(12) United States Patent
Sasmal et al.

(10) Patent No.: US 9,045,479 B2
(45) Date of Patent: Jun. 2, 2015

(54) SUBSTITUTED HETEROCYCLIC COMPOUNDS AS TROPOMYOSIN RECEPTOR KINASE A (TRKA) INHIBITORS

(71) Applicant: Dr. Reddy's Laboratories Ltd., Hyderabad (IN)

(72) Inventors: Pradip Kumar Sasmal, Hyderabad (IN); Shahadat Ahmed, Bangalore (IN); Ganesh Prabhu, Bangalore (IN); Ashok Tehim, Ridgewood, NJ (US); Vidyadhar Paradkar, Branchburg, NJ (US); Marahanakuli Prasanna Dattatreya, Hyderabad (IN); Nanjegowda Jagadeesh Mavinhalli, Bangalore (IN)

(73) Assignee: Dr. Reddy's Laboratories Ltd. (IN)

( * ) Notice: Subject to any disclaimer, the term of this patent is extended or adjusted under 35 U.S.C. 154(b) by 0 days.

(21) Appl. No.: 14/364,518

(22) PCT Filed: Dec. 12, 2012

(86) PCT No.: PCT/IB2012/003022
§ 371 (c)(1),
(2) Date: Jun. 11, 2014

(87) PCT Pub. No.: WO2013/088257
PCT Pub. Date: Jun. 20, 2013

(65) Prior Publication Data
US 2015/0005280 A1    Jan. 1, 2015

(30) Foreign Application Priority Data
Dec. 12, 2011 (IN) .......................... 4329/CHE/2011

(51) Int. Cl.
*C07D 519/00* (2006.01)
*C07D 471/04* (2006.01)

(52) U.S. Cl.
CPC ............ *C07D 471/04* (2013.01); *C07D 519/00* (2013.01)

(58) Field of Classification Search
USPC .......................................... 546/121; 514/300
See application file for complete search history.

(56) References Cited

U.S. PATENT DOCUMENTS

| 2011/0195948 A1 | 8/2011 | Haas et al. | |
| 2013/0331397 A1* | 12/2013 | Molteni et al. | ........... 514/253.04 |

FOREIGN PATENT DOCUMENTS

| JP | 2003231687 A | 8/2003 |
| WO | 2004011461 A1 | 2/2004 |
| WO | 2005005427 A1 | 1/2005 |
| WO | 2007065664 A2 | 6/2007 |
| WO | 2009008748 A1 | 1/2009 |
| WO | 2010048314 A1 | 4/2010 |
| WO | 20120116217 A1 | 8/2012 |

OTHER PUBLICATIONS

Alvares et al., "Building blocks of pain: the regulation of key molecules in spinal sensory neurones during development and following peripheral axotomy", Pain Supplement, 6, 1999, pp. S71-S85.
Belvisi et al., "The nerve growth factor and its receptors in airway inflammatory diseases", Pharmacology & Therapeutics, ScienceDirect, 2008, 117(1), 52-76.
Delafoy et al., "Role of nerve growth factor in the trinitrobenzene sulfonic acid-induced colonic hypersensitivity", Pain, 2003, 105, pp. 489-497.
Dou et al., "Increased nerve growth factor and its receptors in atopic dermatitis: an immunohistochemical study", Arch Dermatol Res, 2006, 298, 31-37.
Ghilardi et al., "Sustained blockade of neurotrophin receptors TrkA, TrkB and TrkC reduces non-malignant skeletal pain but not the maintenance of sensory and sympathetic nerve fibers", Bone, 48, 2011, pp. 389-398.
Gwak et al., "Attenuation of mechanical hyperalgesia following spinal cord injury by administration of antibodies to nerve growth factor in the rat", Neuroscience Letters, 336, 2003, pp. 117-120.
Hayashi et al., "Involvement of NGF in the Rat Model of Persistent Muscle Pain Associated With Taut Band", The Jouranl of Pain, vol. 12, No. 10, Oct. 2011, pp. 1059-1068.
Hu et al., "Decrease in Bladder Overactivity with REN1820 in Rats with Cyclophosphamide Induced Cystitis", The Journal of Urology, vol. 173, 1016-1021, Mar. 2005.
Legault et al., "Highly Efficient Synthesis of O-(2,4-Dinitrophenyl)hydroxylamine. Application to the Synthesis of Substituted N-Benzoyliminopyridinium Ylides", J. Org. Chem., 2003, 68, pp. 7119-7122.
Matayoshi et al., "Actions of brain-derived neurotrophic factor on spinal nociceptive transmission during inflammation in the rat", J Physiol, 569.2, 2005. pp. 685-695.
McMahon et al., "The bioloical effects of endogenous nerve growth factor on adult sensory neurons revealed by a trkA-IgG fusion molecule", Nature Medicine, vol. 1, No. 8, Aug. 1995, pp. 774-780.
Mola et al., "Nerve growth factor and Trk high affinity receptor (TrkA) gene expression in inflammatory bowel disease", Gut, 2000, 46(5), 670-678.
Patapoutian et al., "Trk receptors: mediators of neurotrophin action", Current Opinion Neurobiology, 2001, 11, 272-280.
Ramer et al., "Adrenergic innervation of rat sensory ganglia following proximal or distal painful sciatic neuropathy: distinct mechanisms revealed by anti-NGF treatment", European Journal of Neuroscience, vol. 11, pp. 837-846, 1999.

(Continued)

*Primary Examiner* — Niloofar Rahmani
(74) *Attorney, Agent, or Firm* — Lerner, David, Littenberg, Krumholz & Mentlik, LLP

(57) ABSTRACT

The present application relates to a series of substituted pyrazolo[1,5-a]pyridine compounds, their use as tropomyosin receptor kinase (Trk) family protein kinase inhibitors, method of making and pharmaceutical compositions comprising such compounds.

15 Claims, No Drawings

(56) References Cited

OTHER PUBLICATIONS

Raychaudhuri et al., "K252a, a High-Affinity Nerve Growth Factor Receptor Blocker, Improves Psoriasis: An in vivo Study Using the Severe Combined Immunodeficient Mouse-Human Skin Model", J.Invest Dermatol., 2004, 122(3), 812-819.

Ro et al., "Effect of NGF and anti-NGF on neuropathic pain in rats following chronic constriction injury of the sciatic nerve", Pain, 1999, 79, 265-274.

Shelton et al., "Nerve growth factor mediates hyperalgesia and cachexia in auto-immune arthritis", Pain, 2005, 116, pp. 8-16.

Thompson et al., "Brain-derived neurotrophic factor is an endogenous modulator of nociceptive responses in the spinal cord", Proc. Natl. Acad. Sci. USA 1999, vol. 96, pp. 7714-7718.

Wang et al., "Trk kinase inhibitors as new treatments for cancer and pain", Expert Opinion Ther. Patents, 2009, 19 (3):305-319.

Wei et al., "Activation of Erk in the anterior cingulate cortex during the induction and expression of chronic pain", Molecular Pain, 2008, 4(28), pp. 1-6.

Woolf et al., "Nerve Growth Factor Contributes to the Generation of Inflammatory Sensory Hypersensitivity", Neuroscience, vol. 62, No. 2, pp. 327-331, 1994.

Zahn et al., "Effect of Blockade of Nerve Growth Factor and Tumor Necrosis Factor on Pain Behaviors After Plantar Incision", The Journal of Pain, vol. 5, No. 3, Apr. 2004, pp. 157-163.

International Search Report for Application No. PCT/IB2012/003022 dated May 7, 2013.

* cited by examiner

SUBSTITUTED HETEROCYCLIC COMPOUNDS AS TROPOMYOSIN RECEPTOR KINASE A (TRKA) INHIBITORS

CROSS-REFERENCE TO RELATED APPLICATIONS

The present application is a national phase entry under 35 U.S.C. §371 of International Application No. PCT/IB2012/003022 filed on Dec. 12, 2012, published in English, which claims the priority from Indian Patent Application No. 4329/CHE/2011, filed on Dec. 12, 2011, the disclosures of which are incorporated herein by reference.

TECHNICAL FIELD

The present application relates to a series of substituted pyrazolo[1,5-a]pyridine compounds. The present application is further directed to use such compounds as tropomyosin receptor kinase (Trk) family protein kinase inhibitors. The present application also describes method of making such compounds and pharmaceutical compositions comprising such compounds.

BACKGROUND

TrkA, TrkB and TrkC, which make up the Trk receptor family, are high affinity receptor tyrosine kinases activated by a group of soluble growth factors called neurotrophins (NT) (Curr Opin Neurobiol, 2001, 11, 272-280). Trks play important roles in pain sensation, tumour cell growth and survival signaling (Expert Opin. Ther. Patents, 2009, 19(3):305-319).

Inhibitors of the Trk/neurotrophin pathway have been demonstrated to be effective in numerous animal models of pain. For example, sustained blockade of neurotrophin receptors TrkA, TrkB and TrkC reduces non-malignant skeletal pain (Bone, 2011, 48(2), 389-398). Administration of NGF receptor (TrkA) inhibitor K252a showed significant suppression of mechanical hyperalgesia (relevant to the pathogenesis of myofascial pain syndrome (MPS) in animal models (J. Pain, Article in Press, 2011, 12(10), 1059-1068). Antagonistic NGF and TrkA antibodies have been shown to be efficacious in inflammatory and neuropathic pain animal models (Neuroscience, 1994, 62, 327-331; J. Pain, 2004, 5, 157-163; Nat. Med., 1995, 1, 774-780; Pain, 2005, 116, 8-16; Pain, 2003, 105, 489-497) and neuropathic pain animal models (Eur. J. Neurosci., 1999, 11, 837-846; Pain, 1999, 79, 265-274; Pain, 1999, 81, 245-255; Neurosci. Lett., 2003, 336, 117-120).

NGF secreted by tumor cells and tumor invading macrophages has been shown to directly stimulate TrkA located on peripheral pain fibers. It has also been demonstrated in various tumor models in both mice and rats that neutralizing NGF with a monoclonal antibody inhibits cancer related pain. Further, activation of the BDNF/TrkB pathway has been implicated in numerous studies as a modulator of various types of pain including inflammatory pain (J. Physiol. 2005, 569:685-95), neuropathic pain (Proc. Natl. Acad. Sci. USA 1999, 96:7714-18) and surgical pain (Molecular Pain, 2008, 4(28), 1-11). Since TrkA kinases have been demonstrated to serve as a mediator of NGF driven biological responses, inhibitors of TrkA and/or other Trk kinases may provide an effective treatment for various pain conditions.

Inhibition of the neurotrophin/Trk pathway with NGF antibodies or non-selective small molecule inhibitors of Trk A, B and C has been shown to be effective in treatment of preclinical models of inflammatory diseases such as asthma (Pharmacol. Therapeut., 2008, 117(1), 52-76), interstitial cystitis (J. Urology, 2005, 173(3), 1016-21), inflammatory bowel diseases including ulcerative colitis and Crohn's disease (Gut, 2000, 46(5), 670-678) and inflammatory skin diseases such as atopic dermatitis (Arc Dermatol Res., 2006, 298(1), 31-37), eczema and psoriasis (J. Investig Dermatol., 2004, 122(3), 812-819).

The current treatment regimes for pain conditions utilize several classes of compounds. The opiates apart from being potentially addictive have several adverse effects such as emesis, constipation, dose-related respiratory depression. Nonsteroidal anti-inflammatory analgesics (NSAID) also have drawbacks such as gastric ulceration, dyspepsia and insufficient efficacy in treating severe pain. Accordingly, there is a continuing need for new and more effective treatments for the relief of pain, especially chronic pain. Several classes of small molecule inhibitors of Trk kinases said to be useful for treating pain or cancer are known (Expert Opin. Ther. Patents, 2009, 19(3), 305-319).

U.S. Publication No. 20110195948 describes substituted Pyrazolo[1,5-a]Pyrimidine compounds as Trk kinase inhibitors.

JP Publication No. 2003231687 describes a series of pyrazolyl condensed cyclic compounds as Trk inhibitors.

PCT Publication No. 200505427 describes compounds containing a 1,4,5,6-tetrahydropyrrolo[3,4-c]pyrazole bicyclic scaffold as TrkA inhibitors.

PCT Publication No. 2004011461 describes a series of isothiazole derivatives as Trk inhibitors.

SUMMARY

The present applications relates to pyrazolo[1,5-a]pyridine compounds of formula (I),

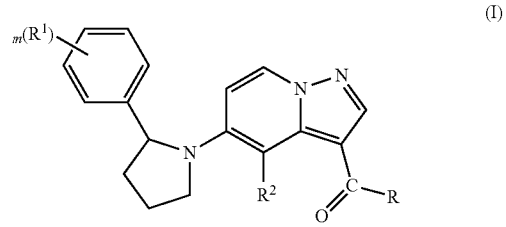

their pharmaceutically acceptable salts, pharmaceutically acceptable solvates or stereoisomers thereof, wherein $R^1$ is independently selected from hydrogen, alkyl, halogen, alkoxy or haloalkoxy;

$R^2$ is selected from hydrogen or fluorine;

wherein when $R^2$ is hydrogen, R is $-NR^3R^4$; and when $R^2$ is fluorine, R is $-NR^3R^4$ or $-OR^x$ wherein Rx is hydrogen or alkyl;

$R^3$ is hydrogen, alkyl, hydroxyalkyl or alkoxyalkyl;

$R^4$ is selected from (i) $-(CR^yR^z)_m-CN$, $-(CR^yR^z)_m COOR^b$, $-(CR^yR^z)_m CONR^cR^d$, $-(CR^yR^z)_m NR^eR^f$, $-(CR^yR^z)_m COR^g$, $-(CR^yR^z)_n-O-(CH_2)_n-OR^h$, alkoxy, haloalkoxy, alkoxyalkyl, thiazolyl, 1,3,4-thiadiazolyl, tetrahydro-2H-thiopyranyl, tetrahydro-2H-thiopyran-1-oxide, tetrahydro-2H-thiopyran-1,1-dioxide, tetrahydrothiophene 1,1-dioxide, (ii) cycloalkyl substituted with hydroxyalkyl, hydroxyalkyl and hydroxyl together, $-(CR^yR^z)_m-COOR^b$, $-CONR^cR^d$, $-NR^eR^f$, $-COR^g$, optionally substituted heterocyclyl, wherein the optional substituent is selected from alkyl or haloalkyl, (iii) heterocyclyl substituted with haloalkyl, alkyl and haloalkyl together, halogen and haloalkyl together, hydroxyalkyl, —SO$_2$-alkyl, —SO$_2$-aryl, —SO$_2$—NR$^e$R$^f$, —CO—NR$^e$R$^f$, —COOR$^b$, —COR$^g$, aralkyl, —(CR$^y$R$^z$)$_n$—NR$^e$R$^f$, optionally substituted heterocyclyl wherein optional substituent is selected from alkyl or SO$_2$—NR$^e$R$^f$, (iv) —(CR$^y$R$^z$)$_m$-aryl substituted with hydroxyalkyl, —SO$_2$-alkyl, —SO$_2$-aryl, —SO$_2$—NR$^e$R$^f$, —CO—NR$^e$R$^f$, —COOR$^b$, aralkyl, —NR$^3$R$^4$, —(CR$^y$R$^z$)$_n$—NR$^e$R$^f$ optionally substituted heterocyclyl wherein optional substituent is selected from halogen, hydroxyl or alkyl; halogen and optionally substituted heterocyclyl together, (v) optionally substituted —(CR$^y$R$^z$)$_n$-heterocyclyl, optionally substituted (C$_7$-C$_{12}$)cycloalkyl, optionally substituted —(CR$^y$R$^z$)$_n$-cycloalkyl, optionally substituted heterocycle containing 3-4 heteroatoms or heterogroups selected from O, S, N, CO, SO or SO$_2$, wherein the optional substituent is selected from cyano, halogen, hydroxy, alkyl, haloalkyl, hydroxyalkyl, alkoxy, haloalkoxy, ⁻COOR$^b$, —(CR$^y$R$^z$)$_n$—CONR$^c$R$^d$, —(CR$^y$R$^z$)$_n$_NR$^e$R$^f$, —SO$_2$R$^g$ or —(CHR$^j$)$_p$—R$^5$, Provided that when R$^2$ is Fluorine, R$^4$ can alternatively be hydroxyalkyl;

Alternatively R$^3$ and R$^4$ together with the nitrogen atom to which they are attached form an optionally substituted 3-10 membered heterocyclic ring wherein the optional substituent is selected from hydroxy, cyano, halogen, alkyl, haloalkyl, hydroxyalkyl, alkoxy, haloalkoxy, —COOR$^b$, —CONR$^c$R$^d$, —NR$^e$R$^f$, —COR$^g$, —O(CH$_2$)$_o$—OR$^h$, —SO$_2$R$^i$, —(CHR$^j$)$_p$—R$^5$ or heterocyclyl optionally substituted with hydroxyl or alkyl;

R$^5$ is independently selected from an optionally substituted group selected from cycloalkyl, aryl, heterocyclyl; wherein the optional substituent is hydroxyl, alkyl, haloalkyl or SO$_2$R$^g$;

R$^b$ is independently selected from hydrogen or alkyl;

R$^c$ is independently selected from hydrogen or alkyl;

R$^d$ is independently selected from hydrogen, alkyl or alkoxy;

R$^e$ is independently selected from hydrogen, alkyl or hydroxyalkyl;

R$^f$ is independently selected from hydrogen or alkyl;

Alternatively R$^e$ and R$^f$, in each occurrence, independent of each other, together with the nitrogen atom to which they are attached form optionally substituted 3-6 membered heterocyclic ring, wherein the optional substituent is selected from hydroxyl, alkyl, acyl, mesyl or COOR$^b$;

R$^g$ is independently selected from alkyl, aryl, heterocyclyl or —NR$^e$R$^f$;

R$^h$ is independently represents alkyl;

R$^i$ is independently selected from alkyl, aryl or —NR$^e$R$^d$;

R$^j$ is independently selected from hydrogen or alkyl;

R$^y$ is independently selected from hydrogen, hydroxy, hydroxyalkyl, alkyl or aryl;

R$^z$ is independently selected from hydrogen or alkyl;

m is independently selected from 0, 1, 2, 3 or 4;

n is independently selected from 1, 2, 3 or 4; and p is 0, 1, 2, 3 or 4.

The present application further relates to methods of treating or preventing conditions, diseases and/or disorders associated with abnormal or deregulated Trk kinase activity by administering effective amount of a compound of formula (I), to a patient in need thereof.

One aspect of the present application provides methods of treating or preventing conditions, diseases and/or disorders associated with abnormal or deregulated TrkA kinase activity by administering effective amount of a compound of formula (I), to a patient in need thereof.

One aspect of the present application provides conditions. diseases and/or disorders treatable or preventable by inhibition of Trk kinase activity, such as pain, inflammation, cancer, restenosis, atherosclerosis, psoriasis, thrombosis, psoriatic arthritis, rheumatoid arthritis, inflammatory bowel disease, ulcerative colitis, Crohn's disease, fibrosis, neurodegenerative disease or a disease, disorder or injury relating to dysmyelination or demyelination by administering a therapeutically effective amount of compound of formula (I), to a patient in need thereof.

The present application also relates to pharmaceutical compositions comprising effective amount of a compound of formula (I), and a pharmaceutically acceptable carrier or diluent, and the use of such compositions in the treatment and/or prevention of diseases associated with inhibiting TrkA in a patient in need thereof, such as pain, inflammation, cancer, restenosis, atherosclerosis, psoriasis, thrombosis, psoriatic arthritis, rheumatoid arthritis, inflammatory bowel disease, ulcerative colitis, Crohn's disease, fibrosis, neurodegenerative disease, a disease, disorder, or injury relating to dysmyelination or demyelination or certain infectious diseases such as *Trypanosoma cruzi* infection

DETAILED DESCRIPTION

'Halogen or Halo' represents fluorine, chlorine, bromine, or iodine.

'Hydroxy' or 'Hydroxyl' represents —OH.

'Alkyl' group refers to linear or branched alkyl group with 1 to 10 carbon atoms. Exemplary alkyl group includes, but is not limited to, methyl, ethyl, n-propyl, iso-propyl, n-butyl, iso-butyl, t-butyl, n-pentyl, iso-pentyl, hexyl, heptyl, octyl and the like.

'Hydroxyalkyl' means at least one hydrogen atom of an alkyl group is replaced by a hydroxyl group. Alkyl group is as defined above. Representative examples of hydroxyalkyl groups include one or more of, but are not limited to hydroxymethyl, hydroxyethyl and the like. Unless otherwise specified, a hydroxyalkyl group typically has from 1 to 10 carbon atoms and 1 to 3 hydroxyl groups.

'Haloalkyl' means at least one halogen atom is substituted on an alkyl group. Both halogen and alkyl have the meaning as defined above. Representative examples of haloalkyl groups include, but are not limited to, fluoromethyl, chloromethyl, fluoroethyl, chloroethyl, difluoromethyl, trifluoromethyl, dichloroethyl, trichloroethyl and the like. Unless otherwise specified, a haloalkyl group typically has from 1 to 10 carbon atoms and 1 to 5 halogen atoms.

'Alkoxy' group refers to an —O(alkyl) group, wherein alkyl group is as defined above. Exemplary alkoxy groups include methoxy, ethoxy, n-propoxy, iso-propoxy, n-butoxy, iso-butoxy, t-butoxy, and the like. Unless otherwise specified, an alkoxy group has from 1 to 10 carbon atoms.

'Alkoxyalkyl' refers to an alkyl group substituted with at least one alkoxy group, wherein alkoxy and alkyl groups are as defined above. Typically, the alkoxy group can have from 1 to 10 carbon atoms, and the alkyl group can have up to 10 carbon atoms. Exemplary alkoxyalkyl groups include, but are not limited to, ethoxymethyl, propoxyethyl, ethoxybutyl and the like.

'Aryl' is a monocyclic or polycyclic aromatic ring system. Exemplary aryl groups include, but are not limited to, phenyl, naphthyl, and the like. Unless otherwise specified, an aryl group typically has from 6 to about 14 carbon atoms but the invention is not limited in that respect.

'Cycloalkyl' group refers to a cyclic alkyl group which may be mono, bicyclic, polycyclic, or a fused/bridged ring system. Exemplary cycloalkyl groups include, but are not limited to, cyclopropyl, cyclobutyl, cyclopentyl, cyclohexyl, cycloheptyl, cyclooctyl, and the like. Unless otherwise specified, a cycloalkyl group typically has from 3 to about 10 carbon atoms. Typical bridged cycloalkyls include, but are not limited to adamantyl, noradamantyl, bicyclo[1.1.0]butanyl, norbornyl(bicyclo[2.2.1]heptanyl), and the like.

'Haloalkoxy' means at least one halogen atom is substituted on an alkoxy group, wherein alkoxy and halogen groups are as defined above. Exemplary haloalkoxy groups include, but not limited to, fluoromethoxy, chloromethoxy, trifluoromethoxy, trichloroethoxy, fluoroethoxy, chloroethoxy, trifloroethoxy, perfluoroethoxy ($—OCF_2CF_3$), trifluoro-t-butoxy, hexafluoro-t-butoxy, perfluoro-t-butoxy ($—OC(CF_3)_3$), and the like. Unless otherwise specified, an haloalkoxy group typically has from 1 to 10 carbon atoms and 1 to 5 halogen atoms.

'Heterocyclyl' or 'Heterocyclic' or 'Heterocycle' is a monocyclic or polycyclic ring system, saturated or unsaturated or aromatic; having at least one heteroatom or heterogroup selected from —O—, —N—, —S—, —SO, —$SO_2$, or —CO. Exemplary saturated heterocyclyl ring groups include, but are not limited to, azetidinyl, pyrrolidinyl, piperidinyl, piperazinyl, tetrahydrofuranyl, tetrahydro-2H-pyranyl, morpholinyl, thiomorpholinyl, thiomorpholine-1,1-dioxide, tetrahydro-2H-thiopyranyl, thiazolidinyl, 1,3-dioxolanyl, 1,4-dioxanyl, 1-oxidotetrahydro-2H-thiopyranyl, 1,1-dioxidotetrahydro-2H-thiopyranyl, hexahydropyrrolo[3,4-c]pyrrol-2(1H)-yl, 2,5-diazabicyclo[2.2.1]heptan-2-yl, azepanyl and the like. Unless otherwise specified, a heterocyclyl group typically has from 3 to about 10 carbon atoms and 1 to 6 heteroatoms or heterogroups.

Exemplary unsaturated heterocyclyl ring groups, aromatic or non-aromatic rings, include, but not limited to, furanyl, oxazolyl, isoxazole, imidazolyl, triazolyl, thiazolyl, pyridinyl, thiazinyl, pyrazinyl, pyrazolyl, tetrazolyl, imidazothiazolyl, furanyl, oxazolyl, isoxazole, imidazolyl, oxadiazolyl, triazolyl, thiazolyl, pyridinyl, thiazinyl, pyrazinyl, pyrazolyl, tetrazolyl, imidazothiazolyl, indolizidinyl, indolyl, oxoindolyl, quinolinyl, 3,4-dihydroisoquinolin-2(1H)-yl, quinoxalinyl, benzoxazolyl, benzo[d]isoxazolyl, benzo[d]thiazolyl, benzo[d][1,3]dioxolyl, 1H-benzo[d][1,2,3]triazolyl, 2-H-indazolyl, 1-H-indazolyl, quinoxalin-2-yl, 1H-benzo[d]imidazolyl, pyrazolo[1,5-a]pyridinyl, dihydrobenzo[b][1,4]dioxinyl, (5,6,7,8-tetrahydroimidazo[1,2-a]pyridin-7-yl), 4,5,6,7-tetrahydropyrazolo[1,5-a]pyrazinyl, 5,6-dihydroimidazo[1,2-a]pyrazin-7(8H)-yl), 5,6,7,8-tetrahydroimidazo[1,2-a]pyrazinyl, Hexahydropyrrolo[1,2-a]pyrazin-2(1H)-yl, 5,6-dihydro-[1,2,4]triazolo[4,3-a]pyrazinyl, pyrazolo[1,5a]pyridinyl and the like. Unless otherwise specified, a heteroaryl group typically has from 3 to about 10 carbon atoms.

'3-10 membered heterocyclic ring' refers to a monocyclic or polycyclic ring system, saturated or unsaturated or aromatic; containing one nitrogen atom and optionally 1-3 additional heteroatoms or heterogroups independently selected from O, S, N, CO, SO, or $SO_2$. Exemplary 3-10 membered heterocyclic rings include (5,6-dihydroimidazo[1,2-a]pyrazin-7(8H)-yl), 5,6,7,8-tetrahydroimidazo[1,2-a]pyrazine-7-yl, 5,6-dihydro-[1,2,4]triazolo[4,3-a]pyrazin-7(8H)-yl, 1H-1,2,4-triazol-1-yl; dihydroisoquinolin-2(1H)-yl, 4,5,6,7-tetrahydropyrazolo[1,5-a]pyrazine-5-yl, pyrrolidin-1-yl; azetidin-1-yl, piperidin-1-yl; piperazin-1-yl, (Hexahydro-1H-pyrido[1,2-a]pyrazin-2(6H)-yl), (Hexahydropyrrolo[1,2-a]pyrazin-2(1H)-yl), hexahydropyrrolo[3,4-c]pyrrol-2(1H)-yl, 2,5-diazabicyclo[2.2.1]heptan-2-yl, azepan-1-yl, 3,8-diazabicyclo[3.2.1]octan-8-yl and the like.

'3-6 membered heterocyclic ring' refers to a monocyclic saturated ring system, containing one nitrogen atom and optionally 1-3 additional heteroatoms or heterogroups independently selected from O, S, N, CO, SO, or $SO_2$. Exemplary 3-6 membered heterocyclic rings include pyrrolidinyl, azetidinyl and the like.

The Trk's are made up of three family members TrkA, TrkB and TrkC that bind to and mediate the signal transduction derived from the Neurotrophins Inhibitors of the Trk/neutrophin pathway have been demonstrated to be highly effective in numerous pre-clinical animal models of pain. The compounds of the invention are modulators of the Trk receptors, particularly TrkA.

As used herein, the term TrkA refers to one of Trk's high affinity binding protein kinase receptors that are activated by Neurotrophins (NT), a group of soluble growth factors Nerve Growth Factor (NGF), Brain-Derived Neurotrophic Factor (BDNF) and Neurotrophin 3-5 (NT 3-5).

'Optionally substituted' means that the substitution is optional and therefore it is possible for the designated atom or group to be unsubstituted. In the event a substitution is desired, then such substitution means that any number of hydrogens on the designated atom is replaced with a selection from the indicated group, provided that the normal valence of the designated atom is not exceeded, and that the substitution results in a stable compound. For example, in formula (I) when a substituent is oxo (i.e., =O), then two hydrogens on the atom are replaced and when the substitution is fluoro, then one hydrogen on the atom is replaced and the like. When more than one substituent is present on an atom or group, the chosen substituents are independent of each other (i.e. same or different).

As used herein and in the appended claims, the singular forms "a", "an", and "the" include plural reference unless the context clearly indicates otherwise.

As used herein, the term 'subject' or 'patient' means mammals, such as humans and other animals, including horses, dogs, cats, rats, mice, sheep, pigs, monkeys, chimpanzees or other apes or primates. In exemplary embodiments, the subject may include subjects for which treatment and/or prevention of the conditions described herein would be beneficial.

For ease of reference, in this application it will be described in terms of administration to human subjects. It will be understood, however, that such descriptions are not limited to administration to humans, but will also include administration to other animals unless explicitly stated otherwise.

A 'therapeutically effective amount' is the amount of compound of the present application that is effective in generating biological or medical response of a subject, for example, reduction or inhibition of an enzyme or a protein activity, or ameliorate symptoms, alleviate conditions, slow or delay disease progression, or prevent a disease.

In one embodiment, the term 'a therapeutically effective amount' refers to the amount of the compound of the present application that, when administered to a subject, is effective in (i) at least partially alleviating, inhibiting, preventing and/or ameliorating a condition, or a disorder or a disease mediated by TrkA, TrkB and/or TrkC, associated with TrkA, TrkB and/or TrkC activity or characterized by activity (normal or abnormal) of TrkA, TrkB and/or TrkC; (ii) reducing or inhibiting the activity of TrkA, TrkB and/or TrkC; or (iii) reducing or inhibiting the expression of TrkA, TrkB and/or TrkC.

In another embodiment, the term "a therapeutically effective amount" refers to the amount of the compound of the present invention that, when administered to a cell, or a tissue, or a non-cellular biological material, or a medium, is effective to at least partially reducing or inhibiting the activity of TrkA, TrkB and/or TrkC; or at least partially reducing or inhibiting the expression of TrkA, TrkB and/or TrkC.

The terms 'treating' or 'to treat' means to alleviate symptoms, eliminate the causation either on a temporary or permanent basis, or to prevent or slow the appearance of symptoms. The term 'treatment' includes alleviation, elimination of causation of or prevention of any of the diseases or disorders described above. The compounds described herein are typically administered in admixture with one or more pharmaceutically acceptable excipients or carriers in the form of a pharmaceutical composition. A 'composition' may contain one compound or a mixture of compounds. A 'pharmaceutical composition' is any composition useful in producing at least one physiological response in a subject to which such pharmaceutical composition is administered.

The term 'substantially pure' means that the isolated material is at least 80% pure, preferably 90% pure, more preferably 95% pure, and even more preferably 99% pure as measured by a suitable analytical techniques known in the art.

Unless defined otherwise, all technical and scientific terms used herein have the same meaning as commonly understood to one of ordinary skill in the art.

One or more compounds of formula (I) can be supplied in the form of a therapeutic composition that is within the scope of the present application.

The term 'Pharmaceutically acceptable salts' refers to any acid or base salt, pharmaceutically acceptable solvates, or any complex of the compound that, when administered to a recipient, is capable of providing (directly or indirectly) a compound as described herein. It should be appreciated, however, that salts that are not pharmaceutically acceptable also lie within the scope of the application. The preparation of salts can be carried out using known methods.

For example, pharmaceutically acceptable salts of compound of formula (I) contemplated refers to salts prepared from acids or bases including inorganic or organic acids and inorganic or organic bases by conventional chemical methods using a compound of formula (I). Generally, such salts may be prepared, for example, by making free base of the compounds and reacting with a stoichiometric quantity of the appropriate acid and vice-versa in water or in an organic solvent, or in a mixture of the two. The compounds of the present applications may form mono, di or tris salts.

When the compound of formula (I) is basic, salts may be prepared from acids, including inorganic or organic acids (acid addition salts). Examples of such acids include, but not limited to formic, acetic, trifluoroacetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), nitric, hydrochloride, hydrobromide, isoethionic, hydroiodide, phosphoric, sulfuric, succinic, tartaric, methanesulfonic, ethanesulfonic, benzenesulfonic, benzoic, mucic, pantothenic, p-toluenesulfonic, camphorsulfonic, 2-hydroxyethanesulfonic, sulfanilic, cyclohexylaminosulfonic, algenic, β-hydroxybutyric, galactaric, and galacturonic acid, and the like.

Salts formed from inorganic bases include sodium, potassium, lithium, calcium, copper, magnesium, manganic salts, manganous, zinc, aluminum, ammonium, ferric, ferrous and the like.

Salts derived from organic bases include salts of primary, secondary, and tertiary amines, substituted amines including naturally occurring substituted amines, cyclic amines, and basic ion exchange resins, such as arginine, betaine, caffeine, choline, N,N-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperid e, polyamine resins, procaine, purines, theobromine, triethylamine, trimethylamine, tripropylamine, tromethamine, and the like.

'Pharmaceutically acceptable salts' in the solid form may exist in more than one crystal structure, and may also be in the form of hydrates.

The term 'stereoisomers' is a general term used for all isomers of an individual molecule that differ only in the orientation of their atoms in space. Where the compounds according to the present application possess one or more asymmetric centers and compounds with asymmetric centers give rise to enantiomers, diastereomers or both as pure or partially purified compounds. It is to be understood that all stereoisomeric forms of the compounds of the invention, including but not limited to, diastereomers, enantiomers and atropsiomers, as well as mixtures thereof such as forms, are included in the scope of the present application. Preparation of such stereoisomeric forms of compound of formula (I), may be achieved by appropriate modification of the methodology known in the art. Their absolute stereochemistry may be determined by the suitable methods. If required, racemic mixtures of the compound of formula (I) may be separated to isolate individual enantiomers or diastereomers. Such separation can be carried out by methods known in the art, such as the coupling of a racemic mixture of compound of formula (I) to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art. Alternatively, any enantiomer or diastereomer of a compound may be obtained by stereoselective synthesis using optically pure starting materials or known reagents.

For any particular compound disclosed herein, wherein the stereochemistry of any particular chiral atom is not specified, then all stereoisomers are contemplated and included as the compounds of the application. Where stereochemistry is specified by a solid wedge or a dashed wedge bond or dashed line representing a particular configuration then that stereoisomer is so specified and defined. Following the standard chemical literature description practice and as used herein, a full wedge bond means above the ring plane, and a dashed wedge bond or dashed line means below the ring plane.

Pharmaceutically acceptable solvates of compound of formula (I) may be hydrates or comprising other solvents of crystallization such as alcohols. Pharmaceutically acceptable solvates of compound of formula (I) may be prepared by conventional methods such as dissolving the compounds of formula (I) in solvents such as water, methanol, ethanol etc., preferably water and recrystallizing by using different crystallization techniques.

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position.

Reference will now be made in detail to the embodiments of the invention, one or more examples of which are set forth below. Each example is provided by way of explanation of the invention, and not by way of limitation of the invention. In fact, it will be apparent to those skilled in the art that various modification and variations can be made in the present invention without departing from the scope or spirit of the invention. For instance, features illustrated or described as part of one embodiment can be used on another embodiment to yield a still further embodiment. Thus it is intended that the present invention cover such modifications and variations as come within the scope of the appended claims and their equivalents. Other objects, features, and aspects of the present invention are disclosed in, or are obvious from, the following detailed description. It is to be understood by one of ordinary skill in the art that the present discussion is a description of exemplary embodiments only, and is not to be construed as limiting the broader aspects of the present application.

Thus in accordance of this application there is provided a series of substituted pyrazolo[1,5-a]pyridine derivatives having the general formula (I),

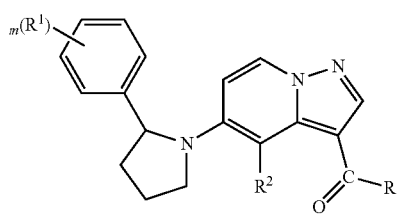

their pharmaceutically acceptable salts, pharmaceutically acceptable solvates or stereoisomers thereof, wherein
$R^1$ is independently selected from hydrogen, alkyl, halogen, alkoxy or haloalkoxy;
$R^2$ is selected from hydrogen or fluorine;
wherein when $R^2$ is hydrogen, R is —$NR^3R^4$; and when $R^2$ is fluorine, R is —$NR^3R^4$ or —$OR^x$ wherein Rx is hydrogen or alkyl;
$R^3$ is hydrogen, alkyl, hydroxyalkyl or alkoxyalkyl;
$R^4$ is selected from
(i) —$(CR^yR^z)_m$—CN, —$(CR^yR^z)_m COOR^b$, —$(CR^yR^z)_m$ $CONR^cR^d$, —$(CR^yR^z)_m NR^eR^f$, —$(CR^yR^z)_m COR^g$, —$(CR^yR^z)_n$—O—$(CH_2)_n$—$OR^h$, alkoxy, haloalkoxy, alkoxyalkyl, thiazolyl, 1,3,4-thiadiazolyl, tetrahydro-2H-thiopyranyl, tetrahydro-2H-thiopyran-1-oxide, tetrahydro-2H-thiopyran-1,1-dioxide, tetrahydrothiophene 1,1-dioxide,
(ii) cycloalkyl substituted with hydroxyalkyl, hydroxyalkyl and hydroxyl together, —$(CR^yR^z)_m$—$COOR^b$, —$CONR^cR^d$, —$NR^eR^f$, —$COR^g$, optionally substituted heterocyclyl, wherein the optional substituent is selected from alkyl or haloalkyl,
(iii) heterocyclyl substituted with haloalkyl, alkyl and haloalkyl together, halogen and haloalkyl together, hydroxyalkyl, —$SO_2$-alkyl, —$SO_2$-aryl, —$SO_2$—$NR^eR^f$, —CO—$NR^eR^f$, —$COOR^b$, —$COR^g$, aralkyl, —$(CR^yR^z)_n$—$NR^eR^f$, optionally substituted heterocyclyl wherein optional substituent is selected from alkyl or $SO_2$—$NR^eR^f$,
(iv) —$(CR^yR^z)_m$-aryl substituted with hydroxyalkyl, —$SO_2$-alkyl, —$SO_2$-aryl, —$SO_2$—$NR^eR^f$, —CO—$NR^eR^f$, —$COOR^b$, aralkyl, —$NR^3R^4$, —$(CR^yR^z)_n$—$NR^eR^f$, an optionally substituted heterocyclyl wherein optional substituent is selected from halogen, hydroxyl or alkyl; halogen and optionally substituted heterocyclyl together,
(v) optionally substituted —$(CR^yR^z)_n$-heterocyclyl, optionally substituted $(C_7-C_{12})$cycloalkyl, optionally substituted —$(CR^yR^z)_n$-cycloalkyl, optionally substituted heterocycle containing 3-4 heteroatoms or heterogroups selected from O, S, N, CO, SO or $SO_2$, wherein the optional substituent is selected from cyano, halogen, hydroxy, alkyl, haloalkyl, hydroxyalkyl, alkoxy, haloalkoxy, ⁻$COOR^b$, —$(CR^yR^z)_n$—$CONR^cR^d$, —$(CR^yR^z)_n$—$NR^eR^f$, —$SO_2R^g$ or —$(CHR^j)_p$—$R^5$,
Provided that when $R^2$ is Fluorine, $R^4$ can alternatively be hydroxyalkyl;
Alternatively $R^3$ and $R^4$ together with the nitrogen atom to which they are attached form an optionally substituted 3-10 membered heterocyclic ring wherein the optional substituent is selected from hydroxy, cyano, halogen, alkyl, haloalkyl, hydroxyalkyl, alkoxy, haloalkoxy, —$COOR^b$, —$CONR^cR^d$, —$NR^eR^f$, —$COR^g$, —$O(CH_2)_o$—$OR^h$, —$SO_2R^i$, —$(CHR^j)_p$—$R^5$ or heterocyclyl optionally substituted with hydroxyl or alkyl;
$R^5$ is independently selected from an optionally substituted group selected from cycloalkyl, aryl, heterocyclyl; wherein the optional substituent is hydroxyl, alkyl, haloalkyl or $SO_2R^g$;
$R^b$ is independently selected from hydrogen or alkyl;
$R^c$ is independently selected from hydrogen or alkyl;
$R^d$ is independently selected from hydrogen, alkyl or alkoxy;
$R^e$ is independently selected from hydrogen, alkyl or hydroxyalkyl;
$R^f$ is independently selected from hydrogen or alkyl;
Alternatively $R^e$ and $R^f$, in each occurrence, independent of each other, together with the nitrogen atom to which they are attached form optionally substituted 3-6 membered heterocyclic ring, wherein the optional substituent is selected from hydroxyl, alkyl, acyl, mesyl or $COOR^b$;
$R^g$ is independently selected from alkyl, aryl, heterocyclyl or —$NR^eR^f$;
$R^h$ is independently represents alkyl;
$R^i$ is independently selected from alkyl, aryl or —$NR^eR^d$;
$R^j$ is independently selected from hydrogen or alkyl;
$R^y$ is independently selected from hydrogen, hydroxy, hydroxyalkyl, alkyl or aryl;
$R^z$ is independently selected from hydrogen or alkyl;
M is independently selected from 0, 1, 2, 3 or 4;
n is independently selected from 1, 2, 3 or 4; and
p is 0, 1, 2, 3 or 4.

In one embodiment, there is provided a compound of formula (Ia),

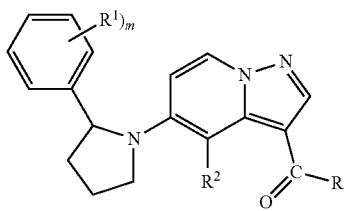

(Ia)

their pharmaceutically acceptable salts, pharmaceutically acceptable solvates or stereoisomers thereof, wherein the values of all the variables are as described for compound of formula (I).

In another embodiment, there is provided a compound of formula (Ib),

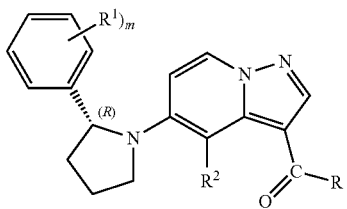

(Ib)

their pharmaceutically acceptable salts, pharmaceutically acceptable solvates or stereoisomers thereof, wherein the values of all the variables are as described for compound of formula (I).

In another embodiment, there is provided a compound of formula (Ic),

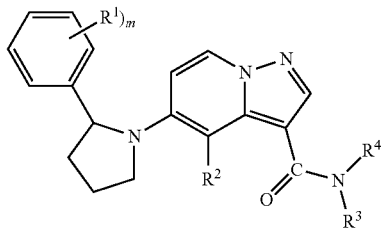

their pharmaceutically acceptable salts, pharmaceutically acceptable solvates or stereoisomers thereof, wherein the values of all the variables are as described for compound of formula (I).

In another embodiment, there is provided a compound of formula (Id),

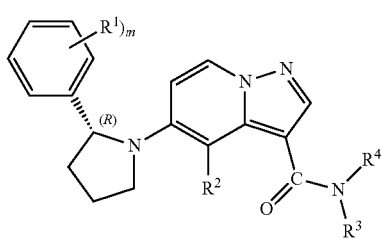

their pharmaceutically acceptable salts, pharmaceutically acceptable solvates or stereoisomers thereof, wherein the values of all the variables are as described for compound of formula (I).

In one embodiment, there is provided a compound of formula (Id), wherein $R^3$ and $R^4$ together with the nitrogen atom to which they are attached form 3-10 membered heterocyclic ring, optionally substituted with hydroxy, cyano, halogen, alkyl, haloalkyl, hydroxyalkyl, alkoxy, haloalkoxy, —COOR$^b$, —CONR$^c$R$^d$, —NR$^e$R$^f$, —COR$^g$, —O(CH$_2$)$_o$—OR$^h$, —SO$_2$R$^i$, —(CHR$^j$)$_p$—R$^5$ or heterocyclyl optionally substituted with hydroxyl or alkyl.

In another embodiment, there is provided a compound of formula (Ie),

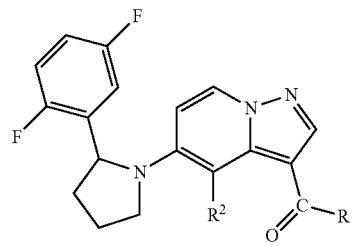

their pharmaceutically acceptable salts, pharmaceutically acceptable solvates or stereoisomers thereof, wherein the values of all the variables are as described for compound of formula (I).

In another embodiment, there is provided a compound of formula (If),

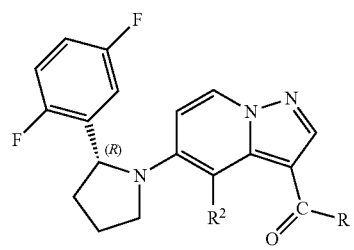

their pharmaceutically acceptable salts, pharmaceutically acceptable solvates or stereoisomers thereof, wherein the values of all the variables are as described for compound of formula (I).

In one embodiment, there is provided a compound of formula (I) or (Ia) or (Ib), or (Ic) or (Id) or (Ie) or (If), wherein when $R^2$ is hydrogen and R is NR$^3$R$^4$.

In one embodiment, there is provided a compound of formula (I) or (Ia) or (Ib), or (Ic) or (Id) or (Ie) or (If), wherein when $R^2$ is fluorine, R is NR$^3$R$^4$ or —OR$^x$.

In one embodiment, there is provided a compound of formula (I) or (Ia) or (Ib), or (Ic) or (Id) or (Ie) or (If), wherein $R^3$ represents hydrogen and $R^4$ represents cycloalkyl substituted with hydroxyalkyl, hydroxyalkyl and hydroxyl together, —(CR$^y$R$^z$)$_m$—COOR$^b$, —CONR$^c$R$^d$, —NR$^e$R$^f$, —COR$^g$, optionally substituted heterocyclyl, wherein optional substituent is selected from alkyl or haloalkyl.

In another embodiment, there is provided a compound of formula (I) or (Ia) or (Ib), or (Ic) or (Id) or (Ie) or (If), wherein $R^3$ represents hydrogen and $R^4$ represents heterocyclyl substituted with haloalkyl, alkyl and haloalkyl together, halogen and haloalkyl together, hydroxyalkyl, —SO$_2$-alkyl, —SO$_2$- aryl, —SO₂—NRᵉRᶠ, —CO—NRᵉRᶠ, —COORᵇ, —CORᵍ, aralkyl, —NR³R⁴, —(CRʸRᶻ)ₙ—NR³R⁴, optionally substituted heterocyclyl, wherein optional substituent is selected from alkyl or SO₂—NRᵉRᶠ.

In another embodiment, there is provided a compound of formula (I) or (Ia) or (Ib), or (Ic) or (Id) or (Ie) or (If), wherein R³ represents hydrogen and R⁴ represents —(CRʸRᶻ)ₘ-aryl substituted with hydroxyalkyl, —SO₂-alkyl, —SO₂-aryl, —SO₂—NRᵉRᶠ, —CO—NRᵉRᶠ, —COORᵇ, aralkyl, —NR³R⁴, —(CRʸRᶻ)ₙ—NRᵉRᶠ, an optionally substituted heterocyclyl wherein optional substituent is selected from halogen, hydroxyl or alkyl, or halogen and optionally substituted heterocyclyl together.

In another embodiment, there is provided a compound of formula (I) or (Ia) or (Ib), or (Ic) or (Id) or (Ie) or (If), wherein R³ represents hydrogen and R⁴ represents an optionally substituted —(CRʸRᶻ)ₙ-heterocyclyl, wherein the optional substituent is selected from cyano, halogen, hydroxy, alkyl, haloalkyl, hydroxyalkyl, alkoxy, haloalkoxy, ⁻COORᵇ, —(CRʸRᶻ)ₙ—CONRᶜRᵈ, —(CRʸRᶻ)ₙ—NRᵉRᶠ, —SO₂Rᵍ or —(CHRʲ)ₚ—R⁵.

In another embodiment, there is provided a compound of formula (I) or (Ia) or (Ib), or (Ic) or (Id) or (Ie) or (If), wherein R³ represents hydrogen and R⁴ represents optionally substituted (C₇-C₁₂)cycloalkyl, wherein the optional substituent is selected from cyano, halogen, hydroxy, alkyl, haloalkyl, hydroxyalkyl, alkoxy, haloalkoxy, ⁻COORᵇ, —(CRʸRᶻ)ₙ—CONRᶜRᵈ, —(CRʸRᶻ)ₙ—NRᵉRᶠ, —SO₂Rᵍ or —(CHRʲ)ₚ—R⁵.

In another embodiment, there is provided a compound of formula (I) or (Ia) or (Ib), or (Ic) or (Id) or (Ie) or (If), wherein R³ represents hydrogen and R⁴ represents optionally substituted —(CRʸRᶻ)ₙ-cycloalkyl, wherein the optional substituent is selected from cyano, halogen, hydroxy, alkyl, haloalkyl, hydroxyalkyl, alkoxy, haloalkoxy, ⁻COORᵇ, —(CRʸRᶻ)ₙ—CONRᶜRᵈ, —(CRʸRᶻ)ₙ—NRᵉRᶠ, —SO₂Rᵍ or —(CHRʲ)ₚ—R⁵.

In another embodiment, there is provided a compound of formula (I) or (Ia) or (Ib), or (Ic) or (Id) or (Ie) or (If), wherein R³ represents hydrogen and R⁴ represents optionally substituted heterocycle containing 3-4 heteroatoms or heterogroups selected from O, S, N, C(=O), S(=O) or S(=O)₂, wherein the optional substituent is independently selected from cyano, halogen, hydroxy, alkyl, haloalkyl, hydroxyalkyl, alkoxy, haloalkoxy, ⁻COORᵇ, —(CRʸRᶻ)ₙ—CONRᶜRᵈ, —(CRʸRᶻ)ₙ—NRᵉRᶠ, —SO₂Rᵍ or —(CHRʲ)ₚ—R⁵.

In another embodiment, there is provided a compound of formula (I) or (Ia) or (Ib), or (Ic) or (Id) or (Ie) or (If), wherein R¹ is fluorine and m is 1 or 2.

In one embodiment, there is provided a compound of formula (I) or (Ia) or (Ib), or (Ic) or (Id) or (Ie) or (If), wherein R³ and R⁴ together form 3-10 membered heterocyclic ring selected from (5,6-dihydroimidazo[1,2-a]pyrazin-7(8H)-yl), 5,6,7,8-tetrahydroimidazo[1,2-a]pyrazine-2-yl, 5,6-dihydro-[1,2,4]triazolo[4,3-a]pyrazin-7(8H)-yl, 1H-1,2,4-triazol-1-yl; dihydroisoquinolin-2(1H)-yl, 4,5,6,7-tetrahydropyrazolo[1,5-a]pyrazine-5-yl, pyrrolidin-1-yl; azetidin-1-yl, piperidin-1-yl, piperazin-1-yl, (Hexahydro-1H-pyrido[1,2-a]pyrazin-2(6H)-yl), (Hexahydropyrrolo[1,2-a]pyrazin-2(1H)-yl), hexahydropyrrolo[3,4-c]pyrrol-2(1H)-yl, 2,5-diazabicyclo[2.2.1]heptan-2-yl, azepan-1-yl, 3,8-diazabicyclo[3.2.1]octan-8-yl and the like.

In one embodiment, there is provided a compound of formula (I) or (Ia) or (Ib), or (Ic) or (Id) or (Ie) or If), wherein R² is fluorine.

In an embodiment, specific compounds of formula (I) without any limitation are enumerated below (List-1):

List-1:

(5-(2-(2,5-difluorophenyl)pyrrolidin-1-yl)pyrazolo[1,5-a]pyridin-3-yl)((S)-3-hydroxypyrrolidin-1-yl)methanone;

(5-(2-(2,5-difluorophenyl)pyrrolidin-1-yl)pyrazolo[1,5-a]pyridin-3-yl)(3-hydroxyazetidine-1-yl)methanone;

(5-(2-(2,5-difluorophenyl)pyrrolidin-1-yl)pyrazolo[1,5-a]pyridin-3-yl)(4-hydroxypiperidin-1-yl)methanone;

(5-(2-(2,5-difluorophenyl)pyrrolidin-1-yl)pyrazolo[1,5-a]pyridin-3-yl)(4-methylpiperazin-1-yl)methanone;

(R)-(5-(2-(2,5-difluorophenyl)pyrrolidin-1-yl)pyrazolo[1,5-a]pyridin-3-yl) (3-hydroxyazetidine-1-yl)methanone;

(5-((R)-2-(2,5-difluorophenyl)pyrrolidin-1-yl)pyrazolo[1,5-a]pyridin-3-yl)((S)-3-hydroxypyrrolidin-1-yl)methanone;

(5-((S)-2-(2,5-difluorophenyl)pyrrolidin-1-yl)pyrazolo[1,5-a]pyridin-3-yl) ((S)-3-hydroxypyrrolidin-1-yl)methanone;

(S)-(5-(2-(2,5-difluorophenyl)pyrrolidin-1-yl)pyrazolo[1,5-a]pyridin-3-yl) (3-hydroxyazetidine-1-yl)methanone;

(5-((R)-2-(2,5-difluorophenyl)pyrrolidin-1-yl)pyrazolo[1,5-a]pyridin-3-yl)(Hexahydro-1H-pyrido[1,2-a]pyrazin-2(6H)-yl)methanone;

(R)-(5-(2-(2,5-difluorophenyl)pyrrolidin-1-yl)pyrazolo[1,5-a]pyridin-3-yl)(5,6-dihydroimidazo[1,2-a]pyrazin-7(8H)-yl)methanone;

(R)-ethyl 7-(5-(2-(2,5-difluorophenyl)pyrrolidin-1-yl)pyrazolo[1,5-a]pyridine-3-carbonyl)-5,6,7,8-tetrahydroimidazo[1,2-a]pyrazine-2-carboxylate;

(5-((R)-2-(2,5-difluorophenyl)pyrrolidin-1-yl)pyrazolo[1,5-a]pyridin-3-yl)(Hexahydropyrrolo[1,2-a]pyrazin-2(1H)-yl)methanone;

(5-((R)-2-(2,5-difluorophenyl)pyrrolidin-1-yl)pyrazolo[1,5-a]pyridin-3-yl)(5-methylhexahydropyrrolo[3,4-c]pyrrol-2(1H)-yl)methanone;

(R)-(5-(2-(2,5-difluorophenyl)pyrrolidin-1-yl)pyrazolo[1,5-a]pyridin-3-yl)(3-(trifluoromethyl)-5,6-dihydro-[1,2,4]triazolo[4,3-a]pyrazin-7 (8H)-yl)methanone;

(R)-(5-(2-(2,5-difluorophenyl)pyrrolidin-1-yl)pyrazolo[1,5-a]pyridin-3-yl) (3-hydroxy-3-methylazetidin-1-yl)methanone;

5-((R)-2-(2,5-difluorophenyl)pyrrolidin-1-yl)-N—((S)-1-phenyl-2-(pyrrolidin-1-yl)ethyl)pyrazolo[1,5-a]pyridine-3-carboxamide;

(5-((R)-2-(2,5-difluorophenyl)pyrrolidin-1-yl)pyrazolo[1,5-a]pyridin-3-yl)(3-(hydroxymethyl)pyrrolidin-1-yl)methanone;

Ethyl 1-(5-((R)-2-(2,5-difluorophenyl)pyrrolidin-1-yl)pyrazolo[1,5-a]pyridine-3-carbonyl)pyrrolidine-3-carboxylate;

1-(5-((R)-2-(2,5-difluorophenyl)pyrrolidin-1-yl)pyrazolo[1,5-a]pyridine-3-carbonyl)pyrrolidine-3-carboxylic acid;

5-((R)-2-(2,5-difluorophenyl)pyrrolidin-1-yl)-N—((S)-2-((S)-3-hydroxypyrrolidin-1-yl)-1-phenylethyl)pyrazolo[1,5-a]pyridine-3-carboxamide;

(R)-Ethyl 2-(5-(2-(2,5-difluorophenyl)pyrrolidin-1-yl)pyrazolo[1,5-a]pyridine-3-carboxamido)acetate;

(R)-2-(5-(2-(2,5-difluorophenyl)pyrrolidin-1-yl)pyrazolo[1,5-a]pyridine-3-carboxamido) acetic acid;

5-((R)-2-(2,5-difluorophenyl)pyrrolidin-1-yl)-N-(3-hydroxyadamantan-1-yl)pyrazolo[1,5-a]pyridine-3-carboxamide (R)-(5-(2-(2,5-difluorophenyl)pyrrolidin-1-yl)pyrazolo[1,5-a]pyridin-3-yl) (piperazin-1-yl)methanone;

2,5-diazabicyclo[2.2.1]heptan-2-yl(5-((R)-2-(2,5-difluorophenyl)pyrrolidin-1-yl)pyrazolo[1,5-a]pyridin-3-yl)methanone;

(R)-Methyl 4-(5-(2-(2,5-difluorophenyl)pyrrolidin-1-yl)pyrazolo[1,5-a]pyridine-3-carboxamido)cyclohexanecarboxylate;

(R)-4-(5-(2-(2,5-difluorophenyl)pyrrolidin-1-yl)pyrazolo[1,5-a]pyridine-3-carboxamido)cyclohexanecarboxylic acid;

(R)-4-amino-1-(5-(2-(2,5-difluorophenyl)pyrrolidin-1-yl)pyrazolo[1,5-a]pyridine-3-carbonyl)piperidine-4-carboxylic acid hydrochloride;

(5-((R)-2-(2,5-difluorophenyl)pyrrolidin-1-yl)pyrazolo[1,5-a]pyridin-3-yl)(8-(((S)-3-hydroxypyrrolidin-1-yl)methyl)-5,6-dihydroimidazo[1,2-a]pyrazin-7(8H)-yl)methanone 2,2,2-trifluoroacetate;

(5-((R)-2-(2,5-difluorophenyl)pyrrolidin-1-yl)pyrazolo[1,5-a]pyridin-3-yl)(4-hydroxyazepan-1-yl)methanone;

(R)-5-(2-(2,5-difluorophenyl)pyrrolidin-1-yl)-N-(2-(pyrrolidin-1-yl)ethyl)pyrazolo[1,5-a]pyridine-3-carboxamide;

(R)-Methyl 4-(5-(2-(2,5-difluorophenyl)pyrrolidin-1-yl)pyrazolo[1,5-a]pyridine-3-carboxamido)tetrahydro-2H-pyran-4-carboxylate;

(R)-(5-(2-(2,5-difluorophenyl)pyrrolidin-1-yl)pyrazolo[1,5-a]pyridin-3-yl)(6,7-dimethoxy-3,4-dihydroisoquinolin-2(1H)-yl)methanone;

Ethyl 3-(5-((R)-2-(2,5-difluorophenyl)pyrrolidin-1-yl)pyrazolo[1,5-a]pyridine-3-carboxamido)cyclohexanecarboxylate;

3-(5-((R)-2-(2,5-difluorophenyl)pyrrolidin-1-yl)pyrazolo[1,5-a]pyridine-3-carboxamido)cyclohexanecarboxylic acid;

(R)-7-(5-(2-(2,5-difluorophenyl)pyrrolidin-1-yl)pyrazolo[1,5-a]pyridine-3-carbonyl)-5,6,7,8-tetrahydroimidazo[1,2-a]pyrazine-2-carboxylic acid;

(R)-5-(2-(2,5-difluorophenyl)pyrrolidin-1-yl)-N-(2-(dimethylamino)-2-oxoethyl)pyrazolo[1,5-a]pyridine-3-carboxamide;

(R)-5-(2-(2,5-difluorophenyl)pyrrolidin-1-yl)-N-(2-(dimethylamino) ethyl)pyrazolo[1,5-a]pyridine-3-carboxamide;

5-((R)-2-(2,5-difluorophenyl)pyrrolidin-1-yl)-N-(1-(5-fluoropyridin-2-yl)ethyl)pyrazolo[1,5-a]pyridine-3-carboxamide;

(5-Benzylhexahydropyrrolo[3,4-c]pyrrol-2 (1H)-yl)(5-((R)-2-(2,5-difluorophenyl)pyrrolidin-1-yl)pyrazolo[1,5-a]pyridin-3-yl)methanone;

(5-((R)-2-(2,5-difluorophenyl)pyrrolidin-1-yl)pyrazolo[1,5-a]pyridin-3-yl)((S)-2-(hydroxymethyl)pyrrolidin-1-yl)methanone;

(R)-Methyl 4-amino-1-(5-(2-(2,5-difluorophenyl)pyrrolidin-1-yl)pyrazolo[1,5-a]pyridine-3-carbonyl)piperidine-4-carboxylate;

(R)-5-(2-(2,5-difluorophenyl)pyrrolidin-1-yl)-N-(2-morpholinoethyl)pyrazolo[1,5-a]pyridine-3-carboxamide;

(5-((R)-2-(2,5-difluorophenyl)pyrrolidin-1-yl)pyrazolo[1,5-a]pyridin-3-yl)((S)-3-(dimethylamino) pyrrolidin-1-yl)methanone;

(R)-4-(5-(2-(2,5-difluorophenyl)pyrrolidin-1-yl)pyrazolo[1,5-a]pyridine-3-carboxamido)tetrahydro-2H-pyran-4-carboxylic acid;

((S)-3-aminopyrrolidin-1-yl)(5-((R)-2-(2,5-difluorophenyl)pyrrolidin-1-yl)pyrazolo[1,5-a]pyridin-3-yl)methanone;

(R)-5-(2-(2,5-difluorophenyl)pyrrolidin-1-yl)-N-(1-(methylsulfonyl)piperidin-4-yl)pyrazolo[1,5-a]pyridine-3-carboxamide;

(R)-5-(2-(2,5-difluorophenyl)pyrrolidin-1-yl)-N-(1-(methylsulfonyl)piperidin-4-yl)pyrazolo[1,5-a]pyridine-3-carboxamide;

5-((R)-2-(2,5-difluorophenyl)pyrrolidin-1-yl)-N—((S)-1-(2-hydroxyethyl)pyrrolidin-3-yl)pyrazolo[1,5-a]pyridine-3-carboxamide;

(R)-5-(2-(2,5-difluorophenyl)pyrrolidin-1-yl)-N-(4-(pyrrolidin-1-ylmethyl)tetrahydro-2H-pyran-4-yl)pyrazolo[1,5-a]pyridine-3-carboxamide;

(R)-5-(2-(2,5-difluorophenyl)pyrrolidin-1-yl)-N-(4-(hydroxymethyl)tetrahydro-2H-pyran-4-yl)pyrazolo[1,5-a]pyridine-3-carboxamide;

(R)-Ethyl 4-(5-(2-(2,5-difluorophenyl)pyrrolidin-1-yl)pyrazolo[1,5-a]pyridine-3-carboxamido) piperidine-1-carboxylate;

(R)-5-(2-(2,5-difluorophenyl)pyrrolidin-1-yl)-N-(1-(2-hydroxyethyl)piperidin-4-yl)pyrazolo[1,5-a]pyridine-3-carboxamide;

(5-((R)-2-(2,5-difluorophenyl)pyrrolidin-1-yl)pyrazolo[1,5-a]pyridin-3-yl)((S)-3-(hydroxymethyl)piperidin-1-yl) methanone;

(5-((R)-2-(2,5-difluorophenyl)pyrrolidin-1-yl)pyrazolo[1,5-a]pyridin-3-yl)((R)-3-(hydroxymethyl)piperidin-1-yl) methanone;

5-((R)-2-(2,5-difluorophenyl)pyrrolidin-1-yl)-N—((S)-1-(methylsulfonyl)pyrrolidin-3-yl)pyrazolo[1,5-a]pyridine-3-carboxamide;

(R)-Methyl 1-benzyl-4-(5-(2-(2,5-difluorophenyl)pyrrolidin-1-yl)pyrazolo[1,5-a]pyridine-3-carboxamido) piperidine-4-carboxylate;

(R)-Methyl 4-(5-(2-(2,5-difluorophenyl)pyrrolidin-1-yl)pyrazolo[1,5-a]pyridine-3-carboxamido) piperidine-4-carboxylate;

(R)—N-(cyanomethyl)-5-(2-(2,5-difluorophenyl)pyrrolidin-1-yl)pyrazolo[1,5-a]pyridine-3-carboxamide;

(R)—N-((2H-tetrazol-5-yl)methyl)-5-(2-(2,5-difluorophenyl)pyrrolidin-1-yl)pyrazolo[1,5-a]pyridine-3-carboxamide;

(R)-1-(5-(2-(2,5-difluorophenyl)pyrrolidin-1-yl)pyrazolo[1,5-a]pyridine-3-carbonyl)piperidine-4-carbonitrile;

5-((R)-2-(2,5-difluorophenyl)pyrrolidin-1-yl)-N-((1r,4R)-4-(methoxycarbamoyl)cyclohexyl)pyrazolo[1,5-a]pyridine-3-carboxamide;

(R)-5-(2-(2,5-difluorophenyl)pyrrolidin-1-yl)-N-((1-(hydroxymethyl)cyclopentyl)methyl)pyrazolo[1,5-a]pyridine-3-carboxamide;

(R)-5-(2-(2,5-difluorophenyl)pyrrolidin-1-yl)-N-(2-methoxyethyl)pyrazolo[1,5-a]pyridine-3-carboxamide;

(5-((R)-2-(2,5-difluorophenyl)pyrrolidin-1-yl)pyrazolo[1,5-a]pyridin-3-yl)(3-(hydroxymethyl)piperazin-1-yl)methanone;

5-((R)-2-(2,5-difluorophenyl)pyrrolidin-1-yl)-N-(1-(5-fluoropyridin-2-yl)ethyl)pyrazolo[1,5-a]pyridine-3-carboxamide (Diastereomer I);

5-((R)-2-(2,5-difluorophenyl)pyrrolidin-1-yl)-N-(1-(5-fluoropyridin-2-yl)ethyl)pyrazolo[1,5-a]pyridine-3-carboxamide (Diastereomer II);

5-((R)-2-(2,5-difluorophenyl)pyrrolidin-1-yl)-N-((1r,4R)-4-(1-ethyl-1H-1,2,4-triazol-5-yl)cyclohexyl)pyrazolo[1,5-a]pyridine-3-carboxamide;

(R)-5-(2-(2,5-difluorophenyl)pyrrolidin-1-yl)-N-(1-sulfamoylpiperidin-4-yl)pyrazolo[1,5-a]pyridine-3-carboxamide;

5-((R)-2-(2,5-difluorophenyl)pyrrolidin-1-yl)-N-(3-(hydroxymethyl)cyclohexyl)pyrazolo[1,5-a]pyridine-3-carboxamide;

(R)-5-(2-(2,5-difluorophenyl)pyrrolidin-1-yl)-N-(1-(hydroxymethyl)cyclopropyl)pyrazolo[1,5-a]pyridine-3-carboxamide;

(R)-5-(2-(2,5-difluorophenyl)pyrrolidin-1-yl)-N-(2-(2-hydroxyethoxy)ethyl)pyrazolo[1,5-a]pyridine-3-carboxamide;

(R)-(4-(1H-tetrazol-5-yl)piperidin-1-yl)(5-(2-(2,5-difluorophenyl)pyrrolidin-1-yl)pyrazolo[1,5-a]pyridin-3-yl)methanone;

5-((R)-2-(2,5-difluorophenyl)pyrrolidin-1-yl)-N-4(S)-tetrahydrofuran-2-yl)methyl)pyrazolo[1,5-a]pyridine-3-carboxamide;

(R)-5-(2-(2,5-difluorophenyl)pyrrolidin-1-yl)-N-(tetrahydro-2H-thiopyran-4-yl)pyrazolo[1,5-a]pyridine-3-carboxamide;

(R)-5-(2-(2,5-difluorophenyl)pyrrolidin-1-yl)-N-(1-(hydroxymethyl)cyclohexyl)pyrazolo[1,5-a]pyridine-3-carboxamide;

5-((R)-2-(2,5-difluorophenyl)pyrrolidin-1-yl)-N—((S)-1-sulfamoylpyrrolidin-3-yl)pyrazolo[1,5-a]pyridine-3-carboxamide;

(R)-5-(2-(2,5-difluorophenyl)pyrrolidin-1-yl)-N-((2-methyl-2H-tetrazol-5-yl)methyl)pyrazolo[1,5-a]pyridine-3-carboxamide;

(R)-5-(2-(2,5-difluorophenyl)pyrrolidin-1-yl)-N-((1-methyl-1H-tetrazol-5-yl)methyl)pyrazolo[1,5-a]pyridine-3-carboxamide (R)-5-(2-(2,5-difluorophenyl)pyrrolidin-1-yl)-N-(2-(4-hydroxypiperidin-1-yl)ethyl)pyrazolo[1,5-a]pyridine-3-carboxamide;

(R)-5-(2-(2,5-difluorophenyl)pyrrolidin-1-yl)-N-(2-(4-methylpiperazin-1-yl)ethyl)pyrazolo[1,5-a]pyridine-3-carboxamide;

5-((R)-2-(2,5-difluorophenyl)pyrrolidin-1-yl)-N-((1r,4R)-4-(hydroxymethyl)cyclohexyl)pyrazolo[1,5-a]pyridine-3-carboxamide;

(5-((R)-2-(2,5-difluorophenyl)pyrrolidin-1-yl)pyrazolo[1,5-a]pyridin-3-yl)(3-(hydroxymethyl)morpholino)methanone;

(5-((R)-2-(2,5-difluorophenyl)pyrrolidin-1-yl)pyrazolo[1,5-a]pyridin-3-yl)(2-(hydroxymethyl) morpholino) methanone;

(R)-5-(2-(2,5-difluorophenyl)pyrrolidin-1-yl)-N-(4-hydroxy-4-(hydroxymethyl)cyclohexyl)pyrazolo[1,5-a]pyridine-3-carboxamide;

(5-((R)-2-(2,5-difluorophenyl)pyrrolidin-1-yl)pyrazolo[1,5-a]pyridin-3-yl)(4-((S)-3-hydroxypyrrolidin-1-yl)piperidin-1-yl)methanone;

(R)-(5-(2-(2,5-difluorophenyl)pyrrolidin-1-yl)pyrazolo[1,5-a]pyridin-3-yl)(4-(3-hydroxyazetidine-1-yl)piperidin-1-yl)methanone;

5-((R)-2-(2,5-difluorophenyl)pyrrolidin-1-yl)-N—((S)-2-hydroxypropyl)pyrazolo[1,5-a]pyridine-3-carboxamide;

(R)-(5-(2-(2,5-difluorophenyl)pyrrolidin-1-yl)pyrazolo[1,5-a]pyridin-3-yl)(4-(1-methyl-1H-tetrazol-5-yl)piperidin-1-yl)methanone;

(R)-(5-(2-(2,5-difluorophenyl)pyrrolidin-1-yl)pyrazolo[1,5-a]pyridin-3-yl)(4-(2-methyl-2H-tetrazol-5-yl)piperidin-1-yl)methanone;

(R)-5-(2-(2,5-difluorophenyl)pyrrolidin-1-yl)-N-(1-oxidotetrahydro-2H-thiopyran-4-yl)pyrazolo[1,5-a]pyridine-3-carboxamide;

(5-((R)-2-(2,5-difluorophenyl)pyrrolidin-1-yl)pyrazolo[1,5-a]pyridin-3-yl)((S)-3-(pyrrolidin-1-ylmethyl)piperidin-1-yl)methanone;

(5-((R)-2-(2,5-difluorophenyl)pyrrolidin-1-yl)pyrazolo[1,5-a]pyridin-3-yl)((R)-3-(pyrrolidin-1-ylmethyl)piperidin-1-yl)methanone;

5-((R)-2-(2,5-difluorophenyl)pyrrolidin-1-yl)-N((2,3-dihydrobenzo[b][1,4]dioxin-2-yl)methyl)pyrazolo[1,5-a]pyridine-3-carboxamide;

(R)-5-(2-(2,5-difluorophenyl)pyrrolidin-1-yl)-N-((1-hydroxycyclobutyl)methyl)pyrazolo[1,5-a]pyridine-3-carboxamide;

(R)-5-(5-(2-(2,5-difluorophenyl)pyrrolidin-1-yl)pyrazolo[1,5-a]pyridine-3-carbonyl)-4,5,6,7-tetrahydropyrazolo[1,5-a]pyrazine-2-carboxylic acid;

(R)-(5-(2-(2,5-difluorophenyl)pyrrolidin-1-yl)pyrazolo[1,5-a]pyridin-3-yl)(3,3-difluoropyrrolidin-1-yl)methanone;

5-((R)-2-(2,5-difluorophenyl)pyrrolidin-1-yl)-N-(2-(3-hydroxypyrrolidin-1-yl)ethyl)pyrazolo[1,5-a]pyridine-3-carboxamide;

(R)-5-(5-(2-(2,5-difluorophenyl)pyrrolidin-1-yl)pyrazolo[1,5-a]pyridine-3-carbonyl)-4,5,6,7-tetrahydropyrazolo[1,5-a]pyrazine-3-carboxylic acid;

N-((1r,4R)-4-(1H-tetrazol-5-yl)cyclohexyl)-5-((R)-2-(2,5-difluorophenyl)pyrrolidin-1-yl)pyrazolo[1,5-a]pyridine-3-carboxamide;

(R)-5-(2-(2,5-difluorophenyl)pyrrolidin-1-yl)-N-(1,1-dioxidotetrahydro-2H-thiopyran-4-yl)pyrazolo[1,5-a]pyridine-3-carboxamide;

5-((R)-2-(2,5-difluorophenyl)pyrrolidin-1-yl)-N-(4-((S)-3-hydroxypyrrolidin-1-yl)cyclohexyl)pyrazolo[1,5-a]pyridine-3-carboxamide;

5-((R)-2-(2,5-difluorophenyl)pyrrolidin-1-yl)-N-((tetrahydro-2H-pyran-3-yl)methyl)pyrazolo[1,5-a]pyridine-3-carboxamide (Diastereomer I);

5-((R)-2-(2,5-difluorophenyl)pyrrolidin-1-yl)-N-((tetrahydro-2H-pyran-3-yl)methyl)pyrazolo[1,5-a]pyridine-3-carboxamide (Diastereomer II);

N-((1R,4R)-4-(1H-1,2,4-triazol-5-yl)cyclohexyl)-5-((R)-2-(2,5-difluorophenyl)pyrrolidin-1-yl)pyrazolo[1,5-a]pyridine-3-carboxamide;

5-((R)-2-(2,5-difluorophenyl)pyrrolidin-1-yl)-N-((1 r,4R)-4-(1-methyl-1H-tetrazol-5-yl)cyclohexyl)pyrazolo[1,5-a]pyridine-3-carboxamide;

5-((R)-2-(2,5-difluorophenyl)pyrrolidin-1-yl)-N-((1r,4R)-4-(2-methyl-2H-tetrazol-5-yl)cyclohexyl)pyrazolo[1,5-a]pyridine-3-carboxamide;

5-((R)-2-(2,5-difluorophenyl)pyrrolidin-1-yl)-N-(5,6,7,8-tetrahydroimidazo[1,2-a]pyridin-7-yl)pyrazolo[1,5-a]pyridine-3-carboxamide;

5-((R)-2-(2,5-difluorophenyl)pyrrolidin-1-yl)-N-((tetrahydrofuran-3-yl)methyl)pyrazolo[1,5-a]pyridine-3-carboxamide (diastereomer 1);

N-((1r,4R)-4-(1,3,4-oxadiazol-2-yl)cyclohexyl)-5-((R)-2-(2,5-difluorophenyl)pyrrolidin-1-yl)pyrazolo[1,5-a]pyridine-3-carboxamide;

(R)-(5-(2-(2,5-difluorophenyl)pyrrolidin-1-yl)pyrazolo[1,5-a]pyridin-3-yl)(4-(5-methyl-1,3,4-oxadiazol-2-yl)piperidin-1-yl)methanone;

(R)-5-(2-(2,5-difluorophenyl)pyrrolidin-1-yl)-N-(4-(3-hydroxyazetidine-1-yl)cyclohexyl)pyrazolo[1,5-a]pyridine-3-carboxamide;

3,8-diazabicyclo[3.2.1]octan-8-yl(5-((R)-2-(2,5-difluorophenyl)pyrrolidin-1-yl)pyrazolo[1,5-a]pyridin-3-yl)methanone;

5-(5-((R)-2-(2,5-difluorophenyl)pyrrolidin-1-yl)pyrazolo[1,5-a]pyridine-3-carboxamido)-4,5,6,7-tetrahydropyrazolo[1,5-a]pyridine-3-carboxylic acid (Diastereomer-I);

5-(5-((R)-2-(2,5-difluorophenyl)pyrrolidin-1-yl)pyrazolo[1,5-a]pyridine-3-carboxamido)-4,5,6,7-tetrahydropyrazolo[1,5-a]pyridine-3-carboxylic acid (Diastereomer-II);

5-((R)-2-(2,5-difluorophenyl)pyrrolidin-1-yl)-N-((tetrahydrofuran-3-yl)methyl)pyrazolo[1,5-a]pyridine-3-carboxamide;

5-((R)-2-(2,5-difluorophenyl)pyrrolidin-1-yl)-N-(octahydroindolizin-7-yl)pyrazolo[1,5-a]pyridine-3-carboxamide;

(R)—N-(Benzo[d][1,3]dioxol-5-yl)-5-(2-(2,5-difluorophenyl)pyrrolidin-1-yl)pyrazolo[1,5-a]pyridine-3-carboxamide;

(R)-(5-(2-(2,5-difluorophenyl)pyrrolidin-1-yl)pyrazolo[1,5-a]pyridin-3-yl) (4-(5-(trifluoromethyl)-1,3,4-oxadiazol-2-yl)piperidin-1-yl)methanone;

5-((R)-2-(2,5-difluorophenyl)pyrrolidin-1-yl)-N-(1,1-dioxidotetrahydrothiophen-3-yl)pyrazolo[1,5-a]pyridine-3-carboxamide;

(R)-5-(2-(2,5-difluorophenyl)pyrrolidin-1-yl)-N-((1-(hydroxymethyl)cyclobutyl)methyl)pyrazolo[1,5-a]pyridine-3-carboxamide;

5-((R)-2-(2,5-difluorophenyl)pyrrolidin-1-yl)-N-((1r,4R)-4-(5-methyl-1,3,4-oxadiazol-2-yl)cyclohexyl)pyrazolo[1,5-a]pyridine-3-carboxamide;

(R)-5-(2-(2,5-difluorophenyl)pyrrolidin-1-yl)-N-(2,3-dihydrobenzo[b][1,4]dioxin-6-yl)pyrazolo[1,5-a]pyridine-3-carboxamide;

(R)—N-(4-(1H-1,2,4-triazol-1-yl)phenyl)-5-(2-(2,5-difluorophenyl)pyrrolidin-1-yl)pyrazolo[1,5-a]pyridine-3-carboxamide;

5-((R)-2-(2,5-difluorophenyl)pyrrolidin-1-yl)-N-(1,1-dioxidotetrahydrothiophen-3-yl)pyrazolo[1,5-a]pyridine-3-carboxamide;

5-((R)-2-(2,5-difluorophenyl)pyrrolidin-1-yl)-N-(1,1-dioxidotetrahydrothiophen-3-yl)pyrazolo[1,5-a]pyridine-3-carboxamide;

5-((R)-2-(2,5-difluorophenyl)pyrrolidin-1-yl)-N-((1r,4R)-4-(5-(trifluoromethyl)-1,3,4-oxadiazol-2-yl)cyclohexyl)pyrazolo[1,5-a]pyridine-3-carboxamide;

5-((R)-2-(2,5-difluorophenyl)pyrrolidin-1-yl)-N-(3-(dimethylcarbamoyl)-4,5,6,7-tetrahydropyrazolo[1,5-a]pyridin-6-yl)pyrazolo[1,5-a]pyridine-3-carboxamide;

(R)-5-(2-(2,5-difluorophenyl)pyrrolidin-1-yl)-N-(2-oxo-2,3-dihydro-1H-benzo[d]imidazol-5-yl)pyrazolo[1,5-a]pyridine-3-carboxamide;

5-((R)-2-(2,5-difluorophenyl)pyrrolidin-1-yl)-N-(octahydro-1H-quinolizin-2-yl)pyrazolo[1,5-a]pyridine-3-carboxamide;

5-((R)-2-(2,5-difluorophenyl)pyrrolidin-1-yl)-N-(4,5,6,7-tetrahydropyrazolo[1,5-a]pyridin-6-yl)pyrazolo[1,5-a]pyridine-3-carboxamide;

(5-((R)-2-(2,5-difluorophenyl)pyrrolidin-1-yl)pyrazolo[1,5-a]pyridin-3-yl) (3-(pyrrolidin-1-ylmethyl)pyrrolidin-1-yl)methanone;

(R)-5-(2-(2,5-difluorophenyl)pyrrolidin-1-yl)-N-(2-methylbenzo[d]oxazol-6-yl)pyrazolo[1,5-a]pyridine-3-carboxamide;

5-((R)-2-(2,5-difluorophenyl)pyrrolidin-1-yl)-N-((1r,4R)-4-(thiazol-2-yl)cyclohexyl)pyrazolo[1,5-a]pyridine-3-carboxamide;

5-(5-((R)-2-(2,5-difluorophenyl)pyrrolidin-1-yl)pyrazolo[1,5-a]pyridine-3-carboxamido)-4,5,6,7-tetrahydropyrazolo[1,5-a]pyridine-2-carboxylic acid;

5-((R)-2-(2,5-difluorophenyl)pyrrolidin-1-yl)-N-((1 r, 4R)-4-(5-methyl-1,2,4-oxadiazol-3-yl)cyclohexyl)pyrazolo[1,5-a]pyridine-3-carboxamide;

(R)—N-(6-(1H-1,2,4-triazol-1-yl)pyridin-3-yl)-5-(2-(2,5-difluorophenyl)pyrrolidin-1-yl)pyrazolo[1,5-a]pyridine-3-carboxamide;

(R)-5-(2-(2,5-difluorophenyl)pyrrolidin-1-yl)-N-(quinoxalin-6-yl)pyrazolo[1,5-a]pyridine-3-carboxamide;

(R)-5-(2-(2,5-difluorophenyl)pyrrolidin-1-yl)-N-(4-(1-methyl-1H-tetrazol-5-yl)phenyl)pyrazolo[1,5-a]pyridine-3-carboxamide;

N-(1-(2,5-difluorophenyl)-2-hydroxyethyl)-5-((R)-2-(2,5-difluorophenyl)pyrrolidin-1-yl)pyrazolo[1,5-a]pyridine-3-carboxamide;

(R)—N-(1-acetylindolin-6-yl)-5-(2-(2,5-difluorophenyl)pyrrolidin-1-yl)pyrazolo[1,5-a]pyridine-3-carboxamide;

(R)-5-(2-(2,5-difluorophenyl)pyrrolidin-1-yl)-N-(5-methyl-1,3,4-thiadiazol-2-yl)pyrazolo[1,5-a]pyridine-3-carboxamide;

(R)-(5-(2-(2,5-difluorophenyl)pyrrolidin-1-yl)pyrazolo[1,5-a]pyridin-3-yl) (4-hydroxy-4-methylpiperidin-1-yl)methanone;

5-((R)-2-(2,5-difluorophenyl)pyrrolidin-1-yl)-N-((1R,2S)-2-hydroxy-2,3-dihydro-1H-inden-1-yl)pyrazolo[1,5-a]pyridine-3-carboxamide;

(R)-5-(2-(2,5-difluorophenyl)pyrrolidin-1-yl)-N-(1,5-dimethyl-3-oxo-2-phenyl-2,3-dihydro-1H-pyrazol-4-yl)pyrazolo[1,5-a]pyridine-3-carboxamide;

7-(5-((R)-2-(2,5-difluorophenyl)pyrrolidin-1-yl)pyrazolo[1,5-a]pyridine-3-carboxamido)-5,6,7,8-tetrahydroimidazo[1,2-a]pyridine-2-carboxylic acid;

(1R,4r)-4-(5-((R)-2-(2,5-difluorophenyl)pyrrolidin-1-yl)pyrazolo[1,5-a]pyridine-3-carboxamido)cyclohexanecarboxylic acid;

(R)—N-(4-(1H-tetrazol-5-yl)phenyl)-5-(2-(2,5-difluorophenyl)pyrrolidin-1-yl)pyrazolo[1,5-a]pyridine-3-carboxamide;

(R)-5-(2-(2,5-difluorophenyl)pyrrolidin-1-yl)-N-(1H-indazol-6-yl)pyrazolo[1,5-a]pyridine-3-carboxamide;

(R)—N-(6-(1H-imidazol-1-yl)pyridin-3-yl)-5-(2-(2,5-difluorophenyl)pyrrolidin-1-yl)pyrazolo[1,5-a]pyridine-3-carboxamide;

(R)—N-(5-(1H-imidazol-1-yl)pyridin-2-yl)-5-(2-(2,5-difluorophenyl)pyrrolidin-1-yl)pyrazolo[1,5-a]pyridine-3-carboxamide;

(R)—N-(3-(1H-tetrazol-5-yl)phenyl)-5-(2-(2,5-difluorophenyl)pyrrolidin-1-yl)pyrazolo[1,5-a]pyridine-3-carboxamide;

(R)-5-(2-(2,5-difluorophenyl)pyrrolidin-1-yl)-N-(4-(2-methyl-2H-tetrazol-5-yl)phenyl)pyrazolo[1,5-a]pyridine-3-carboxamide;

(R)—N-(benzo[d][1,3]dioxol-5-ylmethyl)-5-(2-(2,5-difluorophenyl)pyrrolidin-1-yl)pyrazolo[1,5-a]pyridine-3-carboxamide;

(R)-5-(2-(2,5-difluorophenyl)pyrrolidin-1-yl)-N-((2,3-dihydrobenzo[b][1,4]dioxin-6-yl)methyl)pyrazolo[1,5-a]pyridine-3-carboxamide;

(R)—N-(5-(1H-1,2,4-triazol-1-yl)pyridin-2-yl)-5-(2-(2,5-difluorophenyl)pyrrolidin-1-yl)pyrazolo[1,5-a]pyridine-3-carboxamide;

(R)-5-(2-(2,5-difluorophenyl)pyrrolidin-1-yl)-N-(3-(2-methyl-2H-tetrazol-5-yl)phenyl)pyrazolo[1,5-a]pyridine-3-carboxamide;

(R)-5-(2-(2,5-difluorophenyl)pyrrolidin-1-yl)-N-(6-(1-methyl-1H-tetrazol-5-yl)pyridin-3-yl)pyrazolo[1,5-a]pyridine-3-carboxamide;

(R)-5-(2-(2,5-difluorophenyl)pyrrolidin-1-yl)-N-(6-(2-hydroxyethyl)pyridin-3-yl)pyrazolo[1,5-a]pyridine-3-carboxamide;

(R)-5-(2-(2,5-difluorophenyl)pyrrolidin-1-yl)-N-(3-(1-methyl-1H-tetrazol-5-yl)phenyl)pyrazolo[1,5-a]pyridine-3-carboxamide;

(R)-5-(2-(2,5-difluorophenyl)pyrrolidin-1-yl)-N-(2-methyl-6-(trifluoromethyl)pyridin-3-yl)pyrazolo[1,5-a]pyridine-3-carboxamide;

(R)-5-(2-(2,5-difluorophenyl)pyrrolidin-1-yl)-N-(6-(trifluoromethyl)pyridin-3-yl)pyrazolo[1,5-a]pyridine-3-carboxamide (R)-5-(2-(2,5-difluorophenyl)pyrrolidin-1-yl)-N-(6-(2-methyl-2H-tetrazol-5-yl)pyridin-3-yl)pyrazolo[1,5-a]pyridine-3-carboxamide;

(R)—N-(2-chloro-6-(trifluoromethyl)pyridin-3-yl)-5-(2-(2,5-difluorophenyl)pyrrolidin-1-yl)pyrazolo[1,5-a]pyridine-3-carboxamide;

(R)-5-(2-(2,5-difluorophenyl)pyrrolidin-1-yl)-N-(1-(5-sulfamoylpyridin-2-yl) azetidin-3-yl)pyrazolo[1,5-a]pyridine-3-carboxamide;

5-((R)-2-(2,5-difluorophenyl)pyrrolidin-1-yl)-N-(4-((S)-3-hydroxypyrrolidin-1-yl)phenyl)pyrazolo[1,5-a]pyridine-3-carboxamide;

(R)-5-(2-(2,5-difluorophenyl)pyrrolidin-1-yl)-N-(4-(3-hydroxyazetidine-1-yl)phenyl)pyrazolo[1,5-a]pyridine-3-carboxamide;

(R)—N-(2-(1H-imidazol-1-yl)pyrimidin-5-yl)-5-(2-(2,5-difluorophenyl)pyrrolidin-1-yl)pyrazolo[1,5-a]pyridine-3-carboxamide;

(R)-5-(2-(2,5-difluorophenyl)pyrrolidin-1-yl)-N-(4-(piperazin-1-yl)phenyl)pyrazolo[1,5-a]pyridine-3-carboxamide;

N-(3-chloro-4-((S)-3-hydroxypyrrolidin-1-yl)phenyl)-5-((R)-2-(2,5-difluorophenyl)pyrrolidin-1-yl)pyrazolo[1,5-a]pyridine-3-carboxamide;

(R)—N-(2-(1H-1,2,4-triazol-1-yl)pyrimidin-5-yl)-5-(2-(2,5-difluorophenyl)pyrrolidin-1-yl)pyrazolo[1,5-a]pyridine-3-carboxamide;

(5-((R)-2-(2,5-difluorophenyl)pyrrolidin-1-yl)pyrazolo[1,5-a]pyridin-3-yl)(3-hydroxy-3-methylpyrrolidin-1-yl)methanone;

(R)-5-(2-(2,5-difluorophenyl)pyrrolidin-1-yl)-N-(4-(methylsulfonyl)phenyl)pyrazolo[1,5-a]pyridine-3-carboxamide;

5-((R)-2-(2,5-difluorophenyl)pyrrolidin-1-yl)-N-(4-((3S,5R)-3,5-dimethylpiperazin-1-yl)phenyl)pyrazolo[1,5-a]pyridine-3-carboxamide;

(R)-5-(2-(2,5-difluorophenyl)pyrrolidin-1-yl)-N-(3-methyl-1H-pyrazol-5-yl)pyrazolo[1,5-a]pyridine-3-carboxamide;

(R)-5-(2-(2,5-difluorophenyl)pyrrolidin-1-yl)-N-(6-sulfamoylpyridin-3-yl)pyrazolo[1,5-a]pyridine-3-carboxamide;

(R)—N-(3-chloro-4-(3-hydroxyazetidine-1-yl)phenyl)-5-(2-(2,5-difluorophenyl)pyrrolidin-1-yl)pyrazolo[1,5-a]pyridine-3-carboxamide;

(R)-(5-(2-(2,5-difluorophenyl)pyrrolidin-1-yl)pyrazolo[1,5-a]pyridin-3-yl)(3-hydroxy-3-(hydroxymethyl)azetidin-1-yl)methanone;

(5-((R)-2-(2,5-difluorophenyl)pyrrolidin-1-yl)pyrazolo[1,5-a]pyridin-3-yl) (3-hydroxy-3-(hydroxymethyl)pyrrolidin-1-yl)methanone;

(R)-5-(2-(2,5-difluorophenyl)pyrrolidin-1-yl)-N-(4-(2-oxoimidazolidin-1-yl)phenyl)pyrazolo[1,5-a]pyridine-3-carboxamide;

(R)-5-(2-(2,5-difluorophenyl)pyrrolidin-1-yl)-N-(5-(pyridin-2-yl)-1,3,4-thiadiazol-2-yl)pyrazolo[1,5-a]pyridine-3-carboxamide;

(R)-5-(2-(2,5-difluorophenyl)pyrrolidin-1-yl)-N-(4-sulfamoylphenyl)pyrazolo[1,5-a]pyridine-3-carboxamide;

(R)-5-(2-(2,5-difluorophenyl)pyrrolidin-1-yl)-N-(5-(pyridin-3-yl)-1,3,4-thiadiazol-2-yl)pyrazolo[1,5-a]pyridine-3-carboxamide;

(R)-5-(2-(2,5-difluorophenyl)pyrrolidin-1-yl)-N-(6-(N,N-dimethylsulfamoyl)pyridin-3-yl)pyrazolo[1,5-a]pyridine-3-carboxamide;

(R)-5-(2-(2,5-difluorophenyl)pyrrolidin-1-yl)-N-(6-(N-methylsulfamoyl)pyridin-3-yl)pyrazolo[1,5-a]pyridine-3-carboxamide;

(R)-5-(2-(2,5-difluorophenyl)pyrrolidin-1-yl)-N-(4-(pyridin-3-yl)thiazol-2-yl)pyrazolo[1,5-a]pyridine-3-carboxamide;

(R)-5-(2-(2,5-difluorophenyl)pyrrolidin-1-yl)-N-(4-(pyridin-2-yl)thiazol-2-yl)pyrazolo[1,5-a]pyridine-3-carboxamide;

(R)-5-(2-(5-(difluoromethoxy)-2-fluorophenyl)pyrrolidin-1-yl)pyrazolo[1,5-a]pyridine-3-carboxylic acid;

(R)-(5-(2-(5-(difluoromethoxy)-2-fluorophenyl)pyrrolidin-1-yl)pyrazolo[1,5-a]pyridin-3-yl)(3-hydroxyazetidine-1-yl)methanone;

(5-((R)-2-(5-(difluoromethoxy)-2-fluorophenyl)pyrrolidin-1-yl)pyrazolo[1,5-a]pyridin-3-yl)((S)-3-hydroxypyrrolidin-1-yl)methanone;

(R)-(5-(2-(2-(difluoromethoxy)-5-fluorophenyl)pyrrolidin-1-yl)pyrazolo[1,5-a]pyridin-3-yl)(3-hydroxyazetidine-1-yl)methanone;

(5-((R)-2-(2-(difluoromethoxy)-5-fluorophenyl)pyrrolidin-1-yl)pyrazolo[1,5a]pyridin-3-yl)((S)-3-hydroxypyrrolidin-1-yl)methanone;

(R)-5-(2-(2,5-difluorophenyl)pyrrolidin-1-yl)-4-fluoro-N-(4-hydroxy-4-(hydroxymethyl)cyclohexyl)pyrazolo[1,5a]pyridine-3-carboxamide;

(R)-(5-(2-(2,5-difluorophenyl)pyrrolidin-1-yl)-4-fluoropyrazolo[1,5-a]pyridin-3-yl)(3-hydroxyazetidine-1-yl)methanone;

(R)-5-(2-(2,5-difluorophenyl)pyrrolidin-1-yl)-4-fluoro-N-(tetrahydro-2H-pyran-4-yl)pyrazolo[1,5-a]pyridine-3-carboxamide;

(R)-5-(2-(2,5-difluorophenyl)pyrrolidin-1-yl)-4-fluoropyrazolo[1,5-a]pyridine-3-carboxamide;

5-((R)-2-(2,5-difluorophenyl)pyrrolidin-1-yl)-N—((S)-2,3-dihydroxypropyl)-4-fluoropyrazolo[1,5-a]pyridine-3-carboxamide;

(5-((R)-2-(2,5-difluorophenyl)pyrrolidin-1-yl)-4-fluoropyrazolo[1,5-a]pyridin-3-yl)((S)-3-hydroxypyrrolidin-1-yl)methanone;

(R)-5-(2-(2,5-difluorophenyl)pyrrolidin-1-yl)-4-fluoro-N-((1-(hydroxymethyl)cyclopentyl)methyl)pyrazolo[1,5a]pyridine-3-carboxamide;

5-((R)-2-(2,5-difluorophenyl)pyrrolidin-1-yl)-4-fluoro-N—((S)-1-hydroxypropan-2-yl)pyrazolo[1,5-a]pyridine-3-carboxamide;

N-((1r,4R)-4-(1H-1,2,4-triazol-5-yl)cyclohexyl)-5-((R)-2-(2,5-difluorophenyl)pyrrolidin-1-yl)-4-fluoropyrazolo[1,5-a]pyridine-3-carboxamide;

5-((R)-2-(2,5-difluorophenyl)pyrrolidin-1-yl)-4-fluoro-N—((S)-2-hydroxypropyl)pyrazolo[1,5-a]pyridine-3-carboxamide;

5-((R)-2-(2,5-difluorophenyl)pyrrolidin-1-yl)-4-fluoro-N-((1r,4R)-4-(2-methyl-2H-tetrazol-5-yl)cyclohexyl)pyrazolo[1,5-a]pyridine-3-carboxamide;

5-((R)-2-(2,5-difluorophenyl)pyrrolidin-1-yl)-4-fluoro-N-((1r,4R)-4-(1-methyl-1H-tetrazol-5-yl)cyclohexyl)pyrazolo[1,5-a]pyridine-3-carboxamide;

(R)-5-(2-(2,5-difluorophenyl)pyrrolidin-1-yl)-4-fluoro-N-((1-(hydroxymethyl)cyclobutyl)methyl)pyrazolo[1,5-a]pyridine-3-carboxamide;

(R)-5-(2-(2,5-difluorophenyl)pyrrolidin-1-yl)-N-(3-hydroxycyclobutyl)pyrazolo[1,5-a]pyridine-3-carboxamide; N-((1r,4R)-4-(1H-1,2,4-triazol-5-yl)cyclohexyl)-5-((R)-2-(2,5-difluorophenyl)pyrrolidin-1-yl)-4-fluoropyrazolo[1,5-a]pyridine-3-carboxamide;

(1R,4r)-4-(5-((R)-2-(2,5-difluorophenyl)pyrrolidin-1-yl)-4-fluoropyrazolo[1,5-a]pyridine-3-carboxamido)cyclohexanecarboxylic acid;

5-((R)-2-(2,5-difluorophenyl)pyrrolidin-1-yl)-4-fluoro-N-((1r,4R)-4-hydroxycyclohexyl)pyrazolo[1,5-a]pyridine-3-carboxamide;

5-((R)-2-(2,5-difluorophenyl)pyrrolidin-1-yl)-4-fluoro-N-(3-hydroxycyclohexyl)pyrazolo[1,5-a]pyridine-3-carboxamide;

N-((1r,4R)-4-(1H-tetrazol-5-yl)cyclohexyl)-5-((R)-2-(2,5-difluorophenyl)pyrrolidin-1-yl)-4-fluoropyrazolo[1,5-a]pyridine-3-carboxamide;

5-((R)-2-(2,5-difluorophenyl)pyrrolidin-1-yl)-4-fluoro-N-((1r,4R)-4-(methoxycarbamoyl)cyclohexyl)pyrazolo[1,5-a]pyridine-3-carboxamide;

5-((R)-2-(2,5-difluorophenyl)pyrrolidin-1-yl)-4-fluoro-N-((1r,4R)-4-(hydroxymethyl)cyclohexyl)pyrazolo[1,5-a]pyridine-3-carboxamide;

(1R,4r)-4-(4-fluoro-5-((R)-2-(5-fluoro-2-methoxyphenyl)pyrrolidin-1-yl)pyrazolo[1,5-a]pyridine-3-carboxamido)cyclohexanecarboxylic acid;

(5-((R)-2-(3-(difluoromethoxy)-5-fluorophenyl)pyrrolidin-1-yl)pyrazolo[1,5-a]pyridin-3-yl) ((S)-3-hydroxypyrrolidin-1-yl)methanone;

5-((R)-2-(3-(difluoromethoxy)-5-fluorophenyl)pyrrolidin-1-yl)-N-((1r,4R)-4-(2-methyl-2H-tetrazol-5-yl)cyclohexyl)pyrazolo[1,5-a]pyridine-3-carboxamide;

(R)-5-(2-(3-(difluoromethoxy)-5-fluorophenyl)pyrrolidin-1-yl)-N-(4-hydroxy-4-(hydroxymethyl)cyclohexyl)pyrazolo[1,5-a]pyridine-3-carboxamide;

(1R,4r)-4-(5-((R)-2-(3-(difluoromethoxy)-5-fluorophenyl)pyrrolidin-1-yl)pyrazolo[1,5-a]pyridine-3-carboxamido)cyclohexanecarboxylic acid;

5-((R)-2-(3-(difluoromethoxy)-5-fluorophenyl)pyrrolidin-1-yl)-N-((1r,4R)-4-(1-methyl-1H-tetrazol-5-yl)cyclohexyl)pyrazolo[1,5-a]pyridine-3-carboxamide;

(1R,4r)-4-(5-((R)-2-(5-fluoro-2-methoxyphenyl)pyrrolidin-1-yl)pyrazolo[1,5-a]pyridine-3-carboxamido)cyclohexanecarboxylic acid;

(5-((R)-2-(5-fluoro-2-methoxyphenyl)pyrrolidin-1-yl)pyrazolo[1,5-a]pyridin-3-yl) ((S)-3-hydroxypyrrolidin-1-yl)methanone;

5-((R)-2-(5-fluoro-2-methoxyphenyl)pyrrolidin-1-yl)-N-((1r,4R)-4-(2-methyl-2H-tetrazol-5-yl)cyclohexyl)pyrazolo[1,5-a]pyridine-3-carboxamide;

5-((R)-2-(5-fluoro-2-methoxyphenyl)pyrrolidin-1-yl)-N-((1r,4R)-4-(1-methyl-1H-tetrazol-5-yl)cyclohexyl)pyrazolo[1,5-a]pyridine-3-carboxamide;

5-((R)-2-(5-fluoro-2-methoxyphenyl)pyrrolidin-1-yl)-N-((1r,4R)-4-(methoxycarbamoyl)cyclohexyl)pyrazolo[1,5-a]pyridine-3-carboxamide;

N-((1r,4R)-4-(1H-1,2,4-triazol-5-yl)cyclohexyl)-5-((R)-2-(5-fluoro-2-methoxyphenyl)pyrrolidin-1-yl)pyrazolo[1,5-a]pyridine-3-carboxamide;

N-((1r,4R)-4-(1H-tetrazol-5-yl)cyclohexyl)-5-((R)-2-(5-fluoro-2-methoxyphenyl)pyrrolidin-1-yl)pyrazol[1,5-a]pyridine-3-carboxamide;

3-(5-((R)-2-(5-fluoro-2-methoxyphenyl)pyrrolidin-1-yl)pyrazolo[1,5-a]pyridine-3-carboxamido)cyclohexanecarboxylic acid (Isomer-I);

3-(5-((R)-2-(5-fluoro-2-methoxyphenyl)pyrrolidin-1-yl)pyrazolo[1,5-a]pyridine-3-carboxamido)cyclohexanecarboxylic acid (Isomer-II);

(5-((R)-2-(3,5-difluorophenyl)pyrrolidin-1-yl)pyrazolo[1,5-a]pyridin-3-yl)((S)-3-hydroxypyrrolidin-1-yl)methanone;

5-((R)-2-(3,5-difluorophenyl)pyrrolidin-1-yl)-N-((1r,4R)-4-(1-methyl-1H-tetrazol-5-yl)cyclohexyl)pyrazolo[1,5-a]pyridine-3-carboxamide;

5-((R)-2-(3,5-difluorophenyl)pyrrolidin-1-yl)-N-((1r,4R)-4-(2-methyl-2H-tetrazol-5-yl)cyclohexyl)pyrazolo[1,5-a]pyridine-3-carboxamide;

(R)-5-(2-(3,5-difluorophenyl)pyrrolidin-1-yl)-N-((1-(hydroxymethyl)cyclopentyl)methyl)pyrazolo[1,5-a]pyridine-3-carboxamide;

(R)-5-(2-(3,5-difluorophenyl)pyrrolidin-1-yl)-N-((1-(hydroxymethyl)cyclobutyl)methyl)pyrazolo[1,5-a]pyridine-3-carboxamide;

5-((R)-2-(3,5-difluorophenyl)pyrrolidin-1-yl)-N-(1,1-dioxidotetrahydrothiophen-3-yl)pyrazolo[1,5-a]pyridine-3-carboxamide (Isomer-I);

5-((R)-2-(3,5-difluorophenyl)pyrrolidin-1-yl)-N-(1,1-dioxidotetrahydrothiophen-3-yl)pyrazolo[1,5-a]pyridine-3-carboxamide (Isomer-II);

(R)-5-(2-(3,5-difluorophenyl)pyrrolidin-1-yl)-N-(4-hydroxy-4-(hydroxymethyl)cyclohexyl)pyrazolo[1,5-a]pyridine-3-carboxamide;

(R)—N-(6-(1H-1,2,4-triazol-1-yl)pyridin-3-yl)-5-(2-(3,5-difluorophenyl)pyrrolidin-1-yl)pyrazolo[1,5-a]pyridine-3-carboxamide; or (R)-5-(2-(3,5-difluorophenyl)pyrrolidin-1-yl)-N-(1-(5-sulfamoylpyridin-2-yl)azetidin-3-yl)pyrazolo[1,5-a]pyridine-3-carboxamide;

or their pharmaceutically acceptable salts, pharmaceutically acceptable solvates or stereoisomers thereof.

In one embodiment, there is provided a compound of formula (I) wherein the compounds are:

(R)-5-(2-(2,5-difluorophenyl)pyrrolidin-1-yl)-4-fluoro-N-(4-hydroxy-4-(hydroxymethyl)cyclohexyl)pyrazolo[1,5a]pyridine-3-carboxamide;

(R)-(5-(2-(2,5-difluorophenyl)pyrrolidin-1-yl)-4-fluoropyrazolo[1,5-a]pyridin-3-yl)(3-hydroxyazetidine-1-yl)methanone;

(R)-5-(2-(2,5-difluorophenyl)pyrrolidin-1-yl)-4-fluoro-N-(tetrahydro-2H-pyran-4-yl)pyrazolo[1,5-a]pyridine-3-carboxamide;

(R)-5-(2-(2,5-difluorophenyl)pyrrolidin-1-yl)-4-fluoropyrazolo[1,5-a]pyridine-3-carboxamide;

5-((R)-2-(2,5-difluorophenyl)pyrrolidin-1-yl)-N—((S)-2,3-dihydroxypropyl)-4-fluoropyrazolo[1,5-a]pyridine-3-carboxamide;

(5-((R)-2-(2,5-difluorophenyl)pyrrolidin-1-yl)-4-fluoropyrazolo[1,5-a]pyridin-3-yl)((S)-3-hydroxypyrrolidin-1-yl)methanone;

(R)-5-(2-(2,5-difluorophenyl)pyrrolidin-1-yl)-4-fluoro-N-((1-(hydroxymethyl)cyclopentyl)methyl)pyrazolo[1,5a]pyridine-3-carboxamide;

5-((R)-2-(2,5-difluorophenyl)pyrrolidin-1-yl)-4-fluoro-N—((S)-1-hydroxypropan-2-yl)pyrazolo[1,5-a]pyridine-3-carboxamide;

N-((1r,4R)-4-(1H-1,2,4-triazol-5-yl)cyclohexyl)-5-((R)-2-(2,5-difluorophenyl)pyrrolidin-1-yl)-4-fluoropyrazolo[1,5-a]pyridine-3-carboxamide;

5-((R)-2-(2,5-difluorophenyl)pyrrolidin-1-yl)-4-fluoro-N—((S)-2-hydroxypropyl)pyrazolo[1,5-a]pyridine-3-carboxamide;

5-((R)-2-(2,5-difluorophenyl)pyrrolidin-1-yl)-4-fluoro-N-((1r,4R)-4-(2-methyl-2H-tetrazol-5-yl)cyclohexyl)pyrazolo[1,5-a]pyridine-3-carboxamide;

5-((R)-2-(2,5-difluorophenyl)pyrrolidin-1-yl)-4-fluoro-N-((1r,4R)-4-(1-methyl-1H-tetrazol-5-yl)cyclohexyl)pyrazolo[1,5-a]pyridine-3-carboxamide;

(R)-5-(2-(2,5-difluorophenyl)pyrrolidin-1-yl)-4-fluoro-N-((1-(hydroxymethyl)cyclobutyl)methyl)pyrazolo[1,5-a]pyridine-3-carboxamide;

(R)-5-(2-(2,5-difluorophenyl)pyrrolidin-1-yl)-4-fluoro-N-(3-hydroxycyclobutyl)pyrazolo[1,5-a]pyridine-3-carboxamide;

N-((1r,4R)-4-(1H-1,2,4-triazol-5-yl)cyclohexyl)-5-((R)-2-(2,5-difluorophenyl)pyrrolidin-1-yl)-4-fluoropyrazolo[1,5-a]pyridine-3-carboxamide;

(1R,4r)-4-(5-((R)-2-(2,5-difluorophenyl)pyrrolidin-1-yl)-4-fluoropyrazolo[1,5-a]pyridine-3-carboxamido)cyclohexanecarboxylic acid;

5-((R)-2-(2,5-difluorophenyl)pyrrolidin-1-yl)-4-fluoro-N-((1r,4R)-4-hydroxycyclohexyl)pyrazolo[1,5-a]pyridine-3-carboxamide;

5-((R)-2-(2,5-difluorophenyl)pyrrolidin-1-yl)-4-fluoro-N-(3-hydroxycyclohexyl)pyrazolo[1,5-a]pyridine-3-carboxamide;

N-((1r,4R)-4-(1H-tetrazol-5-yl)cyclohexyl)-5-((R)-2-(2,5-difluorophenyl)pyrrolidin-1-yl)-4-fluoropyrazolo[1,5-a]pyridine-3-carboxamide;

5-((R)-2-(2,5-difluorophenyl)pyrrolidin-1-yl)-4-fluoro-N-((1r,4R)-4-(methoxycarbamoyl)cyclohexyl)pyrazolo[1,5-a]pyridine-3-carboxamide;

5-((R)-2-(2,5-difluorophenyl)pyrrolidin-1-yl)-4-fluoro-N-((1r,4R)-4-(hydroxymethyl)cyclohexyl)pyrazolo[1,5-a]pyridine-3-carboxamide; or (1R,4r)-4-(4-fluoro-5-((R)-2-(5-fluoro-2-methoxyphenyl)pyrrolidin-1-yl)pyrazolo[1,5-a]pyridine-3-carboxamido)cyclohexanecarboxylic acid;

or their pharmaceutically acceptable salts, pharmaceutically acceptable solvates or stereoisomers thereof.

In another embodiment, there is provided a compound of formula (I) wherein the compounds are:

(R)-ethyl 5-(2-(2,5-difluorophenyl)pyrrolidin-1-yl)pyrazolo[1,5-a]pyridine-3-carboxylate;

(R)-5-(2-(2,5-difluorophenyl)pyrrolidin-1-yl)pyrazolo[1,5-a]pyridine-3-carboxylic acid;

5-(2-(2,5-difluorophenyl)pyrrolidin-1-yl)pyrazolo[1,5-a]pyridine-3-carboxylic acid;

5-(2-(2,5-difluorophenyl)pyrrolidin-1-yl)-N,N-dimethylpyrazolo[1,5-a]pyridine-3-carboxamide;

5-(2-(2,5-difluorophenyl)pyrrolidin-1-yl)pyrazolo[1,5-a]pyridine-3-carboxamide;

5-(2-(2,5-difluorophenyl)pyrrolidin-1-yl)-N-(4-fluorophenyl)pyrazolo[1,5-a]pyridine-3-carboxamide;

5-(2-(2,5-difluorophenyl)pyrrolidin-1-yl)-N-(1,3-dihydroxypropan-2-yl)pyrazolo[1,5-a]pyridine-3-carboxamide;

5-((R)-2-(2,5-difluorophenyl)pyrrolidin-1-yl)-N—((S)-2,3-dihydroxypropyl)pyrazolo[1,5-a]pyridine-3-carboxamide;

5-((R)-2-(2,5-difluorophenyl)pyrrolidin-1-yl)-N-((1r,4R)-4-hydroxycyclohexyl)pyrazolo[1,5-a]pyridine-3-carboxamide;

(R)-5-(2-(2,5-difluorophenyl)pyrrolidin-1-yl)-N-(piperidin-1-yl)pyrazolo[1,5-a]pyridine-3-carboxamide;

(R)-5-(2-(2,5-difluorophenyl)pyrrolidin-1-yl)-N-(1,3-dihydroxy-2-methylpropan-2-yl)pyrazolo[1,5-a]pyridine-3-carboxamide;

(R)-5-(2-(2,5-difluorophenyl)pyrrolidin-1-yl)-N-(2-hydroxyethyl)pyrazolo[1,5-a]pyridine-3-carboxamide;

(R)-5-(2-(2,5-difluorophenyl)pyrrolidin-1-yl)-N-(piperidin-4-yl)pyrazolo[1,5-a]pyridine-3-carboxamide;

5-((R)-2-(2,5-difluorophenyl)pyrrolidin-1-yl)-N-(piperidin-3-yl)pyrazolo[1,5-a]pyridine-3-carboxamide;

5-((R)-2-(2,5-difluorophenyl)pyrrolidin-1-yl)-N-(3-hydroxycyclohexyl)pyrazolo[1,5-a]pyridine-3-carboxamide;

(R)-5-(2-(2,5-difluorophenyl)pyrrolidin-1-yl)-N-(4-methylpiperazin-1-yl)pyrazolo[1,5-a]pyridine-3-carboxamide;

(R)-5-(2-(2,5-difluorophenyl)pyrrolidin-1-yl)-N-(1-hydroxy-2-methylpropan-2-yl)pyrazolo[1,5-a]pyridine-3-carboxamide;

5-((R)-2-(2,5-difluorophenyl)pyrrolidin-1-yl)-N—((S)-1-hydroxypropan-2-yl)pyrazolo[1,5-a]pyridine-3-carboxamide;

(R)-5-(2-(2,5-difluorophenyl)pyrrolidin-1-yl)-N-(1-methylpiperidin-4-yl)pyrazolo[1,5-a]pyridine-3-carboxamide;

(R)-5-(2-(2,5-difluorophenyl)pyrrolidin-1-yl)-N-(tetrahydro-2H-pyran-4-yl)pyrazolo[1,5-a]pyridine-3-carboxamide;

(R)-5-(2-(2,5-difluorophenyl)pyrrolidin-1-yl)-N-morpholinopyrazolo[1,5-a]pyridine-3-carboxamide;

5-((R)-2-(2,5-difluorophenyl)pyrrolidin-1-yl)-N-((1R*,2R*)-2-hydroxycyclohexyl)pyrazolo[1,5-a]pyridine-3-carboxamide;

5-((R)-2-(2,5-difluorophenyl)pyrrolidin-1-yl)-N—((S)-2,4-dihydroxybutyl)pyrazolo[1,5-a]pyridine-3-carboxamide;

(R)-5-(2-(2,5-difluorophenyl)pyrrolidin-1-yl)-N-(4-hydroxypiperidin-1-yl)pyrazolo[1,5-a]pyridine-3-carboxamide;

5-((R)-2-(2,5-difluorophenyl)pyrrolidin-1-yl)-N-((S)-pyrrolidin-3-yl)pyrazolo[1,5-a]pyridine-3-carboxamide;

5-((R)-2-(2,5-difluorophenyl)pyrrolidin-1-yl)-N-(tetrahydro-2H-pyran-3-yl)pyrazolo[1,5-a]pyridine-3-carboxamide;

5-((R)-2-(2,5-difluorophenyl)pyrrolidin-1-yl)-N-((1R,2R)-2-hydroxycyclopentyl)pyrazolo[1,5-a]pyridine-3-carboxamide;

(R)—N-cyclopropyl-5-(2-(2,5-difluorophenyl)pyrrolidin-1-yl)pyrazolo[1,5-a]pyridine-3-carboxamide;

(R)—N-(tert-butyl)-5-(2-(2,5-difluorophenyl)pyrrolidin-1-yl)pyrazolo[1,5-a]pyridine-3-carboxamide;

(R)-5-(2-(2,5-difluorophenyl)pyrrolidin-1-yl)-N-(3-hydroxypropyl)pyrazolo[1,5-a]pyridine-3-carboxamide;

N-((1R,4R)-4-cyanocyclohexyl)-5-((R)-2-(2,5-difluorophenyl)pyrrolidin-1-yl)pyrazolo[1,5-a]pyridine-3-carboxamide;

5-((R)-2-(2,5-difluorophenyl)pyrrolidin-1-yl)-N—((S)-1-methylpyrrolidin-3-yl)pyrazolo[1,5-a]pyridine-3-carboxamide;

5-((R)-2-(2,5-difluorophenyl)pyrrolidin-1-yl)-N#R)-2,3-dihydroxypropyl)pyrazolo[1,5-a]pyridine-3-carboxamide;

(R)—N-(4,4-difluorocyclohexyl)-5-(2-(2,5-difluorophenyl)pyrrolidin-1-yl)pyrazolo[1,5-a]pyridine-3-carboxamide;

(R)-5-(2-(2,5-difluorophenyl)pyrrolidin-1-yl)-N-(3-hydroxy-2,2-dimethylpropyl)pyrazolo[1,5-a]pyridine-3-carboxamide;

5-((R)-2-(2,5-difluorophenyl)pyrrolidin-1-yl)-N—((S)-1-hydroxy-3-methylbutan-2-yl)pyrazolo[1,5-a]pyridine-3-carboxamide;

(R)-5-(2-(2,5-difluorophenyl)pyrrolidin-1-yl)-N-(3-hydroxycyclobutyl)pyrazolo[1,5-a]pyridine-3-carboxamide;

5-(5-((R)-2-(2,5-difluorophenyl)pyrrolidin-1-yl)pyrazolo[1,5-a]pyridine-3-carboxamido)-4,5,6,7-tetrahydropyrazolo[1,5-a]pyridine-3-carboxylic acid;

5-((R)-2-(2,5-difluorophenyl)pyrrolidin-1-yl)-N-(2,3-dihydroxy-2-methylpropyl)pyrazolo[1,5-a]pyridine-3-carboxamide;

(R)-5-(2-(2,5-difluorophenyl)pyrrolidin-1-yl)-N-(2-hydroxy-2-methylpropyl)pyrazolo[1,5-a]pyridine-3-carboxamide;

(R)—N-(4-cyanophenyl)-5-(2-(2,5-difluorophenyl)pyrrolidin-1-yl)pyrazolo[1,5-a]pyridine-3-carboxamide;
(R)-5-(2-(2,5-difluorophenyl)pyrrolidin-1-yl)-N-(1,3-dihydroxy-2-(hydroxymethyl) propan-2-yl)pyrazolo[1,5-a]pyridine-3-carboxamide;
(R)-5-(2-(2,5-difluorophenyl)pyrrolidin-1-yl)-N-(pyridin-3-yl)pyrazolo[1,5-a]pyridine-3-carboxamide;
(R)-5-(2-(2,5-difluorophenyl)pyrrolidin-1-yl)-N-(4-methylthiazol-2-yl)pyrazolo[1,5-a]pyridine-3-carboxamide;
(R)-5-(2-(2,5-difluorophenyl)pyrrolidin-1-yl)-N-(pyridin-2-yl)pyrazolo[1,5-a]pyridine-3-carboxamide;
(R)—N-(3-cyanophenyl)-5-(2-(2,5-difluorophenyl)pyrrolidin-1-yl)pyrazolo[1,5-a]pyridine-3-carboxamide;
(R)—N-(6-cyanopyridin-3-yl)-5-(2-(2,5-difluorophenyl) pyrrolidin-1-yl)pyrazolo[1,5-a]pyridine-3-carboxamide;
(R)-5-(2-(2,5-difluorophenyl)pyrrolidin-1-yl)-N-(4-((2-hydroxyethyl)amino)phenyl)pyrazolo[1,5-a]pyridine-3-carboxamide;
(R)—N-(1-(tert-butyl)-3-methyl-1H-pyrazol-5-yl)-5-(2-(2,5-difluorophenyl)pyrrolidin-1-yl)pyrazolo[1,5-a]pyridine-3-carboxamide;
(R)-5-(2-(5-(difluoromethoxy)-2-fluorophenyl)pyrrolidin-1-yl)pyrazolo[1,5-a]pyridine-3-carboxylic acid;
5-((R)-2-(5-(difluoromethoxy)-2-fluorophenyl)pyrrolidin-1-yl)-N—((S)-2,3-dihydroxypropyl)pyrazolo[1,5a]pyridine-3-carboxamide;
5-((R)-2-(5-(difluoromethoxy)-2-fluorophenyl)pyrrolidin-1-yl)-N-((1r,4R)-4-hydroxy cyclo hexyl)pyrazolo[1,5a]pyridine-3-carboxamide;
5-((R)-2-(2-(difluoromethoxy)-5-fluorophenyl)pyrrolidin-1-yl)-N—(S)-2,3-dihydroxypropyl)pyrazolo[1,5-a]pyridine-3-carboxamide;
5-((R)-2-(2-(difluoromethoxy)-5-fluorophenyl)pyrrolidin-1-yl)-N-((1r,4R)-4-hydroxycyclohexyl)pyrazolo[1,5a]pyridine-3-carboxamide;
(R)-5-(2-(2-(difluoromethoxy)-5-fluorophenyl)pyrrolidin-1-yl)pyrazolo[1,5-a]pyridine-3-carboxamide;
5-((R)-2-(3-(difluoromethoxy)-5-fluorophenyl)pyrrolidin-1-yl)-N—((S)-2,3-dihydroxypropyl)pyrazolo[1,5-a]pyridine-3-carboxamide;
(R)-5-(2-(3-(difluoromethoxy)-5-fluorophenyl)pyrrolidin-1-yl)-N-(3-hydroxycyclobutyl)pyrazolo[1,5-a]pyridine-3-carboxamide;
5-((R)-2-(3-(difluoromethoxy)-5-fluorophenyl)pyrrolidin-1-yl)-N-((1r,4R)-4-hydroxycyclohexyl)pyrazolo[1,5-a]pyridine-3-carboxamide;
5-((R)-2-(5-fluoro-2-methoxyphenyl)pyrrolidin-1-yl)-N-((1r,4R)-4-hydroxycyclohexyl)pyrazolo[1,5-a]pyridine-3-carboxamide;
N—((S)-2,3-dihydroxypropyl)-5-(R)-2-(5-fluoro-2-methoxyphenyl)pyrrolidin-1-yl)pyrazolo[1,5-a]pyridine-3-carboxamide;
(R)-5-(2-(5-fluoro-2-methoxyphenyl)pyrrolidin-1-yl)-N-(3-hydroxycyclobutyl)pyrazolo[1,5-a]pyridine-3-carboxamide;
5-((R)-2-(5-fluoro-2-methoxyphenyl)pyrrolidin-1-yl)-N-(3-hydroxycyclohexyl)pyrazolo[1,5-a]pyridine-3-carboxamide (Isomer-I);
5-((R)-2-(5-fluoro-2-methoxyphenyl)pyrrolidin-1-yl)-N-(3-hydroxycyclohexyl)pyrazolo[1, 5-a]pyridine-3-carboxamide;
5-((R)-2-(3,5-difluorophenyl)pyrrolidin-1-yl)-N—((S)-2,3-dihydroxypropyl)pyrazolo[1,5-a]pyridine-3-carboxamide;
(R)-5-(2-(3,5-difluorophenyl)pyrrolidin-1-yl)-N-(1,3-dihydroxy-2-(hydroxymethyl) propan-2-yl)pyrazolo[1,5-a]pyridine-3-carboxamide;
5-((R)-2-(3,5-difluorophenyl)pyrrolidin-1-yl)-N—((R)-1-hydroxypropan-2-yl)pyrazolo[1,5-a]pyridine-3-carboxamide;
5-((R)-2-(3,5-difluorophenyl)pyrrolidin-1-yl)-N-(2,3-dihydroxy-2-methylpropyl)pyrazolo[1,5-a]pyridine-3-carboxamide (Isomer-I); or
5-((R)-2-(3,5-difluorophenyl)pyrrolidin-1-yl)-N-(2,3-dihydroxy-2-methylpropyl)pyrazolo[1,5-a]pyridine-3-carboxamide (Isomer-II);
or their pharmaceutically acceptable salts, pharmaceutically acceptable solvates or stereoisomers thereof.

The compounds of formula (I) can also exist in the form of pharmaceutically acceptable salts, pharmaceutically acceptable solvates or stereoisomers thereof.

The present application relates to the compounds of formula (I), which are inhibitors of TrkA, TrkB and/or TrkC kinase activity, for the treatment or prevention of diseases or conditions or disorders associated with TrkA, TrkB and/or TrkC kinase activity.

One embodiment of the present application further provides methods of treating or preventing conditions, diseases and/or disorders associated TrkA, TrkB and/or TrkC kinase activity, wherein the method includes administration of a therapeutically effective amount of a compound formula (I), to a patient in need thereof.

One embodiment of the present application provides conditions. diseases and/or disorders treatable or preventable by inhibition of Trk kinase activity, such as pain, inflammation, cancer, restenosis, atherosclerosis, psoriasis, thrombosis, psoriatic arthritis, rheumatoid arthritis, inflammatory bowel disease, ulcerative colitis, Crohn's disease, fibrosis, neurodegenerative; a disease, disorder or injury relating to dysmyelination or demyelination or infectious diseases such as *Trypanosoma cruzi* infection by administering a therapeutically effective amount of compound of formula (I), to a patient in need thereof.

One embodiment of the present application further provides methods of treating or preventing conditions, diseases and/or disorders associated TrkA, wherein the method includes administration of a therapeutically effective amount of a compound formula (I), to a patient in need thereof.

In another embodiment, there is provided a method of treating or preventing pain or pain disorder in a patient in need of such a treatment comprising the administration of a therapeutically effective amount of the compound of formula (I), to said patient.

In another embodiment, pain includes chronic and acute pain but is not limited to, pain related to cancer, surgery, bone fracture, skeletal pain caused by tumor metastasis, osteoarthritis, psoriatic arthritis, rheumatoid arthritis, interstitial cystitis, chronic pancreatitis, visceral pain, inflammatory pain, migraine, chronic lower back pain, bladder pain syndrome and neuropathic pain.

In one embodiment, there is provided a method of binding TrkA protein in a patient in need of such a treatment comprising the administration of a therapeutically effective amount of the compound of formula (I) to said patient.

The present application further relates to use of compound of formula (I) for treating or preventing conditions, diseases and/or disorders associated with abnormal or deregulated Trk kinase activity.

One aspect of the present application provides use of compound of formula (I) for treating or preventing conditions, diseases and/or disorders associated with abnormal or deregulated TrkA kinase activity, in a patient in need thereof.

In another embodiment, there is provided an use of the compound for formula (I) for treating or preventing pain or pain disorder in a patient in need of such a treatment, comprising the administration of a therapeutically effective amount of the compound of formula (I), to said patient.

In another embodiment of the present application, pain includes chronic and acute pain but is not limited to, pain related to cancer, surgery, bone fracture, skeletal pain caused by tumor metastasis, osteoarthritis, visceral pain, inflammatory pain and neuropathic pain.

In yet another embodiment, the compounds of the present application may be useful for the pain disorders include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (e.g., postmastectomy syndrome, postthoracotomy syndrome, stump pain); bone and joint pain (osteoarthritis), repetitive motion pain, denial pain, cancer pain, myofascial pain (muscular injury, fibromyalgia); perioperative pain (general surgery, gynecological), chronic pain, dysmenorrhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

In another embodiment of the above aspect, there is provided a method of treating or preventing pain which comprises administering to said subject a pharmaceutical composition comprising an effective amount of a compound of formula (I).

Another embodiment of the application provides the use of such compositions in the treatment and/or prevention of diseases associated with inhibition of TrkA, such as pain, cancer, restenosis, atherosclerosis, psoriasis, thrombosis, neurodegenerative disease, a disease, disorder, or injury relating to dysmyelination or demyelination or certain infectious diseases such as *Trypanosoma crurzi* infection.

In another embodiment, the compounds of formula (I) are useful in treating or preventing neurodegenerative disease.

In one embodiment, neurodegenerative disease is Parkinson's disease or Alzheimer's disease.

In another aspect, the present application provides a method of treating or preventing neurodegenerative disease.

In one embodiment, neurodegenerative disease, as described above, is Parkinson's disease or Alzheimer's disease.

In another embodiment, the present application provides method of treating or preventing certain infectious diseases, for example *Trypanosoma cruzi* infection, by administering effective amount of compound of formula (I) to a patient in need thereof.

In another embodiment, the present application provides method of treating or preventing *Trypanosoma cruzi* infection by administering effective amount of compound of formula (I), to a patient in need thereof.

In one embodiment of the present application, there is provided a pharmaceutical composition comprising a therapeutically effective amount of one or more compounds of formula (I) and pharmaceutically acceptable carrier.

Another embodiment of the present application provides a method of administering TrkA inhibitors in a subject (i.e., a patient), which comprises administering to said subject (i.e., a patient) a pharmaceutical composition comprising a therapeutically effective amount of a compound of formula (I). As used herein the term "subject" and "patient" can be the same and can be used interchangeably.

In another embodiment, there is provided a method of inhibiting TrkA comprising administering to said subject a pharmaceutical composition comprising an effective amount of a compound of formula (I).

In another embodiment, there is provided a method of treating or preventing pain or pain disorder in a patient in need of such a treatment comprising the administration of a therapeutically effective amount of the compound of formula (I) enlisted in List-1, or a stereoisomer thereof or a pharmaceutically acceptable salt thereof to said patient.

The present application further relates to methods of treating a patient for diseases or disorders in which the nerve growth factor (NGF) receptor are involved, in particular TrkA, such as such as pain, cancer, restenosis, atherosclerosis, psoriasis, thrombosis, or a disease, disorder, or injury relating to dysmyelination or demyelination, by administering a therapeutically effective amount of compound of formula (I), as enlisted in List-1, to said patient.

In another embodiment, there is provided a method of treating or preventing pain or pain disorder in a patient in need of such a treatment comprising the administration of a therapeutically effective amount of the compound of formula (I), as enlisted in List-1, to said patient.

In another embodiment, pain includes chronic and acute pain but is not limited to, pain related to cancer, surgery, bone fracture, skeletal pain caused by tumor metastasis, osteoarthritis, visceral pain, inflammatory pain and neuropathic pain.

In one embodiment, there is provided a method of binding NGF receptor TrkA protein in a patient in need of such a treatment comprising the administration of a therapeutically effective amount of the compound of formula (I), as enlisted in List-1, to said patient.

The present application further relates to use of compound of formulation (I) for treating a patient for diseases or disorders in which the NGF receptor are involved, in particular TrkA, such as such as pain, cancer, restenosis, atherosclerosis, psoriasis, thrombosis, or a disease, disorder, or injury relating to dysmyelination or demyelination, by administering a therapeutically effective amount of compound of formula (I), as enlisted in List-1, to said patient.

In another embodiment, there is provided an use of the compound for formula (I) for treating or preventing pain or pain disorder in a patient in need of such a treatment, comprising the administration of a therapeutically effective amount of the compound of formula (I), as enlisted in List-1, to said patient.

In another embodiment, pain includes chronic and acute pain but is not limited to, pain related to cancer, surgery, bone fracture, skeletal pain caused by tumor metastasis, osteoarthritis, visceral pain, inflammatory pain and neuropathic pain.

In another embodiment of the above aspect, there is provided a method of treating or preventing pain which comprises administering to said subject a pharmaceutical composition comprising an effective amount of a compound of formula (I), as enlisted in List-1.

Another embodiment of the application provides the use of such compositions in the treatment or prevention of diseases associated with inhibiting NGF receptor TrkA, such as pain, cancer, restenosis, atherosclerosis, psoriasis, thrombosis, or a disease, disorder, or injury relating to dysmyelination or demyelination.

The pharmaceutical composition of a compound of formula (I) may be administered enterally and/or parenterally. Parenteral administration includes subcutaneous, intramuscular, intradermal, intramammary, intravenous, and other administrative methods known in the art. Enteral administration includes solution, tablets, sustained release capsules, enteric coated capsules, syrups, beverages, foods, and other nutritional supplements. When administered, the present pharmaceutical compositions may be at or near body temperature. In some embodiments, the present pharmaceutical compositions may be below body temperatures. In other embodiments, the present pharmaceutical compositions may be above body temperatures.

The compounds of the present invention may be administered in a wide variety of different dosage forms. For example, they may be combined with various pharmaceutically acceptable inert carriers in the form of, but not limited to, tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers may include solid diluents or fillers, sterile aqueous media, and various nontoxic organic solvents, etc. Moreover, oral pharmaceutical compositions may be sweetened and/or flavored. In general, the compounds of the invention may be present in such dosage forms at concentration levels ranging from about 0.1% to about 90% by weight.

In general, compounds of the present invention for treatment may be administered to a subject in a suitable effective dose in the range of from about 0.01 to about 100 mg per kilogram of body weight of recipient per day, in some embodiments, in the range of from about 0.5 to about 50 mg per kilogram body weight of recipient per day, in still other embodiments, in the range of from about 0.1 to about 20 mg per kilogram body weight of recipient per day. The exemplary dose may be suitably administered once daily, or several sub-doses, e.g. 2 to 5 sub-doses, may be administered at appropriate intervals through the day, or on other appropriate schedules.

An embodiment of the present invention provides the preparation of compounds of formula (I) according to the procedures of the following examples, using appropriate materials. Those skilled in the art will understand that known variations of the conditions and processes of the following preparative procedures can be used to prepare these compounds. Moreover, by utilizing the procedures described in detail, one of ordinary skill in the art can prepare additional compounds of the present invention claimed herein. All temperatures are in degrees Celsius (° C.) unless otherwise noted.

The following acronyms, abbreviations, terms and definitions have been used throughout the reaction scheme and experimental section.

ACN (Acetonitrile), BINAP (2,2'-bis(diphenylphosphino)-1,1'-binaphthyl), CDCl$_3$ (Deuterated chloroform), CHCl$_3$ (Chloroform), CD$_3$OD (Deuterated methanol), Cs$_2$CO$_3$ (Caesium Carbonate) DCM (Dichloromethane), DCE (Dichloroethene), DIPEA [(N,N-diisopropylethylamine) (Hünig's base)], DMF (N,N-dimethylformamide), DMSO (Dimethyl sulfoxide), DMAP (Dimethyl amino pyridine), EtOH (Ethanol), EtOAc (Ethyl acetate), Et$_3$N (Triethylamine), EDCl (1-ethyl-3-(3-dimethylaminopropyl)carbodiimide hydrochloride, HOBt (1-hydroxybenzotriazole), HCl (hydrochloric acid), HATU [O-(-7-azabenzotriazol-1-yl)-N,N,N',N'-tetramethyluronium hexafluorophosphate], MeOH (Methanol), LAH (Lithium aluminium hydride), LiHMDS (Lithium bis(trimethylsilyl)amide), LiOH (Lithium hydroxide), K$_2$CO$_3$ (Potassium Carbonate), KOBu$_t$ (Potassium tert-butoxide), PCC (Pyridinium chlorochromate), Pd (Palladium), Pd(OAc)$_2$ (Palladium (II) acetate), Pd$_2$(dba)$_3$ (Tris(dibenzylideneacetone)dipalladium(0)), POCl$_3$ (Phosphorus oxychloride), NaHCO$_3$ (Sodium Bicarbonate), NaOH (Sodium hydroxide), NaBH$_4$ (Sodium borohydride), Na(OAc)$_3$BH (Sodium triacetoxyborohydride), NaN$_3$ (Sodium azide), NH$_4$Cl (Ammonium chloride), NH$_4$OAc (Ammonium acetate), TFA (Trifluoroacetic acid), THF (Tetrahydrofuran), H$_2$O (Water), ZnBr$_2$ (Zinc bromide).

Another embodiment of the present invention provides a process for the preparation of compounds of formulae (Ii)-(Iix) represent respectively a sub-group of a compound of formula (I), wherein all symbols/variables are as defined earlier unless otherwise stated. The process is represented by Scheme-1.

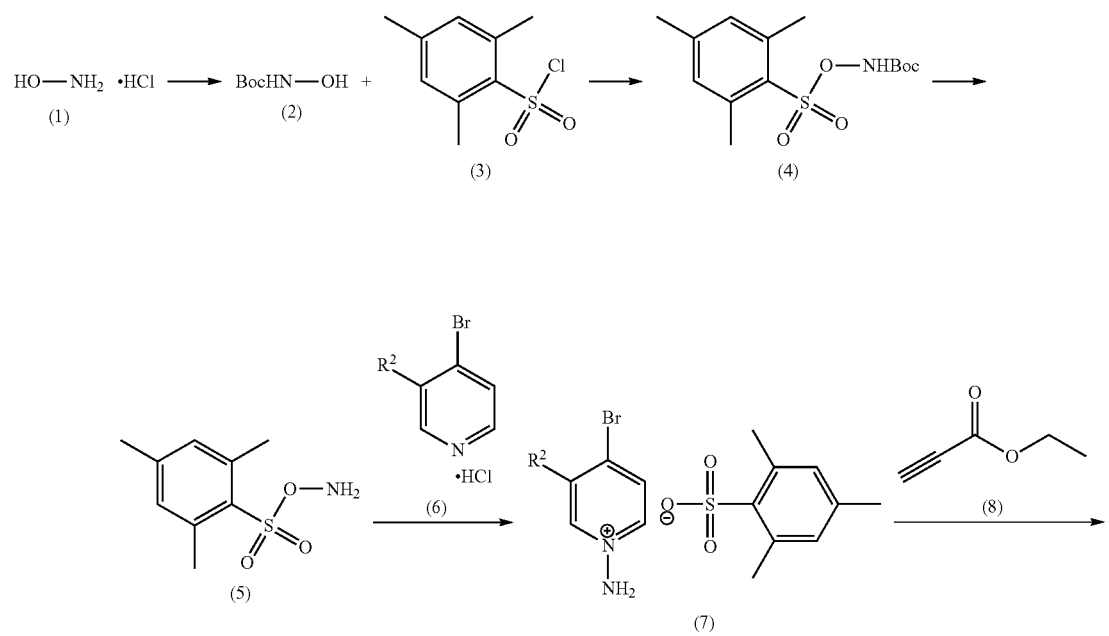

-continued

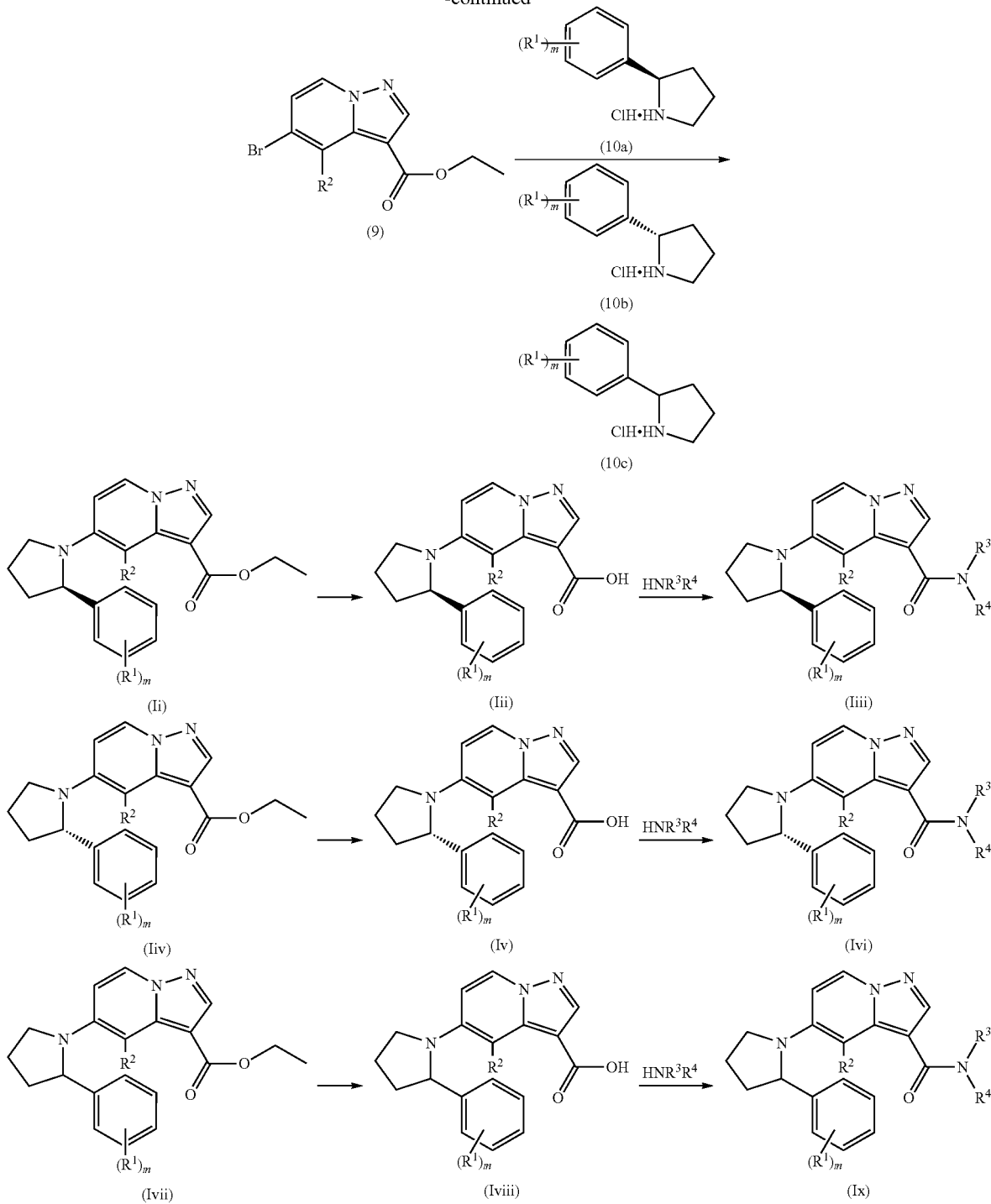

Compound of formula (9) was prepared according to the procedure described in Bioorganic & Medicinal Chemistry Letters 19 (2009) 6122-6126 and WO2010/117787.

A compound of formula (Ii), (Iiv) or (Ivii) can be obtained by reacting a compound of formula (9) with a compound of formula (10a), (10b) or (10c) respectively, in the presence of $Pd_2\,dba_3$, BINAP, $Et_3N$ and $Cs_2CO_3$, in a solvent such as 1,4-dioxane and the like at a temperature of about 60 to about 80° C. for about 12 to about 16 h.

A compound of formula (Ii) to formula (Iii), formula (Iiv) to formula (Iv), formula (Ivii) to formula (Iviii) can be converted using reagents such as 3M LiOH solution, 5N NaOH solution and the like in presence of a suitable solvent such as THF, THF-MeOH and the like.

A compound of formula (Iii) to formula (Iiii), formula (Iv) to formula (Ivi), formula (Iviii) to formula (Iix) can be converted by using suitable reagents such as HATU, DIPEA or HATU, HOBt, DIPEA or EDCI, HOBt, DIPEA or EDCI, DMAP and the like in presence of a suitable solvent such as DMF, DCM and the like at a temperature of about 20 to about 35° C. for about 15 to about 18 h.

In another embodiment there is provided a process for the preparation of a compound of formulae (Ix), (Ixi) & (Ixii), all of which represent respectively a sub-group of a compound of formula (I), wherein all symbols/variables are as defined earlier unless otherwise stated. The process is represented by Scheme-2:

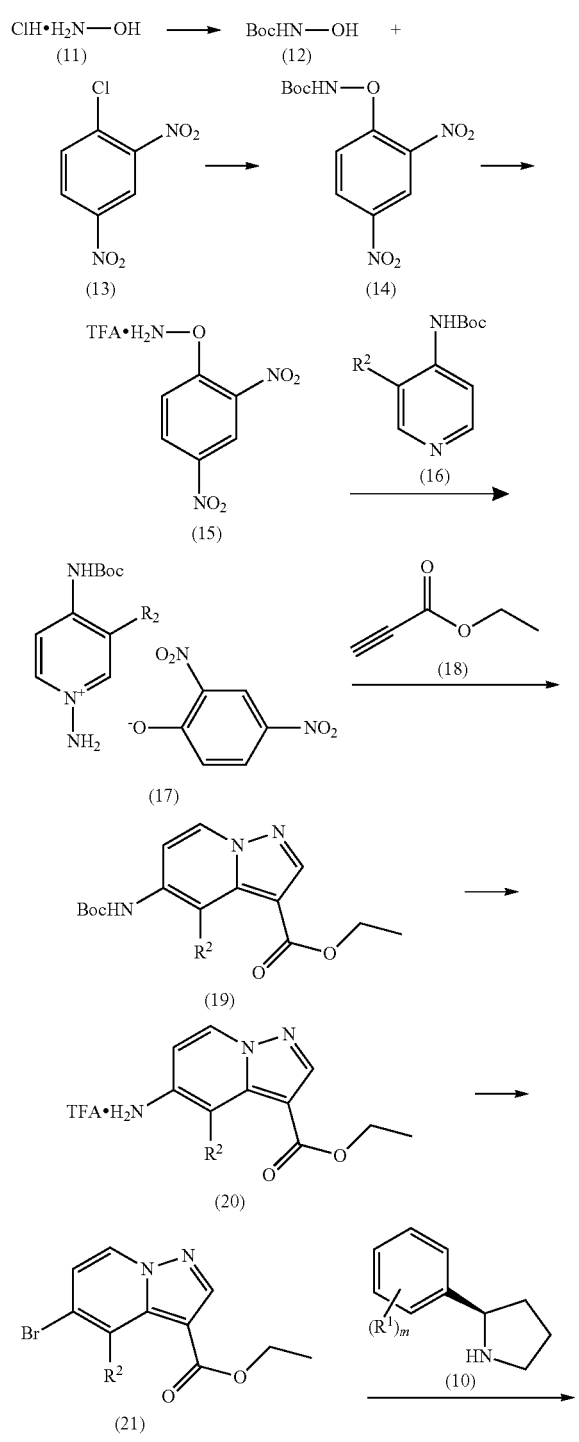

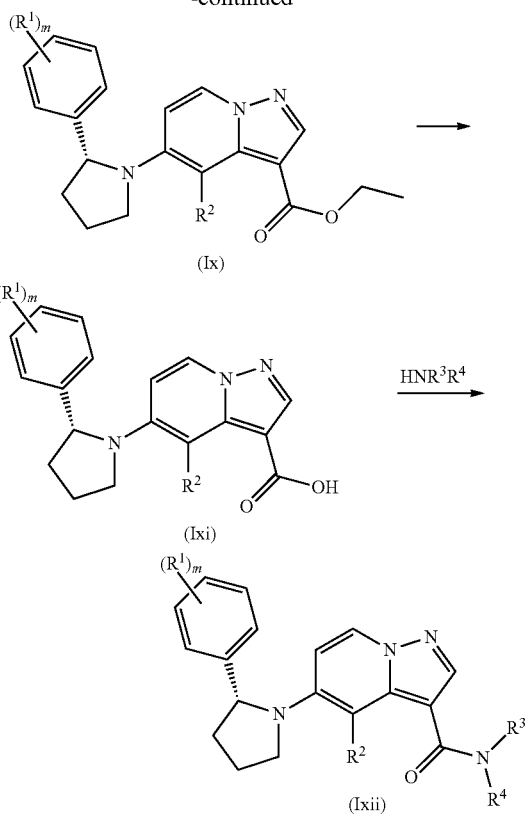

Compound of formula (21) was prepared following a similar procedure as described in J. Org. Chem. 2003, 68, 7119-7122 and WO2009/008748.

A compound of formula (Ix) where $R^1$ and $R^2$ are defined as before can be obtained by reacting a compound of formula (21) with compound of formula (10) in presence of a suitable reagents such as $Pd_2\,dba_3$, BINAP, $CS_2CO_3$, $Et_3N$ or $Pd_2\,dba_3$, BINAP, $KOBu_t$, $Et_3N$, and the like in presence of a suitable solvent such as 1,4-Dioxane, and the like at a temperature of about 80° C. for about 15-18 h.

A compound of formula (Ixi) can be obtained by reacting a compound of formula (Ix) with suitable reagents such as 3M LiOH solution or 5N NaOH solution and the like in presence of a suitable solvent such as THF, THF:MeOH and the like under reflux for about 4-18 h.

A compound of formula (Ixii) can be obtained by reacting a compound of formula (Ixi) with suitable reagents such as HATU, DIPEA or EDCI, HOBt, DIPEA and the like in presence of a suitable solvent such as DMF, DCM and the like at a temperature of about 20-35° C. for about 15-18 h.

As used in the examples and preparations that follow, the terms used therein shall have the meanings indicated: "g" or "gm" refers to grams, "mg" refers to milligrams, "µg" refers to micrograms, "mol" refers to moles, "mmol" refers to millimoles, "L" refers to liters, "mL" or "ml" refers to milliliters, "µL" refers to microliters, "mp" or "m.p." refers to melting point, "mm of Hg" refers to pressure in millimeters of mercury, "cm" refers to centimeters, "nm" refers to nanometers, "conc." refers to concentrated, "M" refers to molar, "mM" refers to millimolar, "µM" refers to micromolar, "nM" refers to nanomolar, "TLC" refers to thin layer chromatography, "HPLC" refers to high performance liquid chromatography, "anhyd" refers to anhydrous; "aq" refers to aqueous; "min"

refers to minute; "mins" refers to minutes; "h" or "hr" refers to hour; "d" refers to day; "atm" refers to atmosphere; "sat." refers to saturated; "s" refers to singlet, "d" refers to doublet; "t" refers to triplet; "q" refers to quartet; "m" refers to multiplet; "dd" refers to "doublet of doublets"; "br" refers to broad; "bs" refers to broad singlet, "LC" refers to liquid chromatograph; "MS" refers to mass spectroscopy; "ESI" refers to electrospray ionization; "CI" refers to chemical ionization; "RT" refers to retention time; "M" refers to molecular ion; "NMR" refers to nuclear magnetic resonance spectroscopy; "MHz" refers to megahertz.

EXAMPLES

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

Synthesis of compounds of formula (I)

Example-1

Synthesis of (R)-ethyl 5-(2-(2,5-difluorophenyl)pyrrolidin-1-yl)pyrazolo[1,5a]pyridine-3-carboxylate

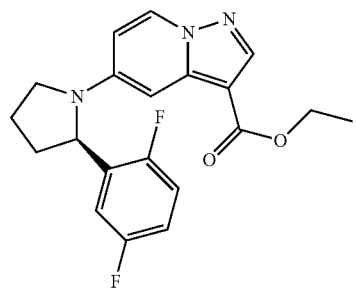 [SMILES: CCOC(=O)c1cnn2ccc(N3CCC[C@@H]3c3cc(F)ccc3F)cc12]

Step-1: Synthesis of 4-chloro-N-methoxy-N-methylbutanamide

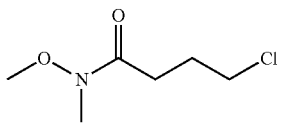

Pyridine (101.28 g, 106.6 mL 1281.79 mmol) was added to a solution of N,O-dimethylhydroxylamine hydrochloride (50 g, 512.72 mmol) in DCM (800 mL) at 0° C. and stirring was continued for 15 min. Chlorobutyrylchloride (72.29 g, 512.72 mmol) was then added to this mixture and was stirred continuously at 0° C. for 2 h. The reaction mixture was diluted with DCM and the organic layer was washed with water followed by brine. The organic layer was separated; dried over anhydrous sodium sulphate and concentrated under reduced pressure to afford 79 g of the title compound as a pale brown liquid.

MS (ESI): m/z 166.1 (M+H)

Step-2: Synthesis of 4-chloro-1-(2,5-difluorophenyl)butan-1-one

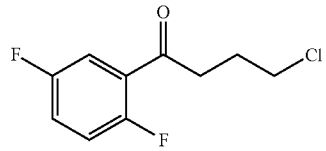 [SMILES: O=C(CCCCl)c1cc(F)ccc1F]

2-Bromo-1,4-difluorobenzene (53.6 g, 277.74 mmol) in THF cooled to −50° C. was added to isopropyl magnesium chloride (2M in THF)(133 mL, 266 mmol). The reaction mixture thus obtained was warmed to 0° C. and stirred for 1 h. The reaction mixture was cooled again to −50° C. 4-chloro-N-methoxy-N-methylbutanamide (40 g, 241.52 mmol) in THF (200 mL) was added dropwise to this reaction mixture with stirring and the stirring was continued at 0° C. for 1 h. The reaction mixture was quenched with saturated aqueous NH$_4$Cl solution, extracted with ethylacetate. The organic layer collected was washed with water (500 mL) and then with brine solution, dried over anhydrous sodium sulfate and concentrated under reduced pressure to afford a crude liquid residue. The residue thus obtained was purified by column chromatography (using 60-120 silica gel and 5% EtOAc in Hexane as eluent) to afford 35 g of the title compound as a colourless liquid.

$^1$H NMR (300 MHz, CDCl$_3$) δ ppm 7.6-7.53 (1H, m), 7.26-7.09 (2H, m), 3.7 (2H, t) 3.22-3.14 (2H, m), 2.28-2.16 (2H, m).

Step-3: Synthesis of (S,E)-N-(4-chloro-1-(2,5-difluorophenyl) butylidene)-2-methylpropane-2-sulfinamide

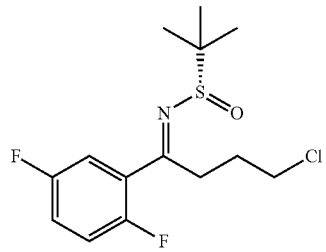 [SMILES: CC(C)(C)[S@](=O)/N=C(\CCCCl)c1cc(F)ccc1F]

Titanium (IV) ethoxide (54.77 g, 240.13 mmol) was added to a solution of 4-chloro-1-(2,5-difluorophenyl)butan-1-one (35 g, 160.09 mmol) and (S)-2-methylpropane-2-sulfinamide (29.1 g, 240.13 mmol) in THF (400 mL) with stirring. The mixture was stirred continuously at 70° C. for 16 h. Reaction mixture was then cooled to a temperature of 20-35° C., quenched with saturated aqueous NH$_4$Cl solution, diluted with ethylacetate and filtered. The filtrate was washed with water followed by brine solution. The organic layer was separated, dried over anhydrous sodium sulfate and concentrated under reduced pressure to afford 44.5 g of the title compound as a colourless liquid.

MS (ESI): m/z 322.3 (M+H)

Step-4: Synthesis of (R)-1-((S)-tert-butylsulfinyl)-2-(2,5-difluorophenyl)pyrrolidine and (S)-1-((S)-tert-butylsulfinyl)-2-(2,5-difluorophenyl)pyrrolidine

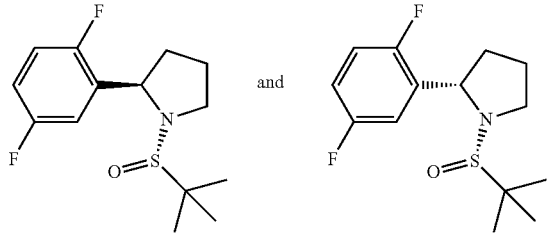 [SMILES: CC(C)(C)[S@](=O)N1CCC[C@@H]1c1cc(F)ccc1F ; CC(C)(C)[S@](=O)N1CCC[C@H]1c1cc(F)ccc1F]

(S,E)-N-(4-chloro-1-(2,5-difluorophenyl)butylidene)-2-methylpropane-2-sulfinamide (44 g, 136.72 mmol) in THF (500 mL) was cooled to −78° C. and to which was added cold (−78° C.) Lithium triethylborohydride (1M in THF) (17.38 g, 165 mL, and 134.67 mmol) dropwise and stirring was continued at −78° C. for 3 h. LiHMDS (1M in THF) (25.26 g, 150 mL, 150 mmol) was then added and stirring was continued at −78° C. to 0° C. for 2 h. The resultant reaction mixture was quenched with saturated NH$_4$Cl solution, diluted with ethylacetate. The ethylacetate layer separated was washed with water followed by brine solution, dried over anhydrous sodium sulphate and concentrated under reduce pressure to afford the crude residue. The residue thus obtained was purified by column chromatography twice (using initially with 60-120 silicagel and 15% EtOAC in Hexane as eluent and again with 230-400 silicagel and 12-14% EtOAc in Hexane as eluent) to afford 14.5 g of the title compound (R)-1-((S)-tert-butylsulfinyl)-2-(2,5-difluorophenyl)pyrrolidine as a pale brown liquid.

$^1$H NMR (300 MHz, CDCl$_3$) δ ppm 7.1-6.85 (3H, m), 5.0 (1H, t) 3.93-3.85 (1H, m), 3.02-2.94 (1H, m), 2.32-2.2 (1H, m), 2.0-1.72 (3H, m), 1.16 (9H, s) and 4 g of the title compound (S)-1-((S)-tert-butylsulfinyl)-2-(2,5-difluorophenyl)pyrrolidine.

$^1$H NMR (300 MHz, CDCl$_3$) $^1$H NMR (300 MHz, CDCl$_3$) δ ppm 7.1-6.8 (3H, m), 5.42-5.2 (1H, d, J=7.5 Hz), 2.3-2.05 (1H, m), 2.0-1.65 (4H, m), 1.1 (9H, s).

Step-5: Synthesis of (R)-2-(2,5-difluorophenyl)pyrrolidine hydrochloride

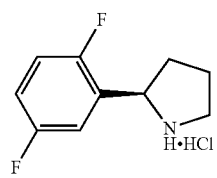

4M HCl solution (in Dioxane) (75 mL) was added to stirred solution of (R)-1-((S)-tert-butylsulfinyl)-2-(2,5-difluorophenyl)pyrrolidine (15 g, 52.19 mmol) in Dioxane (25 mL) and stirring was continued at 20-35° C. for 4 h. After which the reaction mixture was concentrated under reduced pressure to afford the crude product. The crude product was purified by washing with diethyl ether to afford 7.5 g of the title compound as a white solid.

MS (ESI): m/z 184 (M+H)

Step-6: Synthesis of (R)-ethyl 5-(2-(2,5-difluorophenyl)pyrrolidin-1-yl)pyrazolo[1,5a]pyridine-3-carboxylate

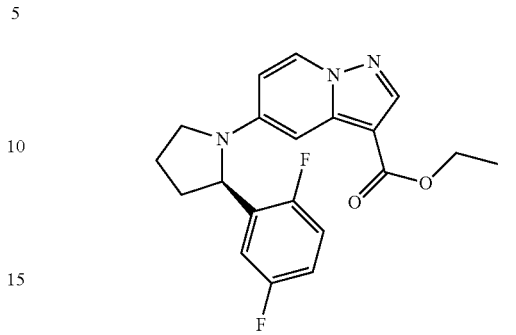

A mixture of ethyl 5-bromopyrazolo[1,5a]pyridine-3-carboxylate (2 g, 7.49 mmol), (R)-2-(2,5-difluorophenyl)pyrrolidine hydrochloride (1.65 g, 7.49 mmol) and Cs$_2$CO$_3$ (7.3 g, 22.47 mmol) in 1,4-Dioxane (35 mL) was degassed with argon gas for 15 min. Pd$_2$(dba)$_3$ (480 mg, 0.52 mmol) and BINAP (380 mg, 0.59 mmol) were added to the above mixture and stirring was continued at 100° C. for 2 h. After completion of the reaction, the reaction mixture was cooled and filtered over a celite bed. The celite bed was washed with ethylacetate. The filtrate thus obtained was further washed with water, dried over anhydrous sodium sulphate and concentrated under reduced pressure to afford the crude product, which was purified by column chromatography (using silica gel 60-120, and 30% EtOAc in Hexane as eluent) to afford 1.8 g of the title compound as a yellow solid.

$^1$H NMR (300 MHz, CDCl$_3$) δ ppm 8.21-8.18 (2H, m), 7.12-7.02 (1H, m), 6.98-6.86 (1H, m), 6.74-6.66 (1H, m), 6.28-6.2 (1H, m), 5.15 (1H, d, J=8 Hz), 6.16-6.13 (1H, m), 5.11 (1H, d, J=8.1 Hz), 4.34-4.27 (2H, m), 3.84 (1H, t) 3.60-3.5 (1H, m), 2.52-2.4 (1H, m), 2.2-2.0 (3H, m), 1.38-1.3 (3H, m).

MS (ESI): m/z 372 (M+H).

Example-2

Synthesis of (R)-5-(2-(2,5-difluorophenyl)pyrrolidin-1-yl)pyrazolo[1,5a]pyridine-3-carboxylic acid

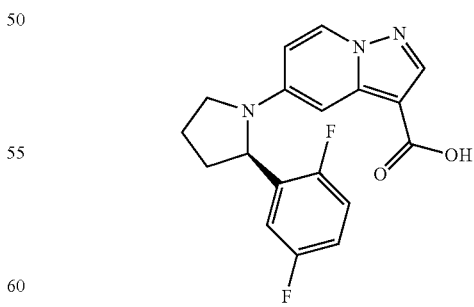

LiOH.H$_2$O (0.679 mg, 16.2 mmol) in water (5 mL) was added to a stirred solution of (R)-ethyl 5-(2-(2,5-difluorophenyl)pyrrolidin-1-yl)pyrazolo[1,5a]pyridine-3-carboxylate (1.8 g, 4.85 mmol) in EtOH (30 mL) and the stirring was continued at reflux temperature for 12-16 h. The reaction mixture was concentrated under reduced pressure to afford the crude product. The crude product thus obtained was diluted with cold water, acidified with 2N aqueous HCl solution, filtered the solid precipitate to afford 1.2 g of the title compound as an off white solid.

MS (ESI): m/z 344(M+H).

Example-3

Synthesis of 5-(2-(2,5-difluorophenyl)pyrrolidin-1-yl)pyrazolo[1,5a]pyridine-3-carboxylic acid

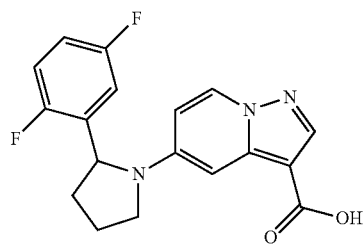 [SMILES: O=C(O)c1cnn2ccc(N3CCCC3c3cc(F)ccc3F)cc12]

Step-1: Synthesis of tert-butyl 2-oxopyrrolidine-1-carboxylate

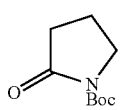

Di-tert-butyldicarbonate (154 g, 154 mL, 704 mmol) was added to solution of 2-Pyrrolidinone (50 g, 587 mmol) and DMAP (36 g, 293.7 mmol) in acetonitrile (500 mL) at 0-5° C. and stirring was continued at 20-35° C. for 2 h. Reaction mixture was concentrated under reduced pressure to afford the residue, which was diluted with EtOAc, washed it with water, dried over anhydrous sodium sulphate and concentrated under reduced pressure to afford 73 g of the title compound.

Step-2: Synthesis of tert-butyl 5-(2,5-difluorophenyl)-2,3-dihydro-1H-pyrrole-1-carboxylate

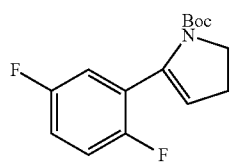 [SMILES: CC(C)(C)OC(=O)N1CCC=C1c1cc(F)ccc1F]

2.0 M Isopropyl magnesium chloride solution in THF (163 mL, 324.3 mmol) was added to a solution of 2-bromo-1,4-difluorobenzene (62.5 g, 324.3 mmol) in THF (350 mL) at −40° C. and stirring was continued at 5° C. for 1 h. tent-Butyl 2-oxopyrrolidine-1-carboxylate (Step-1)(73 g, 392 mmol) in THF (150 mL) was added dropwise to above reaction mixture at −40° C. and stirring was continued at 10° C. for 2 h. Reaction mixture was quenched with saturated NH₄Cl solution, extracted with EtOAc, dried over anhydrous sodium sulphate and concentrated under reduced pressure to afford 76 g of the title compound.

Step-3: Synthesis of 5-(2,5-difluorophenyl)-3,4-dihydro-2H-pyrrole

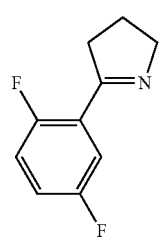

TFA (108 g, 940 mmol) was added to a solution of tert-butyl 5-(2,5-difluorophenyl)-2,3-dihydro-1H-pyrrole-1-carboxylate (53 g, 188 mmol) in DCM (300 mL) at 0° C. and stirring was continued at 20-35° C. for 2 h. The reaction mixture was concentrated under reduced pressure to afford the crude, which was diluted with EtOAc, washed with saturated NaHCO₃ solution, dried over anhydrous sodium sulphate to afford 28.5 g of the title compound.

MS (ESI): m/z 181.9 (M+H)

Step-4: Synthesis of 2-(2,5-difluorophenyl)pyrrolidine

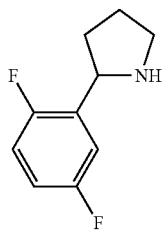

NaBH₄(12 g, 314.9 mmol) was added to a solution of 5-(2,5-difluorophenyl)-3,4-dihydro-2H-pyrrole (28.5 g, 157.4 mmol) in a mixture of MeOH:H₂O(4:1, 250 mL) and stirring was continued at 25-35° C. for 2 h. The reaction mixture was quenched with 1N aqueous HCl solution and basified with 2N aqueous NaOH solution, extracted with DCM, dried over anhydrous sodium sulphate and concentrated under reduced pressure to afford 23 g of the title compound.

MS (ESI): m/z 184 (M+H)

Step-5 Synthesis of Ethyl 5-(2-(2,5-difluorophenyl)pyrrolidin-1-yl)pyrazolo[1,5-a]pyridine-3-carboxylate

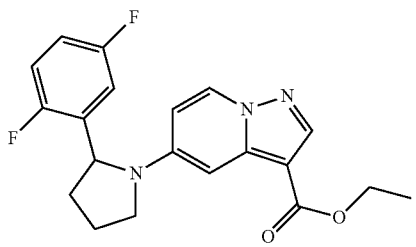 [SMILES: CCOC(=O)c1cnn2ccc(N3CCCC3c3cc(F)ccc3F)cc12]

The title compound was prepared by a procedure substantially similar as in Step-6 of Example—1, using 2-(2,5-difluorophenyl)pyrrolidine in place of (R)-2-(2,5-difluorophenyl)pyrrolidine hydrochloride to afford the crude. The crude compound was purified by column chromatography (using silica gel 60-120, and 5% EtOAc in Hexane as eluent) to afford 135 mg of the title compound.

¹H NMR (400 MHz, DMSO-d₆) δ ppm 8.52-8.50 (1H, d, J=7.6 Hz), 8.12 (1H, s), 7.4-7.3 (1H, m), 7.2-7.1 (1H, m), 6.95-6.9 (1H, m), 6.7 (1H, s), 6.55 (1H, bs), 5.12 (1H, d, J=7.6 Hz), 4.2-4.27 (2H, m), 3.94-3.84 (1H, t), 3.55-3.40 (1H, m), 2.52-2.40 (1H, m), 2.15-1.85 (3H, m), 1.3-1.15 (3H, m),

MS (ESI): 372 (M+H).

Step-6 Synthesis of 5-(2-(2,5-difluorophenyl)pyrrolidin-1-yl)pyrazolo[1,5a]pyridine-3-carboxylic acid

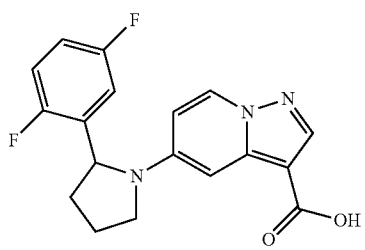 [SMILES: O=C(O)c1cnn2ccc(N3CCCC3c3cc(F)ccc3F)cc12]

5N aqueous solution of NaOH (2 mL) was added to stirred solution of ethyl 5-(2-(2,5-difluorophenyl)pyrrolidin-1-yl)pyrazolo[1,5-a]pyridine-3-carboxylate (50 mg, 0.134 mmol) in a mixture of MeOH (4 mL) and THF (4 mL) and continued stirring at 80° C. for 4 h. The reaction mixture was concentrated under reduced pressure to afford the crude product. The crude product thus obtained was diluted with cold water, acidified with concentrated HCl solution to obtain a solid precipitate. This solid precipitate was filtered and dried well to afford 18 mg of 5-(2-(2,5-difluorophenyl)pyrrolidin-1-yl)pyrazolo[1,5-a]pyridine-3-carboxylic acid as off white solid.

¹H NMR (400 MHz, DMSO-d₆) δ ppm 11.82 (1H, s), 8.46 (1H, d, J=7.6 Hz), 8.08 (1H, s), 7.40-7.30 (1H, m), 7.20-7.10 (1H, m), 6.95-6.88 (1H, m), 6.67 (1H, s), 6.39 (1H, s), 5.15 (1H, d, J=8 Hz), 3.80-3.70 00(1H, t, J=8 Hz), 3.50-3.30 (1H, m), 2.44 (1H, m), 2.10-1.85 (3H, m).

MS (ESI): m/z 344.2 (M+H)

Example-4

(5-(2-(2,5-difluorophenyl)pyrrolidin-1-yl)pyrazolo[1,5-a]pyridin-3-yl)((S)-3-hydroxypyrrolidin-1-yl)methanone

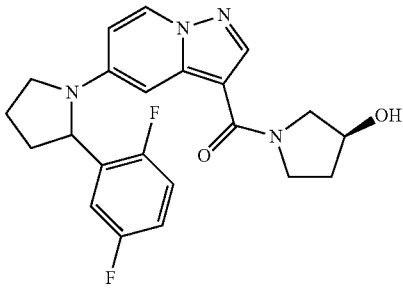 [SMILES: O=C(c1cnn2ccc(N3CCCC3c3cc(F)ccc3F)cc12)N1CC[C@H](O)C1]

5-(2-(2,5-difluorophenyl)pyrrolidin-1-yl)pyrazolo[1,5-a]pyridine-3-carboxylic acid (100 mg, 0.29 mmol) was prepared by the method mentioned in Example-3. DIPEA (93.6 mg, 0.72 mmol) was added to a stirred solution of 5-(2-(2,5-difluorophenyl)pyrrolidin-1-yl)pyrazolo[1,5-a]pyridine-3-carboxylic acid (100 mg, 0.29 mmol) in DMF (1.5 mL) followed by addition of HATU (165 mg, 0.437 mmol) to the reaction mixture. After 2 minutes of stirring, (S)-pyrrolidin-3-ol (81.8 mg, 0.43 mmol) was added and the resulting mixture was stirred at 20-35° C. for 2 h. The reaction mixture was diluted with cold water; extracted with ethyl acetate; dried over sodium sulfate; and concentrated under reduced pressure to get a residue. The residue thus obtained was purified by column chromatography (60-120 silica gel and 3% EtOAc in Hexane as eluent) to afford (5-(2-(2,5-difluorophenyl)pyrrolidin-1-yl)pyrazolo[1,5-a]pyridin-3-yl)((S)-3-hydroxypyrrolidin-1-yl)methanone Example-5

Synthesis of 5-(2-(2,5-difluorophenyl)pyrrolidin-1-yl)-N,N-dimethylpyrazolo[1,5a]pyridine-3-carboxamide

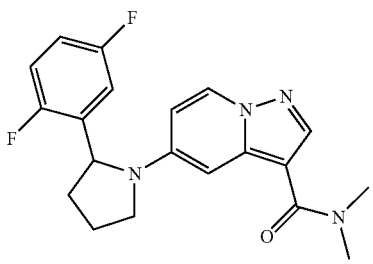 [SMILES: CN(C)C(=O)c1cnn2ccc(N3CCCC3c3cc(F)ccc3F)cc12]

The title compound was prepared by a method substantially similar to that mentioned in Example-4, using dimethyl amine hydrochloride in place of (S)-pyrrolidin-3-ol. The reaction mixture was quenched with cold water, and the solid precipitate obtained was filtered to afford the crude product. The crude product was purified by Preparative TLC (Silicagel GF₂₅₄, 1000 u, 20×20 cm dimension glass plate and 100% EtOAc as eluent) to afford 14 mg of the title compound.

$^1$H NMR (400 MHz, DMSO-d$_6$) δ ppm 8.42 (1H, d, J=7.6 Hz), 8.07 (1H, s), 7.36-7.30 (1H, m), 7.20-7.12 (1H, m), 6.90-6.84 (1H, m), 6.72 (1H, s), 6.39 (1H, d, J=6.4 Hz), 5.11 (1H, d, J=8 Hz), 3.85-3.81 (1H, t, J=8 Hz), 3.5-3.3 (1H, m), 3.03 (6H, s), 2.44 (1H, m), 2.10-1.85 (1H, m).

MS (ESI): m/z 371 (M+H).

Example-6

Synthesis of 5-(2-(2,5-difluorophenyl)pyrrolidin-1-yl)pyrazolo[1,5a]pyridine-3-carboxamide

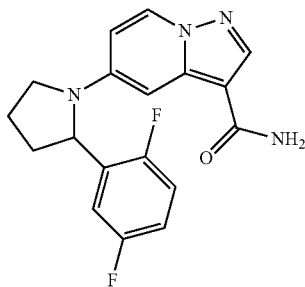 [SMILES: NC(=O)c1cnn2ccc(N3CCCC3c3cc(F)ccc3F)cc12]

DIPEA (750 mg, 5.82 mmol) was added to a stirred solution of 5-(2-2,5-difluorophenyl)pyrrolidin-1-yl)pyrazolo[1,5a]pyridine-3-carboxylic acid (100 mg, 0.29 mmol) in DMF (2 mL) followed by addition of HATU (121 mg, 0.32 mmol) and HOBt (41 mg, 0.305 mmol). After 10 minutes of stirring, NH$_4$Cl (231 mg, 4.36 mmol) was added and the resulting mixture was stirred for 12-16 h at 20-35° C. The reaction mixture was diluted with cold water to obtain a solid precipitate which was then filtered, washed with water, and dried well to afford the crude residue. The crude residue obtained was purified by Preparative TLC (using Silicagel GF$_{254}$, 1000 u, 20×20 cm dimension glass plate and 80% EtOAc in Hexane as eluent) to afford 6 mg of the title compound.

$^1$H NMR (400 MHz, DMSO-d$_6$) δ ppm 8.39 (1H, d, J=7.6 Hz), 8.27 (1H, s), 7.40-7.29 (1H, m), 7.20-7.10 (1H, m), 7.56 (1H, s), 6.91-6.82 (1H, m), 6.33 (1H, d, J=7.2 Hz), 5.11 (1H, d, J=7.4 Hz), 3.86-3.82 (1H, t, J=8 Hz), 3.45-3.30 (2H, m), 2.10-2.00 (1H, m), 1.99-1.88 (2H, m).

MS (ESI): m/z 343.2 (M+H).

Example-7

Synthesis 5-(2-(2,5-difluorophenyl)pyrrolidin-1-yl)-N-(4-fluorophenyl)pyrazolo[1,5a]pyridine-3-carboxamide

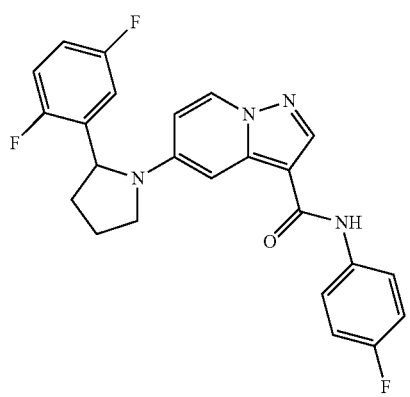 [SMILES: O=C(Nc1ccc(F)cc1)c1cnn2ccc(N3CCCC3c3cc(F)ccc3F)cc12]

The title compound was prepared by a similar method to that mentioned in Example-6 to afford the crude product. The crude product was purified by Preparative TLC (using Silicagel GF$_{254}$, 1000 u coated 20×20 cm dimension glass plate and 30% EtOAc in Hexane as eluent) to afford 8 mg of the title compound.

$^1$H NMR (400 MHz, CDCl$_3$) δ ppm 8.17 (1H, d, J=7.6 Hz), 8.07 (1H, s), 7.56-7.53 (2H, m), 7.42 (1H, s), 7.23 (1H, s), 7.1-7.0 (2H, m), 6.95-6.88 (1H, m), 6.72-6.65 (1H, m), 6.22 (1H, m), 5.15 (1H, d, J=8 Hz), 3.85-3.75 (1H, m), 3.60-3.50 (1H, m), 2.55-2.40 (1H, m), 2.2-2.0 (3H, m).

MS (ESI): m/z 437.3 (M+H).

Example-8

(5-(2-(2,5-difluorophenyl)pyrrolidin-1-yl)pyrazolo[1,5-a]pyridin-3-yl)(3-hydroxyazetidine-1-yl)methanone

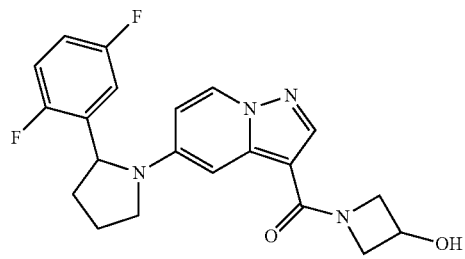 [SMILES: O=C(c1cnn2ccc(N3CCCC3c3cc(F)ccc3F)cc12)N1CC(O)C1]

The title compound was prepared by a similar method as mentioned in Example-4, using 3-Hydroxy azetidine hydrochloride in place of (S)-3-Pyrrolidinol to afford the crude product. The crude product obtained was purified by Preparative TLC (using Silicagel GF$_{254}$, 1000 u, coated 20×20 cm glass plate and 5% MeOH in EtOAc as eluent) to afford mg of (5-(2-(2,5-difluorophenyl)pyrrolidin-1-yl)pyrazolo[1,5-a]pyridin-3-yl)(3-hydroxyazetidine-1-yl)methanone.

Example-9

Synthesis of (5-(2-(2,5-difluorophenyl)pyrrolidin-1-yl)pyrazolo[1,5a]pyridin-3-yl)(4-hydroxypiperidin-1-yl)methanone

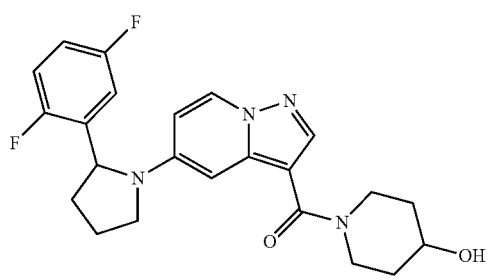 [SMILES: O=C(c1cnn2ccc(N3CCCC3c3cc(F)ccc3F)cc12)N1CCC(O)CC1]

The title compound was prepared by a method substantially similar to that mentioned in Example-8, using 4-piperidinol in place of 3-Hydroxyazetidine hydrochloride to afford the crude product. The crude product was purified by Preparative HPLC [Column: 21.2×150×5 um, Zorbax, XDB,C-18 (#22), Mobile phase-A: 0.1% TFA in water, B:ACN, Gradient (Time/% B): 0/30, 2/40, 10/70 and Flow rate:20 mL/min] to afford 22.1 mg of the title compound.

$^1$H NMR (400 MHz, DMSO-d$_6$) δ ppm 8.44 (1H, d, J=8 Hz), 7.96 (1H, s), 7.36-7.30 (1H, m), 7.18-7.13 (1H, m), 6.91-6.86 (1H, m), 6.46 (1H, s), 6.38 (1H, d, J=6.4 Hz), 5.12 (1H, d, J=8 Hz), 3.92-3.70 (3H, m), 3.71-3.67 (1H, m), 3.16-3.08 (3H, m), 2.1-1.85 (3H, m), 1.8-1.65 (2H, m), 1.4-1.2 (2H, m).

MS (ESI): m/z 427.3 (M+H)

Example-10

Synthesis of 5-(2-(2,5-difluorophenyl)pyrrolidin-1-yl)-N-(1,3-dihydroxypropan-2-yl)pyrazolo[1,5a]pyridine-3-carboxamide

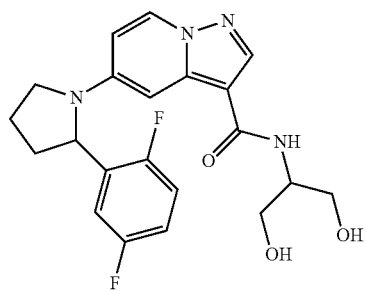 [SMILES: O=C(NC(CO)CO)c1cnn2ccc(N3CCCC3c3cc(F)ccc3F)cc12]

The title compound was prepared by a method substantially similar to that mentioned in Example-4, using 2-aminopropane-1,3-diol in place (S)-pyrrolidin-3-ol to afford the crude product. The crude product obtained was purified by Preparative HPLC [Column:LUNA-C18-250*21.2 mm, Mobile phase-A: 10 mM NH$_4$OAc, B: MeOH:ACN(1:1), Gradient (Time/% B): 0/40, 2/40, 10/90 and Flow rate:20 mL/min] to afford 9 mg of the title compound. $^1$H NMR (400 MHz, DMSO-d$_6$) δ ppm 8.42 (1H, d, J=8 Hz), 8.35 (1H, s), 7.41-7.30 (2H, m), 7.2-7.1 (1H, m), 6.95 (1H, s), 6.90-6.80 (1H, m), 6.38 (1H, d, J=6.4 Hz) 5.12 (1H, d, J=8 Hz), 4.65 (2H, m), 3.95-3.80 (2H, m), 3.50-3.40 (5H, m), 2.1-2.0 (1H, m), 2.0-1.85 (3H, m).

MS (ESI): m/z 417.1 (M+H).

Example-11

Synthesis of (5-(2-(2,5-difluorophenyl)pyrrolidin-1-yl)pyrazolo[1,5a]pyridin-3-yl)(4-methylpiperazin-1-yl)methanone

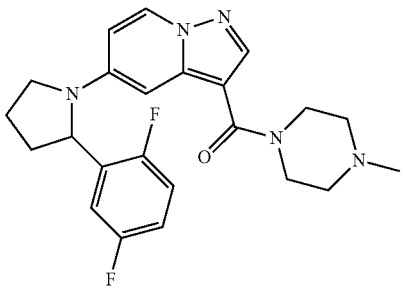 [SMILES: CN1CCN(C(=O)c2cnn3ccc(N4CCCC4c4cc(F)ccc4F)cc23)CC1]

The title compound was prepared by a method substantially similar to that mentioned in Example-6, using 1-Methyl piperazine in place of NH$_4$Cl. The reaction mixture was diluted with cold water, extracted with ethylacetate, washed the ethylacetate layer with water, dried over anhydrous sodium sulfate and concentrated under reduced pressure to afford the crude residue. The crude residue was purified by Preparative HPLC [using Column:21.2×150×5 um, Zorbax, XDB,C-18(#022), Mobile phase-A: 10 mM NH$_4$OAc, B:ACN, Gradient (Time/% B): 0/30, 2/40, 10/70 and Flow rate:20 mL/min] to afford 20 mg of the title compound(5-(2-(2,5-difluorophenyl)pyrrolidin-1-yl)pyrazolo[1,5-a]pyridin-3-yl)(4-methylpiperazin-1-yl)methanone. $^1$H NMR (400 MHz, DMSO-d$_6$) δ ppm 8.24 (1H, d, J=8 Hz), 7.90 (1H, s), 7.20-7.030 (1H, m), 6.95-6.90 (1H, m), 6.79-6.78 (1H, m), 6.72-6.65 (1H, m), 6.17 (1H dd, J=2.4, 7.6 Hz), 5.11 (1H, d, J=8 Hz), 3.80-3.70 (5H, m), 3.55-3.49 (1H, m), 2.48-2.40 (5H, m), 2.33 (3H, s), 2.11-1.98 (3H, m).

MS (ESI): m/z 426.3 (M+H).

Example-12

Synthesis of (R)-(5-(2-(2,5-difluorophenyl)pyrrolidin-1-yl)pyrazolo[1,5a]pyridin-3-yl) (3-hydroxyazetidine-1-yl)methanone

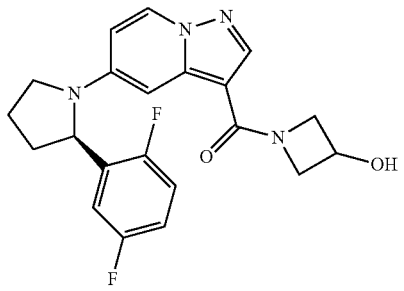 [SMILES: O=C(c1cnn2ccc(N3CCC[C@@H]3c3cc(F)ccc3F)cc12)N1CC(O)C1]

The title compound was prepared by a method substantially similar to that mentioned in Example-4, using (R)-5-(2-(2,5-difluorophenyl)pyrrolidin-1-yl)pyrazolo[1,5a]pyridine-3-carboxylic acid (Example-2) and 3-Hydroxy azetidine hydrochloride in place of (S)-3-Pyrrolidinol to afford the crude product. The crude product was purified by Preparative HPLC [Column: Water X-bridge, C-18, 5 u, OBD,19×150 mm, Mobile phase-A: Water, B:ACN, Gradient (Time/% B): 0/30, 2/40, 10/10 and Flow rate:15 mL/min] to afford 98 mg of the title compound(R)-(5-(2-(2,5-difluorophenyl)pyrrolidin-1-yl)pyrazolo[1,5-a]pyridin-3-yl)(3-hydroxyazetidine-1-yl)methanone as a white solid. $^1$H NMR (400 MHz, DMSO-d$_6$) δ ppm 8.46 (1H, d, J=8 Hz), 8.02 (1H, s), 7.38-7.3 (1H m), 7.2-7.18 (1H, m), 6.95 (1H, s), 6.92-6.84 (1H, m), 6.46 (1H, m), 5.72 (1H, d, J=6.4 Hz), 5.17 (1H, d, J=8.4 Hz), 4.54-4.45 (2H, m), 3.95-3.55 (3H, m), 3.50-3.40 (1H, m), 2.5-2.4 (1H, m), 2.1-1.8 (3H, m).

MS (ESI): m/z 399.1 (M+H).

Example-13

Synthesis of (5-((R)-2-(2,5-difluorophenyl)pyrrolidin-1-yl)pyrazolo[1,5a]pyridin-3-yl)((S)-3-hydroxypyrrolidin-1-yl)methanone

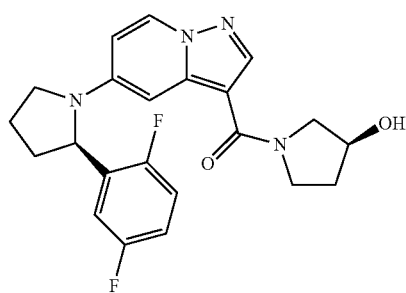 [SMILES: O=C(c1cnn2ccc(N3CCC[C@@H]3c3cc(F)ccc3F)cc12)N1CC[C@H](O)C1]

The title compound was prepared by the method substantially similar to that mentioned in Example-4, using (S)-3-Pyrrolidinol to afford the crude product, which was purified by Preparative HPLC [Column: water x-bridge, C-18, 5 u, OBD, 19×150 mm, Mobile phase-A: 0.1% TFA in water, B:ACN, Gradient (Time/% B): 0/20, 2/30, 10/90 and Flow rate:15 mL/min] 120 mg of the title compound as an off white solid.

$^1$H NMR (400 MHz, DMSO-d$_6$) δ ppm 8.45 (1H, d, J=8 Hz), 8.15 (1H, bs), 7.36-7.30 (1H, m), 7.18-7.12 (1H, m), 7.01 (1H, s), 6.90-6.85 (1H, m), 6.40 (1H, d, J=6.4 Hz), 5.13 (1H, d, J=8.4 Hz), 4.93 (1H, bs), 4.29 (1H, bs), 3.9-3.60 (3H, m), 3.6-3.4 (4H, m), 2.04-2.00 (1H, m), 2.0-1.70 (3H, m).

MS (ESI): m/z 413.1 (M+H)

Example-14

Synthesis of (5-((S)-2-(2,5-difluorophenyl)pyrrolidin-1-yl)pyrazolo[1,5a]pyridin-3-yl) ((S)-3-hydroxypyrrolidin-1-yl)methanone

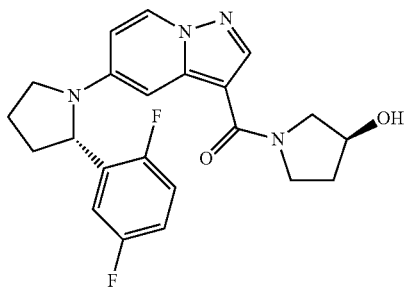 [SMILES: O=C(c1cnn2ccc(N3CCC[C@H]3c3cc(F)ccc3F)cc12)N1CC[C@H](O)C1]

(S)-5-(2-(2,5-difluorophenyl)pyrrolidin-1-yl)pyrazolo[1,5-a]pyridine-3-carboxylic acid (100 mg, 0.29 mmol) was prepared by the Buchwald coupling (Scheme-1) of ethyl 5-bromopyrazolo[1,5a]pyridine-3-carboxylate and (S)-2-(2,5-difluorophenyl)pyrrolidine hydrochloride. A method substantially similar to that mentioned in Example-1, using (S)-5-(2-(2,5-difluorophenyl)pyrrolidin-1-yl)pyrazolo[1,5-a]pyridine-3-carboxylic acid (100 mg, 0.29 mmol) and (S)-3-Pyrrolidinol (38 mg, 0.44 mmol) afforded the crude product, which was purified by Preparative HPLC [Column:LUNA-C18-250*21.2 mm, Mobile phase-A: 0.1% TFA in water, B: ACN, Gradient (Time/% B): 0/50, 2/50, 10/90 and Flow rate:20 mL/min] to obtain 55 mg of the title compound as an off white solid.

$^1$H NMR (400 MHz, DMSO-d$_6$) δ ppm 8.45 (1H, d, J=8 Hz), 8.2 (1H, bs), 7.38-7.30 (1H, m), 7.20-7.12 (1H, m), 7.01 (1H, s), 6.9-6.84 (1H, m), 6.40 (1H, d), 5.12 (1H, d, J=8.0 Hz), 4.95 (1H, d, J=5.6 Hz), 4.3 (1H, bs), 3.90-3.60 (3H, m), 3.6-3.4 (4H, m), 2.04 (1H, m), 2.0-1.7 (3H, m).

MS (ESI): m/z 413 (M+H).

Example-15

Synthesis of (S)-(5-(2-(2,5-difluorophenyl)pyrrolidin-1-yl)pyrazolo[1,5a]pyridin-3-yl) (3-hydroxyazetidine-1-yl)methanone

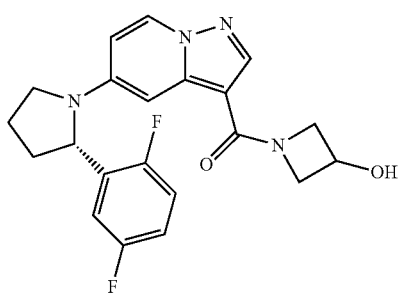 [SMILES: O=C(c1cnn2ccc(N3CCC[C@H]3c3cc(F)ccc3F)cc12)N1CC(O)C1]

The title compound was prepared by the method substantially similar to that mentioned in Example-14, using 3-Hydroxy azetidine hydrochloride in place of (S)-3-Pyrrolidinol to afford the crude product. The crude product obtained was purified by Preparative HPLC [Column: 21.2×150×5 um, Zorbax, XDB,C-18(#26), Mobile phase-A: 0.1% TFA in water, B:ACN, Gradient (Time/% B): 0/30, 2/40, 10/70 and Flow rate:20 mL/min] to afford 60 mg of the title compound as off white solid.

$^1$H NMR (400 MHz, DMSO-$d_6$) δ ppm 8.46 (1H, d, J=8 Hz), 8.02 (1H, s), 7.38-7.3 (1H, m), 7.2-7.18 (1H, m), 6.95 (1H, s), 6.90-6.84 (1H, m), 6.41 (1H, d), 5.71 (1H, d, J=6.4 Hz), 5.1 (1H, d, J=8.4 Hz), 4.52-4.20 (2H, m), 4.05-3.80 (2H, m), 3.5-3.4 (1H, m), 2.5-2.4 (1H, m), 2.1-2.0 (1H, m), 2.1-1.85 (2H, m).

MS (ESI): m/z 399.1 (M+H).

Example-16

Synthesis of (5-((R)-2-(2,5-difluorophenyl)pyrrolidin-1-yl)pyrazolo[1,5a]pyridin-3-yl)(Hexahydro-1H-pyrido[1,2-a]pyrazin-2 (6H)-yl)methanone

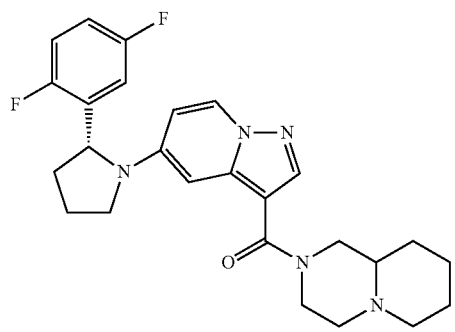 [SMILES: O=C(c1cnn2ccc(N3CCC[C@@H]3c3cc(F)ccc3F)cc12)N1CCN2CCCCC2C1]

DIPEA (71 mg, 00.1 mL, 0.55 mmol) was added to a stirred solution of (R)-5-(2-(2,5-difluorophenyl)pyrrolidin-1-yl) pyrazolo[1,5-a]pyridine-3-carboxylic acid (75 mg, 0.22 mmol) in DMF (1.5 mL) followed by addition of EDCl (63 mg, 0.33 mmol) and HOBt (32 mg, 0.24 mmol). After 10 minutes of stirring the reaction mixture, octahydro-1H-pyrido[1,2-a]pyrazine (46 mg, 0.33 mmol) was added and the resulting mixture was stirred for 16 h at 20-35° C. The reaction mixture was diluted with cold water and extracted with ethyl acetate. The ethyl acetate layer was washed with water and brine solution. The ethyl acetate portion was dried over anhydrous sodium sulfate and concentrated under reduced pressure to afford the crude compound, which was refluxed in hexane, filtered, and the filtrate was concentrated under reduced pressure to afford 45 mg of the title compound as a yellow solid.

MS (ESI): m/z 466.3 (M+H)

Example-17

Synthesis of (R)-(5-(2-(2,5-difluorophenyl)pyrrolidin-1-yl)pyrazolo[1,5-a]pyridin-3-yl)(5,6-dihydroimidazo[1,2-a]pyrazin-7(8H)-yl)methanone

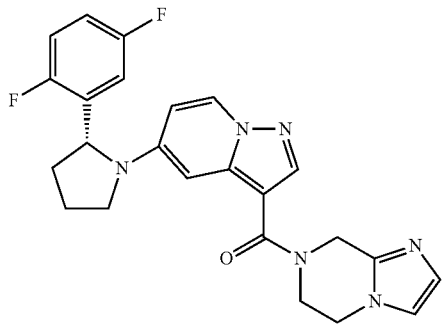 [SMILES: O=C(c1cnn2ccc(N3CCC[C@@H]3c3cc(F)ccc3F)cc12)N1CCn2ccnc2C1]

The title compound was prepared by a method substantially similar to that mentioned in Example-16, using 5,6,7,8-tetrahydroimidazo[1,2-a]pyrazine in place of octahydro-1H-pyrido[1,2-a]pyrazine to afford the crude compound, which was purified by recrystallisation (DCM: Hexane) to afford 40 mg of the title compound as a yellow solid.

$^1$H NMR (300 MHz, CDCl$_3$) δ ppm 8.16 (1H, d, J=7.8 Hz), 7.98 (1H, s), 7.1-7.0 (2H, m), 7.0-6.8 (3H, m), 6.74-6.64 (1H, m), 6.22-6.18 (1H, m), 5.13 (1H, d, J=8.4 Hz), 5.05 (2H, s), 4.2-4.15 (4H, m), 3.8-3.7 (1H, m), 3.6-3.45 (1H, m), 2.55-2.4 (1H, m), 2.15-2.0 (3H, m).

MS (ESI): m/z 449.2 (M+H)

Example-18

Synthesis of (R)-ethyl 7-(5-(2-(2,5-difluorophenyl) pyrrolidin-1-yl)pyrazolo[1,5-a]pyridine-3-carbonyl)-5,6,7,8-tetrahydroimidazo[1,2-a]pyrazine-2-carboxylate

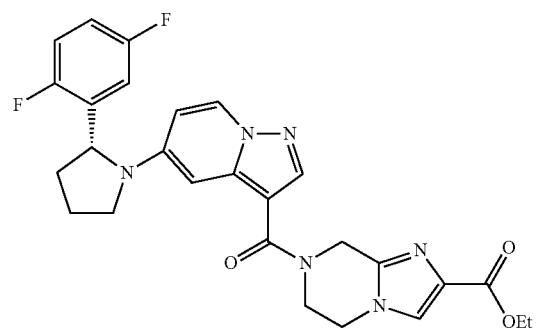 [SMILES: CCOC(=O)c1cn2c(n1)CN(C(=O)c1cnn3ccc(N4CCC[C@@H]4c4cc(F)ccc4F)cc13)CC2]

Step-1

Synthesis of ethyl imidazo[1,2-a]pyrazine-2-carboxylate

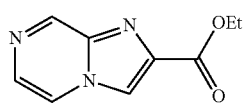 [SMILES: CCOC(=O)c1cn2ccncc2n1]

Ethyl bromopyruvate (2.153 g, 11.04 mmol) was added to a solution of 3-aminopyrazine (1 g, 10.51 mmol) in DME (10 mL) and the mixture was stirred continuously at 20-35° C. for 2 h. The reaction mixture was filtered and the solid which precipitated out was dried well, dissolved in EtOH (10 mL) and stirred under reflux for 2 h. This reaction mixture was then concentrated under reduced pressure to obtain a crude residue. The residue was diluted with aqueous sodium bicarbonate solution, and extracted with chloroform. The organic layer separated was washed with water and then with brine solution; dried over anhydrous sodium sulphate and concentrated under reduced pressure to afford the crude product. The crude product was further purified by column chromatography (using Silica gel 60-120 mesh and 60% EtOAc in Hexane as eluent) to afford 450 mg of the title compound the as a yellow solid.

MS (ESI): m/z 192 (M+H).

Step-2

Synthesis of ethyl 5,6,7,8-tetrahydroimidazo[1,2-a]pyrazine-2-carboxylate hydrochloride

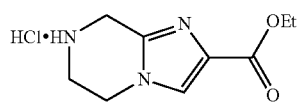

10% Pd/C (40 mg) was added to a solution of ethyl imidazo[1,2-a]pyrazine-2-carboxylate (410 mg, 2.15 mmol) and conc.HCl (0.5 mL) in EtOH (9.5 mL) and stirring was continued under a hydrogen atmosphere for 16 h. The reaction mixture was filtered over a celite bed and the filtrate was concentrated under reduced pressure to afford the crude product, which was purified by washing with diethyl ether and dried to afford 400 mg of the title compound as a yellow hygroscopic solid.

MS (ESI): m/z 196 (M+H)

Step-3

Synthesis of (R)-ethyl 7-(5-(2-(2,5-difluorophenyl)pyrrolidin-1-yl)pyrazolo[1,5-a]pyridine-3-carbonyl)-5,6,7,8-tetrahydroimidazo[1,2-a]pyrazine-2-carboxylate

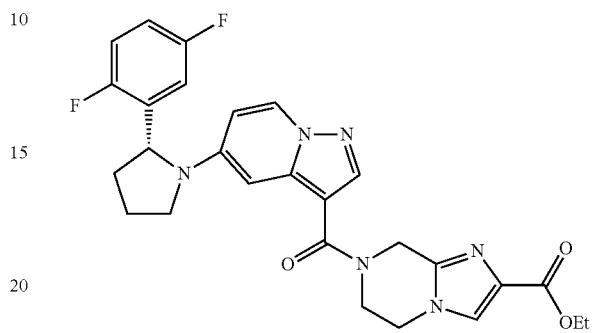

The title compound was prepared by a method substantially similar to that mentioned in Example-16, using ethyl 5,6,7,8-tetrahydroimidazo[1,2-a]pyrazine-2-carboxylate hydrochloride in place of octahydro-1H-pyrido[1,2-a]pyrazine to afford the crude compound. The crude compound thus obtained was purified by Preparative HPLC [Column: 21.2× 150×5 um, Zorbax, XDB,C-18(#26), Mobile phase-A: 0.01% TFA in water, B:ACN, Gradient (Time/% B): 0/40, 2/50, 10/90 and Flow rate:20 mL/min] to afford 18 mg of the title compound as an off-white solid.

$^1$H NMR (300 MHz, CDCl$_3$) δ ppm 8.10 (1H, d, J=7.2 Hz), 7.9 (1H, s), 7.53 (1H s), 7.05-6.95 (1H, m), 6.95-6.70 (2H, m), 6.65-6.55 (1H, m), 6.14 (1H, d, J=6.0 Hz), 5.1-5.0 (3H, m), 4.3-4.25 (2H, q), 4.2-4.0 (4H, m), 3.7 (1H, m), 3.55-3.40 (1H, m), 2.5-2.3 (1H, m), 2.1-1.9 (3H, m), 1.4-1.28 (3H, t).

MS (ESI): m/z 521.2 (M+H).

Example-19

Synthesis of (5-((R)-2-(2,5-difluorophenyl)pyrrolidin-1-yl)pyrazolo[1,5-a]pyridin-3-yl)(Hexahydropyrrolo[1,2-a]pyrazin-2 (1H)-yl)methanone

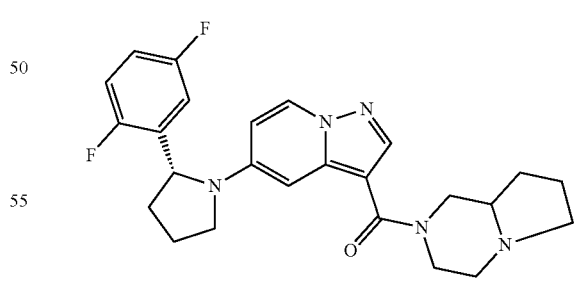

The title compound was prepared by a method substantially similar to that mentioned in Example-16, using Octahydropyrrolo[1,2-a]pyrazine in place of octahydro-1H-pyrido[1,2-a]pyrazine to afford the crude product. The crude product was purified by recrystallization from a mixture of DCM and Hexane to afford 35 mg of the title compound as a yellow solid.

MS (ESI): m/z 452.2 (M+H).

Example-20

Synthesis of (5-((R)-2-(2,5-difluorophenyl)pyrrolidin-1-yl)pyrazolo[1,5-a]pyridin-3-yl)(5-methyl-hexahydropyrrolo[3,4-c]pyrrol-2 (1H)-yl)methanone

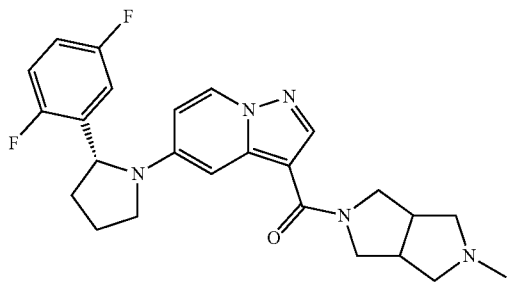 [SMILES: CN1CC2CN(C(=O)c3cnn4ccc(N5CCC[C@@H]5c5cc(F)ccc5F)cc34)CC2C1]

The title compound was prepared by a similar method to that mentioned in Example-4 to afford the crude product. The crude product thus obtained was purified by Preparative HPLC [Column: 21.2×250×7 um, Zorbax, XDB,C-18, Mobile phase-A: 0.01% TFA in water, B:ACN, Gradient (Time/% B): 0/30, 2/40, 10/80 and Flow rate:20 mL/min] 65 mg of the title compound.

$^1$H NMR (400 MHz, CD$_3$OD) δ ppm 8.30 (1H, d, J=7.6 Hz), 8.13 (1H, s), 7.2-7.18 (1H m), 7.04-6.98 (2H, m), 6.8-6.72 (1H, m), 6.58-6.50 (1H, m), 5.19 (1H, d, J=8.0 Hz), 4.1-3.7 (6H, m), 3.65-3.53 (2H, m), 3.45-3.30 (2H, m), 3.25-3.10 (1H, m), 3.0-2.9 (4H, m), 2.55-2.45 (1H, m), 2.25-1.95 (3H, m).

MS (ESI): m/z 452.3 (M+H).

Example-21

Synthesis of (R)-(5-(2-(2,5-difluorophenyl)pyrrolidin-1-yl)pyrazolo[1,5-a]pyridin-3-yl)(3-(trifluoromethyl)-5,6-dihydro-[1,2,4]triazolo[4,3-a]pyrazin-7(8H)-yl)methanone

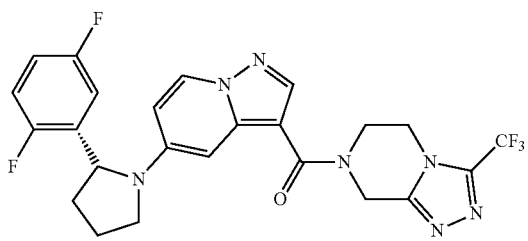

The title compound was prepared by a method substantially similar to that mentioned in Example-4, using 3-(trifluoromethyl)-5,6,7,8-tetrahydro-[1,2,4]triazolo[4,3-a]pyrazine hydrochloride in place of (S)-3-Pyrrolidinol to afford the crude product, which was purified by Preparative HPLC [Column: AG/PP/C18/15-028, Mobile phase-A: Water, B: ACN, Gradient (Time/% B): 0/40, 2/50, 10/80 and Flow rate:20 mL/min] to afford 20 mg of the title compound as a yellow solid.

$^1$H NMR (300 MHz, CD$_3$OD) δ ppm 8.33 (1H, d, J=6.9 Hz), 8.15 (1H, s), 7.22-7.14 (1H m), 7.05-6.95 (1H, m), 6.85-6.73 (2H, m), 6.54 (1H, d, J=7.8 Hz), 5.2 (1H, d, J=8.4 Hz), 5.14 (2H, s), 4.4 (2H, t), 4.22-4.18 (2H, m), 3.9-3.8 (1H, m), 3.62-3.52 (1H, m), 2.56-2.51 (1H, m), 2.2-2.0 (3H, m).

MS (ESI): m/z 518.2 (M+H)

Example-22

Synthesis of 5-((R)-2-(2,5-difluorophenyl)pyrrolidin-1-yl)-N—((S)-2,3-dihydroxypropyl) pyrazolo[1,5a]pyridine-3-carboxamide

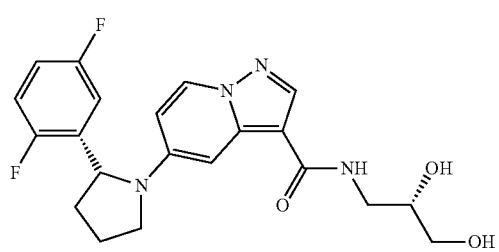

The title compound was prepared by a similar method to that mentioned in Example-6 to afford the crude product, which was purified by Preparative TLC (Silicagel GF$_{254}$, 1000 u, 20×20 cm dimension glass plate and 5% MeOH in DCM as eluent) to afford 30 mg of the title compound as an off white solid.

$^1$H NMR (400 MHz, CD$_3$OD) δ ppm 8.3-8.2 (2H, m), 7.22-7.14 (1H m), 7.08-6.96 (2H, m), 6.84-6.74 (1H, m), 6.44 (1H, d, J=7.6 Hz), 5.19 (1H, d, J=8.0 Hz), 3.9-3.7 (2H, m), 3.60-3.48 (4H, m), 3.4-3.3 (1H, m), 2.6-2.45 (1H, m), 2.2-2.0 (3H, m).

MS (ESI): m/z 417.2 (M+H).

Example-23

Synthesis of (R)-(5-(2-(2,5-difluorophenyl)pyrrolidin-1-yl)pyrazolo[1,5a]pyridin-3-yl) (3-hydroxy-3-methylazetidin-1-yl)methanone

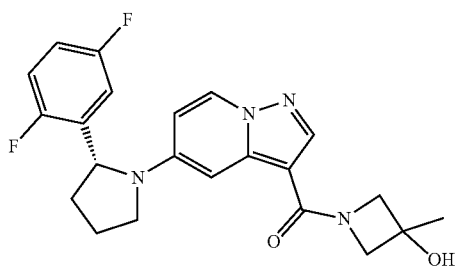 [SMILES: CC1(O)CN(C(=O)c2cnn3ccc(N4CCC[C@@H]4c4cc(F)ccc4F)cc23)C1]

Step-1

Synthesis of tert-butyl 3-hydroxyazetidine-1-carboxylate

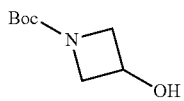

Cold aqueous NaOH (3.65 g, 91.25 mmol in 25 mL of water) was added to cold (0° C.) solution of azetidin-3-ol hydrochloride (4 g, 36.5 mmol) in water (15 mL) followed by addition of di-tert-butyl dicarbonate (8.4 mL, 38.33 mmol). The reaction mixture was stirred continuously at 20-35° C. for 12-14 h. The reaction mixture was diluted with ethyl acetate; the organic layer was separated, washed with water followed by brine solution, dried over anhydrous sodium sulphate and concentrated under reduce pressure to afford the crude compound, which was purified by column chromatography (using 60-120 silica gel and 30% EtOAc in Hexane as eluent) to afford 3.5 g of the title compound.

$^1$H NMR (400 MHz, DMSO) δ ppm 5.6 (1H, s), 4.4 (1H, bs), 4.0 (2H, t), 3.6-3.5 (2H, m), 1.4 (9H, s).

Step-2

Synthesis of tert-butyl 3-oxoazetidine-1-carboxylate

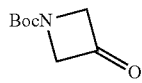

PCC (4.94 g, 22.8 mmol) was added portion wise to a stirred solution of tert-butyl-3-hydroxyazetidine-1-carboxylate (3.3 g, 19 mmol) in DCM (50 mL) at 20-35° C. and the reaction mixture was stirred continuously at the same temperature for 12-16 h. The reaction mixture was filtered and the filtrate was washed with water, dried over anhydrous sodium sulphate and concentrated under reduced pressure to afford the crude product, which was purified by column chromatography (using 60-120 silica gel and 10% EtOAc in Hexane as eluent) to afford 650 mg of the title compound.

$^1$H NMR (400 MHz, DMSO) δ ppm 4.66 (4H, s), 1.4 (9H, s).

Step-3

Synthesis of tert-butyl 3-hydroxy-3-methylazetidine-1-carboxylate

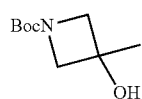

Methyl magnesium bromide (3.0M in Diethyl ether) (1.5 mL, 4.5 mmol) was added to cold (−10° C.) solution of tert-butyl 3-oxoazetidine-1-carboxylate (650 mg, 3.8 mmol) in THF (10 mL) and stirring was continued at 20-35° C. for 1 h. After which the reaction mixture was quenched with saturated aqueous NH$_4$Cl solution and extracted with ethylacetate. The organic layer separated was washed with water, dried over anhydrous sodium sulphate and concentrated under reduced pressure to afford the residue. The residue was purified by column chromatography (using 60-120 silica gel and 50% EtOAc in Hexane as eluent) to afford 430 mg of the title compound.

$^1$H NMR (400 MHz, DMSO) δ ppm 5.56 (1H, s), 3.7-3.5 (4H, m), 1.4 (9H, s), 1.3 (3H, s).

Step-4

Synthesis of 3-methylazetidin-3-ol hydrochloride

4M solution of HCl in EtOAc (3 mL) was added dropwise to a stirred cold (0° C.) solution of tert-butyl 3-hydroxy-3-methylazetidine-1-carboxylate (100 mg, 0.53 mmol) in EtOAc (1 mL) and stirring was continued at 20-35° C. for 2 h. The reaction mixture was concentrated under reduced pressure to afford 80 mg (crude), which was taken to the next step without purification.

Step-5

Synthesis of (R)-(5-(2-(2,5-difluorophenyl)pyrrolidin-1-yl)pyrazolo[1,5-a]pyridin-3-yl)(3-hydroxy-3-methylazetidin-1-yl)methanone

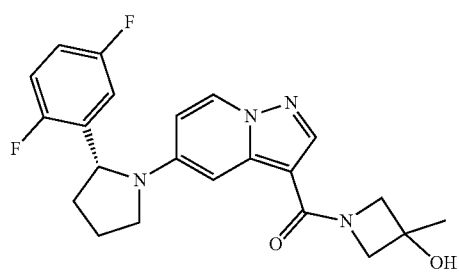 [SMILES: CC1(O)CN(C(=O)c2cnn3ccc(N4CCC[C@@H]4c4cc(F)ccc4F)cc23)C1]

The title compound was prepared by a method substantially similar to that mentioned in Example-6, using 3-methylazetidin-3-ol hydrochloride in place of NH$_4$Cl along with HOBt (49 mg, 0.29 mmol) to afford the crude product, which was purified by Preparative TLC (Silicagel GF$_{254}$, 1000 u, 20×20 cm dimension glass plate and 10% MeOH in DCM as eluent) to afford 37 mg of the title compound as a white solid.

$^1$H NMR (300 MHz, CD$_3$OD) δ ppm 8.30 (1H, d, J=7.5 Hz), 8.02 (1H, s), 7.22-7.14 (1H, m), 7.08 (1H, d, J=2.4 Hz), 7.05-6.98 (1H, m), 6.84-6.78 (1H, m), 6.53 (1H, dd, J=2.7, 7.8 Hz), 5.2 (1H, d, J=7.8 Hz), 4.4-3.95 (4H, m), 3.87 (1H, t), 3.62-3.52 (1H, m), 2.61-2.45 (1H, m), 2.2-2.0 (3H, m), 1.5 (3H, s).

MS (ESI): m/z 413.1 (M+H).

Example-24

Synthesis of 5-((R)-2-(2,5-difluorophenyl)pyrrolidin-1-yl)-N—((S)-1-phenyl-2-(pyrrolidin-1-yl)ethyl)pyrazolo[1,5a]pyridine-3-carboxamide

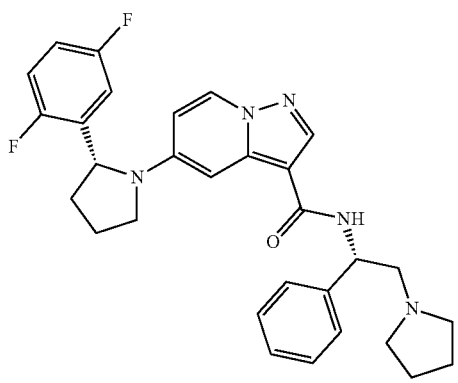 [SMILES: O=C(N[C@H](CN1CCCC1)c1ccccc1)c1cnn2ccc(N3CCC[C@@H]3c3cc(F)ccc3F)cc12]

The title compound was prepared by a method substantially similar to that mentioned in Example-23, using (S)-1-phenyl-2-(pyrrolidin-1-yl)ethanamine in place of 3-methylazetidin-3-ol hydrochloride to afford 33 mg of the title compound.

$^1$H NMR (300 MHz, CDCl$_3$) δ ppm 8.15-8.05 (2H, m), 7.4-7.1 (5H, m), 7.22-7.14 (1H, m), 7.1-6.7 (3H, m), 6.7-6.55 (1H, m), 6.15-6.05 (1H, m), 5.15-5.0 (2H, m), 3.8-3.6 (1H, m), 3.55-3.4 (1H, m), 3.1-2.9 (1H, m), 2.8-2.3 (5H, m), 2.15-1.9 (2H, m), 1.9-1.7 (6H, m), MS (ESI): m/z 516.3 (M+H).

Example-25

(5-((R)-2-(2,5-difluorophenyl)pyrrolidin-1-yl)pyrazolo[1,5a]pyridin-3-yl)(3-(hydroxymethyl)pyrrolidin-1-yl)methanone

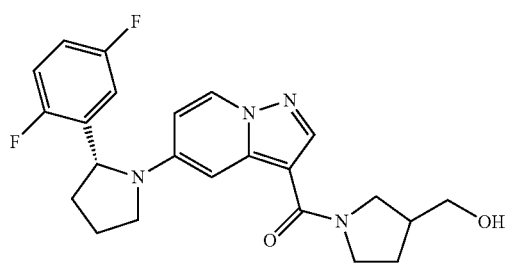 [SMILES: O=C(c1cnn2ccc(N3CCC[C@@H]3c3cc(F)ccc3F)cc12)N1CCC(CO)C1]

The title compound was prepared by a method substantially similar to that mentioned in Example-23, using pyrrolidin-3-ylmethanol in place of 3-methylazetidin-3-ol hydrochloride, to afford the crude product, which was purified by recrystallisation from MeOH to afford 52 mg of the title compound as a white solid.

MS (ESI): m/z 427.2 (M+H).

Example-26

Synthesis of 5-((R)-2-(2,5-difluorophenyl)pyrrolidin-1-yl)-N-((1r,4R)-4-hydroxycyclohexyl)pyrazolo[1,5a]pyridine-3-carboxamide

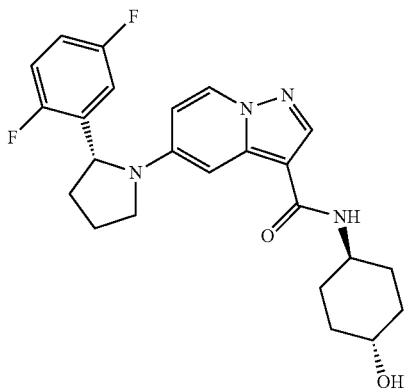 [SMILES: O=C(N[C@H]1CC[C@H](O)CC1)c1cnn2ccc(N3CCC[C@@H]3c3cc(F)ccc3F)cc12]

The title compound was prepared by a method substantially similar to that mentioned in Example-23, using trans-4-aminocyclohexanol in place of 3-methylazetidin-3-ol hydrochloride to afford the crude product, which was purified by Preparative TLC (Silicagel GF$_{254}$, 1000 u, 20×20 cm dimension glass plate and 5% MeOH in EtOAc as eluent) to afford 23 mg of the title compound as a brown solid.

$^1$H NMR (400 MHz, CDCl$_3$) δ ppm 8.13 (1H, d, J=7.6 Hz), 7.9 (1H, s), 7.18 (1H, d, J=2.0 Hz), 7.1-7.0 (1H, m), 6.94-6.89 (1H, m), 6.7-6.65 (1H, m), 6.17 (1H, dd, J=2.4, 7.6 Hz), 5.47 (1H, d, J=8 Hz), 5.13 (1H, d, J=8 Hz), 3.99-3.95 (1H, m), 3.80 (1H, t, J=8.4 Hz), 3.7-3.6 (1H, m), 3.6-3.5 (1H, m), 2.5-2.4 (1H, m), 2.11-2.07 (2H, m), 2.06-1.9 (3H, m), 1.55-1.4 (3H, m), 1.4-1.27 (3H, m).

MS (ESI): m/z 441.2 (M+H).

Example-27

Synthesis of (R)-5-(2-(2,5-difluorophenyl)pyrrolidin-1-yl)-N-(piperidin-1-yl)pyrazolo[1,5a]pyridine-3-carboxamide

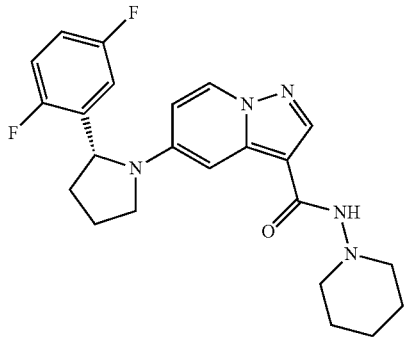

A method substantially similar to that mentioned in Example-16 was employed using 1-aminopiperidine in place of Octahydropyrrolo[1,2-a]pyrazine to afford a crude product, which was purified by Preparative HPLC [Column: 21.2× 150×5 um, Zorbax, XDB,C-18(#26), Mobile phase-A: 0.1% TFA in water, B:ACN, Gradient (Time/% B): 0/30, 2/40, 10/70 and Flow rate:20 mL/min] to afford 50 mg of the title compound.

¹H NMR (400 MHz, DMSO-d₆) δ ppm 8.75 (1H, bs), 8.42 (1H, d, J=8.0 Hz), 8.59 (1H, bs), 7.35-7.29 (1H, m), 7.2-7.1 (1H, m), 7.0-6.8 (2H, m), 6.4 (1H, d, J=6.4 Hz), 5.12 (1H, d, J=8 Hz), 3.86 (1H, t, J=8.8 Hz), 3.5-3.4 (1H, m), 3.0-2.7 (3H, m), 2.5-2.4 (1H, m), 2.1-2.0 (1H, m), 2.0-1.85 (3H, m), 1.7-1.5 (5H, m), 1.4-1.3 (1H, bs).

MS (ESI): m/z 426.2 (M+H).

Example-28

Synthesis of (R)-5-(2-(2,5-difluorophenyl)pyrrolidin-1-yl)-N-(1,3-dihydroxy-2-methylpropan-2-yl)pyrazolo[1,5a]pyridine-3-carboxamide

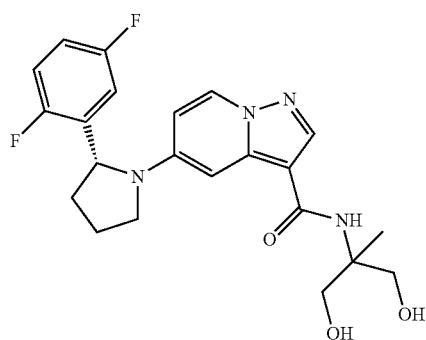 [SMILES: CC(CO)(CO)NC(=O)c1cnn2ccc(N3CCC[C@@H]3c3cc(F)ccc3F)cc12]

The title compound was prepared by the method substantially similar to that mentioned in Example-6, using 2-amino-2-methylpropane-1,3-diol to afford the crude solid, which was purified by Preparative TLC(Silicagel GF₂₅₄, 1000 u, 20×20 cm dimension glass plate and 5% MeOH in DCM as eluent) to afford 14 mg of the title compound as a white solid.

¹H NMR (400 MHz, DMSO-d₆) δ ppm 8.4 (1H, d, J=8 Hz), 8.33 (1H, s), 7.35-7.29 (1H, m), 7.18-7.13 (1H, m), 6.94 (1H, s), 6.9-6.8 (2H, m), 6.33 (1H, d, J=7.6 Hz), 5.15 (1H, d, J=8 Hz), 5.0 (2H, t), 3.89-3.80 (1H, m), 3.62-3.38 (5H, m), 2.46-2.4 (1H, m), 2.1-2.0 (1H, m), 2.0-1.85 (2H, m), 1.2 (3H, s).

MS (ESI): m/z 431.1 (M+H).

Example-29

Synthesis of (R)-5-(2-(2,5-difluorophenyl)pyrrolidin-1-yl)-N-(2-hydroxyethyl)pyrazolo[1,5a]pyridine-3-carboxamide

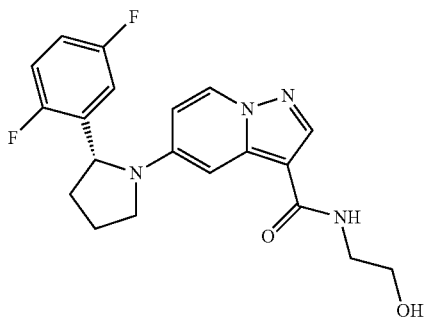 [SMILES: O=C(NCCO)c1cnn2ccc(N3CCC[C@@H]3c3cc(F)ccc3F)cc12]

The title compound was prepared by the method substantially similar to that mentioned in Example-6, using 2-aminoethanol to afford the crude product, which was purified by Preparative TLC(Silicagel GF₂₅₄, 1000 u, 20×20 cm dimension glass plate and 5% MeOH in DCM as eluent) to afford 20 mg of the title compound as an off white solid.

¹H NMR (400 MHz, DMSO-d₆) δ ppm 8.39 (1H, d, J=7.6), 8.28 (1H, s), 7.86-7.8 (1H, t), 7.36-7.26 (1H, m), 7.16-7.08 (1H, m), 6.94 (1H, s), 6.88-6.8 (1H, m), 6.36 (1H, d), 5.13 (1H, d, J=7.6 Hz), 4.7 (1H, t), 3.85 (1H, t), 3.5-3.35 (3H, m), 3.3-3.2 (2H, m), 2.5-2.4 (1H, m), 2.1-1.8 (3H, m).

MS (ESI): m/z 387.1 (M+H).

Example-30

Synthesis of Ethyl 1-(5-((R)-2-(2,5-difluorophenyl)pyrrolidin-1-yl)pyrazolo[1,5a]pyridine-3-carbonyl)pyrrolidine-3-carboxylate

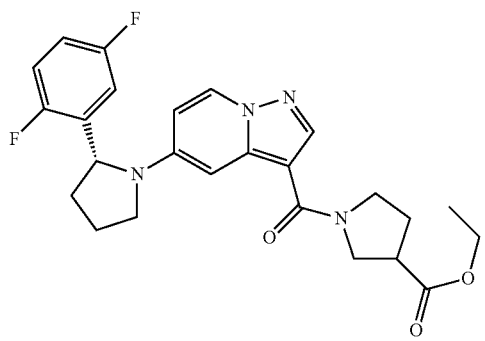 [SMILES: CCOC(=O)C1CCN(C(=O)c2cnn3ccc(N4CCC[C@@H]4c4cc(F)ccc4F)cc23)C1]

Step-1

Synthesis of ethyl pyrrolidine-3-carboxylate

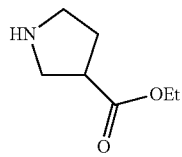

Thionyl chloride (5 mL) was added to a cold (0° C.) stirred solution of pyrrolidine-3-carboxylicacid (500 mg, 4.34 mmol) in EtOH (25 mL) and continued stirring at 80° C. for 12-16 h. The reaction mixture was concentrated under reduced pressure to afford 600 mg (crude) of ethyl pyrrolidine-3-carboxylate, which was used as such in the next step without purification.

MS (ESI): m/z 144 (M+H).

Step-2

Synthesis of Ethyl 1-(5-((R)-2-(2,5-difluorophenyl)pyrrolidin-1-yl)pyrazolo[1,5a]pyridine-3-carbonyl)pyrrolidine-3-carboxylate

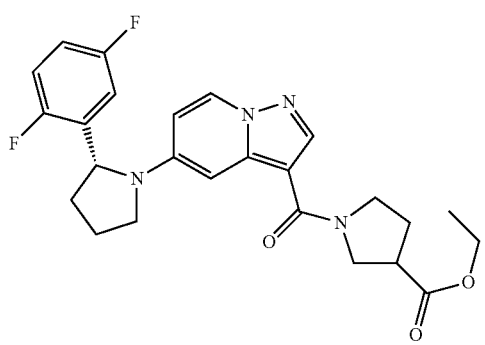 [SMILES: CCOC(=O)C1CCN(C(=O)c2cnn3ccc(N4CCC[C@@H]4c4cc(F)ccc4F)cc23)C1]

The title compound was prepared by a method substantially similar to that mentioned in Example-23, using ethyl pyrrolidine-3-carboxylate in place of 3-Azetidinol hydrochloride to afford the crude product, which was purified by Preparative TLC (Silicagel GF$_{254}$, 1000 u, 20×20 cm dimension glass plate and 100% EtOAc as eluent) to afford 56 mg of the title compound as a white solid.

MS (ESI): m/z 469.2 (M+H).

Example-31

1-(5-((R)-2-(2,5-difluorophenyl)pyrrolidin-1-yl)pyrazolo[1,5a]pyridine-3-carbonyl)pyrrolidine-3-carboxylic acid

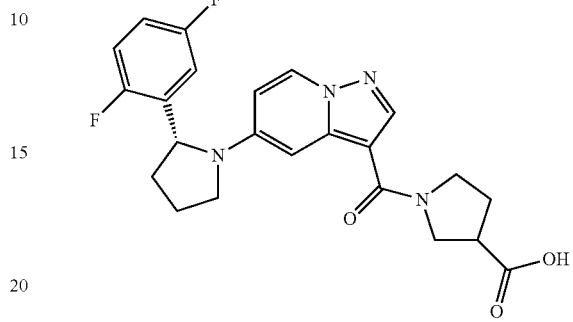

LiOH.H$_2$O (14 mg, 0.32 mmol) in water (0.5 mL) was added to a stirred solution of ethyl 1-(5-((R)-2-(2,5-difluorophenyl)pyrrolidin-1-yl)pyrazolo[1,5-a]pyridine-3-carbonyl)pyrrolidine-3-carboxylate (50 mg, 0.1 mmol) in THF (3 mL) and MeOH (1 mL) at 20-35° C. and the mixture was stirred for 1 h. The reaction mixture was concentrated under reduced pressure to afford the crude product. The crude product thus obtained was diluted with cold water, acidified with 2N aqueous HCl solution and filtered. The solid residue obtained was washed with water followed by Hexane to afford 40 mg of the title compound as a white solid.

MS (ESI): m/z 441.1 (M+H).

Example-32

Synthesis of (R)-5-(2-(2,5-difluorophenyl)pyrrolidin-1-yl)-N-(piperidin-4-yl)pyrazolo[1,5a]pyridine-3-carboxamide

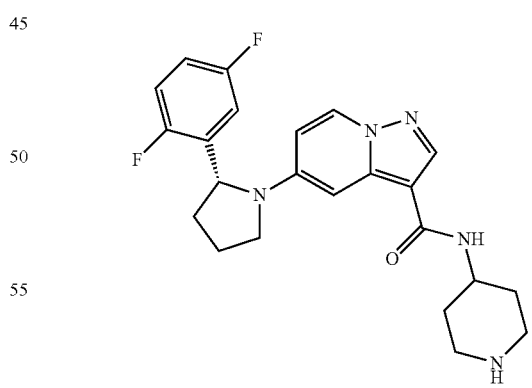

(R)-tert-butyl-4-(5-(2-(2,5-difluorophenyl)pyrrolidin-1-yl)pyrazolo[1,5-a]pyridine-3-carboxamido) piperidine-1-carboxylate (39 mg, 0.2 mmol) was prepared by a method substantially similar to that mentioned in Example-23 (using tert-butyl 4-aminopiperidine-1-carboxylate in place of 3-Azetidinol hydrochloride). Trifluoroacetic acid (156 mg, 1.4 mmol) was added to a cold (0° C.) stirred solution of (R)-tert-butyl 4-(5-2-2,5-difluorophenyl)pyrrolidin-1-yl)pyrazolo[1,5-a]pyridine-3-carboxamido)piperidine-1-carboxylate (39 mg, 0.2 mmol) in DCM (1.2 mL). The mixture was stirred continuously at 20-35° C. for 4 h. The reaction mixture was concentrated under reduced pressure to afford a residue. The residue obtained was diluted with DCM, washed with aqueous saturated sodium bicarbonate solution, dried over sodium sulfate and concentrated under reduced pressure to obtain a crude product, which was purified by dissolving in DCM and reprecipitated with n-Hexane. The precipitate was filtered off and dried to afford 39 mg of the title compound as a brown solid. $^1$H NMR (300 MHz, CD$_3$OD) δ ppm 8.3 (2H, m), 7.22-7.1 (1H, m), 7.1-6.95 (2H, m), 6.85-6.75 (1H, m), 6.5 (1H, d, J=7.8 Hz), 5.2 (1H, d, J=7.8 Hz), 4.1-3.8 (2H, m), 3.6-3.5 (1H, m), 3.2 (2H, d, J=11.7 Hz), 2.9 (2H, t, J=12.6 Hz), 2.5-2.45 (1H, m), 2.2-1.9 (5H, m), 1.7-1.5 (2H, m).

MS (ESI): m/z 426.1 (M+H).

Example-33

Synthesis of 5-((R)-2-(2,5-difluorophenyl)pyrrolidin-1-yl)-N-(piperidin-3-yl)pyrazolo[1,5a]pyridine-3-carboxamide

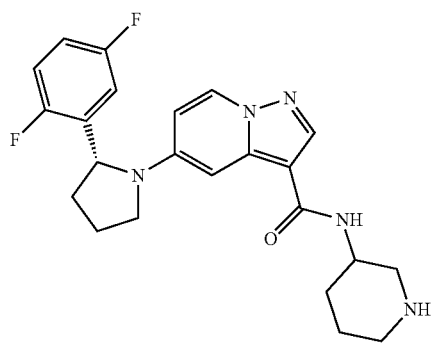 [SMILES: O=C(NC1CCCNC1)c1cnn2ccc(N3CCC[C@@H]3c3cc(F)ccc3F)cc12]

A method substantially similar to that mentioned in Example-32 was employed using tert-butyl 3-aminopiperidine-1-carboxylate to afford 21 mg of the title compound as a brown solid.

MS (ESI): 426.2 (M+H).

Example-34

Synthesis of 5-((R)-2-(2,5-difluorophenyl)pyrrolidin-1-yl)-N—((S)-2-((S)-3-hydroxypyrrolidin-1-yl)-1-phenylethyl)pyrazolo[1,5a]pyridine-3-carboxamide

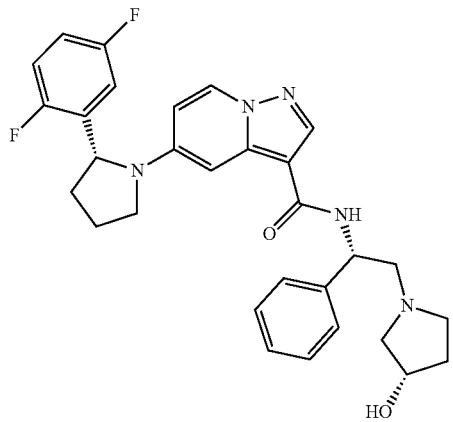 [SMILES: O=C(N[C@H](CN1CC[C@H](O)C1)c1ccccc1)c1cnn2ccc(N3CCC[C@@H]3c3cc(F)ccc3F)cc12]

A method substantially similar to that mentioned in Example-23, was employed using (S)-1-((S)-2-amino-2-phenylethyl)pyrrolidin-3-ol in place of 3-azetidinol hydrochloride to afford a crude product, which was purified by Preparative [Column AG/PP/C18-15/028, Mobile phase-A: 0.1% TFA in water, B: ACN, Gradient (Time/% B): 0/30, 2/40, 10/90 and Flow rate: 20 mL/min] to obtain 25 mg of the title compound as a pale brown solid.

$^1$H NMR (300 MHz, CD$_3$OD) δ ppm 8.4 (1H, s), 8.29 (1H, d, J=7.8 Hz), 7.48-7.24 (4H, m), 7.22-7.18 (1H, m), 7.06-6.96 (2H, m), 6.82-6.74 (1H, m), 6.5-6.42 (1H, m), 5.4-5.3 (1H, m), 5.2 (1H, d, J=7.8 Hz), 4.45-4.35 (1H, m), 3.9-3.8 (1H, m), 3.6-3.5 (1H, m), 3.25-3.0 (3H, m), 3.0-2.7 (2H, m), 2.6-2.4 (1H, m), 2.3-1.9 (4H, m), 1.9-1.75 (1H, m).

MS (ESI): m/z 532.2 (M+H).

Example-35

Synthesis of (R)-Ethyl 2-(5-(2-(2,5-difluorophenyl)pyrrolidin-1-yl) pyrazolo[1,5a]pyridine-3-carboxamido) acetate

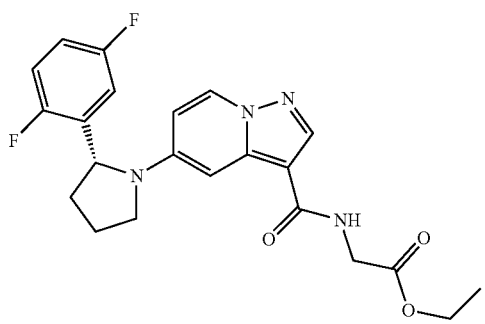 [SMILES: CCOC(=O)CNC(=O)c1cnn2ccc(N3CCC[C@@H]3c3cc(F)ccc3F)cc12]

A method substantially similar to that mentioned in Example-16 was employed using Glycine ethylester hydrochloride in place of Octahydropyrrolo[1,2-a]pyrazine to afford 75 mg of the title compound as a pale brown solid.

$^1$H NMR (300 MHz, CD$_3$OD) δ ppm 8.13 (1H, d, J=7.8 Hz), 8.04 (1H, s), 7.17-(1H, d, J=2.7 Hz), 7.1-7.0 (1H, m), 6.95-6.6.85 (1H, m), 6.71-6.66 (1H, m), 6.2-6.6.1 (2H, m), 5.14 (1H, d, J=7.8 Hz), 4.35-4.20 (4H, m), 3.85-3.75 (1H, m), 3.6-3.5 (1H, m), 2.50-2.40 (1H, m), 2.2-1.9 (3H, m), 1.31 (3H, t, J=7.2 Hz).

MS (ESI): m/z 429.1 (M+H).

Example-36

Synthesis of (R)-2-(5-(2-(2,5-difluorophenyl)pyrrolidin-1-yl)pyrazolo[1,5a]pyridine-3-carboxamido) acetic acid

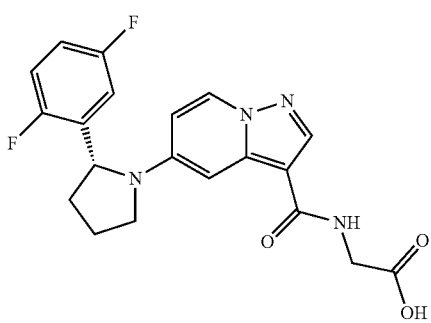 [SMILES: O=C(O)CNC(=O)c1cnn2ccc(N3CCC[C@@H]3c3cc(F)ccc3F)cc12]

A method substantially similar to that mentioned in Example-31 was used to afford 18 mg of the title compound.

$^1$H NMR (300 MHz, DMSO-d$_6$) δ ppm 12.6 (1H, bs), 8.44 (1H, d, J=7.5 Hz), 8.31 (1H, s), 8.25 (1H, t, J=6.0 Hz), 7.4-7.28 (1H, m), 7.2-7.1 (1H, m), 6.94 (1H, s), 6.9-6.8 (1H, m), 6.4 (1H, d, J=7.8 Hz), 5.15 (1H, d, J=7.8 Hz), 3.9-3.8 (3H, m), 3.5-3.35 (1H, m), 3.3-3.2 (1H, m), 2.5-2.4 (1H, m), 2.1-1.8 (3H, m).

MS (ESI): m/z 401.1 (M+H).

Example-37

Synthesis of 5-((R)-2-(2,5-difluorophenyl)pyrrolidin-1-yl)-N-(3-hydroxyadamantan-1-yl)pyrazolo[1,5a]pyridine-3-carboxamide

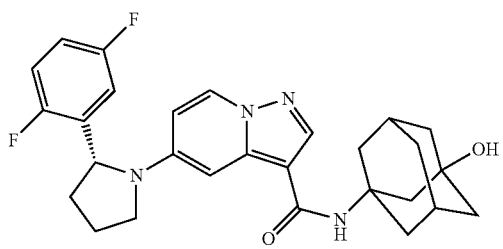 [SMILES: O=C(NC12CC3CC(CC(O)(C3)C1)C2)c1cnn2ccc(N3CCC[C@@H]3c3cc(F)ccc3F)cc12]

A method substantially similar to that mentioned in Example-6, was employed using 3-amino adamantanol to afford the crude compound, which was purified by Flash chromatography (Biotage, Column: Silicagel 12 g pack size, Mobile Phase: EtOAc in n-Hexane: 0 to 100% as eluent) to afford 25 mg of the title compound as a pale green solid.

MS (ESI): m/z 493.2 (M+H).

Example-38

Synthesis of (R)-(5-(2-(2,5-difluorophenyl)pyrrolidin-1-yl)pyrazolo[1,5-a]pyridin-3-yl) (piperazin-1-yl)methanone

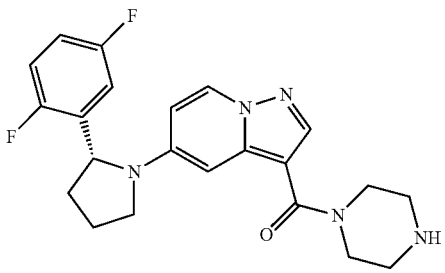 [SMILES: O=C(c1cnn2ccc(N3CCC[C@@H]3c3cc(F)ccc3F)cc12)N1CCNCC1]

A method substantially similar to that mentioned in Example-32 was employed using tert-butylpiperazine-1-carboxylate, to afford 50 mg of the title compound as a yellow solid.

$^1$H NMR (300 MHz, DMSO-d$_6$) δ ppm 8.45 (1H, d, J=7.5 Hz), 7.97 (1H, s), 7.4-7.3 (1H, m), 7.2-7.1 (1H, m), 6.95-6.8 (1H, m), 6.5-6.35 (2H, m), 5.12 (1H, d, J=7.8 Hz), 3.9 (1H, t), 3.5-3.4 (5H, m), 2.7-2.6 (4H, m), 2.5-2.4 (1H, m), 2.1-1.8 (3H, m).

MS (ESI): m/z 412.3 (M+H).

Example-39

Synthesis of 2,5-diazabicyclo[2.2.1]heptan-2-yl(5-((R)-2-(2,5-difluorophenyl)pyrrolidin-1-yl)pyrazolo[1,5-a]pyridin-3-yl)methanone

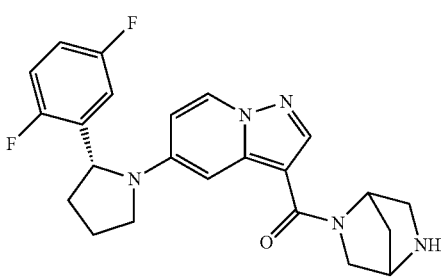 [SMILES: O=C(c1cnn2ccc(N3CCC[C@@H]3c3cc(F)ccc3F)cc12)N1CC2CC1CN2]

Step-1

Synthesis of tert-butyl 2,5-diazabicyclo[2.2.1]heptane-2-carboxylate

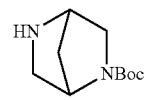

Di-tert-butyldicarbonate (0.38 g, 0.38 mL, 1.7 mmol) was added dropwise for 10 minutes to a cold (−30° C.) stirred solution of 2,5-diazabicyclo[2.2.1]heptanedihydrobromide (1 g, 3.8 mmol) and triethylamine (776 mg, 1.07 mL, 7.6 mmol) in MeOH (30 mL). The reaction mixture was stirred at 25° C. for 12-16 h. The reaction mixture was concentrated under reduced pressure; diluted with water and filtered. The filtrate was extracted with DCM; the organic layer was washed with brine, dried over anhydrous sodium sulphate and concentrated under reduced pressure to afford 200 mg of the title compound as a white solid.

MS (ESI): m/z 199.0 (M+H)

Step-2

Synthesis of tert-butyl 5-(5-((R)-2-(2,5-difluorophenyl)pyrrolidin-1-yl)pyrazolo[1,5a]pyridine-3-carbonyl)-2,5-diazabicyclo[2.2.1]heptane-2-carboxylate

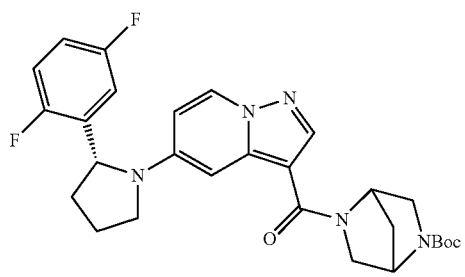 [SMILES: CC(C)(C)OC(=O)N1CC2CC1CN2C(=O)c1cnn2ccc(N3CCC[C@@H]3c3cc(F)ccc3F)cc12]

A method substantially similar to that mentioned in Example-16, was used to afford 40 mg of the title compound as a white solid. MS (ESI): m/z 524.2 (M+H).

Step-3

Synthesis of 2,5-diazabicyclo[2.2.1]heptan-2-yl(5-((R)-2-(2,5-difluorophenyl)pyrrolidin-1-yl)pyrazolo[1,5-a]pyridin-3-yl)methanone

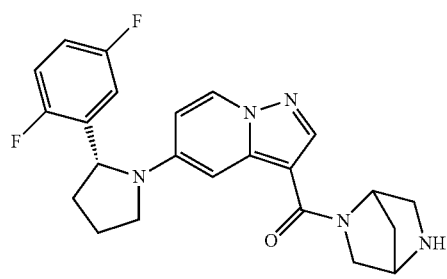 [SMILES: O=C(c1cnn2ccc(N3CCC[C@@H]3c3cc(F)ccc3F)cc12)N1CC2CC1CN2]

A method substantially similar to that mentioned in Example-32 was employed wherein 4N HCl in Dioxane was used in place of TFA, to afford 16 mg of the title compound as a brownish yellow solid.

¹H NMR (300 MHz, DMSO-d₆) δ ppm 8.42 (1H, d, J=7.5 Hz), 8.1 (1H, s), 7.4-7.25 (1H, m), 7.2-6.95 (2H, m), 6.9-6.8 (1H, m), 6.375 (1H, m), 5.10 (1H, d, J=7.5 Hz), 4.61 (1H, s), 4.0-3.4 (4H, m), 3.0-2.7 (2H, bs), 2.5-2.4 (1H, m), 2.1-1.5 (5H, m).

MS (ESI): m/z 424.2 (M+H).

Example-40

Synthesis of (R)-Methyl 4-(5-(2-(2,5-difluorophenyl)pyrrolidin-1-yl)pyrazolo[1,5a]pyridine-3-carboxamido)cyclohexanecarboxylate

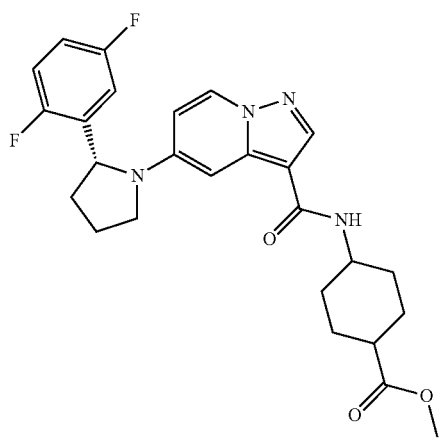 [SMILES: COC(=O)C1CCC(NC(=O)c2cnn3ccc(N4CCC[C@@H]4c4cc(F)ccc4F)cc23)CC1]

Step-1

Synthesis of Methyl 4-aminocyclohexanecarboxylate

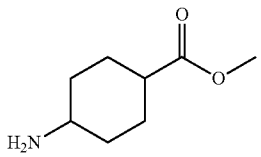

Thionyl chloride (4.15 g, 34.92) was added to a cold (0° C.) stirred solution of 4-aminocyclohexane carboxylic acid (1 g, 6.98 mmol) in MeOH (10 mL). The reaction mixture was stirred under reflux conditions for 12-16 h. The reaction mixture was then concentrated under reduced pressure. The residue obtained was diluted with ice cold water, basified with aqueous sodium bicarbonate solution and extracted with DCM. The DCM layer was washed with water followed by brine solution, dried over anhydrous sodium sulphate and concentrated under reduced pressure to afford 650 mg of the title compound as a brown liquid. MS (ESI): m/z 158 (M+H)

Step-2

Synthesis of (R)-Methyl 4-(5-(2-(2,5-difluorophenyl)pyrrolidin-1-yl)pyrazolo[1,5a]pyridine-3-carboxamido)cyclohexanecarboxylate

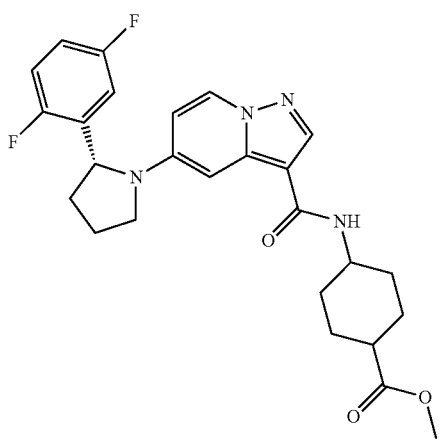 [SMILES: COC(=O)C1CCC(NC(=O)c2cnn3ccc(N4CCC[C@@H]4c4cc(F)ccc4F)cc23)CC1]

A method substantially similar to that mentioned in Example-16, was used to afford a crude compound, which was purified by Preparative HPLC [Column: Zorbax, Eclipse, C-18, Mobile phase-A: 0.1% TFA in water, B:ACN, Gradient (Time/% B): 0/10, 2/20, 10/60 and Flow rate:20 mL/min] to obtain 16 mg of the title compound as a white solid.

$^1$H NMR (300 MHz, DMSO-$d_6$) δ ppm 8.41-8.38 (2H, m), 7.6 (1H, d, J=7.5 Hz), 7.4-7.3 (1H, m), 7.2-7.1 (1H, m), 7.0-6.8 (2H, m), 6.4 (1H, d, J=6.6 Hz), 5.12 (1H, d, J=8.1 Hz), 3.9-3.75 (1H, m), 3.65 (3H, s), 3.5-3.35 (3H, m), 2.65-2.5 (2H, m), 2.5-2.4 (1H, m), 2.1-1.8 (4H, m), 1.7-1.3 (5H, m).
MS (ESI): m/z 483.2 (M+H).

Example-41

Synthesis of (R)-4-(5-(2-(2,5-difluorophenyl)pyrrolidin-1-yl)pyrazolo[1,5a]pyridine-3-carboxamido)cyclohexanecarboxylic acid

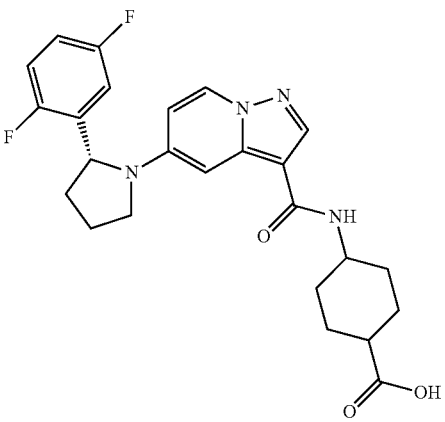 [SMILES: O=C(NC1CCC(C(=O)O)CC1)c1cnn2ccc(N3CCC[C@@H]3c3cc(F)ccc3F)cc12]

A method substantially similar to that mentioned in Example-31 was used to afford a crude product, which was purified by Preparative HPLC [Column: AG/PPC/C18-15/028, Mobile phase-A: 0.1% TFA in water, B: ACN, Gradient (Time/% B): 0/20, 2/30, 10/70 and Flow rate:20 mL/min] to afford 8 mg of the title compound as a white solid.

$^1$H NMR (400 MHz, DMSO-$d_6$) δ ppm 12.1 (1H, bs), 8.41-8.37 (2H, m), 7.56 (1H, d, J=7.6 Hz), 7.36-7.3 (1H, m), 7.2-7.1 (1H, m), 6.95 (1H, s), 6.9-6.8 (1H, m), 6.4 (1H, d, J=6.0 Hz), 5.11 (1H, d, J=8.4 Hz), 3.86-3.75 (2H, m), 3.5-3.4 (2H, m), 2.5-2.4 (1H, m), 2.1-1.85 (6H, m), 1.7-1.4 (7H, m).
MS (ESI): m/z 469.2 (M+H).

Example-42

Synthesis of (R)-4-amino-1-(5-(2-(2,5-difluorophenyl)pyrrolidin-1-yl)pyrazolo[1,5a]pyridine-3-carbonyl)piperidine-4-carboxylic acid hydrochloride

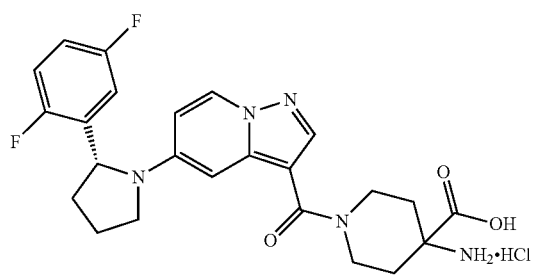

Step-1

Synthesis of (R)-methyl-4-((tert-butoxycarbonyl)amino)-1-(5-(2-(2,5-difluorophenyl)pyrrolidin-1-yl)pyrazolo[1,5-a]pyridine-3-carbonyl)piperidine-4-carboxylate

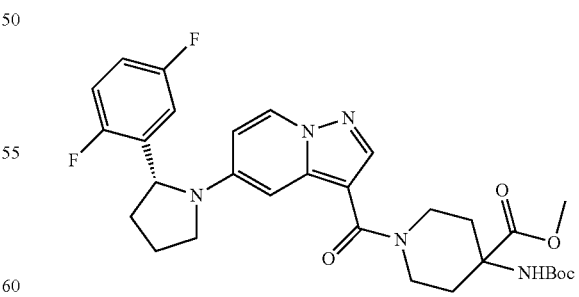

A method substantially similar to that mentioned in Example-16, was employed using methyl 4-((tert-butoxycarbonyl)amino)piperidine-4-carboxylate (0.124 g, 0.48 mmol) to afford 240 mg of the title compound(R)-methyl 4-((tert-butoxycarbonyl)amino)-1-(5-(2-(2,5-difluorophenyl)pyrrolidin-1-yl)pyrazolo[1,5-a]pyridine-3-carbonyl)piperidine-4-carboxylate as a pale green solid. MS (ESI): m/z 584.2 (M+H).

Step-2

Synthesis of (R)-4-((tert-butoxycarbonyl)amino)-1-(5-(2-(2,5-difluorophenyl)pyrrolidin-1-yl)pyrazolo[1,5-a]pyridine-3-carbonyl)piperidine-4-carboxylic acid

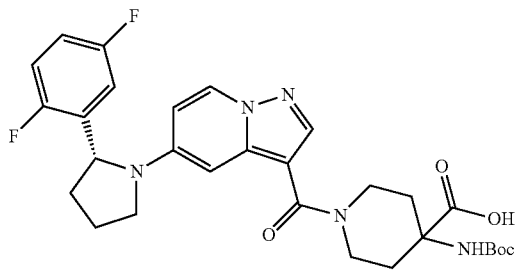

LiOH.H₂O (43 mg, 1 mmol) in water (2 mL) was added to a stirred solution of (R)-methyl 4-((tert-butoxycarbonyl)amino)-1-(5-(2-(2,5-difluorophenyl)pyrrolidin-1-yl)pyrazolo[1,5-a]pyridine-3-carbonyl)piperidine-4-carboxylate (120 mg, 0.2 mmol) in THF (6 mL), MeOH (2 mL) and water (2 mL) at 20-35° C. The reaction mixture was stirred for 6 h; thereafter it was concentrated under reduced pressure to afford a crude product. The crude product thus obtained was diluted with cold water, acidified with 2N aqueous HCl solution, extracted with ethyl acetate, dried over anhydrous sodium sulphate and concentrated under reduced pressure to afford 100 mg of the title compound as a pale green solid. MS (ESI): m/z 570.2 (M+H).

Step-3

Synthesis of (R)-4-amino-1-(5-(2-(2,5-difluorophenyl)pyrrolidin-1-yl)pyrazolo[1,5-a]pyridine-3-carbonyl)piperidine-4-carboxylic acid hydrochloride

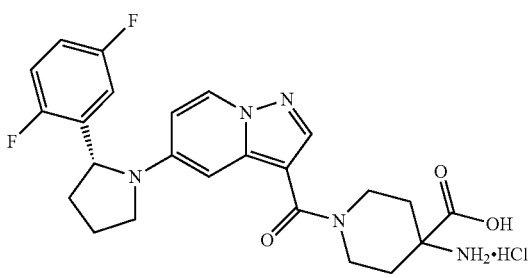

(R)-4-((tert-butoxycarbonyl)amino)-1-(5-(2-(2,5-difluorophenyl)pyrrolidin-1-yl)pyrazolo[1,5-a]pyridine-3-carbonyl)piperidine-4-carboxylic acid (100 mg, 0.17 mmol) added to 4N HCl in Dioxane (5 mL) was stirred at 20-35° C. for 3 h. The reaction mixture was concentrated under reduced pressure to afford crude. The crude obtained was washed with diethyl ether and dried to afford 58 mg of the title compound as a pale brown solid.

¹H NMR (300 MHz, DMSO-d₆) δ ppm 8.63 (4H, bs), 8.45 (1H, d, J=7.8 Hz), 8.04 (1H, s), 7.38-7.28 (1H, m), 7.2-7.1 (1H, m), 6.9-6.8 (1H, m), 6.6 (1H, s), 6.4 (1H, d, J=6.9 Hz), 5.13 (1H, d, J=7.8 Hz), 3.9-3.7 (8H, m), 2.5-2.4 (1H, m), 2.15-1.7 (10H, m).
MS (ESI): m/z 470.2 (M+H) (Free base).

Example-43

Synthesis of (5-((R)-2-(2,5-difluorophenyl)pyrrolidin-1-yl)pyrazolo[1,5a]pyridin-3-yl)(8-(((S)-3-hydroxypyrrolidin-1-yl)methyl)-5,6-dihydroimidazo[1,2-a]pyrazin-7(8H)-yl)methanone 2,2,2-trifluoroacetate

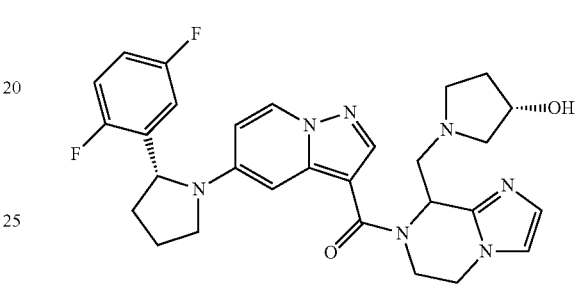

A method substantially similar to that mentioned in Example-6, was employed using (3S)-1-((5,6,7,8-tetrahydroimidazo[1,2-a]pyrazin-8-yl)methyl)pyrrolidin-3-ol (WO95/21843) to afford a crude product. The crude product obtained was purified by Preparative HPLC [Column:21.2× 150×5 um, Zorbax, XDB,C-18(#026), Mobile phase-A: 0.1% TFA in water, B:ACN, Gradient (Time/% B): 0/20, 2/30, 10/90 and Flow rate:20 mL/min] to afford 5.1 mg of the title compound as a pale brown solid.
¹H NMR (300 MHz, CD₃OD) δ ppm 8.35 (1H, t, J=7.8 Hz), 8.2 (1H, s), 7.5 (2H, s), 7.2-7.1 (1H, m), 7.05-6.9 (2H, m), 6.83-6.7 (1H, m), 6.6-6.5 (1H, m), 6.37-6.22 (1H, m), 5.25 (1H, d, J=6.6 Hz), 4.85-4.55 (3H, m), 4.55-4.15 (2H, m), 4.1-3.45 (9H, m), 2.6-2.25 (2H, m), 2.25-2.1 (4H, m).
MS (ESI): m/z 548.2 (M+H) (free base).

Example-44

5-((R)-2-(2,5-difluorophenyl)pyrrolidin-1-yl)-N-(3-hydroxycyclohexyl)pyrazolo[1,5a]pyridine-3-carboxamide

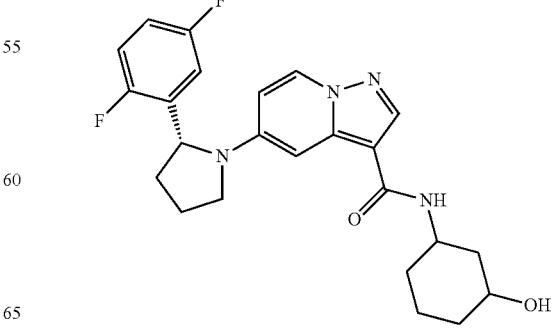

A method substantially similar to that mentioned in Example-6, was employed using 3-aminocyclohexanol to obtain a crude product, which was purified by Preparative HPLC [Column: AG/PP/C18/15-028, Mobile phase-A: 0.1% TFA in water, B: ACN, Gradient (Time/% B): 0/40, 2/50, 8/90 and Flow rate:20 mL/min] to afford 30 mg of the title compound as a white solid.

MS (ESI): m/z 441.2 (M+H)

Example-45

Synthesis of (5-((R)-2-(2,5-difluorophenyl)pyrrolidin-1-yl)pyrazolo[1,5-a]pyridin-3-yl)(4-hydroxyazepan-1-yl)methanone

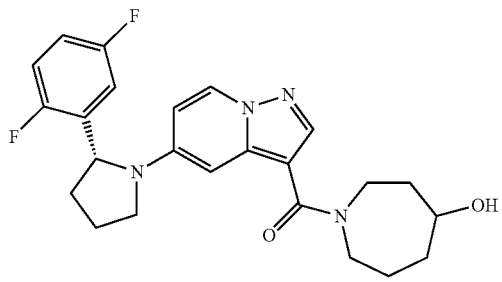 [SMILES: O=C(c1cnn2ccc(N3CCC[C@@H]3c3cc(F)ccc3F)cc12)N1CCCC(O)CC1]

A method substantially similar to that mentioned in Example-23, was employed using azepan-4-ol to afford the crude product, which was purified by Preparative TLC (Silicagel GF$_{254}$, 1000 u, 20×20 cm dimension glass plate and 10% MeOH in DCM as eluent) to afford 54 mg of the title compound.

MS (ESI): m/z 441.2 (M+H).

Example-46

Synthesis of (R)-5-(2-(2,5-difluorophenyl)pyrrolidin-1-yl)-N-(2-(pyrrolidin-1-yl)ethyl)pyrazolo[1,5a]pyridine-3-carboxamide

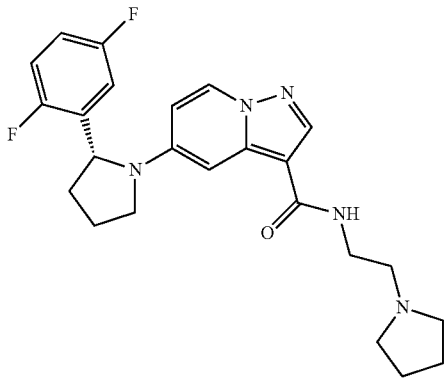 [SMILES: O=C(NCCN1CCCC1)c1cnn2ccc(N3CCC[C@@H]3c3cc(F)ccc3F)cc12]

A method substantially similar to that mentioned in Example-16, was employed using 1-(2-aminoethyl)pyrrolidine to afford 35 mg of the title compound as white solid.

$^1$H NMR (300 MHz, CDCl$_3$) δ ppm 8.28 (1H, d, J=8.1 Hz), 8.20 (1H, s), 7.23-7.1 (1H, m), 7.08-6.95 (2H, m), 6.83-6.75 (1H, m), 6.46 (1H, d, J=7.5 Hz), 5.21 (1H, d, J=8.7 Hz), 3.9-3.8 (1H, m), 3.6-3.48 (3H, m), 2.8-2.6 (6H, m), 2.6-2.1 (1H, m), 2.22-2.0 (3H, m), 1.9-1.8 (3H, m).

MS (ESI): m/z 440.2 (M+H).

Example-47

Synthesis of (R)-Methyl 4-(5-(2-(2,5-difluorophenyl)pyrrolidin-1-yl)pyrazolo[1,5a]pyridine-3-carboxamido)tetrahydro-2H-pyran-4-carboxylate

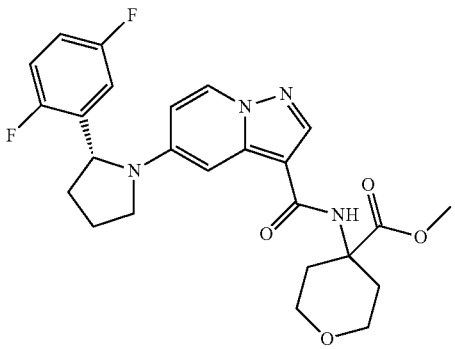 [SMILES: COC(=O)C1(NC(=O)c2cnn3ccc(N4CCC[C@@H]4c4cc(F)ccc4F)cc23)CCOCC1]

A method substantially similar to that mentioned in Example-16, was employed using methyl 4-aminotetrahydro-2H-pyran-4-carboxylate to afford 100 mg of the title compound as a green solid.

$^1$H NMR (300 MHz, CDCl$_3$) δ ppm 8.14 (1H, d, J=7.8 Hz), 8.02 (1H, s), 7.15-7.0 (2H, m), 6.96-6.85 (1H, m), 6.72-6.6 (1H, m), 6.2 (1H, dd, J=2.7 Hz), 5.8 (1H, s), 5.15 (1H, d, J=8.1 Hz), 3.96-3.82 (2H, m), 3.82-3.64 (6H, m), 3.6-3.44 (1H, m), 2.56-2.24 (3H, m), 2.2-1.98 (5H, m).

MS (ESI): m/z 485.2 (M+H).

Example-48

Synthesis of (R)-(5-(2-(2,5-difluorophenyl)pyrrolidin-1-yl)pyrazolo[1,5-a]pyridin-3-yl)(6,7-dimethoxy-3,4-dihydroisoquinolin-2 (1H)-yl)methanone

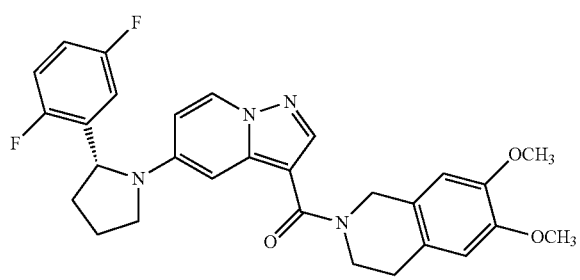 [SMILES: COc1cc2c(cc1OC)CN(C(=O)c1cnn3ccc(N4CCC[C@@H]4c4cc(F)ccc4F)cc13)CC2]

A method substantially similar to that mentioned in Example-16, was employed using 6,7-dimethoxy-1,2,3,4-tetrahydroisoquinoline hydrochloride to afford 42.4 mg of the title compound as a pale yellow solid.

$^1$H NMR (300 MHz, CDCl$_3$) δ ppm 8.15 (1H, d, J=7.5 Hz), 8.0 (1H, s), 7.1-7.0 (1H, m), 6.95-6.85 (2H, m), 6.75-6.65 (2H, m), 6.6 (1H, s), 6.2 (1H, dd, J=2.7, 7.8 Hz), 5.2 (1H, d, J=7.8 Hz), 4.8 (2H, s), 4.0-3.9 (2H, m), 3.87 (3H, s), 3.84 (s, 3H), 3.8-3.7 (1H, m), 3.55-3.45 (1H, m), 2.95-2.855 (2H, m), 2.5-2.4 (1H, m), 2.1-1.95 (3H, m).
MS (ESI): m/z 519.2 (M+H).

Example-49

Synthesis of (R)-5-(2-(2,5-difluorophenyl)pyrrolidin-1-yl)-N-(4-methylpiperazin-1-yl)pyrazolo[1,5a]pyridine-3-carboxamide

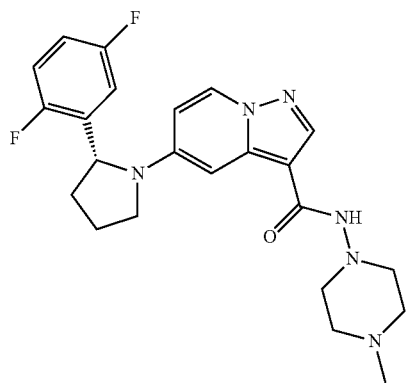

A method substantially similar to that mentioned in Example-27, was employed using 4-methylpiperazin-1-amine to afford a crude product, which was purified by Preparative TLC (Silicagel $GF_{254}$, 1000 u, 20×20 cm dimension glass plate and 5% MeOH in DCM as eluent) 30 mg of the title compound as an off white solid.
$^1$H NMR (400 MHz, DMSO+$D_2O$) δ ppm 8.4 (1H, d, J=8.0 Hz), 8.3 (1H, bs), 7.35-7.25 (1H, m), 7.2-7.1 (1H, m), 6.95-6.8 (2H, m), 6.5 (1H, bs), 5.15 (1H, d, J=8.0 Hz), 3.5-3.4 (1H, m), 2.9-2.7 (4H, m), 2.5-2.4 (6H, m), 2.2 (3H, s) 2.14-2.04 (2H, m), 2.0-1.86 (2H, m).
MS (ESI): 441.2 (M+H).

Example-50

Synthesis of Ethyl 3-(5-((R)-2-(2,5-difluorophenyl)pyrrolidin-1-yl)pyrazolo[1,5a]pyridine-3-carboxamido)cyclohexanecarboxylate

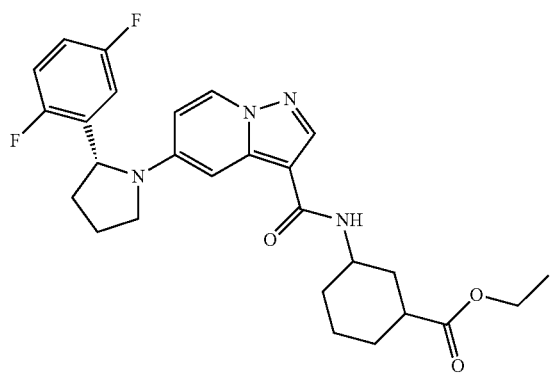 [SMILES: CCOC(=O)C1CCCC(NC(=O)c2cnn3ccc(N4CCC[C@@H]4c4cc(F)ccc4F)cc23)C1]

Ethyl 3-aminocyclohexanecarboxylate was prepared by the method substantially similar to that mentioned method similar to Example-40 using 3-amino cyclohexane carboxylic acid (Fluorochem). A method substantially similar to that mentioned in Example-23, was employed using ethyl 3-aminocyclohexanecarboxylate to afford 135 mg of the title compound as an off white solid.
MS (ESI): m/z 497.2 (M+H).

Example-51

Synthesis of 3-(5-((R)-2-(2,5-difluorophenyl)pyrrolidin-1-yl)pyrazolo[1,5a]pyridine-3-carboxamido)cyclohexanecarboxylic acid

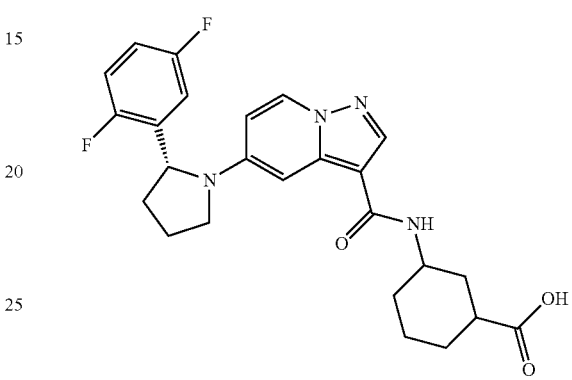

The title compound was prepared by the method substantially similar to that mentioned in Example-41, to afford 32 mg of the title compound as white solid.
MS (ESI): m/z 469.2 (M+H).

Example-52

Synthesis of (R)-5-(2-(2,5-difluorophenyl)pyrrolidin-1-yl)-N-(1-hydroxy-2-methylpropan-2-yl)pyrazolo[1,5a]pyridine-3-carboxamide

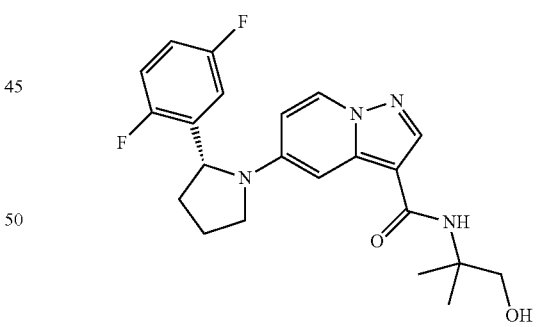

A method substantially similar to that mentioned in Example-26, using 2-amino-2-methylpropan-1-ol to afford a crude product, which was purified by flash chromatography (Biotage, Column: Silicagel 12 g pack size, Mobile Phase: EtOAc in n-Hexane: 0 to 60% as eluent) to afford 19.6 mg of the title compound as grey solid.
$^1$H NMR (400 MHz, DMSO $d_6$) δ ppm 8.4 (2H, m), 7.35-7.28 (1H, m), 7.2-7.1 (1H, m), 7.0-6.94 (2H, m), 6.9-6.84 (1H, m), 6.34 (1H, d, J=6.8 Hz), 5.15 (1H, d, J=8.0 Hz), 5.08 (1H, t), 3.9 (1H, t), 3.5-3.4 (3H, m), 2.5-2.4 (1H, m), 2.1-1.85 (3H, m), 1.3 (6H, s).
MS (ESI): m/z 415.2 (M+H).

Example-53

Synthesis of (R)-7-(5-(2-(2,5-difluorophenyl)pyrrolidin-1-yl)pyrazolo[1,5-a]pyridine-3-carbonyl)-5,6,7,8-tetrahydroimidazo[1,2-a]pyrazine-2-carboxylic acid

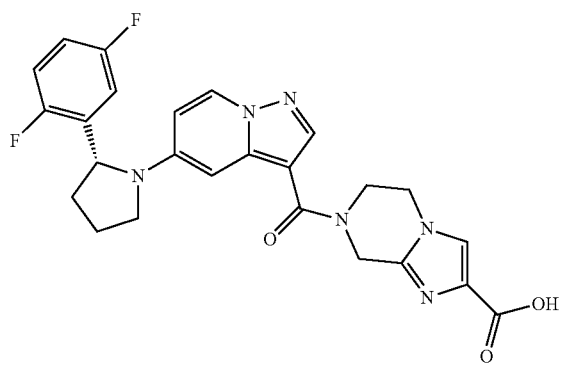 [SMILES: O=C(O)c1cn2c(n1)CN(C(=O)c1cnn3ccc(N4CCC[C@@H]4c4cc(F)ccc4F)cc13)CC2]

Step-1

Synthesis of Ethyl imidazo[1,2-a]pyrazine-2-carboxylate

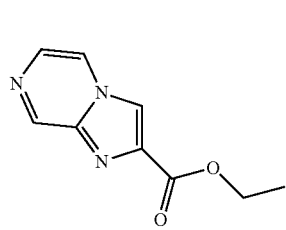

Ethyl bromopyruvate (2.15 g, 11.04 mmol) was added to stirred solution of 2-aminopyrazine (1 g, 10.5 mmol) in 1,2-Dimethoxy ethane (10 mL). The reaction mixture was stirred at 20-35° C. for 2 h. The mixture was then filtered to obtain a solid precipitate which was dried well, dissolved in EtOH (10 mL) and refluxed for 2 h. This mixture was concentrated, diluted with aqueous saturated sodium bicarbonate solution, extracted with chloroform. The chloroform layer was washed with water followed by brine solution, dried over anhydrous sodium sulphate and concentrated under reduced pressure to afford the crude product, which was purified by column chromatography (using 60-120 silica gel and 60% EtOAc in Hexane as eluent) to afford 450 mg of the title compound.

$^1$H NMR (400 MHz, CDCl$_3$) δ ppm 9.22 (1H, s), 8.28 (1H, s), 8.12-8.08 (1H, m), 8 (1H, d, J=4.8 Hz), 4.52-4.47 (2H, m), 1.5 (3H, t).

Step-2

Synthesis of Ethyl 5,6,7,8-tetrahydroimidazo[1,2-a]pyrazine-2-carboxylate hydrochloride

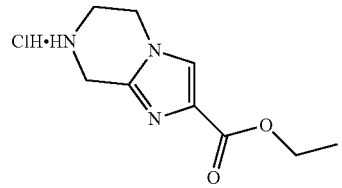

10% Pd/C (40 mg) was added to a stirred solution of Ethyl imidazo[1,2-a]pyrazine-2-carboxylate (410 mg, 2.15 mmol) and conc.HCl (0.5 mL) in EtOH (9.5 mL) under inert atmosphere. The reaction mixture was stirred continuously under hydrogen atmosphere for 16 h. The reaction mixture was filtered over a celite bed-and the filtrate was concentrated under reduced pressure to afford a solid product, which was washed with diethyl ether and dried to afford 400 mg of the title compound as a yellow solid.

MS (ESI): m/z 196 (M+H).

Step-3

Synthesis of (R)-ethyl 7-(5-(2-(2,5-difluorophenyl)pyrrolidin-1-yl)pyrazolo[1,5-a]pyridine-3-carbonyl)-5,6,7,8-tetrahydroimidazo[1,2-a]pyrazine-2-carboxylate A method substantially similar to that mentioned in Example-16, was employed using Ethyl 5,6,7,8-tetrahydroimidazo[1,2-a]pyrazine-2-carboxylate to afford the residue, which was purified by Preparative [Column AG/PP/C18-15/028, Mobile phase-A: 0.1% TFA in water, B: ACN, Gradient (Time/% B): 0/20, 2/30, 10/70 and Flow rate:20 mL/min] to afford 50 mg of the title compound as an off white solid.

MS (ESI): m/z 521.2 (M+H).

Step-4

Synthesis of (R)-7-(5-(2-(2,5-difluorophenyl)pyrrolidin-1-yl)pyrazolo[1,5-a]pyridine-3-carbonyl)-5,6,7,8-tetrahydroimidazo[1,2-a]pyrazine-2-carboxylic acid

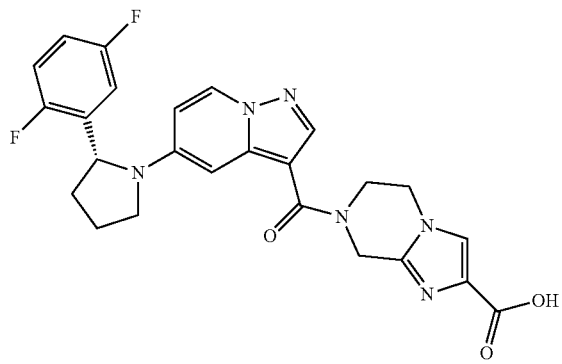 [SMILES: O=C(O)c1cn2c(n1)CN(C(=O)c1cnn3ccc(N4CCC[C@@H]4c4cc(F)ccc4F)cc13)CC2]

A method substantially similar to that mentioned in Example-41 was used to afford 18 mg of the title compound a pale brown solid.

$^1$H NMR (400 MHz, DMSO-d$_6$) δ ppm 8.4 (1H, d, J=7.6 Hz), 8.2 (1H, s), 7.94 (1H, s), 7.38-7.3 (1H, m), 7.2-7.12 (1H, m), 6.92-6.84 (1H, m), 6.7 (1H, s), 6.46 (1H, bs), 5.15 (1H, d, J=8.0 Hz), 4.83 (2H, s), 4.2 (2H, t), 4.06 (2H, t), 3.9-3.8 (1H, t), 3.16 (2H, s), 2.5-2.4 (1H, m), 2.1-1.85 (3H, m).

MS (ESI): m/z 492.9 (M+H).

Example-54

Synthesis of (R)-5-(2-(2,5-difluorophenyl)pyrrolidin-1-yl)-N-(2-(dimethylamino)-2-oxoethyl)pyrazolo[1,5a]pyridine-3-carboxamide

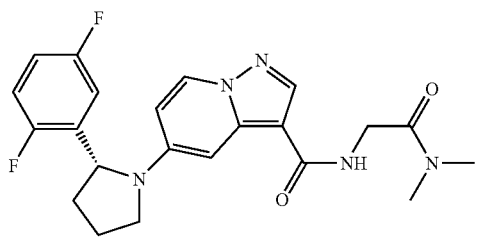 [SMILES: CN(C)C(=O)CNC(=O)c1cnn2ccc(N3CCC[C@@H]3c3cc(F)ccc3F)cc12]

A method substantially similar to that mentioned in Example-16, was employed using 2-amino-N,N-dimethylacetamide hydrochloride to afford a crude product, which was purified by Preparative HPLC [using Column:21.2×150×5 um, Zorbax, XDB,C-18(#022), Mobile phase-A: 0.1% TFA in water, B: MeOH:ACN(1:1), Gradient (Time/% B): 0/50, 2/60, 10/80 and Flow rate:20 mL/min] to afford 15 mg of the title compound a pale green solid.

$^1$H NMR (400 MHz, DMSO-d$_6$) δ ppm 8.43 (1H, d, J=7.6 Hz), 8.35 (1H, s), 8.0 (1H, t), 7.4-7.3 (1H, m), 7.2-7.1 (1H, m), 6.95-6.83 (2H, m), 6.4 (1H, d, J=6.0 Hz), 5.12 (1H, d, J=8 Hz), 4.06 (2H, t), 3.88-3.8 (1H, t), 3.48-3.4 (1H, m), 3.1 (3H, s), 2.86 (3H, s), 2.5-2.4 (1H, m), 2.1-2.0 (1H, m), 2.0-1.84 (2H, m).

MS (ESI): m/z 428.1 (M+H).

Example-55

Synthesis of (R)-5-(2-(2,5-difluorophenyl)pyrrolidin-1-yl)-N-(2-(dimethylamino) ethyl)pyrazolo[1,5a]pyridine-3-carboxamide

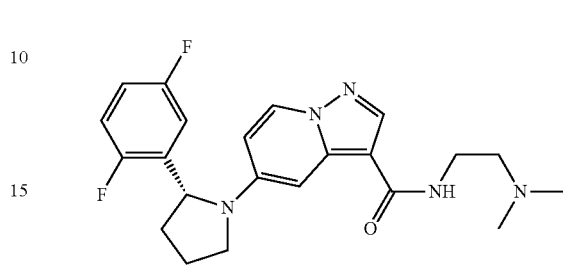

A method substantially similar to that mentioned in Example-16, was employed using N1,N1-dimethylethane-1,2-diamine to afford a crude product which was purified by Preparative HPLC [Column: AG/PP/C18/15-028, Mobile phase-A: 0.1% TFA in water, B: ACN, Gradient (Time/% B): 0/20, 2/30, 10/70 and Flow rate:20 mL/min] to 3.8 mg of the title compound as a pale brown solid.

$^1$H NMR (400 MHz, CDCl$_3$) δ ppm 8.15 (1H, d, J=7.6 Hz), 8.02 (1H, s), 7.21 (1H, d, J=2.4 Hz), 7.1-7.0 (1H, m), 6.95-6.85 (1H, m), 6.72-6.66 (1H, m), 6.42 (1H, bs), 6.16 (1H, dd, J=2.8, 7,6 Hz), 5.15 (1H, d, J=8.0 Hz), 3.80 (1H, t), 3.6-3.46 (3H, m), 2.54-2.4 (3H, m), 2.34 (6H, s), 2.14-2.0 (3H, m).

MS (ESI): m/z 414.2 (M+H).

Example-56

Synthesis of 5-((R)-2-(2,5-difluorophenyl)pyrrolidin-1-yl)-N—((S)-1-hydroxypropan-2-yl)pyrazolo[1,5a]pyridine-3-carboxamide

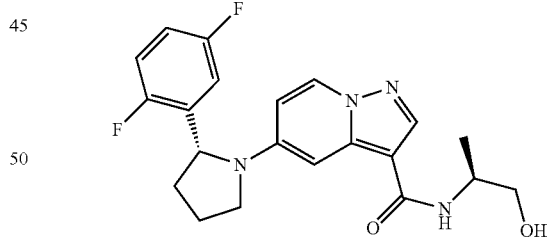

A method substantially similar to that mentioned in Example—6, was employed using (S)-2-aminopropan-1-ol to afford a crude product, which was purified by Flash chromatography (Biotage, Column: Silicagel 12 g pack size, Mobile Phase: EtOAc in n-Hexane: 0 to 60% as eluent) to afford 10.4 mg of the title compound as a green solid.

$^1$H NMR (400 MHz, CDCl$_3$) δ ppm 8.15 (1H, d, J=7.5 Hz), 8.0 (1H, s), 7.15 (1H, s), 7.1-7.0 (1H, m), 7.0-6.8 (1H, m), 6.75-6.6 (1H, m), 6.2 (1H, d), 5.8 (1H, bs), 5.25 (1H, d, J=7.8 Hz), 4.35 (1H, bs), 3.85-3.7 (2H, m), 3.7-3.48 (3H, m), 2.55-2.35 (1H, m), 2.15-1.95 (3H, m), 1.35-1.31 (3H, d, J=6.6 Hz).

MS (ESI): m/z 401.1 (M+H).

Example-57

Synthesis of 5-((R)-2-(2,5-difluorophenyl)pyrrolidin-1-yl)-N-(1-(5-fluoropyridin-2-yl)ethyl)pyrazolo[1,5a]pyridine-3-carboxamide

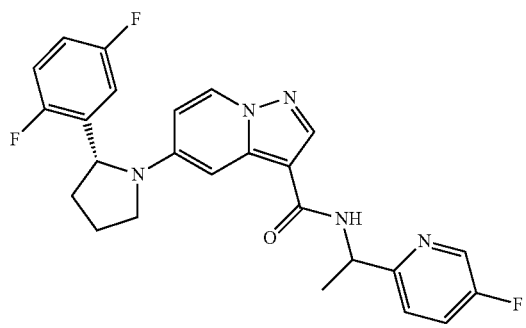 [SMILES: CC(NC(=O)c1cnn2ccc(N3CCC[C@@H]3c3cc(F)ccc3F)cc12)c1ccc(F)cn1]

Step-1

Synthesis of N-(1-(5-fluoropyridin-2-yl)ethyl)acetamide

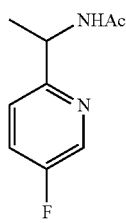

10% Pd/C (100 mg) was added to a solution of N-(1-(5-fluoropyridin-2-yl) vinyl)acetamide (440 g, 2.2 mmol) in EtOH (10 mL) and the mixture was stirred continuously under hydrogen atmosphere at 20-35° C. for 1.5 h. The reaction mixture was filtered over a celite bed-and the filtrate was concentrated under reduced pressure to afford 415 g of the title compound as a yellowish brown liquid. MS (ESI): m/z 183 (M+H).

Step-2

Synthesis of 1-(5-fluoropyridin-2-yl)ethanamine

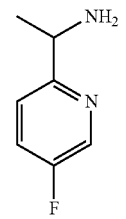

A mixture of 5N aqueous NaOH solution (5 mL) and N-(1-(5-fluoropyridin-2-yl)ethyl)acetamide (180 mg, 0.4 mmol) was heated under reflux conditions for 12-16 h. After completion of the reaction, the reaction mixture was cooled to a temperature of 20-35° C. The reaction mixture was extracted with DCM, dried over anhydrous sodium sulphate and concentrated under reduced pressure to afford 45 mg of the title compound as a yellow liquid.
MS (ESI): m/z 141 (M+H).

Step-3

Synthesis of 5-((R)-2-(2,5-difluorophenyl)pyrrolidin-1-yl)-N-(1-(5-fluoropyridin-2-yl)ethyl)pyrazolo[1,5a]pyridine-3-carboxamide

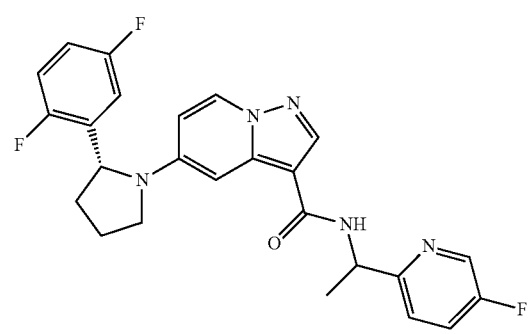 [SMILES: CC(NC(=O)c1cnn2ccc(N3CCC[C@@H]3c3cc(F)ccc3F)cc12)c1ccc(F)cn1]

A method substantially similar to that mentioned in Example-16, was employed using 1-(5-fluoropyridin-2-yl)ethanamine in place of octahydro-1H-pyrido[1,2-a]pyrazine to afford a crude product, which was purified by Preparative TLC (Silicagel GF$_{254}$, 1000 u, 20×20 cm dimension glass plate and 50% EtOAc in Hexane as eluent) to afford 60 mg of the title compound as an off white solid.
MS (ESI): m/z 466.1 (M+H).

Example-58

Synthesis of (R)-5-(2-(2,5-difluorophenyl)pyrrolidin-1-yl)-N-(1-methylpiperidin-4-yl)pyrazolo[1,5a]pyridine-3-carboxamide

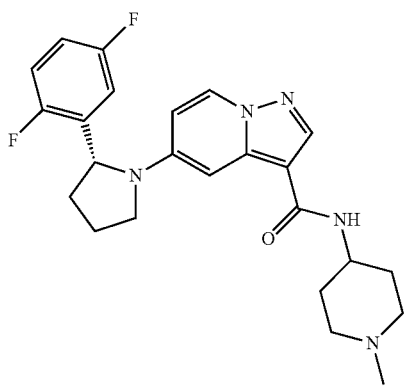 [SMILES: CN1CCC(NC(=O)c2cnn3ccc(N4CCC[C@@H]4c4cc(F)ccc4F)cc23)CC1]

A method substantially similar to that mentioned in Example-16, was employed using 1-Methyl-piperidin-4-ylamine (Fluorochem), to afford the crude product, which was purified by Preparative TLC(Silicagel GF$_{254}$, 1000 u, 20×20 cm dimension glass plate and 50% EtOAc in Hexane as eluent) to afford 15 mg of the title compound as an off-white solid.

$^1$H NMR (400 MHz, DMSO-d$_6$) δ ppm 8.42 (1H, d, J=7.6 Hz), 8.33 (1H, s), 7.65 (1H, d, J=7.6 Hz), 7.4-7.3 (1H, m), 7.2-7.1 (1H, m), 6.95-6.85 (2H, m), 6.4 (1H, d, J=6.4 Hz), 5.12 (1H, d, J=8.0 Hz), 3.9-3.8 (1H, m), 3.8-3.76 (1H, m), 2.9-2.8 (2H, m), 2.46-2.4 (1H, m), 2.28-2.18 (3H, m), 2.1-1.84 (5H, m), 1.8-1.7 (2H, m), 1.6-1.48 (2H, m).

MS (ESI): m/z 440.2 (M+H)

Example-59

Synthesis of (5-Benzylhexahydropyrrolo[3,4-c]pyrrol-2 (1H)-yl)(5-((R)-2-(2,5-difluorophenyl)pyrrolidin-1-yl)pyrazolo[1,5a]pyridin-3-yl)methanone

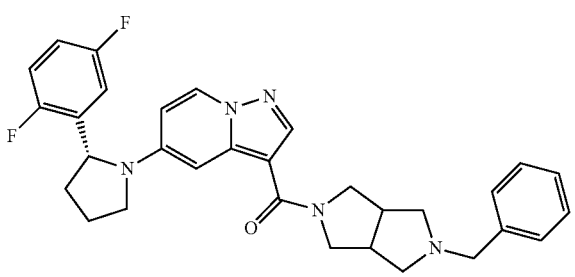 [SMILES: O=C(c1cnn2ccc(N3CCC[C@@H]3c3cc(F)ccc3F)cc12)N1CC2CN(Cc3ccccc3)CC2C1]

A method substantially similar to that mentioned in Example-16, was employed using 2-benzyloctahydropyrrolo[3,4-c]pyrrole (US 2004/0186107A1) to afford a residue, which was purified by Preparative HPLC [Column: AG/PP/C18/15-028, Mobile phase-A: 0.1% TFA in water, B: ACN, Gradient (Time/% B): 0/20, 2/30, 9/90 and Flow rate:20 mL/min] to afford 30 mg of the title compound as a light pink solid.

$^1$H NMR (300 MHz, CD$_3$OD) δ ppm 8.32 (1H, d, J=7.5 Hz), 8.16 (1H, s), 7.54 (5H, s), 7.24-7.12 (1H, m), 7.06-6.96 (2H, m), 6.84-6.72 (1H, m), 6.58 (1H, d), 5.22 (1H, d), 4.42 (2H, s), 4.02-3.7 (6H, m), 3.68-3.50 (2H, m), 3.50-3.35 (1H, m), 3.2-3.0 (3H, m), 2.6-2.5 (1H, m), 2.2-2.0 (3H, m).

MS (ESI): m/z 528.2 (M+H).

Example-60

Synthesis of (R)-5-(2-(2,5-difluorophenyl)pyrrolidin-1-yl)-N-(tetrahydro-2H-pyran-4-yl)pyrazolo[1,5a]pyridine-3-carboxamide

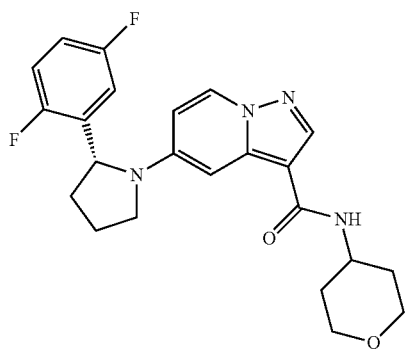

The title compound was prepared by the method substantially similar to that mentioned in Example-16, using tetrahydro-2H-pyran-4-amine to afford the crude compound. The crude compound was purified by Preparative TLC (using Silicagel GF$_{254}$, 1000 u coated 20×20 cm dimension glass plate and 100% EtOAc as eluent) to afford 31 mg of the title compound.

$^1$H NMR (300 MHz, DMSO-d$_6$) δ ppm 8.40-8.38 (1H, d, J=7.5 Hz), 8.34 (1H, s), 7.7 (1H, d, J=7.8 Hz), 7.4-7.24 (1H, m), 7.22-7.06 (1H, s), 6.98-6.82 (2H, m), 6.4-6.35 (1H, d, J=6 Hz), 5.10-5.07 (1H, d, J=7.6 Hz), 4.0-3.8 (4H, m), 3.5-3.3 (2H, m), 2.5-2.4 (1H, m), 2.1-1.8 (3H, m), 1.8-1.6 (2H, m), 1.6-1.4 (2H, m).

MS (ESI): m/z 427.0 (M+H).

Example-61

Synthesis of (5-((R)-2-(2,5-difluorophenyl)pyrrolidin-1-yl)pyrazolo[1,5-a]pyridin-3-yl)((S)-2-(hydroxymethyl)pyrrolidin-1-yl)methanone

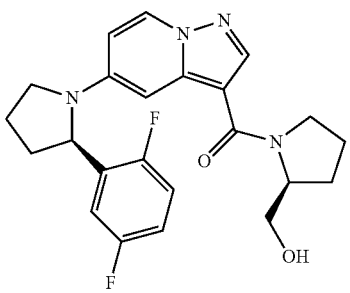 [SMILES: O=C(c1cnn2ccc(N3CCC[C@@H]3c3cc(F)ccc3F)cc12)N1CCC[C@H]1CO]

The title compound was prepared by the method substantially similar to that mentioned in Example-23, using (S)-pyrrolidin-2-ylmethanol to afford the crude, which was purified by column chromatography (using silica gel 60-120, and 60% EtOAc in Hexane as eluent) to afford 16.3 mg of the title compound.

$^1$H NMR (300 MHz, CD$_3$OD) δ ppm 8.3 (1H, d, J=7.8 Hz), 8.14 (1H, s), 7.28-7.1 (1H, m), 7.08-6.94 (1H, m), 6.94-6.84

(1H, s), (2H, m), 6.84-6.72 (1H, m), 6.52 (1H, m), 6.22 (1H, m), 5.2 (1H, d, J=7.5 Hz), 4.4-4.2 (1H, m), 3.9-3.5 (6H, m), 2.6-2.49 (1H, m), 2.25-1.7 (7H, m).

MS (ESI): m/z 427.1 (M+H).

Example-62

Synthesis of (R)-5-(2-(2,5-difluorophenyl)pyrrolidin-1-yl)-N-morpholinopyrazolo[1,5-a]pyridine-3-carboxamide

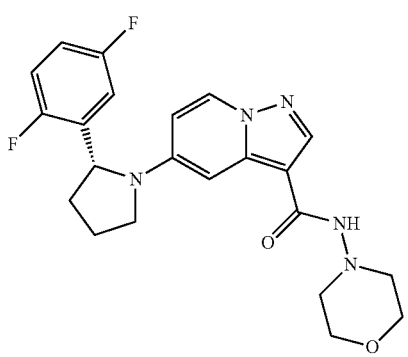 [SMILES: O=C(NN1CCOCC1)c1cnn2ccc(N3CCC[C@@H]3c3cc(F)ccc3F)cc12]

The title compound was prepared by the method substantially similar to that mentioned in Example-16, using 1-aminomorpholine (WO 2007/127688) to afford 70 mg of the title compound.

$^1$H NMR (300 MHz, DMSO-$d_6$) δ ppm 8.9-8.75 (1H, m), 8.4 (1H, d, J=7.5 Hz), 8.3-8.2 (1H, m), 7.36-7.26 (1H, m), 7.2-7.1 (1H, m), 7.0-6.82 (2H, m), 6.36 (1H, d, J=7.5 Hz), 5.1 (1H, d, J=7.8 Hz), 3.86-3.6 (5H, m), 3.50-3.36 (2H, m), 2.90-2.74 (4H, m), 2.5-2.4 (1H, m), 2.1-1.85 (3H, m).

MS (ESI): m/z 428.1 (M+H).

Example-63

Synthesis of (R)-Methyl 4-amino-1-(5-(2-(2,5-difluorophenyl)pyrrolidin-1-yl)pyrazolo[1,5-a]pyridine-3-carbonyl)piperidine-4-carboxylate

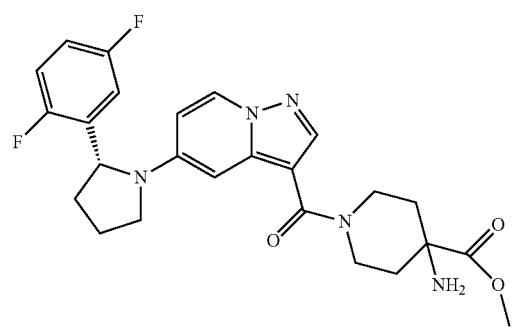 [SMILES: COC(=O)C1(N)CCN(C(=O)c2cnn3ccc(N4CCC[C@@H]4c4cc(F)ccc4F)cc23)CC1]

Step-1

Synthesis of (R)-Methyl 4-((tert-butoxycarbonyl)amino)-1-(5-(2-(2,5-difluorophenyl)pyrrolidin-1-yl)pyrazolo[1,5a]pyridine-3-carbonyl)piperidine-4-carboxylate

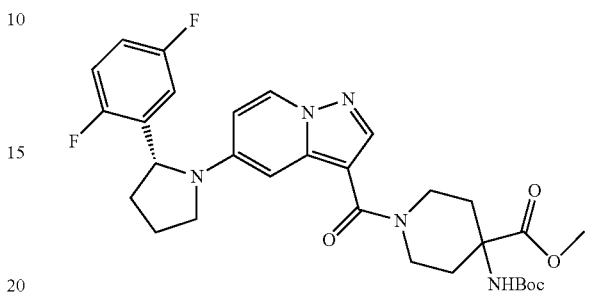

The title compound was prepared by the method substantially similar to that mentioned in Example-16, using methyl 4-((tert-butoxycarbonyl)amino)piperidine-4-carboxylate in place of octahydro-1H-pyrido[1,2-a]pyrazine to afford 240 mg of the title compound.

MS (ESI): m/z 584.2 (M+H)

Step-2

Synthesis of (R)-Methyl 4-amino-1-(5-(2-(2,5-difluorophenyl)pyrrolidin-1-yl)pyrazolo[1,5-a]pyridine-3-carbonyl)piperidine-4-carboxylate

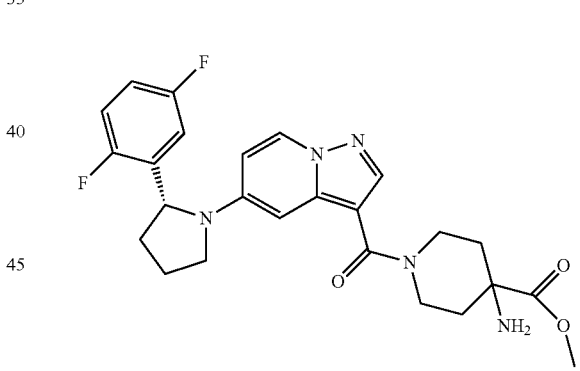

A mixture of 4M HCl solution in Dioxane (1 mL) and (R)-methyl 4-((tert-butoxycarbonyl)amino)-1-(5-(2-(2,5-difluorophenyl)pyrrolidin-1-yl)pyrazolo[1,5-a]pyridine-3-carbonyl)piperidine-4-carboxylate (50 g, 0.085 mmol) was stirred at 20-35° C. for 3 h. After which the reaction mixture was concentrated under reduced pressure to afford the crude. The residue obtained was dissolved in water, extracted with ethylacetate, washed with saturated NaHCO$_3$ solution followed by brine and dried over anhydrous sodium sulfate, concentrated under reduced pressure to afford 15 mg of the title compound.

$^1$H NMR (400 MHz, DMSO) δ ppm 8.5 (1H, d, J=7.2 Hz), 8.0 (1H, s), 7.4-7.25 (1H, m), 7.2-7.1 (1H, m), 6.9-6.8 (1H, m), 6.55 (1H, s), 6.4 (1H, s), 5.15 (1H, d, J=6.8 Hz), 3.9-3.6 (6H, m), 3.52-3.40 (4H, m), 2.1-1.7 (6H, m), 1.6-1.42 (2H, m).

MS (ESI): m/z 484.2 (M+H).

Example-64

Synthesis of (R)-5-(2-(2,5-difluorophenyl)pyrrolidin-1-yl)-N-(2-morpholinoethyl)pyrazolo[1,5a]pyridine-3-carboxamide

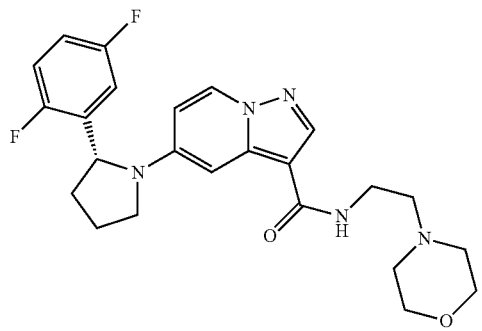 [SMILES: O=C(NCCN1CCOCC1)c1cnn2ccc(N3CCC[C@@H]3c3cc(F)ccc3F)cc12]

The title compound was prepared by the method substantially similar to that mentioned in Example-16, using 2-morpholinoethanamine in place of octahydro-1H-pyrido[1,2-a]pyrazine to afford 60 mg of the title compound.

$^1$H NMR (400 MHz, CD$_3$OD) δ ppm 8.25 (1H, d, J=7.6 Hz), 8.2 (1H, s), 7.2-7.1 (1H, m), 7.1-6.95 (2H, m), 6.80-6.75 (1H, m), 6.45-6.4 (1H, m), 5.2 (1H, d, J=8.4 Hz), 3.9 (1H, t), 3.72-3.64 (4H, m), 3.66-3.44 (3H, m), 2.64-2.42 (7H, m), 2.2-2.0 (3H, m).

MS (ESI): m/z 456.2 (M+H).

Example-65

Synthesis of (5-((R)-2-(2,5-difluorophenyl)pyrrolidin-1-yl)pyrazolo[1,5-a]pyridin-3-yl)((S)-3-(dimethylamino) pyrrolidin-1-yl)methanone

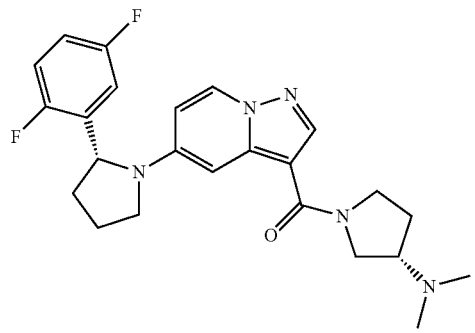 [SMILES: CN(C)[C@H]1CCN(C(=O)c2cnn3ccc(N4CCC[C@@H]4c4cc(F)ccc4F)cc23)C1]

The title compound was prepared by the method substantially similar to that mentioned in Example-16, using (S)—N,N-dimethylpyrrolidin-3-amine in place of octahydro-1H-pyrido[1,2-a]pyrazine to afford 35 mg of the title compound.

$^1$H NMR (400 MHz, CD$_3$OD) δ ppm 8.3 (1H, d, J=8.0 Hz), 8.18 (1H, s), 7.22-7.18 (1H, m), 7.08-6.96 (2H, m), 6.82-6.74 (1H, m), 6.5 (1H, m), 5.2 (1H, d), 4.0-3.78 (3H, m), 3.6-3.5 (1H, m), 2.9-2.8 (1H, bs), 2.58-2.44 (1H, bs), 2.38 (6H, s), 2.28-2.08 (2H, m), 2.07-1.98 (2H, m), 1.96-1.8 (1H, s).

MS (ESI): m/z 440.2 (M+H).

Example-66

Synthesis of (R)-4-(5-(2-(2,5-difluorophenyl)pyrrolidin-1-yl)pyrazolo[1,5-a]pyridine-3-carboxamido) tetrahydro-2H-pyran-4-carboxylic acid

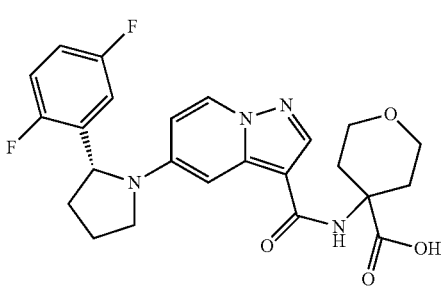 [SMILES: O=C(NC1(C(=O)O)CCOCC1)c1cnn2ccc(N3CCC[C@@H]3c3cc(F)ccc3F)cc12]

Step-1

Synthesis of (R)-Methyl 4-(5-(2-(2,5-difluorophenyl)pyrrolidin-1-yl)pyrazolo[1,5a]pyridine-3-carboxamido)tetrahydro-2H-pyran-4-carboxylate

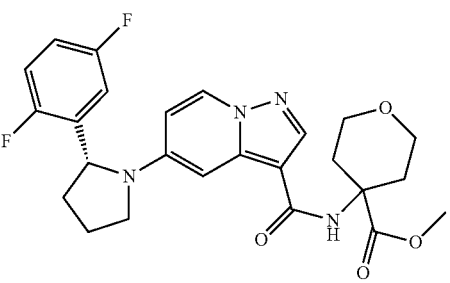 [SMILES: COC(=O)C1(NC(=O)c2cnn3ccc(N4CCC[C@@H]4c4cc(F)ccc4F)cc23)CCOCC1]

The title compound was prepared by the method substantially similar to that mentioned in Example-16, using methyl 4-aminotetrahydro-2H-pyran-4-carboxylate hydrochloride (MaybridgeBB) in place of octahydro-1H-pyrido[1,2-a]pyrazine to afford crude. The impure product was purified by Preparative TLC (using Silicagel GF$_{254}$, 1000 u coated 20×20 cm dimension glass plate and 60% EtOAc in Hexane as eluent) to afford 18 mg of the title compound.

MS (ESI): m/z 485.5 (M+H).

Step-2

Synthesis of (R)-4-(5-(2-(2,5-difluorophenyl)pyrrolidin-1-yl)pyrazolo[1,5-a]pyridine-3-carboxamido)tetrahydro-2H-pyran-4-carboxylic acid

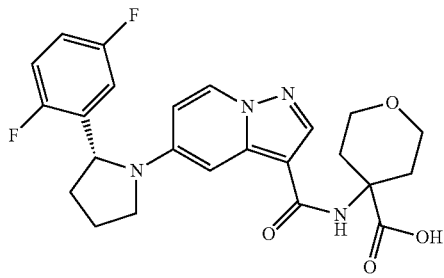 [SMILES: O=C(NC1(C(=O)O)CCOCC1)c1cnn2ccc(N3CCC[C@@H]3c3cc(F)ccc3F)cc12]

NaOH (3 mg, 0.07 mmol) in water (0.1 mL) was added to a stirred solution of (R)-Methyl 4-(5-(2-(2,5-difluorophenyl)pyrrolidin-1-yl)pyrazolo[1,5a]pyridine-3-carboxamido) tetrahydro-2H-pyran-4-carboxylate (18 mg, 0.04 mmol) in MeOH (1 mL) at 20-35° C. and stirring was continued for 16 h. The reaction mixture was concentrated under reduced pressure to afford the crude. The crude thus obtained was diluted with cold water, acidified with 2N aqueous HCl solution, extracted into ethylacetate, dried over sodium sulphate, concentrated under reduced pressure to afford the impure product. The crude compound was purified by preparative TLC (using Silicagel $GF_{254}$, 1000 u coated 20×20 cm dimension glass plate and 10% MeOH in $CHCl_3$ as eluent) to afford 6 mg of the title compound.

$^1$H NMR (400 MHz, $CD_3OD$) δ ppm) 8.4 (1H, s), 8.25 (1H, d, J=8.0 Hz), 7.2-7.1 (1H, m), 7.03-6.95 (2H, m), 6.8-6.7 (1H, m), 6.41-6.39 (1H, d, J=5.2 Hz), 5.20-5.18 (1H, d, J=8.0 Hz), 3.90-3.65 (5H, m), 3.6-3.5 (1H, m), 2.55-2.45 (1H, m), 2.3-1.9 (7H, m).

MS (ESI): m/z 470.7 (M+H).

Example-67

Synthesis of ((S)-3-aminopyrrolidin-1-yl)(5-((R)-2-(2,5-difluorophenyl)pyrrolidin-1-yl)pyrazolo[1,5-a]pyridin-3-yl)methanone

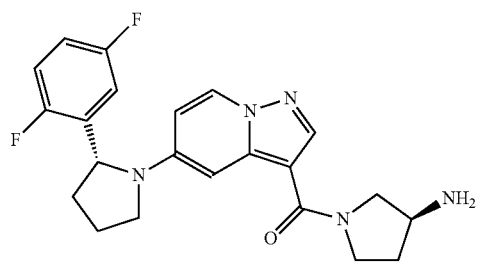 [SMILES: N[C@H]1CCN(C(=O)c2cnn3ccc(N4CCC[C@@H]4c4cc(F)ccc4F)cc23)C1]

Step-1

Synthesis of Tert-butyl(S)-1-(5-((R)-2-(2,5-difluorophenyl)pyrrolidin-1-yl)pyrazolo[1,5-a]pyridine-3-carbonyl)pyrrolidin-3-yl)carbamate

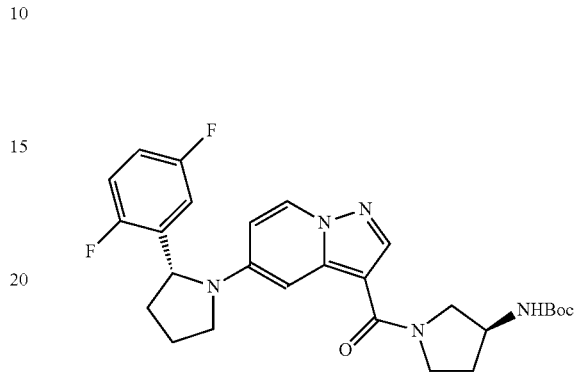

The title compound was prepared by the method substantially similar to that mentioned in Example-16, using (S)-tert-butyl pyrrolidin-3-ylcarbamate in place of octahydro-1H-pyrido[1,2-a]pyrazine to afford 100 mg of the title compound.

MS (ESI): m/z 512.2 (M+H).

Step-2

Synthesis of ((S)-3-aminopyrrolidin-1-yl)(5-((R)-2-(2,5-difluorophenyl)pyrrolidin-1-yl)pyrazolo[1,5a]pyridin-3-yl)methanone

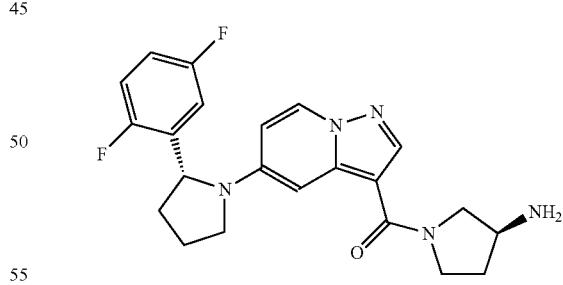

The title compound was prepared by the method substantially similar to that mentioned in Example-32 using TFA to afford 30 mg of the title compound.

$^1$H NMR (400 MHz, DMSO) δ ppm 8.44-8.42 (1H, d, J=7.6 Hz), 8.2 (1H, s), 7.4-7.3 (1H, m), 7.2-7.1 (1H, m), 7.0 (1H, s), 6.9-6.8 (1H, m), 6.42-6.38 (1H, d, J=6.0 Hz), 5.12-5.10 (1H, d, J=8.0 Hz), 3.9-3.8 (2H, m), 3.7-3.4 (5H, m), 3.15-3.0 (2H, m), 2.5-2.4 (1H, m), 2.2-1.85 (4H, m), 1.7-1.5 (1H, m).

MS (ESI): m/z 412.1 (M+H).

Example-68

Synthesis of (R)-5-(2-(2,5-difluorophenyl)pyrrolidin-1-yl)-N-(1-(methylsulfonyl)piperidin-4-yl)pyrazolo[1,5-a]pyridine-3-carboxamide

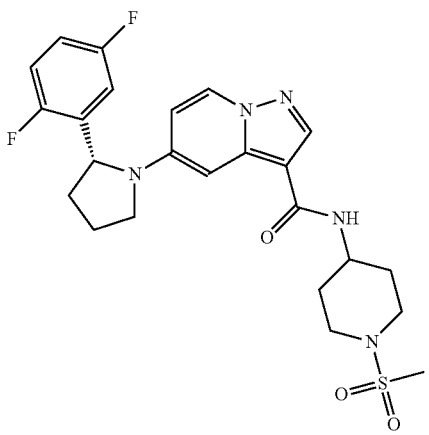 [SMILES: CS(=O)(=O)N1CCC(NC(=O)c2cnn3ccc(N4CCC[C@@H]4c4cc(F)ccc4F)cc23)CC1]

Step-1

Synthesis of (R)-tert-butyl 4-(5-(2-(2,5-difluorophenyl)pyrrolidin-1-yl)pyrazolo[1,5-a]pyridine-3-carboxamido)piperidine-1-carboxylate

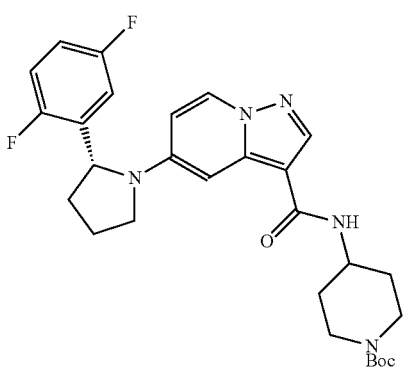 [SMILES: CC(C)(C)OC(=O)N1CCC(NC(=O)c2cnn3ccc(N4CCC[C@@H]4c4cc(F)ccc4F)cc23)CC1]

The title compound was prepared by the similar coupling method as mentioned in Example-16, using tert-butyl 4-aminopiperidine-1-carboxylate in place of octahydro-1H-pyrido[1,2-a]pyrazine to afford 120 mg of the title compound.

MS (ESI): m/z 512.2 (M+H).

Step-2

Synthesis of (R)-5-(2-(2,5-difluorophenyl)pyrrolidin-1-yl)-N-(piperidin-4-yl)pyrazolo[1,5-a]pyridine-3-carboxamide

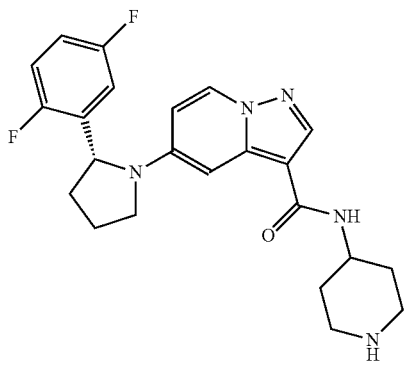 [SMILES: O=C(NC1CCNCC1)c1cnn2ccc(N3CCC[C@@H]3c3cc(F)ccc3F)cc12]

The title compound was prepared by the method substantially similar to that mentioned in Example-32 using TFA to afford 39 mg of the title compound.

MS (ESI): m/z 426.1 (M+H)

Step-3

Synthesis of (R)-5-(2-(2,5-difluorophenyl)pyrrolidin-1-yl)-N-(1-(methylsulfonyl)piperidin-4-yl)pyrazolo[1,5-a]pyridine-3-carboxamide

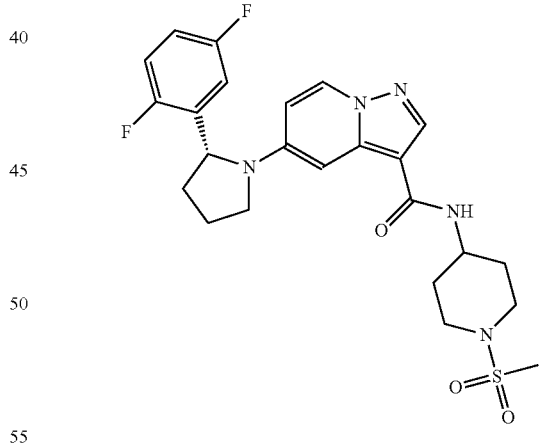

Methane sulfonyl chloride (10 mg, 0.09 mmol) was added to cold (0-5° C.) solution of (R)-5-(2-(2,5-difluorophenyl)pyrrolidin-1-yl)-N-(piperidin-4-yl)pyrazolo[1,5-a]pyridine-3-carboxamide (35 mg, 0.08 mmol) and Et$_3$N (10 mg, 0.1 mmol) in DCM (1 mL); stirring was continued at 25-35° C. for 4 h. Reaction mixture was diluted with DCM, washed with water, aqueous NaHCO$_3$ solution followed by brine to afford the crude compound, which was purified by preparative TLC (using Silicagel GF$_{254}$, 1000 u coated 20×20 cm dimension glass plate and 10% MeOH in CHCl$_3$ as eluent) to afford 53.63 mg of the title compound.

¹H NMR (300 MHz, CD₃OD) δ ppm 8.3-8.12 (3H, m), 8.2 (1H, s), 7.24-6.9 (3H, m), 7.2-6.82 (1H, m), 6.46-6.36 (1H, m), 5.2 (1H, d, J=8.7 Hz), 4.1-3.7 (4H, m), 3.6-3.5 (1H, m), 3.0-2.8 (5H, m), 3.7-2.55 (1H, m), 2.2-1.95 (5H, m), 1.75-1.55 (2H, m).
MS (ESI): m/z 503.7 (M+H).

Example-69

Synthesis of (R)-5-(2-(2,5-difluorophenyl)pyrrolidin-1-yl)-N-(1-(methylsulfonyl)piperidin-4-yl)pyrazolo[1,5-a]pyridine-3-carboxamide

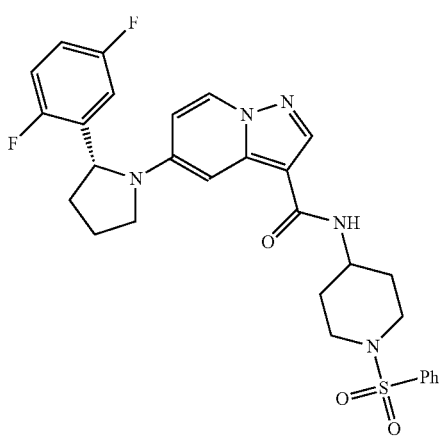 [SMILES: O=C(NC1CCN(S(=O)(=O)c2ccccc2)CC1)c1cnn2ccc(N3CCC[C@@H]3c3cc(F)ccc3F)cc12]

The title compound was prepared by the method substantially similar to that mentioned in Example-68 using benzene sulfonyl chloride in place methane sulfonyl chloride (in THF instead of DCM) to afford 16.5 mg of the title compound.
¹H NMR (300 MHz, CD₃OD) δ ppm 8.35-8.2 (2H, m), 7.85-7.55 (3H, m), 7.2-7.1 (1H, m), 7.1-6.9 (2H, m), 6.8-6.7 (1H, m), 6.5 (1H, m), 5.2 (1H, d, J=7.8 Hz), 4.0-3.4 (5H, m), 2.6-2.3 (3H, m), 2.2-1.9 (5H, m), 1.7-1.55 (1H, m).
MS (ESI): m/z 566.2 (M+H).

Example-70

Synthesis of 5-((R)-2-(2,5-difluorophenyl)pyrrolidin-1-yl)-N-((1R*,2R*)-2-hydroxycyclohexyl)pyrazolo[1,5-a]pyridine-3-carboxamide

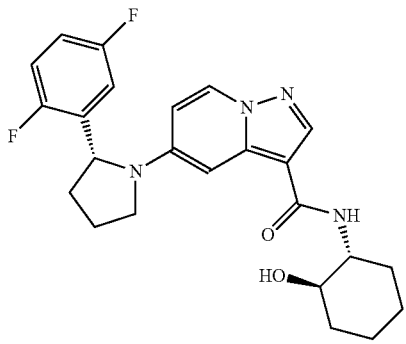 [SMILES: O=C(N[C@@H]1CCCC[C@H]1O)c1cnn2ccc(N3CCC[C@@H]3c3cc(F)ccc3F)cc12]

The title compound was prepared by the similar coupling method as mentioned in Example-6, using (trans)-2-aminocyclohexanol to afford 8.1 mg of the title compound.
MS (ESI): m/z 441.2 (M+H).

Example-71

Synthesis of 5-((R)-2-(2,5-difluorophenyl)pyrrolidin-1-yl)-N—((S)-1-(2-hydroxyethyl)pyrrolidin-3-yl)pyrazolo[1,5-a]pyridine-3-carboxamide

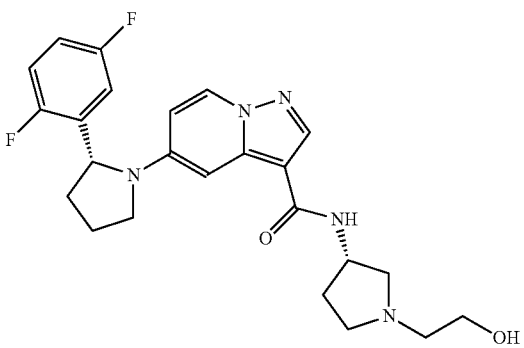 [SMILES: O=C(N[C@H]1CCN(CCO)C1)c1cnn2ccc(N3CCC[C@@H]3c3cc(F)ccc3F)cc12]

Step-1

Synthesis of (S)-Tert-butyl (1-(2-hydroxyethyl)pyrrolidin-3-yl)carbamate

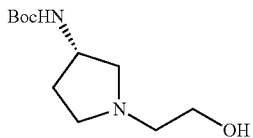

2-Bromoethanol (338 mg, 2.703 mmol) was added to a solution of (S)-tert-butyl pyrrolidin-3-ylcarbamate (500 mg, 2.7 mmol) and Et₃N (328 mg, 3.24 mmol) in acetonitrile (5 mL) in a seal tube and stirring was continued at 60° C. for 32 h. Reaction mixture was concentrated under reduced pressure to afford the crude, which was diluted with EtOAc, washed it with water followed by brine solution and dried over anhydrous sodium sulphate, concentrated under reduced pressure to afford 430 mg of the title compound.
MS (ESI): m/z 230.8 (M+H).

Step-2

Synthesis of (S)-2-(3-aminopyrrolidin-1-yl)ethanol hydrochloride

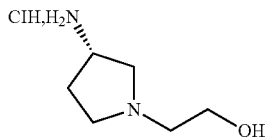

4M HCl solution (in dioxane) (1.5 mL) was added to a stirred solution of (S)-tert-butyl (1-(2-hydroxyethyl)pyrrolidin-3-yl)carbamate (400 mg, 1.73 mmol) in Dioxane (1 mL) and stirring was continued at 20-35° C. for 2 h. After which the reaction mixture was concentrated under reduced pressure to afford the crude. The crude obtained was purified by washing with diethyl ether and dried to afford 300 mg (crude) of the title compound.

MS (ESI): m/z 131.1 (M+H, free base).

Step-3

Synthesis of 5-((R)-2-(2,5-difluorophenyl)pyrrolidin-1-yl)-N—((S)-1-(2-hydroxyethyl)pyrrolidin-3-yl)pyrazolo[1,5-a]pyridine-3-carboxamide

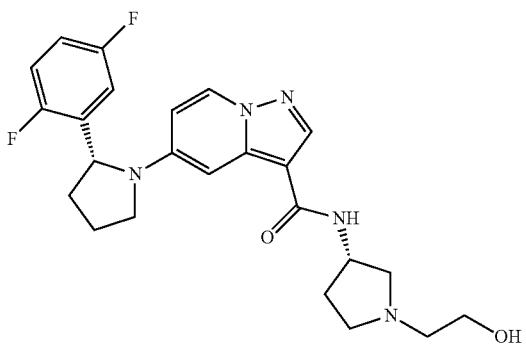 [SMILES: O=C(N[C@H]1CCN(CCO)C1)c1cnn2ccc(N3CCC[C@@H]3c3cc(F)ccc3F)cc12]

The title compound was prepared by the method substantially similar to that mentioned in Example-6, using (S)-2-(3-aminopyrrolidin-1-yl)ethanol hydrochloride in place of $NH_4Cl$ to afford the crude compound. The crude compound was purified by Preparative TLC (using Silicagel $GF_{254}$, 1000 u coated 20×20 cm dimension glass plate and 10% MeOH in DCM as eluent) to afford 32 mg of the title compound.

$^1$H NMR (300 MHz, DMSO-$d_6$) δ ppm 8.41-8.35 (2H, m), 7.8 (1H, d, J=7.2 Hz), 7.38-7.28 (1H, m), 7.20-7.10 (1H, m), 6.95 (1H, s), 6.82-6.90 (1H, m), 6.38-6.32 (1H, m), 5.12-5.09 (1H, d, J=7.6 Hz), 4.50-4.30 (2H, m), 3.85-3.75 (1H, m), 3.52-3.40 (4H, m), 2.80-2.60 (3H, m), 2.5-2.4 (2H, m), 2.15-1.85 (4H, m), 1.72-1.60 (1H, m).

MS (ESI): m/z 456.4 (M+H).

Example-72

Synthesis of (R)-5-(2-(2,5-difluorophenyl)pyrrolidin-1-yl)-N-(4-(pyrrolidin-1-ylmethyl)tetrahydro-2H-pyran-4-yl)pyrazolo[1,5-a]pyridine-3-carboxamide

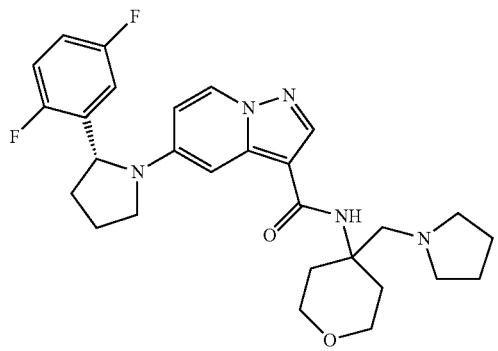 [SMILES: O=C(NC1(CN2CCCC2)CCOCC1)c1cnn2ccc(N3CCC[C@@H]3c3cc(F)ccc3F)cc12]

The title compound was prepared by the method substantially similar to that mentioned in Example-16, using 4-(pyrrolidin-1-ylmethyl)tetrahydro-2H-pyran-4-amine hydrochloride in place of octahydro-1H-pyrido[1,2-a]pyrazine to afford the crude compound. The crude compound was purified by Preparative TLC (using Silicagel $GF_{254}$, 1000 u coated 20×20 cm dimension glass plate and 10% MeOH in DCM as eluent) to afford 31.7 mg of the title compound.

$^1$H NMR (400 MHz, DMSO-$d_6$) δ ppm 8.5 (1H, s), 8.4-8.3 (1H, d, J=7.6 Hz), 7.4-7.3 (1H, m), 7.2-7.1 (1H, m), 7.0-6.8 (3H, m), 6.30-6.28 (1H, d, J=6 Hz), 5.2-5.1 (1H, d, J=8.4 Hz), 3.9-3.8 (1H, t), 3.70-3.60 (2H, m), 3.60-3.50 (2H, t), 3.50-3.40 (2H, m), 2.80 (2H, bs), 2.3-2.2 (2H, m), 2.1-2.0 (1H, m), 2.0-1.8 (2H, m), 1.7-1.5 (6H, m).

MS (ESI): m/z 509.7 (M+H).

Example-73

Synthesis of (R)-5-(2-(2,5-difluorophenyl)pyrrolidin-1-yl)-N-(4-(hydroxymethyl)tetrahydro-2H-pyran-4-yl)pyrazolo[1,5-a]pyridine-3-carboxamide

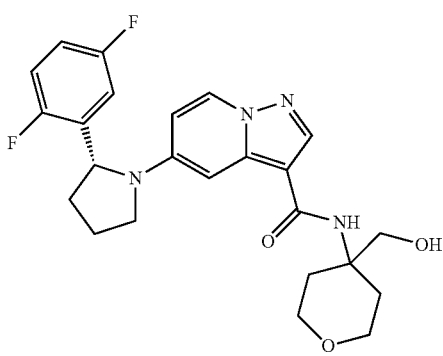 [SMILES: O=C(NC1(CO)CCOCC1)c1cnn2ccc(N3CCC[C@@H]3c3cc(F)ccc3F)cc12]

The title compound was prepared by the method substantially similar to that mentioned in Example-6, using (4-aminotetrahydro-2H-pyran-4-yl)methanol in place of $NH_4Cl$ to afford the crude compound. The crude compound was purified by Preparative TLC (using Silicagel $GF_{254}$, 1000 u coated 20×20 cm dimension glass plate and 100% EtOAc in Hexane as eluent) to afford 21 mg of the title compound.

$^1$H NMR (300 MHz, $CD_3OD$) δ ppm 8.36 (1H, s), 8.25-8.23 (1H, d, J=7.8 Hz), 7.22-6.92 (4H, m), 6.85-6.75 (1H, m), 6.46-6.38 (1H, m), 5.20-5.17 (1H, d, J=8.4 Hz), 3.9-3.4 (8H, m), 2.60-1.95 (6H, m), 1.85-1.65 (2H, m), 1.37-1.35 (1H, d, J=6.6 Hz).

MS (ESI): m/z 456.7 (M+H).

Example-74

Synthesis of (R)-Ethyl 4-(5-(2-(2,5-difluorophenyl)pyrrolidin-1-yl)pyrazolo[1,5a]pyridine-3-carboxamido) piperidine-1-carboxylate

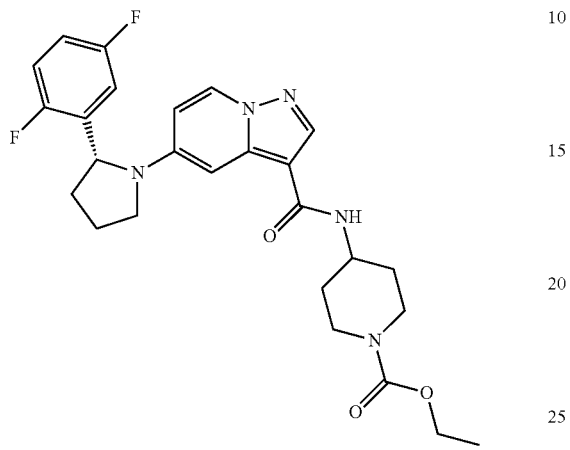

The title compound was prepared by the method substantially similar to that mentioned in Example-68 using Ethyl chloroformate in place Benzene sulfonyl chloride to afford the crude, which was purified by washing with mixture of EtOAc and Hexane to afford 15.3 mg of the title compound.

$^1$H NMR (300 MHz, CD$_3$OD) δ ppm 8.28-8.2 (2H, m), 7.2-7.1 (1H, m), 7.04-6.94 (2H, m), 6.84-6.72 (1H, m), 6.5-6.4 (1H, m), 5.2 (1H, d, J=7.8 Hz), 4.2-3.95 (4H, m), 3.9-3.8 (1H, m), 3.6-3.5 (1H, m), 3.05-2.85 (2H, m), 2.6-2.45 (1H, m), 2.2-1.85 (5H, m), 1.6-1.4 (2H, m), 1.3-1.2 (3H, t).

MS (ESI): m/z 497.8 (M+H).

Example-75

Synthesis of 5-((R)-2-(2,5-difluorophenyl)pyrrolidin-1-yl)-N—((S)-2,4-dihydroxybutyl)pyrazolo[1,5-a]pyridine-3-carboxamide

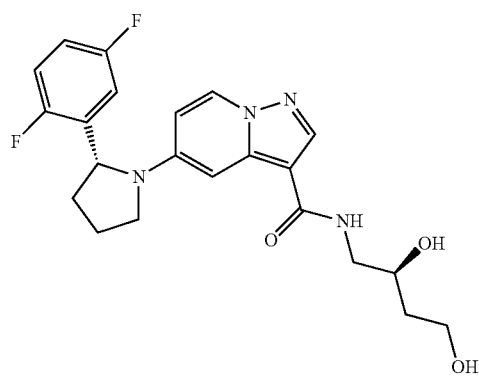 [SMILES: O=C(NC[C@@H](O)CCO)c1cnn2ccc(N3CCC[C@@H]3c3cc(F)ccc3F)cc12]

Step-1

Synthesis of (S)-methyl 4-amino-3-hydroxybutanoate hydrochloride

Thionyl chloride (3 mL) was added to a cold (0° C.) stirred solution of (S)-4-amino-3-hydroxybutanoic acid (300 mg, 2.9 mmol) in MeOH (3 mL) and continued stirring at 62° C. for 12 h. The reaction mixture was concentrated under reduced pressure to afford 300 mg of the title compound.

MS (ESI): m/z 134 (M+H)

Step-2

Synthesis of (S)-methyl 4-(5-((R)-2-(2,5-difluorophenyl)pyrrolidin-1-yl)pyrazolo[1,5-a]pyridine-3-carboxamido)-3-hydroxybutanoate The title compound was prepared by the similar coupling method as mentioned in Example-6, using (S)-methyl 4-amino-3-hydroxybutanoate hydrochloride to afford 100 mg of the title compound.

MS (ESI): m/z 458.9 (M+H).

Step-3

Synthesis of 5-((R)-2-(2,5-difluorophenyl)pyrrolidin-1-yl)-N—((S)-2,4-dihydroxybutyl)pyrazolo[1,5-a]pyridine-3-carboxamide

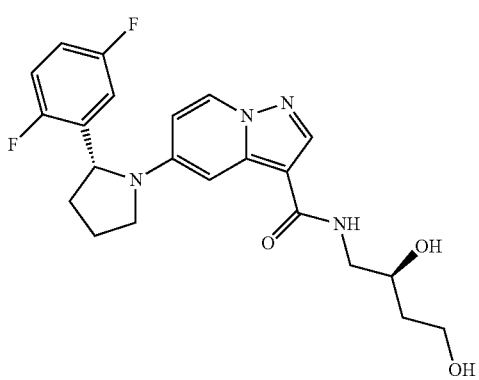 [SMILES: O=C(NC[C@@H](O)CCO)c1cnn2ccc(N3CCC[C@@H]3c3cc(F)ccc3F)cc12]

LAH (12 mg, 0.33 mmol) was added portionwise to a solution of (S)-methyl 4-(5-((R)-2-(2,5-difluorophenyl)pyrrolidin-1-yl)pyrazolo[1,5-a]pyridine-3-carboxamido)-3-hydroxybutanoate (100 mg, 0.22 mmol) in THF (2 mL) at 0-5° C. and continued stirring at the same temperature for 1 h. EtOAc was added to the above reaction mixture followed by NH$_4$Cl solution and water. Organic layer separated was dried over anhydrous sodium sulphate and concentrated under reduced pressure to afford the crude product, which was purified by Preparative TLC (using Silicagel GF$_{254}$, 1000 u coated 20×20 cm dimension glass plate and 7% MeOH in CHCl$_3$ as eluent) to afford 10.3 mg of the title compound.

$^1$H NMR (300 MHz, CD$_3$OD) δ ppm 8.3-8.2 (2H, m), 7.20-6.95 (3H, m), 6.8-6.7 (1H, m), 6.45-6.42 (1H, d, J=6.0 Hz), 5.2-5.17 (1H, d, J=8.1 Hz), 3.96-3.80 (2H, m), 3.78-3.66 (2H, t), 3.60-3.40 (2H, m), 2.55-2.45 (1H, m), 2.2-1.96 (3H, m), 1.84-1.54 (2H, m).

MS (ESI): m/z 431.1 (M+H).

Example-76

Synthesis of (R)-5-(2-(2,5-difluorophenyl)pyrrolidin-1-yl)-N-(1-(2-hydroxyethyl)piperidin-4-yl)pyrazolo[1,5-a]pyridine-3-carboxamide

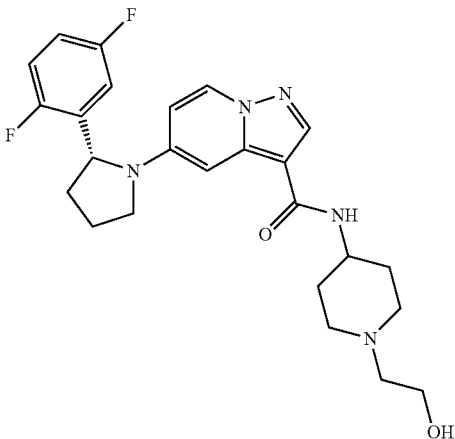 [SMILES: O=C(NC1CCN(CCO)CC1)c1cnn2ccc(N3CCC[C@@H]3c3cc(F)ccc3F)cc12]

2-Bromoethanol (18 mg, 0.14 mmol) was added to stirred solution of (R)-5-(2-(2,5-difluorophenyl)pyrrolidin-1-yl)-N-(piperidin-4-yl)pyrazolo[1,5-a]pyridine-3-carboxamide (50 mg, 0.12 mmol) (Example-32) in acetonitrile (0.5 mL) and stirring was continued at 70° C. for 4 h. The reaction mixture was diluted with EtOAc, washed the organic layer with water and dried over anhydrous sodium sulphate, concentrated under reduced pressure to afford the crude product, which was purified by Preparative HPLC [Column:21.2×150×5 um, waters× bridge C-18, Mobile phase-A: 0.1% TFA in water, B:ACN, Gradient (Time/% B): 0/20, 2/30, 1870 and Flow rate:20 mL/min] to afford 4.1 mg of the title compound.

$^1$H NMR (300 MHz, CD$_3$OD) δ ppm 8.25-8.20 (2H, m), 7.2-6.95 (3H, m), 6.8-6.7 (1H, m), 6.45-6.43 (1H, m), 5.20-5.16 (1H, d, J=8.4 Hz), 4.10-3.65 (5H, m), 3.60-3.45 (2H, m), 3.05-2.95 (2H, d, J=12.3 Hz), 2.6-2.45-(3H, m), 2.3-1.85 (7H, m), 1.75-1.55 (2H, m).

MS (ESI): m/z 470.4 (M+H).

Example-77

Synthesis of (5-((R)-2-(2,5-difluorophenyl)pyrrolidin-1-yl)pyrazolo[1,5a]pyridin-3-yl)((S)-3-(hydroxymethyl)piperidin-1-yl)methanone

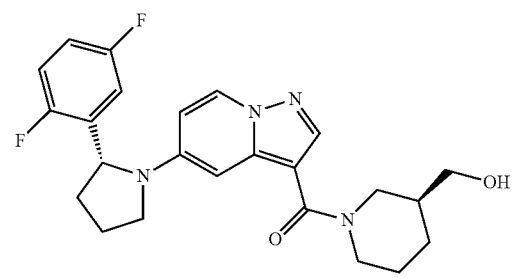 [SMILES: O=C(c1cnn2ccc(N3CCC[C@@H]3c3cc(F)ccc3F)cc12)N1CCC[C@H](CO)C1]

The title compound was prepared by the similar coupling method as mentioned in Example-23, using (S)-piperidin-3-ylmethanol in place of octahydro-1H-pyrido[1,2-a]pyrazine to afford crude. The crude compound was purified by Preparative HPLC [Column:21.2×150×5 um, Zorbax, XDB,C-18, Mobile phase-A: 0.1% TFA in water, B:ACN:MeOH (1:1), Isocratic: A: 52% and B:48%, Flow rate:20 mL/min] 21 mg of the title compound.

$^1$H NMR (400 MHz, CDCl$_3$) δ ppm 8.16-8.14 (1H, d, J=7.6 Hz), 7.95 (1H, s), 7.1-7.04 (1H, m), 6.95-6.87 (1H, m), 6.8-6.68 (2H, m), 6.20-6.16 (1H, m), 5.20-5.17 (1H, d, J=8.0 Hz), 3.9-3.4 (8H, m), 2.5-2.4 (1H, m), 2.2-1.8 (5H, m), 1.5-1.4 (3H, m).

MS (ESI): m/z 441.4 (M+H).

Example-78

Synthesis of (5-((R)-2-(2,5-difluorophenyl)pyrrolidin-1-yl)pyrazolo[1,5a]pyridin-3-yl)((R)-3-(hydroxymethyl)piperidin-1-yl)methanone

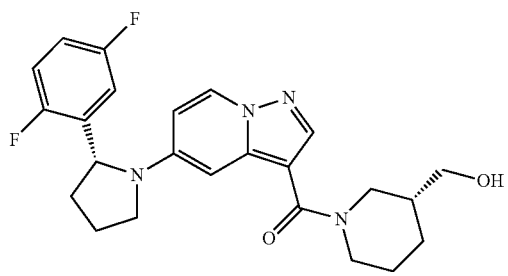 [SMILES: O=C(c1cnn2ccc(N3CCC[C@@H]3c3cc(F)ccc3F)cc12)N1CCC[C@@H](CO)C1]

The title compound was prepared by the similar coupling method as mentioned in Example-23, using (R)-piperidin-3-ylmethanol in place of NH$_4$Cl to afford the crude, which was purified by Preparative HPLC [Column: 21.2×150×5 u, Zorbax, Eclipse, C-18, Mobile phase-A: 10 mmol NH$_4$OAc in Water, B:ACN, Gradient (Time/% B): 0/30, 2/30, 10/90 and Flow rate:20 mL/min] 30 mg of the title compound.

$^1$H NMR (400 MHz, CDCl$_3$) δ ppm 8.16-8.14 (1H, d, J=7.6 Hz), 7.93 (1H, s), 7.10-7.04 (1H, m), 6.95-6.87 (1H, m), 6.84 (1H, s), 6.74-6.68 (1H, m), 6.2-6.15 (1H, m), 5.12-5.10 (1H, d, J=8.0 Hz), 3.95-3.70 (2H, m), 3.6-3.4 (5H, m), 2.5-2.4 (1H, m), 2.15-1.4 (9H, m).

MS (ESI): m/z 440.9 (M+H)

Example-79

Synthesis of (R)-5-(2-(2,5-difluorophenyl)pyrrolidin-1-yl)-N-(4-hydroxypiperidin-1-yl)pyrazolo[1,5-a]pyridine-3-carboxamide

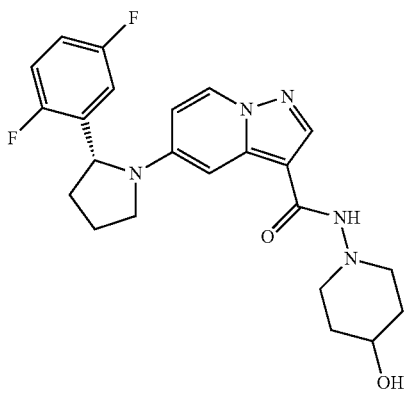 [SMILES: O=C(NN1CCC(O)CC1)c1cnn2ccc(N3CCC[C@@H]3c3cc(F)ccc3F)cc12]

The title compound was prepared by the method substantially similar to that mentioned in Example-6, using 1-aminopiperidin-4-ol (WO 2007/127688) in place of NH$_4$Cl to afford 53.1 mg of the title compound.

$^1$H NMR (400 MHz, DMSO-d$_6$) δ ppm 8.74 (1H, s) 8.42 (1H, d, J=7.6 Hz), 8.26 (1H, s) 7.34-7.30 (1H, m), 7.20-7.12 (1H, m), 6.95-6.88 (1H, m), 6.41-6.35 (1H, d, J=6.4 Hz), 5.15-5.13 (1H, d, J=8 Hz), 4.63 (1H, s) 3.88-3.81 (1H, m), 3.60-3.40 (2H, m), 2.95-2.88 (2H, m), 2.75-2.65 (2H, m), 2.10-1.85 (3H, m), 1.75 (1H, bs), 1.55-1.45 (2H, m).

MS (ESI): m/z 442.2 (M+H).

Example-80

Synthesis of 5-((R)-2-(2,5-difluorophenyl)pyrrolidin-1-yl)-N—((S)-1-(methylsulfonyl)pyrrolidin-3-yl)pyrazolo[1,5-a]pyridine-3-carboxamide

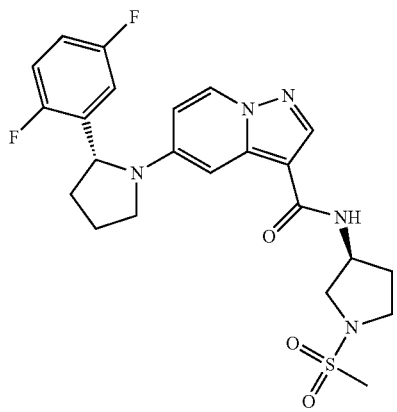 [SMILES: CS(=O)(=O)N1CC[C@H](NC(=O)c2cnn3ccc(N4CCC[C@@H]4c4cc(F)ccc4F)cc23)C1]

Step-1

Synthesis of (S)-tert-butyl (1-(methylsulfonyl)pyrrolidin-3-yl)carbamate

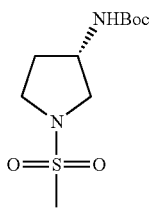 [SMILES: CC(C)(C)OC(=O)N[C@H]1CCN(S(C)(=O)=O)C1]

Methane sulfonyl chloride (204 mg, 1.78 mmol) was added to a solution of (S)-tert-butyl pyrrolidin-3-ylcarbamate (300 mg, 1.62 mmol) and Et₃N (197 mg, 1.94 mmol) in DCM (6 mL) at 0-5° C.; stirring was continued at 20-35° C. for 2 h. The reaction mixture was diluted with DCM, washed with water, aqueous NaHCO₃ solution followed by brine to afford 250 mg of the title compound.

Step-2

Synthesis of (S)-1-(methylsulfonyl)pyrrolidin-3-amine hydrochloride

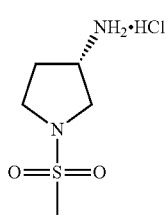

4M HCl solution (in Dioxane) (2 mL) and (S)-tert-butyl (1-(methylsulfonyl)pyrrolidin-3-yl)carbamate (200 mg, 0.99 mmol) was stirred at 20-35° C. for 2 h. The solid precipitate thus obtained was filtered, washed with hexane and dried to afford 120 mg of the title compound.

MS (ESI): m/z 164.9 (M+H).

Step-3

Synthesis of 5-((R)-2-(2,5-difluorophenyl)pyrrolidin-1-yl)-N—((S)-1-(methylsulfonyl)pyrrolidin-3-yl) pyrazolo[1,5-a]pyridine-3-carboxamide

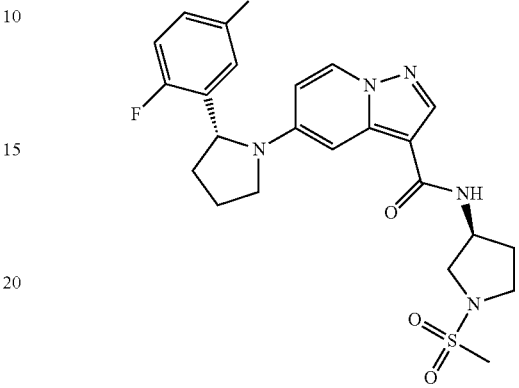

The title compound was prepared by the method substantially similar to that mentioned in Example-16, using (S)-1-(methylsulfonyl)pyrrolidin-3-amine hydrochloride to afford 89.9 mg of the title compound.

¹H NMR (400 MHz, DMSO-d₆) δ ppm 8.43-8.41 (1H, d, J=8 Hz), 8.34 (1H, s), 7.90-7.89 (1H, d, J=6.4 Hz), 7.40-7.30 (1H, m), 7.20-7.12 (1H, m), 6.95 (1H, s), 6.92-6.84 (1H, m), 6.39-6.38 (1H, d, J=6.0 Hz), 5.13-5.11 (1H, d, J=8.0 Hz), 4.5-4.4 (1H, m), 3.9-3.8 (1H, m), 3.56-3.40 (3H, m), 3.16-3.10 (1H, m), 2.91 (3H, s), 2.2-2.0 (2H, m), 2.0-1.86 (3H, m), 1.24 (1H, m).

MS (ESI): 489.8 (M+H).

Example-81

Synthesis of (R)-Methyl 1-benzyl-4-(5-(2-(2,5-difluorophenyl)pyrrolidin-1-yl)pyrazolo[1,5a]pyridine-3-carboxamido) piperidine-4-carboxylate

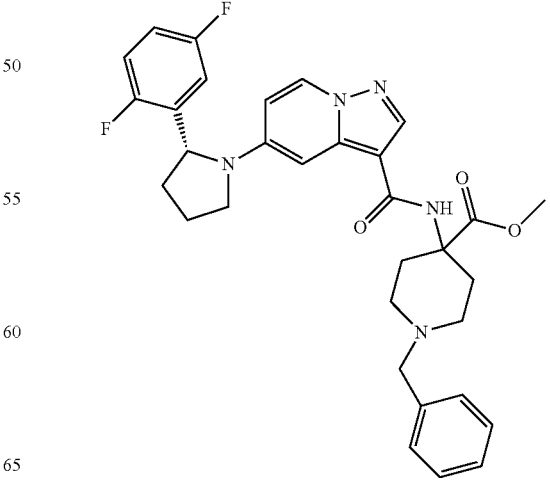

The title compound was prepared by the method substantially similar to that mentioned in Example-16, using methyl 4-amino-1-benzylpiperidine-4-carboxylate dihydrochloride to afford crude. The crude compound was purified by Preparative TLC (using Silicagel GF$_{254}$, 1000 u coated 20×20 cm dimension glass plate and 10% MeOH in CHCl$_3$ as eluent) to afford 7 mg of the title compound.

$^1$H NMR (300 MHz, DMSO-d$_6$) δ ppm 8.5-8.35 (2H, m), 7.75 (1H, s), 7.4-7.1 (7H, m), 6.95-6.8 (2H, m), 6.31-6.29 (1H, d, J=5.4 Hz), 5.16-5.13 (1H, d, J=7.8 Hz), 3.9-3.78 (1H, m), 3.6 (3H, s), 3.5-3.4 (3H, m), 2.6-2.5 (1H, m), 2.38-1.84 (9H, m).

MS (ESI): m/z 574.2 (M+H).

Example-82

Synthesis of 5-((R)-2-(2,5-difluorophenyl)pyrrolidin-1-yl)-N-((S)-pyrrolidin-3-yl)pyrazolo[1,5a]pyridine-3-carboxamide

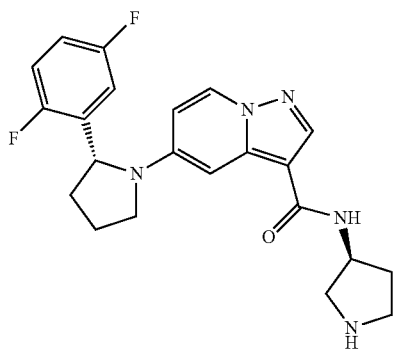 [SMILES: O=C(N[C@H]1CCNC1)c1cnn2ccc(N3CCC[C@@H]3c3cc(F)ccc3F)cc12]

Step-1

(S)-Tert-butyl 3-(5-((R)-2-(2,5-difluorophenyl)pyrrolidin-1-yl)pyrazolo[1,5a]pyridine-3-carboxamido)pyrrolidine-1-carboxylate

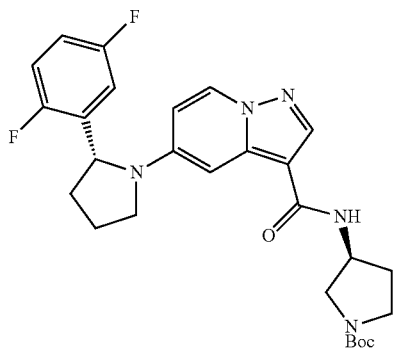 [SMILES: CC(C)(C)OC(=O)N1CC[C@H](NC(=O)c2cnn3ccc(N4CCC[C@@H]4c4cc(F)ccc4F)cc23)C1]

The title compound was prepared by the method substantially similar to that mentioned in Example-16, using (S)-tert-butyl 3-aminopyrrolidine-1-carboxylatehydrochloride to afford 115 mg of the title compound.

MS (ESI): m/z 456.1 (M-56).

Step-2

Synthesis of 5-((R)-2-(2,5-difluorophenyl)pyrrolidin-1-yl)-N-((S)-pyrrolidin-3-yl)pyrazolo[1,5a]pyridine-3-carboxamide

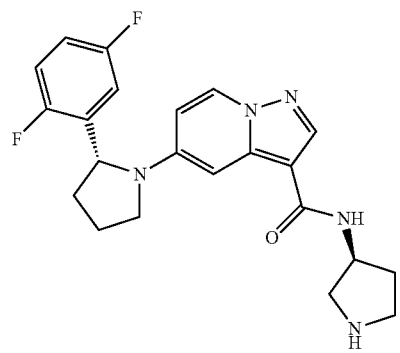 [SMILES: O=C(N[C@H]1CCNC1)c1cnn2ccc(N3CCC[C@@H]3c3cc(F)ccc3F)cc12]

4M HCl solution (in Dioxane) (2 mL) was added to a stirred solution of (R)-methyl 4-((tert-butoxycarbonyl)amino)-1-(5-(2-(2,5-difluorophenyl)pyrrolidin-1-yl)pyrazolo[1,5-pyridine-3-carbonyl)piperidine-4-carboxylate (110 mg, 0.215 mmol) in Dioxane (1 mL) and stirring was continued at 25° C. for 2 h. After which the reaction mixture was concentrated under reduced pressure to afford the crude. The crude thus obtained was purified by washing with diethyl ether and further stirred in sat. NaHCO$_3$ solution filtered and dried to afford 72.6 mg of the title compound as white solid.

$^1$H NMR (400 MHz, DMSO-d$_6$) δ ppm 8.40 (1H, d, J=7.5 Hz), 8.35 (1H, s), 7.90-7.75 (1H, m), 7.4-7.3 (1H, m), 7.20-7.10 (1H, m), 6.95 (1H, s), 6.95-6.88 (1H, m), 6.40-6.32 (1H, d, J=6.3 Hz), 5.12-5.10 (1H, d, J=7.8 Hz), 4.4-4.2 (1H, m), 3.90-3.80 (1H, m), 3.0-2.50 (4H, m), 2.1-1.85 (5H, m), 1.60-1.50 (1H, m).

MS (ESI): 411.9 (M+H).

Example-83

Synthesis of 5-((R)-2-(2,5-difluorophenyl)pyrrolidin-1-yl)-N-(tetrahydro-2H-pyran-3-yl)pyrazolo[1,5-a]pyridine-3-carboxamide

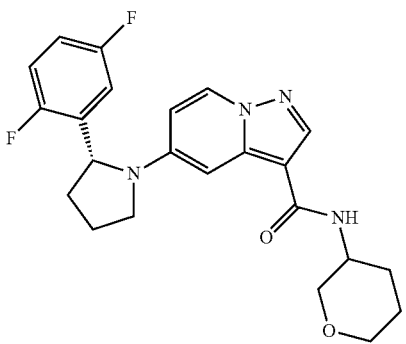 [SMILES: O=C(NC1CCCOC1)c1cnn2ccc(N3CCC[C@@H]3c3cc(F)ccc3F)cc12]

The title compound was prepared by the method substantially similar to that mentioned in Example-16, using tetrahydro-2H-pyran-3-amine to afford 42 mg of the title compound.

MS (ESI): m/z 427.3 (M+H).

Example-84

Synthesis of 5-((R)-2-(2,5-difluorophenyl)pyrrolidin-1-yl)-N-((1R,2R)-2-hydroxycyclopentyl)pyrazolo[1,5-a]pyridine-3-carboxamide

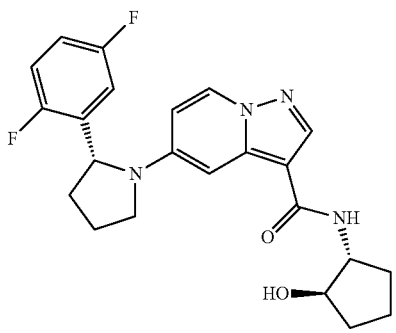 [SMILES: O=C(N[C@@H]1CCC[C@H]1O)c1cnn2ccc(N3CCC[C@@H]3c3cc(F)ccc3F)cc12]

The title compound was prepared by the similar coupling method as mentioned in Example-6, using (1R,2R)-2-aminocyclopentanol to afford crude. The crude compound was purified by recrystallisation from mixture of EtOAc and Hexane to afford 40 mg of the title compound $^1$H NMR (300 MHz, DMSO-d$_6$) δ ppm 8.4-8.3 (1H, d, J=7.5 Hz), 8.35 (1H, s), 7.65-7.55 (1H, d, J=6.3 Hz), 7.4-7.3 (1H, m), 7.2-7.1 (1H, m), 7.0-6.8 (2H, m), 6.4-6.3 (1H, d, J=6.3 Hz), 5.15-5.05 (1H, d, J=7.8 Hz), 4.85-4.8 (1H, t), 4.0-3.8 (3H, m), 3.5-3.35 (1H, m), 2.5-2.35 (2H, m), 2.15-1.7 (5H, m), 1.7-1.5 (2H, m), 1.5-1.3 (2H, m).

MS (ESI): m/z 426.9 (M+H)

Example-85

Synthesis of (R)-Methyl 4-(5-(2-(2,5-difluorophenyl)pyrrolidin-1-yl)pyrazolo[1,5a]pyridine-3-carboxamido) piperidine-4-carboxylate

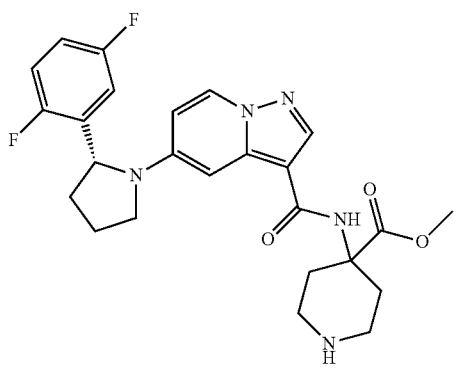 [SMILES: COC(=O)C1(NC(=O)c2cnn3ccc(N4CCC[C@@H]4c4cc(F)ccc4F)cc23)CCNCC1]

10% Pd/C (20 mg) was added to a solution of (R)-Methyl 1-benzyl-4-(5-(2-(2,5-difluorophenyl)pyrrolidin-1-yl)pyrazolo[1,5a]pyridine-3-carboxamido) piperidine-4-carboxylate (Example-81) (130 mg, 0.22 mmol) in MeOH (10 mL) and the mixture was stirred continuously under hydrogen atmosphere at 20-35° C. for 6 h. The reaction mixture was filtered over a celite bed and the filtrate was concentrated under reduced pressure to afford the crude. The crude compound was purified by Preparative HPLC [Column: 21.2×250×7 um, Zorbax, XDB C-18, Mobile phase-A: 0.1% TFA in Water, B:ACN, Gradient (Time/% B): 0/10, 2/20, 8/60 and Flow rate:20 mL/min] to afford 10 mg of the title compound.

$^1$H NMR (300 MHz, CD$_3$OD) δ ppm 8.35 (1H, s), 8.3-8.2 (1H, d, J=7.8 Hz), 7.2-7.1 (1H, m), 7.05-6.9 (2H, m), 6.8-6.7 (1H, m), 6.45-6.35 (1H, m), 5.2-5.15 (1H, d J=8.1 Hz), 3.8-3.7 (1H, m), 3.68 (3H, s), 3.65-3.45 (1H, m), 3.1-2.9 (4H, m), 2.6-2.4 (1H, m), 2.25-1.9 (8H, m).

MS (ESI): m/z 484.4 (M+H).

Example-86

Synthesis of (R)—N-(cyanomethyl)-5-(2-(2,5-difluorophenyl)pyrrolidin-1-yl)pyrazolo[1,5-a]pyridine-3-carboxamide

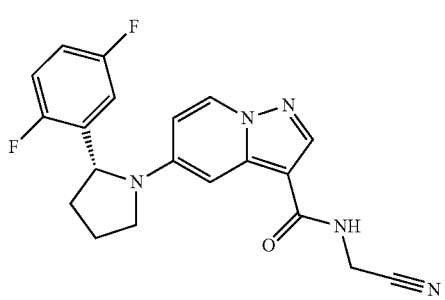 [SMILES: N#CCNC(=O)c1cnn2ccc(N3CCC[C@@H]3c3cc(F)ccc3F)cc12]

The title compound was prepared by the method substantially similar to that mentioned in Example-6 using 2-aminoacetonitrile sulfate, to afford the crude, which was purified by Preparative TLC (using Silicagel GF$_{254}$, 1000 u coated 20×20 cm dimension glass plate and 10% MeOH in DCM as eluent).

$^1$H NMR (400 MHz, CDCl$_3$) δ ppm 8.15-8.13 (1H, d, J=7.6 Hz), 7.97 (1H, s), 7.16 (1H, m), 7.09-7.04 (1H, m), 6.95-6.89 (1H, m), 6.69-6.65 (1H, m), 6.21-6.18 (1H, dd, J=2.4, 8.0 Hz), 5.98 (1H, t), 5.15-5.13 (1H, d, J=8.4 Hz), 4.38-4.36 (2H, d, J=5.6 Hz), 3.80 (1H, t), 3.58-3.52 (1H, q), 2.50-2.44 (1H, m), 2.15-2.04 (4H, m).

MS (ESI): m/z 382.2 (M+H).

Example-87

Synthesis of (R)—N-((2H-tetrazol-5-yl)methyl)-5-(2-(2,5-difluorophenyl)pyrrolidin-1-yl)pyrazolo[1,5-a]pyridine-3-carboxamide

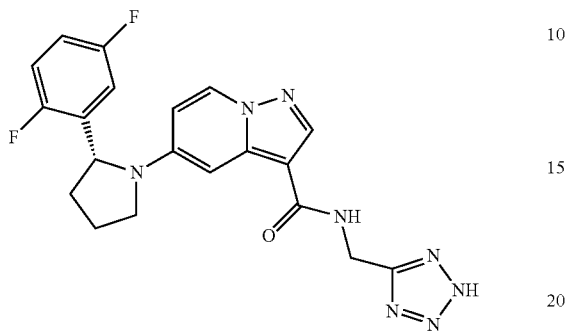

NaN$_3$ (31 mg, 0.47 mmol) and ZnBr$_2$ (27 mg, 0.12 mmol) were added to a solution of (R)—N-(cyanomethyl)-5-(2-(2,5-difluorophenyl)pyrrolidin-1-yl)pyrazolo[1,5-a]pyridine-3-carboxamide (90 mg, 0.24 mmol) in a mixture of 2-propanol (1 mL) and water (1 mL); continued stirring at 50° C. for 12 h. The reaction mixture was quenched with aqueous 2N HCl solution and extracted with EtOAc, dried over anhydrous sodium sulphate, concentrated under reduced pressure to afford the crude. The crude product obtained was purified by dissolving in DCM and reprecipitated with n-Pentane, filtered and dried to afford 55 mg, of the title compound.

$^1$H NMR (400 MHz, DMSO-d$_6$) δ ppm 8.62 (1H, t), 8.44-8.42 (1H, d, J=7.6 Hz), 8.32 (1H, s), 7.35-7.29 (1H, m), 7.16-7.12 (1H, m), 6.93 (1H, bs), 6.88-6.83 (1H, m), 6.38-6.37 (1H, m), 5.12-5.10 (1H, d, J=8.0 Hz), 4.69-4.67 (2H, m), 3.83 (1H, t), 3.45-3.33 (2H, m), 2.03-1.88 (3H, m).

MS (ESI): m/z 425.2 (M+H)

Example-88

Synthesis of (R)-1-(5-(2-(2,5-difluorophenyl)pyrrolidin-1-yl)pyrazolo[1,5-a]pyridine-3-carbonyl)piperidine-4-carbonitrile

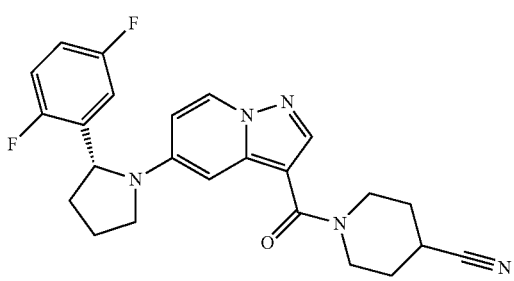 [SMILES: N#CC1CCN(C(=O)c2cnn3ccc(N4CCC[C@@H]4c4cc(F)ccc4F)cc23)CC1]

The title compound was prepared by the method substantially similar to that mentioned in Example-16, using 4-cyano piperidine to afford the crude, which was purified by column chromatography (using silica gel 60-120, and 5% EtOAc in Hexane as eluent) to afford 120 mg of the title compound.

$^1$H NMR (300 MHz, CD$_3$OD) δ ppm 8.29-8.26 (1H, d, J=7.8 Hz), 7.97 (1H, s), 7.22-7.16 (1H, m), 7.05-7.01 (1H, m), 6.82-6.76 (1H, m), 6.52-6.47 (2H, m), 5.17-5.14 (1H, d, J=7.6 Hz), 3.85-3.83 (3H, m), 3.59-3.42 (4H, m), 3.08-3.03 (1, m), 2.54-2.49 (1H, m), 2.14-1.91 (6H, m).

MS (ESI): m/z 436.2 (M+H)

Example-89

Synthesis of 5-((R)-2-(2,5-difluorophenyl)pyrrolidin-1-yl)-N-((1r,4R)-4-(methoxycarbamoyl)cyclohexyl)pyrazolo[1,5-a]pyridine-3-carboxamide

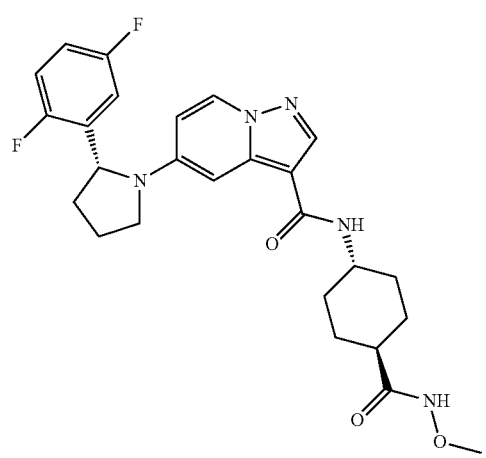 [SMILES: CONC(=O)[C@H]1CC[C@H](NC(=O)c2cnn3ccc(N4CCC[C@@H]4c4cc(F)ccc4F)cc23)CC1]

Step-1

Synthesis of (1r,4r)-4-(((benzyloxy)carbonyl)amino)cyclohexanecarboxylic acid

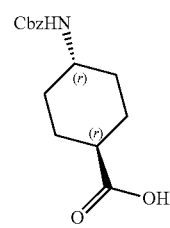 [SMILES: O=C(N[C@H]1CC[C@H](C(=O)O)CC1)OCc1ccccc1]

NaOH (890 mg, 22.2 mmol) in water (52 mL) was added to a stirred solution of trans-4-aminocyclohexanecarboxylic acid (2 g, 11.13 mmol) in THF (26 mL) at 0-5° C. followed by addition of benzylchloroformate (2.08 g, 12.2 mmol) and stirring was continued at 20-35° C. for 3 h. The reaction mixture was concentrated under reduced pressure to afford the crude, which was diluted with EtOAc, washed with water, dried over anhydrous sodium sulphate and concentrated under reduced pressure to afford 2.2 g of the title compound.

¹H NMR (300 MHz, DMSO-d₆) δ ppm 7.5-7.2 (5H, m), 5.0 (2H, s), 3.3-3.1 (1H, m), 2.3-1.7 (5H, m), 1.5-1.1 (4H, m).

Step-2

Synthesis of Benzyl((1r,4r)-4-(methoxycarbamoyl)cyclohexyl)carbamate

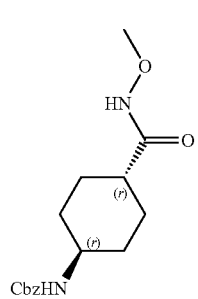 [SMILES: CONC(=O)[C@H]1CC[C@H](NC(=O)OCc2ccccc2)CC1]

The title compound was synthesized by the method substantially similar to that mentioned in the Example-16 using O-methyl hydroxylamine hydrochloride to afford 400 mg of the title compound.

MS (ESI): m/z 306.9 (M+H).

Step-3

Synthesis of (1r,4r)-4-amino-N-methoxycyclohexanecarboxamide

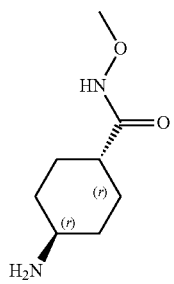

10% Pd/C (30 mg) was added to a solution of Benzyl ((1r,4r)-4-(methoxycarbamoyl)cyclohexyl) carbamate (300 mg, 0.98 mmol) in MeOH (3 mL) and the mixture was stirred continuously under hydrogen atmosphere at 20-35° C. for 4.0 h. The reaction mixture was filtered over a celite bed and the filtrate was concentrated under reduced pressure to afford 160 mg (crude) of the title compound.

MS (ESI): m/z 173 (M+H).

Step-4

Synthesis of 5-((R)-2-(2,5-difluorophenyl)pyrrolidin-1-yl)-N-((1r,4R)-4-(methoxycarbamoyl)cyclohexyl)pyrazolo[1,5-a]pyridine-3-carboxamide

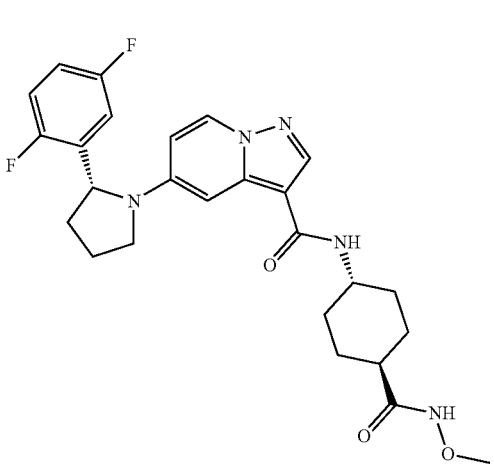 [SMILES: CONC(=O)[C@H]1CC[C@H](NC(=O)c2cnn3ccc(N4CCC[C@@H]4c4cc(F)ccc4F)cc23)CC1]

The title compound was prepared by the method substantially similar to that mentioned in Example-16 using (1r,4r)-4-amino-N-methoxycyclohexanecarboxamide to afford the crude, which was purified by Preparative TLC (using Silica-gel GF₂₅₄, 1000 u coated 20×20 cm dimension glass plate and 80% EtOAc in Hexane as eluent) to afford 20 mg of the title compound.

¹H NMR (300 MHz, CD₃OD) δ ppm 8.24-8.22 (2H, m), 7.19-7.12 (1H, m), 7.02-6.98 (2H, m), 6.80-6.75 (1H, m), 6.45-6.42 (1H, dd, J=2.4, 7.8 Hz), 5.18-5.16 (1H, d, J=7.8 Hz), 3.84-3.82 (2H, m), 3.66 (3H, s), 3.58-3.53 (1H, m), 2.53-2.48 (1H, m), 2.12-2.01 (7H, m), 1.88-1.84 (2H, m), 1.70-1.63 (2H, m), 1.43-1.30 (3H, m).

MS (ESI): m/z 498.5 (M+H).

Example-90

Synthesis of (R)—N-cyclopropyl-5-(2-(2,5-difluorophenyl)pyrrolidin-1-yl)pyrazolo[1,5-a]pyridine-3-carboxamide

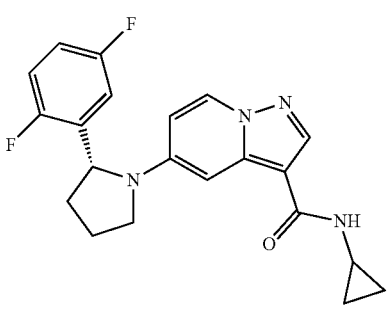 [SMILES: O=C(NC1CC1)c1cnn2ccc(N3CCC[C@@H]3c3cc(F)ccc3F)cc12]

The title compound was prepared by the method substantially similar to that mentioned in Example-16, using cyclopropylamine in place of octahydro-1H-pyrido[1,2-a]pyrazine to afford the crude compound. The crude compound was purified by Preparative TLC (using Silicagel GF$_{254}$, 1000 u coated 20×20 cm dimension glass plate and 80% EtOAc in Hexane as eluent) to afford 29 mg of the title compound.

$^1$H NMR (400 MHz, CDCl$_3$) δ ppm 8.13-8.111 (1H, d, J=7.6 Hz), 7.91 (1H, bs), 7.26-7.0 (1H, m), 6.95-6.85 (1H, m), 6.70-6.65 (1H, m), 6.2-6.1 (1H, dm, J=4.8 Hz) 5.83 (1H, bs), 5.2-5.1 (1H, d, J=8.4 Hz), 3.8-3.7 (1H, m), 3.60-3.50 (1H, m), 2.9-2.8 (1H, m), 2.5-2.4 (1H, m), 2.2-1.95 (3H, m), 1.25 (1H,$) 0.9-0.75 (2H, m), 0.7-0.5 (2H, m).

MS (ESI): m/z 383.2 (M+H).

Example-91

Synthesis of (R)-5-(2-(2,5-difluorophenyl)pyrrolidin-1-yl)-N-((1-(hydroxymethyl)cyclopentyl)methyl)pyrazolo[1,5-a]pyridine-3-carboxamide

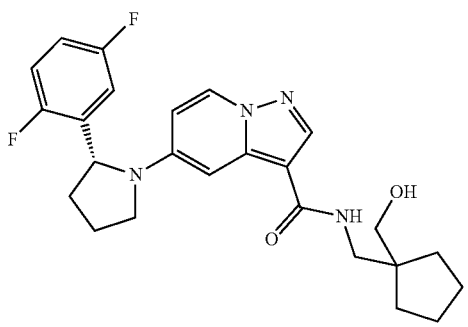 [SMILES: O=C(NCC1(CO)CCCC1)c1cnn2ccc(N3CCC[C@@H]3c3cc(F)ccc3F)cc12]

The title compound was prepared by the similar coupling method as mentioned in Example-23, using (1-(aminomethyl)cyclopentyl)methanol in place of octahydro-1H-pyrido[1,2-a]pyrazine to afford crude. The crude compound was purified by washing with mixture of DCM and n-Hexane to afford 88 mg of the title compound.

$^1$H NMR (300 MHz, CDCl$_3$) δ ppm 8.2-8.1 (1H, d, J=7.5 Hz), 8.0 (1H, s), 7.3 (1H, d, J=2.4 Hz), 7.1-7.0 (1H, m), 7.0-6.9 (1H, m), 6.8-6.6 (1H, m), 6.2-6.1 (2H, s), 5.2-5.1 (1H, d, J=7.8 Hz), 4.5 (1H, bs), 3.90-3.70 (1H, m), 3.60-3.50 (1H, m), 3.40 (2H, d), 3.3 (2H, s), 2.5-2.4 (1H, m), 2.1-2.0 (3H, m), 1.7-1.6 (4H, m), 1.6-1.5 (3H, m), 1.5-1.3 (2H, m).

MS (ESI): m/z 455.2 (M+H)

Example-92

Synthesis of (R)-5-(2-(2,5-difluorophenyl)pyrrolidin-1-yl)-N-(2-methoxyethyl)pyrazolo[1,5-a]pyridine-3-carboxamide

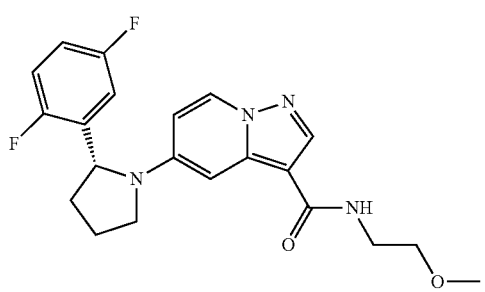 [SMILES: COCCNC(=O)c1cnn2ccc(N3CCC[C@@H]3c3cc(F)ccc3F)cc12]

The title compound was prepared by the method substantially similar to that mentioned in Example-16, using 2-methoxyethaneamine in place of octahydro-1H-pyrido[1,2-a]pyrazine to afford 60 mg of the title compound.

$^1$H NMR (400 MHz, DMSO-d$_6$) δ ppm 8.45-8.35 (1H, d, J=8.0 Hz), 8.3 (1H, s), 7.95-7.85 (1H, t), 7.4-7.25 (1H, m), 7.2-7.1 (1H, m), 7.0-6.9 (1H, s), 6.9-6.8 (1H, m), 6.83 (1H, m), 6.4-6.3 (1H, d, J=6.8 Hz), 5.2-5.05 (1H, d, J=8.0 Hz), 3.9-3.8 (1H, t), 3.50-3.30 (6H, m), 3.3-3.2 (3H, s) 2.5-2.4 (2H, m), 2.15-2.0 (1H, m), 2.0-1.8 (2H, m).

MS (ESI): m/z 401.2 (M+H).

Example-93

Synthesis of (5-((R)-2-(2,5-difluorophenyl)pyrrolidin-1-yl)pyrazolo[1,5-a]pyridin-3-yl)(3-(hydroxymethyl)piperazin-1-yl)methanone

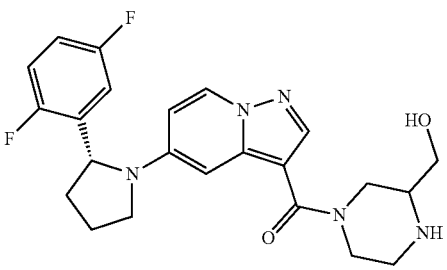 [SMILES: O=C(c1cnn2ccc(N3CCC[C@@H]3c3cc(F)ccc3F)cc12)N1CCNC(CO)C1]

Step-1

Synthesis of tert-butyl 4-(5-((R)-2-(2,5-difluorophenyl)pyrrolidin-1-yl)pyrazolo[1,5-a]pyridine-3-carbonyl)-2-(hydroxymethyl)piperazine-1-carboxylate

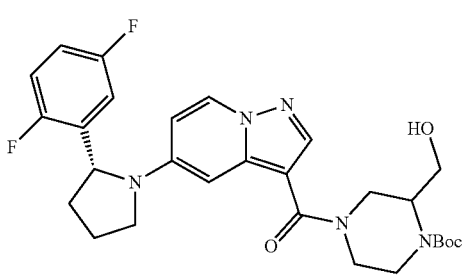 [SMILES: CC(C)(C)OC(=O)N1CCN(C(=O)c2cnn3ccc(N4CCC[C@@H]4c4cc(F)ccc4F)cc23)CC1CO]

The title compound was prepared by a coupling method substantially similar to that mentioned in Example-16, using tert-butyl 2-(hydroxymethyl)piperazine-1-carboxylate to afford 140 mg of the title compound.

MS (ESI): 541.9 (M+H).

Step-2

Synthesis of (5-((R)-2-(2,5-difluorophenyl)pyrrolidin-1-yl)pyrazolo[1,5-a]pyridin-3-yl)(3-(hydroxymethyl)piperazin-1-yl)methanone

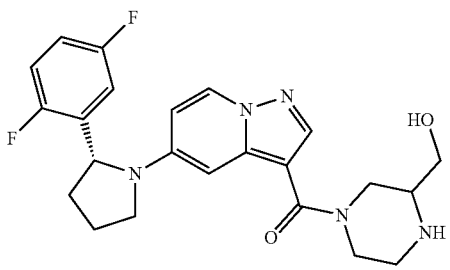 [SMILES: O=C(c1cnn2ccc(N3CCC[C@@H]3c3cc(F)ccc3F)cc12)N1CCNC(CO)C1]

4M HCl solution (in Dioxane) (5 mL) was added to a stirred solution of tert-butyl 4-(5-((R)-2-(2,5-difluorophenyl)pyrrolidin-1-yl)pyrazolo[1,5-a]pyridine-3-carbonyl)-2-(hydroxyl methyl)piperazine-1-carboxylate (150 mg, 0.276 mmol) in Dioxane (2 mL) and stirring was continued at 20-35° C. for 4 h. After which the reaction mixture was concentrated under reduced pressure to afford the crude product. The crude product was purified by Preparative HPLC [Column:LUNA-C18-250*21.2 mm, Mobile phase-A: 0.1% TFA in water, B: ACN, Gradient (Time/% B): 0/30, 2/30, 10/60 and Flow rate:20 mL/min] 110 mg of the title compound.

MS (ESI): m/z 441.9 (M+H).

Example-94

Synthesis of 5-((R)-2-(2,5-difluorophenyl)pyrrolidin-1-yl)-N-(1-(5-fluoropyridin-2-yl)ethyl)pyrazolo[1,5-a]pyridine-3-carboxamide (Diastereomer 1)

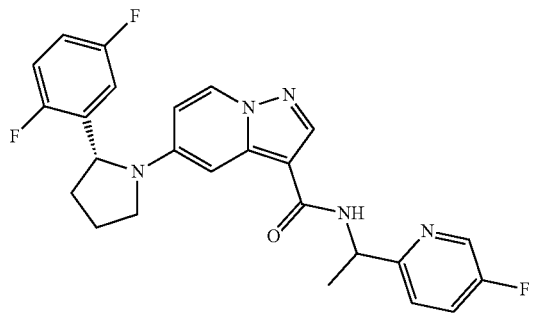 [SMILES: CC(NC(=O)c1cnn2ccc(N3CCC[C@@H]3c3cc(F)ccc3F)cc12)c1ccc(F)cn1]

The title compound was prepared as mixture of diastereomers by the method substantially similar to that mentioned in Example-57 to afford the crude product, which was further purified by Chiral HPLC[Column:AG/CHIRALPAK AD-H/02, Mobile phase: n-Hexane:60% and IPA:40%, Flow rate: 1 mL/min] to afford 20 mg of the title compound. (and 20 mg Example-96 as the other isomer as mentioned below).

$^1$H NMR (400 MHz, DMSO-d$_6$) δ ppm 8.52-8.46 (2H, m), 8.41 (1H, d, J=7.6 Hz), 8.22 (1H, d, J=7.6 Hz), 7.70-7.64 (1H, m), 7.46-7.40 (1H, m), 7.36-7.28 (1H, m), 7.2-7.1 (1H, m), 6.94-6.82 (2H, m), 6.35 (1H, m), 5.15 (2H, m), 3.81 (1H, m), 3.45-3.35 (1H, m), 2.55-2.40 (1H, m), 2.1-1.85 (3H, m), 1.45 (3H, d, J=7.2 Hz).

MS (ESI): m/z 466.9 (M+H).

Example-95

Synthesis of 5-((R)-2-(2,5-difluorophenyl)pyrrolidin-1-yl)-N-(1-(5-fluoropyridin-2-yl)ethyl)pyrazolo[1,5-a]pyridine-3-carboxamide (Diastereomer II)

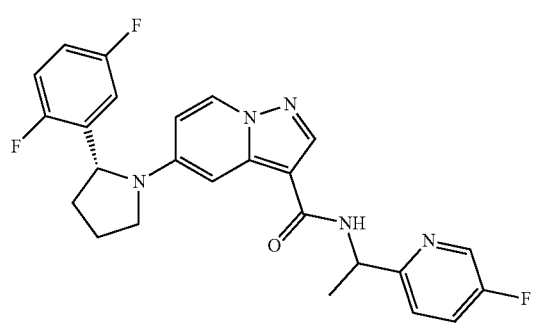 [SMILES: CC(NC(=O)c1cnn2ccc(N3CCC[C@@H]3c3cc(F)ccc3F)cc12)c1ccc(F)cn1]

$^1$H NMR (400 MHz, DMSO-d$_6$) δ ppm 8.50-8.40 (3H, m), 8.21 (1H, d, J=8 Hz), 7.70-7.64 (1H, m), 7.42 (1H, m), 7.3 (1H, m), 7.13 (1H, m), 6.92 (1H, s), 6.90-6.82 (1H, m), 6.34 (1H, m), 5.20-5.08 (2H, m), 3.81 (1H, m), 3.45-3.40 (1H, m), 2.55-2.40 (1H, m), 2.1-1.85 (3H, m), 1.46 (3H, d, J=7.2 Hz).

MS (ESI): m/z 466.9 (M+H).

Example-96

Synthesis of 5-((R)-2-(2,5-difluorophenyl)pyrrolidin-1-yl)-N-((1r,4R)-4-(1-ethyl-1H-1,2,4-triazol-5-yl)cyclohexyl)pyrazolo[1,5-a]pyridine-3-carboxamide

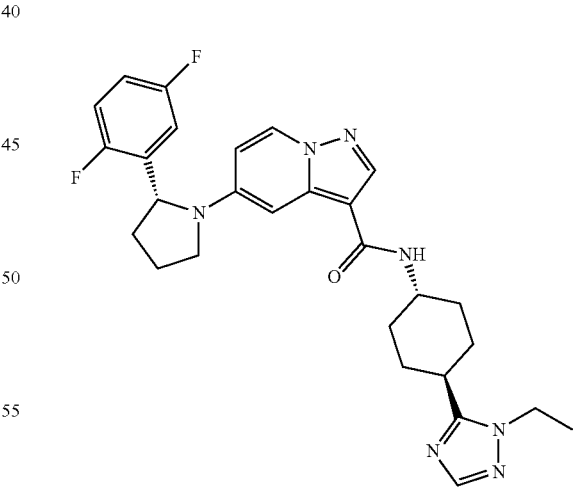

The title compound was prepared by the method substantially similar to that mentioned in Example-16, using (1r,4r)-4-(1-ethyl-1H-1,2,4-triazol-5-yl)cyclohexanamine to afford the crude, which was purified Preparative TLC (using Silica-gel GF$_{254}$, 1000 u coated 20×20 cm dimension glass plate and 100% EtOAc as eluent) to afford 20 mg of the title compound.

$^1$H NMR (300 MHz, CD$_3$OD) δ ppm 8.31-8.22 (2H, m), 7.20-7.12 (1H, m), 7.04-6.97 (2H, m), 6.81-6.75 (1H, m), 6.45-6.41 (1H, dd, J=2.4, 7.8 Hz), 5.19-5.16 (1H, d, J=7.8 Hz), 4.20 (2H, q), 3.94-3.82 (2H, m), 3.59-3.50 (1H, m), 2.92-2.72 (1H, m), 2.53-2.48 (1H, m), 2.12-1.96 (8H, m), 1.83-1.68 (2H, m), 1.56-1.41 (5H, m).

MS (ESI): m/z 520.3 (M+H).

Example-97

Synthesis of (R)-5-(2-(2,5-difluorophenyl)pyrrolidin-1-yl)-N-(1-sulfamoylpiperidin-4-yl)pyrazolo[1,5-a]pyridine-3-carboxamide

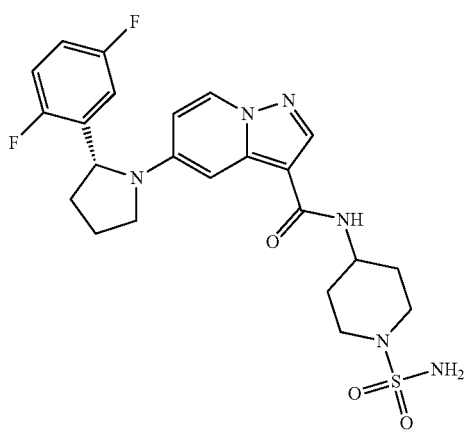 [SMILES: NS(=O)(=O)N1CCC(NC(=O)c2cnn3ccc(N4CCC[C@@H]4c4cc(F)ccc4F)cc23)CC1]

Sulfamide (9 mg, 0.093 mmol) was added to solution of (R)-5-(2-(2,5-difluorophenyl)pyrrolidin-1-yl)-N-(piperidin-4-yl)pyrazolo[1,5-a]pyridine-3-carboxamide (25 mg, 0.058 mmol) (Example-32) in 1,4-Dioxane (0.5 mL) and stirring was continued at 110° C. for 4 h. The reaction mixture was concentrated to afford the residue, which was quenched with water, extracted with EtOAc, dried over anhydrous sodium sulfate and concentrated under reduced pressure to afford the crude. The crude product was purified by Preparative TLC (using Silicagel $GF_{254}$, 1000 u coated 20×20 cm dimension glass plate and 10% MeOH in DCM as eluent) to afford 8 mg, of the title compound.

$^1$H NMR (300 MHz, CD$_3$OD) δ ppm 8.26-8.23 (2H, m), 7.20-7.13 (1H, m), 7.03-7.00 (2H, m), 6.81-6.75 (1H, m), 6.48-6.44 (1H, m), 5.19-5.16 (1H, d, J=8.4 Hz), 3.93-3.86 (2H, m), 3.68-3.54 (3H, m), 2.77-2.69 (2H, m), 2.53-2.49 (1H, m), 2.12-1.98 (5H, m), 1.71-1.65 (2H, m).

MS (ESI): m/z 505.2 (M+H)

Example-98

Synthesis of (R)—N-(tert-butyl)-5-(2-(2,5-difluorophenyl)pyrrolidin-1-yl)pyrazolo[1,5-a]pyridine-3-carboxamide

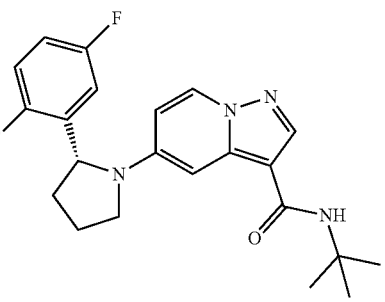

The title compound was prepared by the method substantially similar to that mentioned in Example-16, using tert-butyl amine in place of octahydro-1H-pyrido[1,2-a]pyrazine to afford crude. The crude compound was purified by Preparative TLC (using Silicagel $GF_{254}$, 1000 u coated 20×20 cm dimension glass plate and 70% EtOAc in Hexane as eluent) to afford 20 mg of the title compound.

$^1$H NMR (400 MHz, CDCl$_3$) δ ppm 8.15-8.05 (1H, d, J=7.6 Hz), 7.9 (1H, s), 7.20-7.15 (1H, d, J=2.0 Hz), 7.1-7.0 (1H, m), 7.0-6.85 (1H, m), 6.75-6.6 (1H, m), 6.15-6.1 (1H, dd), 5.51 (1H, s), 5.2-5.1 (1H, d, J=8.4 Hz), 3.85-3.75 (1H, t), 3.60-3.50 (1H, m), 2.5-2.40 (1H, m), 2.2-2.0 (3H, m), 1.5 (9H, s).

MS (ESI): m/z 399.2 (M+H).

Example-99

Synthesis of 5-((R)-2-(2,5-difluorophenyl)pyrrolidin-1-yl)-N-(3-(hydroxymethyl)cyclohexyl)pyrazolo[1,5-a]pyridine-3-carboxamide

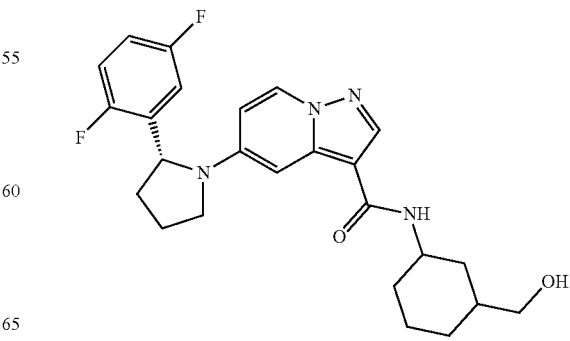

Step-1

Synthesis of ethyl 3-amino cyclohexanecarboxylate

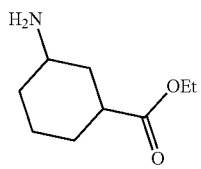

Conc.HCl (1 mL) was added to a solution of 3-aminocyclohexanecarboxylic acid (500 mg, 3.49 mmol) in EtOH (20 mL) and stirring was continued at reflux temperature for 3 h. The reaction mixture was concentrated under reduced pressure to afford the crude, which was washed with 10% aqueous NaHCO$_3$ solution, extracted with DCM, dried over anhydrous sodium sulphate to afford 300 mg of the title compound.

MS (ESI): m/z 172 (M+H).

Step-2

Synthesis of (3-aminocyclohexyl)methanol

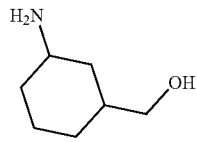

LAH (107 mg, 2.8 mmol) was added portionwise to a solution of ethyl 3-aminocyclohexanecarboxylate (320 mg, 1.87 mmol) in THF (5 mL) at 0° C. and continued stirring at 25-30° C. for 15 h. The reaction mixture was quenched with aqueous saturated sodium sulphate solution, filtered the solid precipitate, washed the solid with THF; the filtrate collected was concentrated under reduced pressure to afford 200 mg of the title compound.

MS (ESI): m/z 130 (M+H).

Step-3

Synthesis of 5-((R)-2-(2,5-difluorophenyl)pyrrolidin-1-yl)-N-(3-(hydroxymethyl)cyclohexyl)pyrazolo[1,5-a]pyridine-3-carboxamide

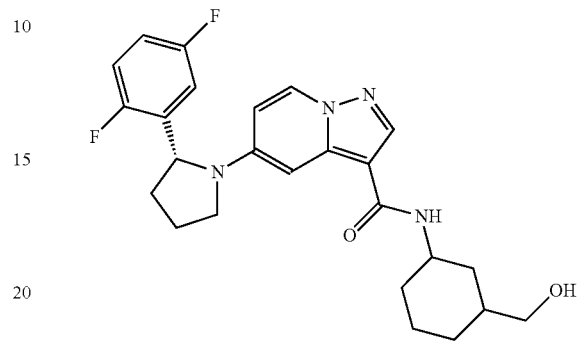

The title compound was prepared by the method substantially similar to that mentioned in Example-6 using (3-aminocyclohexyl)methanol (Step-2) to afford the crude, which was purified by washing with Diethyl ether and n-Hexane to afford 42 mg of the title compound.

MS (ESI): 455.4 (M+H).

Example-100

Synthesis of (R)-5-(2-(2,5-difluorophenyl)pyrrolidin-1-yl)-N-(3-hydroxypropyl)pyrazolo[1,5-a]pyridine-3-carboxamide

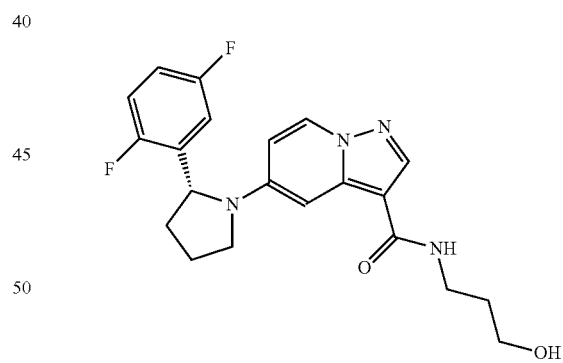

The title compound was prepared by the method substantially similar to that mentioned in Example-6 using (3-aminopropanol to afford the crude, which was purified by washing with Diethyl ether and n-Hexane to afford 49 mg of the title compound.

$^1$H NMR (400 MHz, DMSO-d$_6$) δ ppm 8.4 (1H, d, J=7.6 Hz), 8.28 (1H, s), 7.86-7.80 (1H, m), 7.38-7.30 (1H, m), 7.18-7.12 (1H, m), 6.95 (1H, s), 6.90-6.84 (1H, m), 6.38-6.32 (1H, m), 5.12 (1H, d), 4.5 (1H, t), 3.9-3.8 (1H, m), 3.50-3.40 (3H, m), 3.3-3.2 (1H, m), 2.5-2.4 (1H, m), 2.1-1.85 (3H, m), 1.68-1.60 (2H, m).

MS (ESI): m/z 401.2 (M+H).

Example-101

Synthesis of (R)-5-(2-(2,5-difluorophenyl)pyrrolidin-1-yl)-N-(1-(hydroxymethyl)cyclopropyl)pyrazolo[1,5-a]pyridine-3-carboxamide

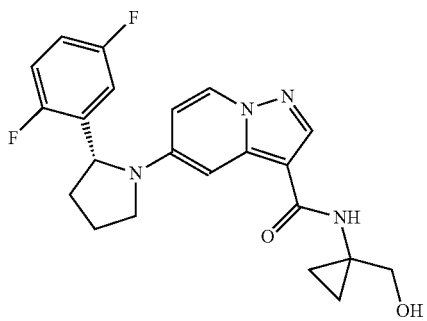 [SMILES: O=C(NC1(CO)CC1)c1cnn2ccc(N3CCC[C@@H]3c3cc(F)ccc3F)cc12]

The title compound was prepared by the method substantially similar to that mentioned in Example-6, using (1-aminocyclopropyl)methanol hydrochloride in place of $NH_4Cl$ to afford the crude compound. The crude compound was purified by Preparative HPLC [Column:21.2×150×5 um, Zorbax, XDB,C-18, Mobile phase-A: 0.1% TFA in water, B:ACN: MeOH (1:1), Isocratic: A: 52% and B:48%, Flow rate:20 mL/min] to afford 42 mg of the title compound $^1$H NMR (400 MHz, $CD_3OD$) δ ppm 8.3-8.25 (1H, d, J=7.6 Hz), 8.2 (1H, s), 7.25-7.15 (1H, m), 7.1-7.0 (2H, m), 6.85-6.75 (1H, m), 6.5-6.4 (1H, dd), 5.3-5.15 (1H, d, J=8.0 Hz), 3.9-3.8 (1H, m), 3.7-3.6 (2H, s), 3.6-3.5 (1H, m), 2.6-2.45 (1H, m), 2.2-1.95 (3H, m), 1.0-0.8 (4H, m).

MS (ESI): m/z 413.9 (M+H).

Example-102

Synthesis of (R)-5-(2-(2,5-difluorophenyl)pyrrolidin-1-yl)-N-(2-(2-hydroxyethoxy)ethyl)pyrazolo[1,5-a]pyridine-3-carboxamide

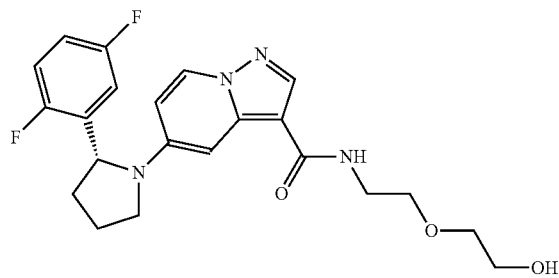 [SMILES: O=C(NCCOCCO)c1cnn2ccc(N3CCC[C@@H]3c3cc(F)ccc3F)cc12]

The title compound was prepared by the method substantially similar to that mentioned in Example-6, using 2-(2-aminoethoxy)ethanol to afford the crude, which was purified by Preparative TLC (using Silicagel $GF_{254}$, 1000 u coated 20×20 cm dimension glass plate and 6% MeOH in $CHCl_3$ as eluent) to afford 18 mg of the title compound.

$^1$H NMR (400 MHz, DMSO-$d_6$) δ ppm 8.42-8.40 (1H, d, J=8.0 Hz), 8.29 (1H, s), 7.89 (1H, t), 7.34-7.30 (1H, m), 7.17-7.14 (1H, m), 6.96 (1H, bs), 6.89-6.86 (1H, m), 6.37-6.35 (1H, dd, J=8.0 Hz), 5.12-5.10 (1H, d, J=8.0 Hz), 4.62 (1H, t), 3.84 (1H, t), 3.52-3.35 (8H, m), 2.46-2.40 (1H, m), 2.04-1.89 (3H, m).

MS (ESI): m/z 431.4 (M+H).

Example-103

Synthesis of (R)-(4-(1H-tetrazol-5-yl)piperidin-1-yl)(5-(2-(2,5-difluorophenyl)pyrrolidin-1-yl)pyrazolo[1,5-a]pyridin-3-yl)methanone

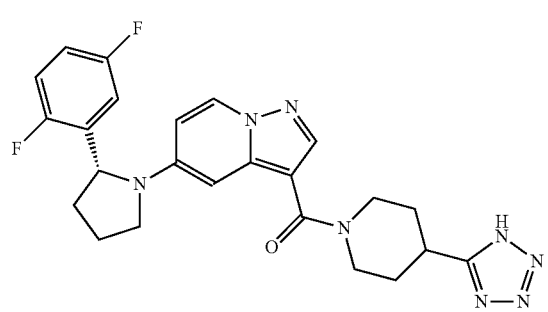 [SMILES: O=C(c1cnn2ccc(N3CCC[C@@H]3c3cc(F)ccc3F)cc12)N1CCC(c2nnn[nH]2)CC1]

The title compound was prepared by the method substantially similar to that mentioned in Example-88, using 2-(R)-1-(5-(2-(2,5-difluorophenyl)pyrrolidin-1-yl)pyrazolo[1,5-a]pyridine-3-carbonyl)piperidine-4-carbonitrile (Example-89) to afford the crude, which was purified by Preparative HPLC [Column: 21.2×150×5 um, Zorbax, XDB,C-18, Mobile phase-A: 0.1% TFA in water, B:ACN, Gradient (Time/% B): 0/10, 2/20, 10/70 and Flow rate:20 mL/min] to afford 35 mg of the title compound.

$^1$H NMR (300 MHz, $CD_3OD$) δ ppm 8.29-8.26 (1H, d, J=8.4 Hz), 7.99 (1H, s), 7.19-7.15 (1H, m), 7.01-6.95 (1H, m), 6.81-6.79 (1H, m), 6.51 (2H, bs), 5.12 (1H, d, J=7.6 Hz), 4.34 (2H, t), 3.85 (1H, t), 3.55-3.50 (1H, m), 3.3-3.1 (2H, m), 2.51-2.50 (2H, m), 2.12-2.03 (4H, m), 1.90-1.70 (2H, m).

MS (ESI): m/z 479.5 (M+H).

Example-104

Synthesis of N-((1R,4R)-4-cyanocyclohexyl)-5-((R)-2-(2,5-difluorophenyl)pyrrolidin-1-yl)pyrazolo[1,5-a]pyridine-3-carboxamide

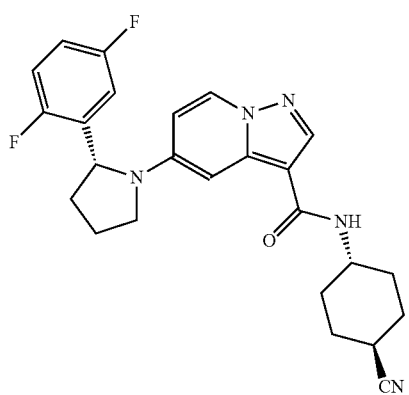 [SMILES: N#C[C@H]1CC[C@H](NC(=O)c2cnn3ccc(N4CCC[C@@H]4c4cc(F)ccc4F)cc23)CC1]

Step-1

Synthesis of benzyl((1r,4r)-4-carbamoylcyclohexyl)carbamate

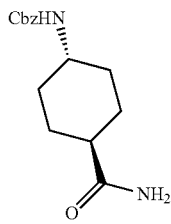 [SMILES: NC(=O)[C@H]1CC[C@H](NC(=O)OCc2ccccc2)CC1]

Isobutyl chloroformate (3.698 g, 3.5 mL, 27.08 mmol) and N-methylmorpholine (4.56 g, 4.96 mL, 45.13 mmol) were added to a solution of (1r,4r)-4-(((benzyloxy) carbonyl)amino)cyclohexanecarboxylic acid (Step-1 product of Example-90) (5 g, 18.05 mmol) in THF (100 mL) at −78° C. and stirring was continued at same temperature for 1.5 h. Ammonia gas was purged at −78° C. for 0.5 h and continued stirring at 25-35° C. for 1 h. The solid precipitate thus obtained was filtered, washed with water, dried well to afford the first crop and the filtrate collected was extracted with EtOAc, dried over anhydrous sodium sulphate and concentrated under reduced pressure to afford second crop which upon mixing with first crop gave 3.8 g of the title compound.

$^1$H NMR (300 MHz, DMSO-$d_6$) δ ppm 7.4-7.1 (7H, m), 6.7 (1H, s), 5.0 (2H, s), 3.3-3.1 (1H, m), 2.05-1.9 (1H, m), 1.83-1.7 (4H, m), 1.4-1.1 (4H, m).

Step-2

Synthesis of benzyl((1r,4r)-4-cyanocyclohexyl)carbamate

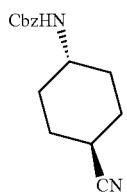 [SMILES: N#C[C@H]1CC[C@H](NC(=O)OCc2ccccc2)CC1]

Imidazole (492 mg, 7.2 mmol) was added to a solution of benzyl ((1r,4r)-4-carbamoylcyclohexyl)carbamate (1 g, 3.6 mmol) in Pyridine (10 mL) at −30° C. followed by addition of POCl$_3$ (2.19 g, 14.4 mmol) and stirring was continued at same temperature for 0.5 h. The reaction was quenched with ice, extracted with EtOAc, washed with water followed by aqueous 1N HCl solution, dried over anhydrous sodium sulphate and concentrated under reduced pressure to afford 650 mg of the title compound.

$^1$H NMR (400 MHz, DMSO-$d_6$) δ ppm 7.4-7.2 (5H, m), 5.0 (2H, s), 3.4-3.3 (1H, m), 2.7-2.6 (1H, m), 2.05-1.9 (2H, m), 1.8-1.7 (2H, m), 1.6-1.5 (2H, m), 1.3-1.1 (2H, m).

Step-3

Synthesis of (1r,4r)-4-aminocyclohexanecarbonitrile

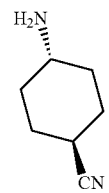

TMSI (542 mg, 2.7 mmol) was added to a solution of benzyl ((1r,4r)-4-cyanocyclohexyl)carbamate (500 mg, 1.93 mmol) in DCM (5 mL) at 0-5° C. and stirring was continued at 20-35° C. for 2 h. Reaction mixture was quenched with MeOH (5 mL), concentrated under reduced pressure to afford the residue, which was diluted with water, adjusted the pH to 8 and then extracted with mixture of 5% MeOH in DCM, dried over anhydrous sodium sulphate and concentrated under reduced pressure to afford 240 mg (crude) of (1r,4r)-4-aminocyclohexanecarbonitrile. MS (ESI): m/z 125.3 (M+H).

Step-4

Synthesis of N-((1R,4R)-4-cyanocyclohexyl)-5-((R)-2-(2,5-difluorophenyl)pyrrolidin-1-yl)pyrazolo[1,5-a]pyridine-3-carboxamide

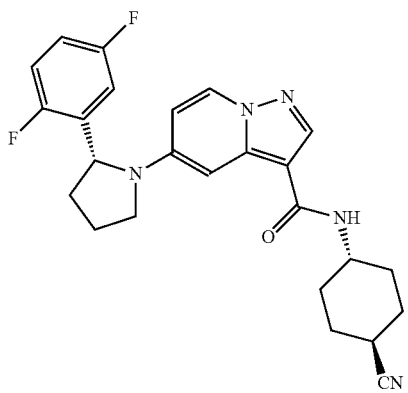 [SMILES: N#C[C@H]1CC[C@H](NC(=O)c2cnn3ccc(N4CCC[C@@H]4c4cc(F)ccc4F)cc23)CC1]

The title compound was prepared by the similar coupling method as mentioned in Example-16, using (1r,4r)-4-aminocyclohexanecarbonitrile to afford the crude, which was purified by column chromatography (using silica gel 60-120, and 20% EtOAc in Hexane as eluent) to afford 12 mg of the title compound.

$^1$H NMR (300 MHz, CD$_3$OD) δ ppm 8.25-8.21 (2H, m), 7.17-7.13 (1H, m), 7.01-6.99 (2H, m), 6.80-6.76 (1H, m), 6.46-6.44 (1H, m), 5.19-5.16 (1H, d, J=8.4 Hz), 3.84-3.78 (2H, m), 3.60-3.50 (1H, m), 2.63-2.48 (2H, m), 2.18-2.00 (8H, m), 1.72-1.67 (2H, m), 1.45-1.29 (2H, m).

MS (ESI): m/z 449.9 (M+H).

Example-105

Synthesis of 5-((R)-2-(2,5-difluorophenyl)pyrrolidin-1-yl)-N—(((S)-tetrahydrofuran-2-yl)methyl)pyrazolo[1,5-a]pyridine-3-carboxamide

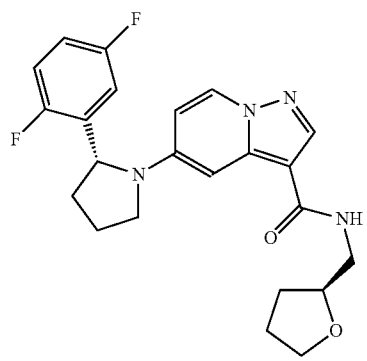 [SMILES: O=C(NC[C@@H]1CCCO1)c1cnn2ccc(N3CCC[C@@H]3c3cc(F)ccc3F)cc12]

The title compound was prepared by a method substantially similar to that mentioned in Example-16, to afford the crude, which was purified by column chromatography (using silica gel 60-120, and 5% EtOAc in Hexane as eluent) to afford 40 mg of the title compound. $^1$H NMR (300 MHz, DMSO-d$_6$) δ ppm 8.41-8.39 (1H, d, J=7.6 Hz), 8.34 (1H, s), 7.92 (1H, t), 7.37-7.29 (1H, m), 7.19-7.12 (1H, m), 6.95 (1H, bs), 6.90-6.84 (1H, m), 6.36-6.34 (1H, m), 5.12-5.10 (1H, d, J=7.8 Hz), 3.93-3.76 (3H, m), 3.65-3.60 (1H, q), 3.44-3.42 (1H, m), 3.31-3.20 (4H, m), 2.46-2.43 (1H, m), 2.04-1.78 (6H, m), 1.54 (1H, m), 1.25-1.23 (1H, m).
MS (ESI): m/z 427.4 (M+H).

Example-106

Synthesis of (R)-5-(2-(2,5-difluorophenyl)pyrrolidin-1-yl)-N-(tetrahydro-2H-thiopyran-4-yl)pyrazolo[1,5-a]pyridine-3-carboxamide

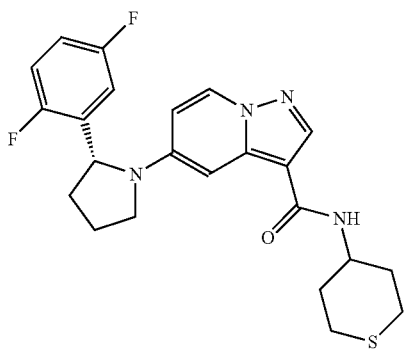

The title compound was prepared by the method substantially similar to that mentioned in Example-16, using tetrahydro-2H-thiopyran-4-yl-amine to afford the crude, which was purified by Preparative TLC (using Silicagel GF$_{254}$, 1000 u coated 20×20 cm dimension glass plate and 50% EtOAc in n-Hexane as eluent) to afford 22.4 mg of the title compound.
$^1$H NMR (300 MHz, DMSO-d$_6$) δ ppm 8.42-8.39 (1H, d, J=7.8 Hz), 8.32 (1H, s), 7.69-7.67 (1H, m), 7.40-7.25 (1H, m), 7.20-7.10 (1H, m), 6.95-6.80 (2H, m), 6.40-6.39 (1H, m), 5.11-5.08 (1H, d, J=8.4 Hz), 3.9-3.7 (2H, m), 2.69-2.66 (5H, m), 2.01-2.00 (4H, m), 1.91-1.81 (2H, m), 1.65-1.55 (2H, m).
MS (ESI): m/z 442.8 (M+H).

Example-107

Synthesis of (R)-5-(2-(2,5-difluorophenyl)pyrrolidin-1-yl)-N-(1-(hydroxymethyl)cyclohexyl)pyrazolo[1,5-a]pyridine-3-carboxamide

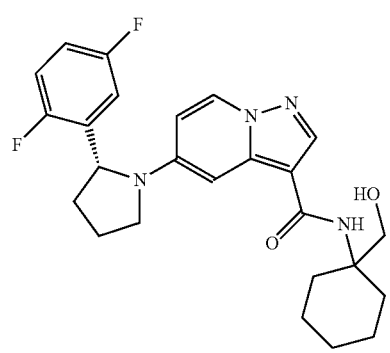 [SMILES: O=C(NC1(CO)CCCCC1)c1cnn2ccc(N3CCC[C@@H]3c3cc(F)ccc3F)cc12]

The title compound was prepared by the method substantially similar to that mentioned in Example-16, using (1-aminocyclohexyl)methanol to afford the crude, which was purified by Preparative HPLC [Column: 21.2×250×7 um, Zorbax, XDB,C-18(#22), Mobile phase-A: 0.1% TFA in water, B:ACN, Gradient (Time/% B): 0/50, 2/60, 8/80 and Flow rate:20 mL/min] to afford 34 mg of the title compound.
$^1$H NMR (300 MHz, DMSO-d$_6$) δ ppm 8.26-8.22 (2H, m), 7.20-7.12 (1H, m), 7.04-6.97 (2H, m), 6.97 (1H, s), 6.80-6.74 (1H, m), 6.43-6.39 (1H, dd, J=2.4, 7.5 Hz), 5.20-5.17 (1H, d, J=7.6 Hz), 3.85-3.81 (1H, m), 3.73-3.71 (2H, m), 3.55-3.53 (1H, m), 2.52-2.4 (1H, m), 2.20-2.01 (5H, m), 1.54-1.50 (7H, m).
MS (ESI): m/z 454.9 (M+H)

Example-108

Synthesis of 5-((R)-2-(2,5-difluorophenyl)pyrrolidin-1-yl)-N—((S)-1-methylpyrrolidin-3-yl)pyrazolo[1,5-a]pyridine-3-carboxamide

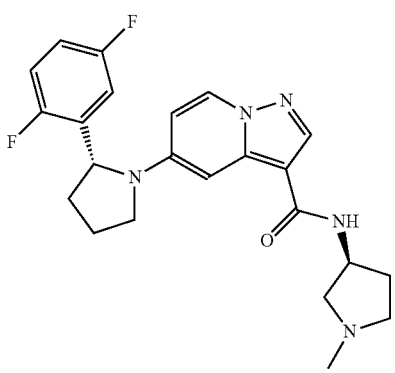 [SMILES: CN1CC[C@H](NC(=O)c2cnn3ccc(N4CCC[C@@H]4c4cc(F)ccc4F)cc23)C1]

The title compound was prepared by the method substantially similar to that mentioned in Example-16, (S)-1-Methylpyrrolidin-3-amine hydrochloride to afford the crude, which was purified by washing with Diethyl ether and n-Hexane to afford 38 mg of the title compound.

¹H NMR (400 MHz, DMSO-d₆) δ ppm 8.46-8d.40 (2H, m), 7.88 (1H, d, J=7.2 Hz), 7.42-7.34 (1H, m), 7.24-7.18 (1H, m), 7.0 (1H, s), 6.94-6.88 (1H, m), 6.4 (1H, d, J=6 Hz), 5.15 (1H, d, J=8 Hz), 4.44-4.36 (1H, m), 3.92-3.86 (1H, t), 3.5-3.42 (1H, m), 2.72-2.58 (2H, m), 2.55-2.40 (3H, m), 2.28 (3H, s), 2.2-1.9 (4H, m), 1.76-1.68 (1H, m).
MS (ESI): m/z 426.5 (M+H).

Example-109

Synthesis of 5-((R)-2-(2,5-difluorophenyl)pyrrolidin-1-yl)-N—((S)-1-sulfamoylpyrrolidin-3-yl)pyrazolo[1,5-a]pyridine-3-carboxamide

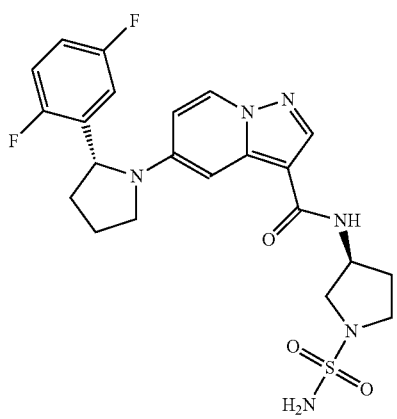 [SMILES: NS(=O)(=O)N1CC[C@H](NC(=O)c2cnn3ccc(N4CCC[C@@H]4c4cc(F)ccc4F)cc23)C1]

The title compound was prepared by the method substantially similar to that mentioned in Example-98, using 5-((R)-2-(2,5-difluorophenyl)pyrrolidin-1-yl)-N—((S)-pyrrolidin-3-yl)pyrazolo[1,5-a]pyridine-3-carboxamide (Example-82) and Sulfamide to afford the crude, which was purified by Preparative HPLC [Column: 21.2×250×7 um, Zorbax, XDB, C-18(#22), Mobile phase-A: 10 mmol.NH₄OAc in water, B:ACN, Gradient (Time/% B): 0/30, 2/30, 8/90 and Flow rate:20 mL/min] to afford 26 mg of the title compound.
¹H NMR (400 MHz, DMSO-d₆) δ ppm 8.44-8.40 (1H, d, J=7.6 Hz), 8.35 (1H, s), 7.9 (1H, d, J=6.8 Hz), 7.38-7.30 (1H, m), 7.20-7.12 (1H, m), 6.95 (1H, s), 6.90-6.84 (1H, m), 6.80 (2H, s), 6.42-6.36 (1H, m), 5.12 (1H, d, J=7.6 Hz), 4.41 (1H, m), 3.85 (1H, m), 3.5-3.4 (2H, m), 3.3-3.1 (2H, m), 3.0-2.92 (1H, m), 2.5-2.4 (1H, m), 2.2-2.1 (1H, m), 2.1-1.85 (4H, m).
MS (ESI): m/z 491.8 (M+H).

Example-110

Synthesis of 5-((R)-2-(2,5-difluorophenyl)pyrrolidin-1-yl)-N—((R)-2,3-dihydroxypropyl)pyrazolo[1,5-a]pyridine-3-carboxamide

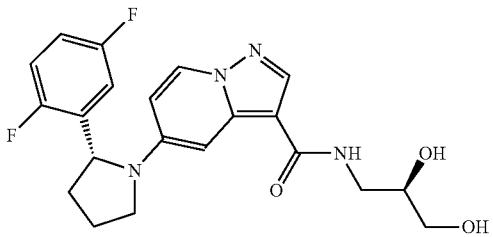 [SMILES: O=C(NC[C@@H](O)CO)c1cnn2ccc(N3CCC[C@@H]3c3cc(F)ccc3F)cc12]

The title compound was prepared by the method substantially similar to that mentioned in Example-6, using (1-(R)-3-aminopropane-1,2-diol to afford 33 mg of the title compound.
¹H NMR (400 MHz, DMSO-d₆) δ ppm 8.42-8.40 (1H, d, J=7.6 Hz), 8.33 (1H, s), 7.90-7.84 (1H, m), 7.36-7.28 (1H, m), 7.2-7.12 (1H, m), 6.95 (1H, s), 6.9-6.84 (1H, m), 6.4-6.32 (1H, m), 5.12 (1H, d, J=8 Hz), 4.84 (1H, d, J=4.8 Hz), 4.59 (1H, t), 3.84 (1H, m), 3.6-3.4 (2H, m), 3.16-3.08 (1H, m), 2.5-2.4 (1H, m), 2.1-1.85 (3H, m), 1.24 (1H, m), 0.86 (1H, m).
MS (ESI): m/z 417.4 (M+H).

Example-111

Synthesis of (R)-5-(2-(2,5-difluorophenyl)pyrrolidin-1-yl)-N-((2-methyl-2H-tetrazol-5-yl)methyl)pyrazolo[1,5-a]pyridine-3-carboxamide

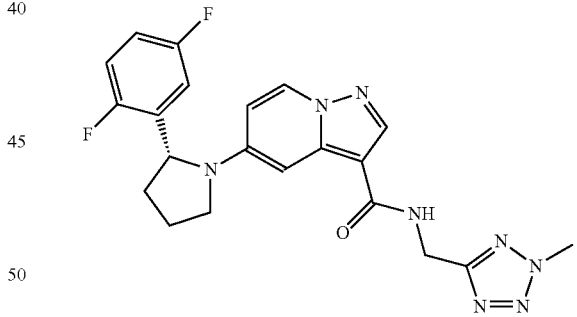

Step-1

Synthesis of Benzyl(cyanomethyl)carbamate

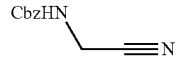

NaHCO₃ (1.09 g, 12.97 mmol) in water (5 mL) was added to a stirred solution of 2-aminoacetonitrile sulfate (1.0 g, 6.48 mmol) in 1,4-Dioxane (10 mL) at 0-5° C. followed by addition of Benzylchloroformate (1.3 g, 1.11 mL, 7.78 mmol) and stirring was continued at 20-35° C. for 15 h. Reaction mixture was diluted with DCM and washed it with water, dried over anhydrous sodium sulphate and concentrated under reduced pressure to afford the crude, which was purified by Column chromatography (using Silica gel 60-120 and 10% MeOH in DCM as eluent) to afford 700 mg of the title compound.

$^1$H NMR (300 MHz, CDCl$_3$) δ ppm 7.5-7.3 (5H, m), 5.25 (2H, s), 4.2 (2H, d, J=6.3 Hz).

Step-2

Synthesis of Benzyl((2H-tetrazol-5-yl)methyl)carbamate

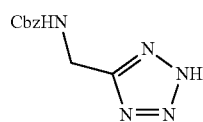 [SMILES: O=C(NCc1nn[nH]n1)OCc1ccccc1]

The title compound was prepared by the method substantially similar to that mentioned in Example-88 to afford 360 mg, of the title compound.

MS (ESI): m/z 233.9 (M+H).

Step-3

Synthesis of benzyl((2-methyl-2H-tetrazol-5-yl)methyl)carbamate and benzyl ((1-methyl-2H-tetrazol-5-yl)methyl)carbamate

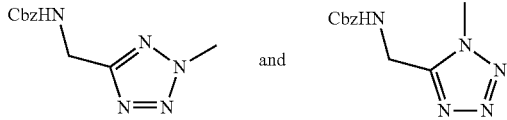 [SMILES: Cn1nnc(CNC(=O)OCc2ccccc2)n1 ; Cn1nnnc1CNC(=O)OCc1ccccc1]

Methyl iodide (211 mg, 1.48 mmol) was added to a mixture of benzyl ((2H-tetrazol-5-yl)methyl)carbamate (350 mg, 1.5 mmol) and K$_2$CO$_3$ (408 mg, 2.9 mmol) in DMF (3.5 mL) at 0-5° C. and stirring was continued at 25-35° C. for 16 h. Reaction mixture was quenched with ice, extracted with EtOAc, washed the organic layer with water, dried over anhydrous sodium sulphate and concentrated under reduced pressure to afford crude. The crude compound was purified by Flash chromatography (Biotage, Column: Silicagel 12 g pack size, Mobile Phase: EtOAc in n-Hexane: 0 to 100% as eluent) to afford 130 mg, of the title compound. benzyl ((2-methyl-2H-tetrazol-5-yl)methyl)carbamate.

$^1$H NMR (300 MHz, CDCl$_3$) δ ppm 7.48-7.29 (5H, m), 5.5-5.4 (1H, bs), 5.19 (2H, s), 4.71-4.6 (2H, d, J=6.0 Hz), 4.33 (3H, s), and 180 mg of the title compound benzyl ((1-methyl-1H-tetrazol-5-yl)methyl)carbamate.

$^1$H NMR (300 MHz, CDCl$_3$) δ ppm 7.48-7.29 (5H, m), 5.9-5.5 (1H, bs), 5.18 (2H, s), 4.7-4.59 (2H, d, J=6.3 Hz), 4.12 (3H, s).

Step-4

Synthesis of (2-methyl-2H-tetrazol-5-yl)methanamine

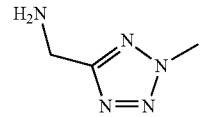

10% Pd/C (13 mg) was added to a solution benzyl ((2-methyl-2H-tetrazol-5-yl)methyl)carbamate (130 g, 0.52 mmol) in MeOH (3.0 mL) and the mixture was stirred continuously under hydrogen atmosphere at 20-35° C. for 4 h. The reaction mixture was filtered over a celite bed-and the filtrate was concentrated under reduced pressure to afford 45 g of the title compound.

MS (ESI): m/z 114 (M+H).

Step-5

Synthesis of (R)-5-(2-(2,5-difluorophenyl)pyrrolidin-1-yl)-N-((2-methyl-2H-tetrazol-5-yl)methyl)pyrazolo[1,5-a]pyridine-3-carboxamide

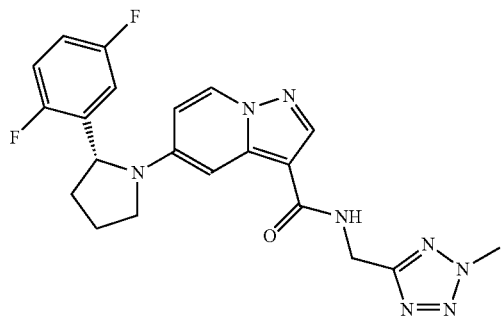 [SMILES: Cn1nnc(CNC(=O)c2cnn3ccc(N4CCC[C@@H]4c4cc(F)ccc4F)cc23)n1]

The title compound was prepared by the method substantially similar to that mentioned in Example-16, using (2-methyl-2H-tetrazol-5-yl)methanamine to afford the crude, which was purified by dissolving in DCM and reprecipitated with n-Hexane and dried to afford 30 mg of the title compound.

$^1$H NMR (400 MHz, DMSO-d$_6$) δ ppm 8.52-8.50 (1H, d, J=7.6 Hz), 8.43-8.41 (1H, d, J=7.6 Hz), 8.33 (1H, s), 7.4-7.3 (1H, m), 7.2-7.1 (1H, m), 6.95 (1H, s), 6.9-6.7 (1H, m), 6.45-6.35 (1H, m), 5.12 (1H, d, J=7.6 Hz), 4.64-4.60 (2H, m), 4.32 (3H, s), 3.84-3.82 (1H, m), 3.55-3.4 (1H, m), 2.52-2.4 (1H, m), 2.05-1.85 (3H, m).

MS (ESI): m/z 439.5 (M+H).

Example-112

Synthesis of (R)-5-(2-(2,5-difluorophenyl)pyrrolidin-1-yl)-N-((1-methyl-1H-tetrazol-5-yl)methyl)pyrazolo[1,5-a]pyridine-3-carboxamide

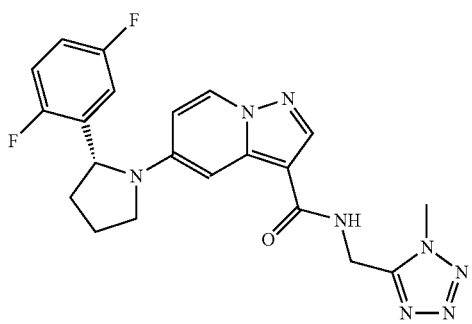 [SMILES: Cn1nnnc1CNC(=O)c1cnn2ccc(N3CCC[C@@H]3c3cc(F)ccc3F)cc12]

The title compound was prepared by the method substantially similar to that mentioned in Example-16, using (1-methyl-2H-tetrazol-5-yl)methanamine (Step-3, Example-112) to afford the crude, which was purified by dissolving in DCM and reprecipitated with n-Hexane, filtered and dried to afford 26 mg of the title compound.

$^1$H NMR (400 MHz, DMSO-d$_6$) δ ppm 8.61 (1H, t), 8.43-8.41 (1H, d, J=7.6 Hz), 8.32 (1H, s), 7.4-7.3 (1H, m), 7.2-7.1 (1H, m), 6.93 (1H, s), 6.9-6.7 (1H, m), 6.45-6.35 (1H, m), 5.12 (1H, d, J=7.6 Hz), 4.76-4.60 (2H, m), 4.08 (3H, s), 3.84-3.82 (1H, m), 3.55-3.4 (1H, m), 2.52-2.4 (1H, m), 2.05-1.85 (3H, m), MS (ESI): m/z 438.9 (M+H).

Example-113

Synthesis of (R)-5-(2-(2,5-difluorophenyl)pyrrolidin-1-yl)-N-(2-(4-hydroxypiperidin-1-yl)ethyl)pyrazolo[1,5-a]pyridine-3-carboxamide

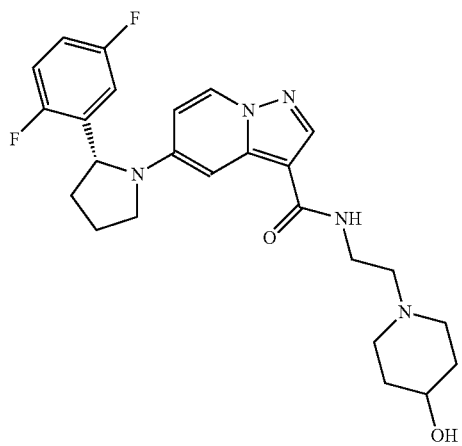 [SMILES: O=C(NCCN1CCC(O)CC1)c1cnn2ccc(N3CCC[C@@H]3c3cc(F)ccc3F)cc12]

The title compound was prepared by the method substantially similar to that mentioned in Example-6, using 1-(2-Aminoethyl)-4-piperidinol dihydrochloride, to afford the crude, which was purified by Preparative TLC (using Silica-gel GF$_{254}$, 1000 u coated 20×20 cm dimension glass plate and 10% MeOH in DCM as eluent) to afford 25 mg of the title compound.

$^1$H NMR (300 MHz, DMSO-d$_6$) δ ppm 8.43-8.41 (1H, d, J=7.6 Hz) 8.25 (1H, s), 7.4-7.25 (1H, m), 7.2-7.05 (1H, m), 6.95-6.8 (2H, m), 6.45-6.3 (1H, bs), 5.15-5.05 (1H, d, J=7.5 Hz), 3.9-3.8 (1H, t), 2.2-1.84 (6H, m), 1.82-1.7 (3H, m), 1.7-1.35 (3H, m).

MS (ESI): m/z 469.9 (M+H).

Example-114

Synthesis of (R)-5-(2-(2,5-difluorophenyl)pyrrolidin-1-yl)-N-(2-(4-methylpiperazin-1-yl)ethyl)pyrazolo[1,5-a]pyridine-3-carboxamide

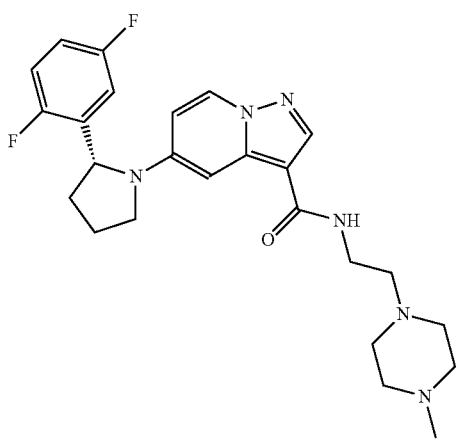 [SMILES: CN1CCN(CCNC(=O)c2cnn3ccc(N4CCC[C@@H]4c4cc(F)ccc4F)cc23)CC1]

The title compound was prepared by the method substantially similar to that mentioned in Example-16, using 2-(4-Methyl-piperazin-1-yl)-ethylamine, to afford the crude, which was purified by Preparative TLC (using Silicagel GF$_{254}$, 1000 u coated 20×20 cm dimension glass plate and 10% MeOH in DCM as eluent) to afford 28 mg of the title compound.

$^1$H NMR (300 MHz, CDCl$_3$) δ ppm 8.17-8.1 (1H, d, J=7.5 Hz), 7.95 (1H, s), 7.2 (1H, d, J=2.4 Hz), 7.1-7.0 (1H, m), 6.95-6.8 (1H, m), 6.7-6.6 (1H, m), 6.4-6.3 (1H, t), 6.15-6.1 (1H, dd, J=2.7, 7.8 Hz), 5.15-5.1 (1H, d, J=7.5 Hz), 3.85-3.7 (1H, m), 3.60-3.45 (3H, m), 2.7-2.35 (9H, m), 2.3 (3H, s), 2.15-1.9 (3H, m), 1.3-1.2 (1H, s).

MS (ESI): m/z 469.6 (M+H).

Example-115

Synthesis of (R)—N-(4,4-difluorocyclohexyl)-5-(2-(2,5-difluorophenyl)pyrrolidin-1-yl)pyrazolo[1,5-a]pyridine-3-carboxamide

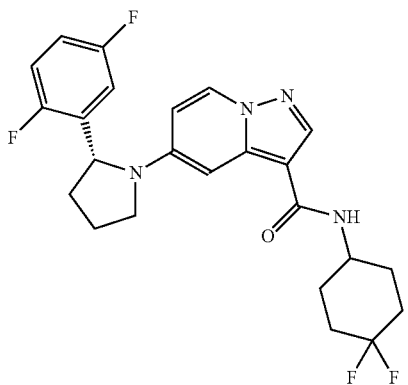 [SMILES: O=C(NC1CCC(F)(F)CC1)c1cnn2ccc(N3CCC[C@@H]3c3cc(F)ccc3F)cc12]

The title compound was prepared by the method substantially similar to that mentioned in Example-16, using 4,4-Difluorocyclohexylamine hydrochloride to afford the crude, which was purified by Preparative HPLC [Column: 21.2×150×5 um, Zorbax, XDB,C-18(#22), Mobile phase-A: 10 mmol NH₄OAc in water, B:ACN, Gradient (Time/% B): 0/40, 2/60, 8/80 and Flow rate:20 mL/min] to afford 17 mg of the title compound.

$^1$H NMR (300 MHz, DMSO-$d_6$) δ ppm 8.45-8.4 (1H, d, J=7.5 Hz), 8.35 (1H, s), 7.65-7.60 (1H, m), 7.4-7.3 (1H, m), 7.2-7.1 (1H, m), 6.95-6.8 (2H, m), 6.45-6.35 (1H, m), 5.215.10 (1H, d, J=7.4 Hz), 4.0-3.8 (2H, m), 2.15-1.95 (5H, m), 1.95-175 (5H, m), 1.6-1.4 (2H, m).

MS (ESI): m/z 461.5 (M+H).

Example-116

Synthesis of 5-((R)-2-(2,5-difluorophenyl)pyrrolidin-1-yl)-N-((1r,4R)-4-(hydroxymethyl)cyclohexyl)pyrazolo[1,5-a]pyridine-3-carboxamide

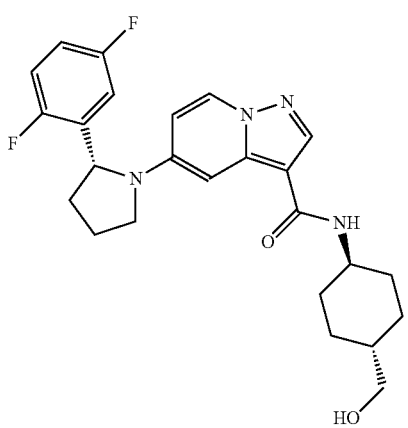 [SMILES: O=C(N[C@H]1CC[C@H](CO)CC1)c1cnn2ccc(N3CCC[C@@H]3c3cc(F)ccc3F)cc12]

The title compound was prepared by the method substantially similar to that mentioned in Example-6 using trans-4-Aminocyclohexanemethanol hydrochloride to afford the crude, which was purified by recrystallisation from mixture of EtOAc and n-Hexane to afford 45 mg of the title compound.

$^1$H NMR (300 MHz, DMSO-$d_6$) δ ppm 8.41-8.38 (1H, d, J=7.6 Hz), 8.32 (1H, s), 7.58-7.55 (1H, d, J=8.1 Hz), 7.4-7.3 (1H, m), 7.2-7.1 (1H, m), 6.94 (1H, bs), 6.92-6.82 (1H, m), 6.37-6.35 (1H, m), 5.12 (1H, d, J=7.6 Hz), 4.42 (1H, t), 3.83 (1H, t), 3.7-3.6 (1H, m), 3.44-3.43 (1H, m), 3.22 (1H, t), 2.52-2.4 (1H, m), 2.15-1.6 (8H, m), 1.3-1.15 (4H, m), 0.97-0.93 (2H, m).

MS (ESI): m/z 454.9 (M+H).

Example-117

Synthesis of (5-((R)-2-(2,5-difluorophenyl)pyrrolidin-1-yl)pyrazolo[1,5-a]pyridin-3-yl)(3-(hydroxymethyl)morpholino)methanone

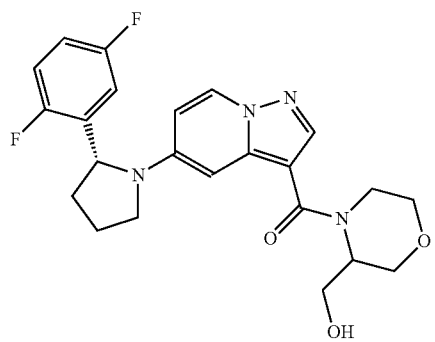 [SMILES: O=C(c1cnn2ccc(N3CCC[C@@H]3c3cc(F)ccc3F)cc12)N1CCOCC1CO]

The title compound was prepared by the method substantially similar to that mentioned in Example-6, using morpholino-3-methanol to afford the crude, which was purified by Preparative TLC (using Silicagel GF$_{254}$, 1000 u coated 20×20 cm dimension glass plate and 6% MeOH in CHCl₃ as eluent) to afford 15 mg of the title compound.

MS (ESI): m/z 442.9 (M+H).

Example-118

Synthesis of (5-((R)-2-(2,5-difluorophenyl)pyrrolidin-1-yl)pyrazolo[1,5-a]pyridin-3-yl)(2-(hydroxymethyl) morpholino) methanone

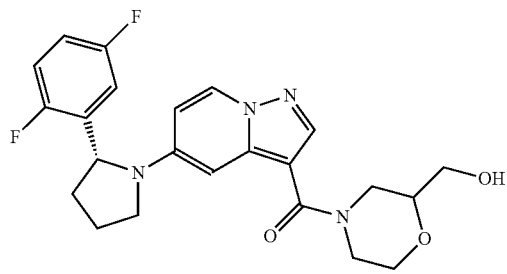 [SMILES: O=C(c1cnn2ccc(N3CCC[C@@H]3c3cc(F)ccc3F)cc12)N1CCOC(CO)C1]

The title compound was prepared by the method substantially similar to that mentioned in Example-6, using morpholino-3-methanol to afford the crude, which was purified by Preparative TLC (using Silicagel GF$_{254}$, 1000 u coated 20×20 cm dimension glass plate and 6% MeOH in CHCl$_3$ as eluent) to afford 15 mg of the title compound (5-((R)-2-(2,5-difluorophenyl)pyrrolidin-1-yl)pyrazolo[1,5-a]pyridin-3-yl) (2-(hydroxymethyl) morpholino) methanone.

MS (ESI): m/z 442.8 (M+H).

Example-119

Synthesis of (R)-5-(2-(2,5-difluorophenyl)pyrrolidin-1-yl)-N-(4-hydroxy-4-(hydroxymethyl)cyclohexyl) pyrazolo[1,5-a]pyridine-3-carboxamide

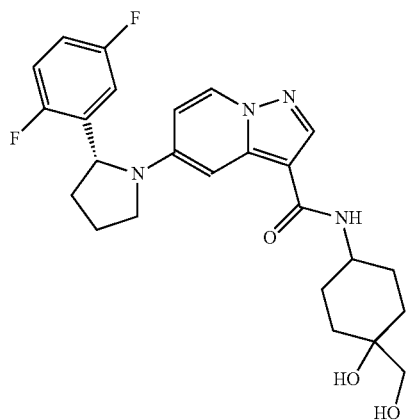 [SMILES: O=C(NC1CCC(O)(CO)CC1)c1cnn2ccc(N3CCC[C@@H]3c3cc(F)ccc3F)cc12]

The title compound was prepared by the method substantially similar to that mentioned in Example-16, using 4-amino-1-(hydroxymethyl)cyclohexanol to afford the crude, which was purified by Preparative TLC (using Silicagel GF$_{254}$, 1000 u coated 20×20 cm dimension glass plate and 7% MeOH in CHCl$_3$ as eluent) to afford 12 mg of the title compound.

$^1$H NMR (400 MHz, DMSO-d$_6$) δ ppm 8.39-8.35 (2H, m), 7.62-7.60 (1H, d, J=7.6 Hz), 7.34-7.30 (1H, m), 7.2-7.1 (1H, m), 6.95-6.9 (1H, m), 6.9-6.8 (1H, s), 6.40-6.30 (1H, m), 5.10-5.08 (1H, d, J=7.6 Hz), 4.56 (1H, t), 4.2-4.27 (2H, m), 3.96 (1H, bs), 3.83 (1H, t), 3.65-3.55 (1H, m), 3.17-3.15 (1H, d, J=5.6 Hz), 2.04-1.88 (4H, m), 1.71-1.33 (10H, m).

MS (ESI): m/z 470.9 (M+H).

Example-120

Synthesis of (5-((R)-2-(2,5-difluorophenyl)pyrrolidin-1-yl)pyrazolo[1,5-a]pyridin-3-yl)(4-((S)-3-hydroxypyrrolidin-1-yl)piperidin-1-yl)methanone

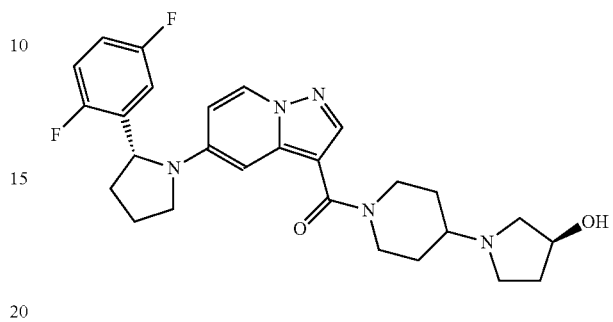

Step-1

Synthesis of (S)-tert-butyl 4-(3-hydroxypyrrolidin-1-yl)piperidine-1-carboxylate

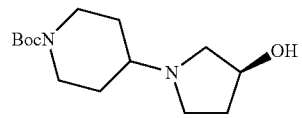 [SMILES: CC(C)(C)OC(=O)N1CCC(N2CC[C@H](O)C2)CC1]

Acetic acid (90 mg, 1.2 mmol) was added to solution of tert-butyl 4-oxopiperidine-1-carboxylate (300 mg, 1.5 mmol) and (S)-pyrrolidin-3-ol (140 mg, 1.7 mmol) in DCE (3 mL) at 10-15° C. and stirring was continued at the same temperature for 10 minutes. Sodium triacetoxyborohydride (957 mg, 4.5 mmol) was added portionwise to the reaction mixture and stirring was continued at 20-35° C. for 16 h. The reaction mixture was diluted with DCM, washed with water, dried over anhydrous sodium sulphate and concentrated under reduced pressure to afford 200 mg of the title compound.

MS (ESI): m/z 271 (M+H).

Step-2

Synthesis of (S)-1-(piperidin-4-yl)pyrrolidin-3-ol hydrochloride

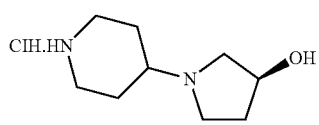

(S)-tert-butyl 4-(3-hydroxypyrrolidin-1-yl)piperidine-1-carboxylate (200 mg, 0.73 mmol) was added to a solution of 4M HCl in Dioxane (4 mL) at 0-5° C. and stirring was continued at 20-35° C. for 3 h. The reaction mixture was concentrated under reduced pressure to afford the crude product. The crude product was purified by washing with diethyl ether to afford 80 mg of the title compound.

MS (ESI): m/z 171 (M+H).

Step-3

Synthesis of (5-((R)-2-(2,5-difluorophenyl)pyrrolidin-1-yl)pyrazolo[1,5-a]pyridin-3-yl)(4-((S)-3-hydroxypyrrolidin-1-yl)piperidin-1-yl)methanone

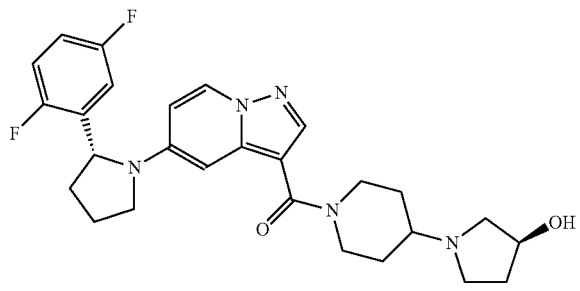 [SMILES: O=C(c1cnn2ccc(N3CCC[C@@H]3c3cc(F)ccc3F)cc12)N1CCC(N2CC[C@H](O)C2)CC1]

The title compound was prepared by the method substantially similar to that mentioned in Example-6, using (S)-1-(piperidin-4-yl)pyrrolidin-3-ol hydrochloride to afford the crude, which was purified by Preparative TLC (using Silicagel $GF_{254}$, 1000 u coated 20×20 cm dimension glass plate and 70% EtOAc in n-Hexane as eluent) to afford 23 mg of the title compound.

$^1$H NMR (400 MHz, DMSO-$d_6$) δ ppm 8.45-8.35 (1H, d, J=8.0 Hz), 8.0-7.95 (1H, s), 7.4-7.3 (1H, m), 7.2-7.1 (1H, m), 6.95-6.8 (1H, m), 6.5 (1H, s), 6.4-6.3 (1H, m), 5.15-5.0 (1H, d, J=8.8 Hz), 4.3-4.2 (1H, s), 4.2-4.0 (2H, m), 3.9-3.8 (1H, t), 3.0-2.8 (5H, m), 2.1-1.95 (3H, m), 1.95-1.8 (4H, m), 1.7-1.60 (1H, bs), 1.5-1.3 (2H, m).

MS (ESI): m/z 496.5 (M+H).

Example-121

Synthesis of (R)-(5-(2-(2,5-difluorophenyl)pyrrolidin-1-yl)pyrazolo[1,5-a]pyridin-3-yl)(4-(3-hydroxyazetidine-1-yl)piperidin-1-yl)methanone

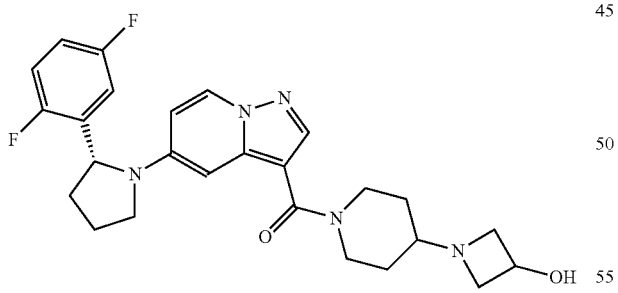

The title compound was prepared by the method substantially similar to that mentioned in Example-6, using 1-(piperidin-4-yl)azetidin-3-ol hydrochloride (prepared by method substantially similar to that mentioned in Step-1 to Step-2 in Example-121 using tert-butyl-4-oxopiperidine-1-carboxylate and 3-Azetidinolhydrochloride) to afford 30 mg of the title compound.

$^1$H NMR (400 MHz, DMSO-$d_6$) δ ppm 8.5-8.4 (1H, d, J=7.6 Hz), 7.95 (1H, s), 7.4-7.3 (1H, m), 7.2-7.1 (1H, m), 6.95-6.8 (1H, m), 6.5-6.45 (1H, bs), 6.4-6.3 (1H, d, J=6.8 Hz), 5.15-5.05 (1H, d, J=8.0 Hz), 4.25-4.15 (1H, m), 4.0-3.75 (3H, m), 3.65-3.5 (2H, m), 3.1-2.9 (2H, m), 2.9-2.7 (2H, bs), 2.1-1.3 (4H, m), 1.7-1.5 (2H, m), 1.2-1.0 (3H, m).

MS (ESI): m/z 482.6 (M+H).

Example-122

Synthesis of (R)-5-(2-(2,5-difluorophenyl)pyrrolidin-1-yl)-N-(3-hydroxy-2,2-dimethylpropyl)pyrazolo[1,5-a]pyridine-3-carboxamide

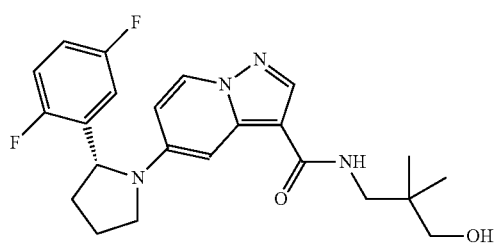 [SMILES: CC(C)(CO)CNC(=O)c1cnn2ccc(N3CCC[C@@H]3c3cc(F)ccc3F)cc12]

The title compound was prepared by the method substantially similar to that mentioned in Example-6, using 3-amino-2,2-dimethylpropan-1-ol to afford the crude, which was purified by Preparative TLC (using Silicagel $GF_{254}$, 1000 u coated 20×20 cm dimension glass plate and 5% MeOH in DCM as eluent) to afford 22 mg of the title compound.

$^1$H NMR (400 MHz, CD$_3$OD) δ ppm 8.45-8.4 (1H, d, J=7.6 Hz), 8.36 (1H, s), 7.95-7.8 (1H, t), 7.4-7.3 (1H, m), 7.2-7.1 (1H, m), 7.0-6.85 (2H, m), 6.4-6.3 (1H, d, J=4.8 Hz), 5.2-5.1 (1H, d, J=8.0 Hz), 4.8-4.7 (1H, t), 3.9-3.8 (1H, t), 3.5-3.35 (2H, m), 3.15-2.95 (4H, m), 2.1-2.0 (1H, m), 2.0-1.8 (2H, m), 0.9-0.7 (6H, s).

MS (ESI): m/z 429.9 (M+H).

Example-123

Synthesis of 5-((R)-2-(2,5-difluorophenyl)pyrrolidin-1-yl)-N—((S)-2-hydroxypropyl)pyrazolo[1,5-a]pyridine-3-carboxamide

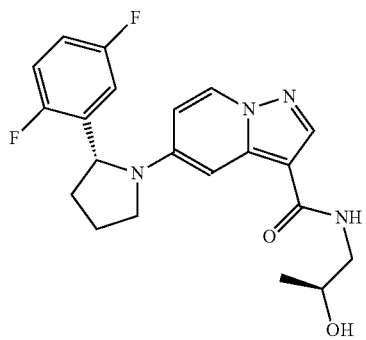 [SMILES: C[C@H](O)CNC(=O)c1cnn2ccc(N3CCC[C@@H]3c3cc(F)ccc3F)cc12]

The title compound was prepared by the method substantially similar to that mentioned in Example-6, using (S)-1-aminopropan-2-ol to afford 24.5 mg of the title compound.

$^1$H NMR (400 MHz, DMSO-$d_6$) δ ppm 8.41-8.40 (1H, d, J=7.6 Hz), 8.32 (1H, s), 7.86-7.8 (1H, m), 7.38-7.30 (1H, m), 7.2-7.1 (1H, m), 6.95 (1H, s), 6.9-6.84 (1H, m), 6.4-6.34 (1H, m), 5.12-5.10 (1H, d, J=8 Hz), 4.75-4.74 (1H, d, J=4.8 Hz), 3.9-3.8 (1H, m), 3.74-3.66 (1H, m), 3.5-3.4 (1H, m), 3.22-3.04 (2H, m), 2.55-2.40 (1H, m), 2.1-1.85 (3H, m), 1.05-1.03 (3H, d, J=6.4 Hz).
MS (ESI): m/z 401.6 (M+H).

Example-124

Synthesis of (R)-(5-(2-(2,5-difluorophenyl)pyrrolidin-1-yl)pyrazolo[1,5-a]pyridin-3-yl)(4-(1-methyl-1H-tetrazol-5-yl)piperidin-1-yl)methanone

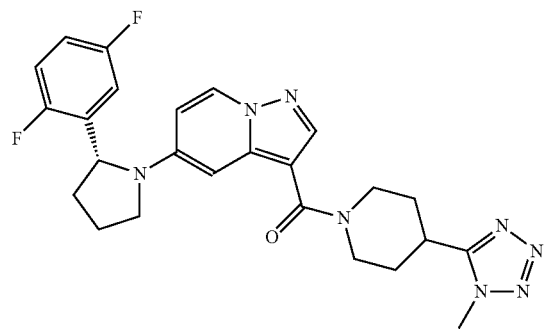 [SMILES: Cn1nnnc1C1CCN(C(=O)c2cnn3ccc(N4CCC[C@@H]4c4cc(F)ccc4F)cc23)CC1]

Step-1

Synthesis of Benzyl 4-cyanopiperidine-1-carboxylate

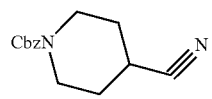 [SMILES: N#CC1CCN(C(=O)OCc2ccccc2)CC1]

The title compound was prepared by the method substantially similar to that mentioned in Example-88, to afford 1.6 g of the title compound.
$^1$H NMR (400 MHz, CDCl$_3$) δ ppm 7.42-7.3 (5H, m), 5.1 (2H, s), 3.8-3.7 (2H, m), 3.5-3.4 (2H, m), 2.9-2.8 (1H, m), 2.0-1.7 (4H, m).

Step-2

Synthesis of Benzyl 4-(1H-tetrazol-5-yl)piperidine-1-carboxylate

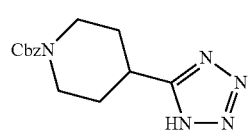 [SMILES: O=C(OCc1ccccc1)N1CCC(c2nnn[nH]2)CC1]

NaN$_3$ (1.7 g, 26.14 mmol) and NH$_4$Cl (1.75 g, 32.7 mmol) were added to the solution of benzyl 4-cyanopiperidine-1-carboxylate (1.6 g, 26.14 mmol) in DMF (16 mL) and stirring was continued at 90° C. for 24 h. The reaction mixture was quenched with 10% aqueous citric acid solution, extracted with EtOAc, dried over anhydrous sodium sulphate and concentrated under reduced pressure to afford 1.45 g of the title compound.
MS (ESI): m/z 288.5 (M+H).

Step-3

Synthesis of Benzyl 4-(1-methyl-1H-tetrazol-5-yl)piperidine-1-carboxylate and Benzyl 4-(2-methyl-2H-tetrazol-5-yl)piperidine-1-carboxylate

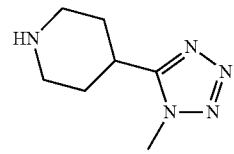

The title compounds were prepared by the method substantially similar to that mentioned in Example-112 (Step-3), to afford 0.6 g of the title compound Benzyl 4-(1-methyl-1H-tetrazol-5-yl)piperidine-1-carboxylate.
$^1$H NMR (300 MHz, DMSO-d$_6$) δ ppm 7.4-7.2 (5H, m), 5.1 (2H, s), 4.1 (1H, s), 4.0 (3H, s), 3.1-2.9 (2H, m), 2.0-1.9 (2H, m), 1.7-1.5 (2H, m). and 0.7 g (of the title compound Benzyl 4-(2-methyl-2H-tetrazol-5-yl)piperidine-1-carboxylate.
$^1$H NMR (300 MHz, DMSO-d$_6$) δ ppm 7.4-7.2 (5H, m), 5.1 (2H, s), 4.3 (3H, s), 4.05-3.95 (2H, m), 3.2-3.0 (3H, m), 2.1-1.9 (2H, m), 1.7-1.5 (2H, m).

Step-4

Synthesis of 4-(1-Methyl-1H-tetrazol-5-yl)piperidine

The title compounds were prepared by the method substantially similar to that mentioned in Example-112 (Step-4), to afford 0.2 g of the title compound.
MS (ESI): m/z 168.3 (M+H).

Step-5

Synthesis of (R)-(5-(2-(2,5-difluorophenyl)pyrrolidin-1-yl)pyrazolo[1,5-a]pyridin-3-yl)(4-(1-methyl-1H-tetrazol-5-yl)piperidin-1-yl)methanone

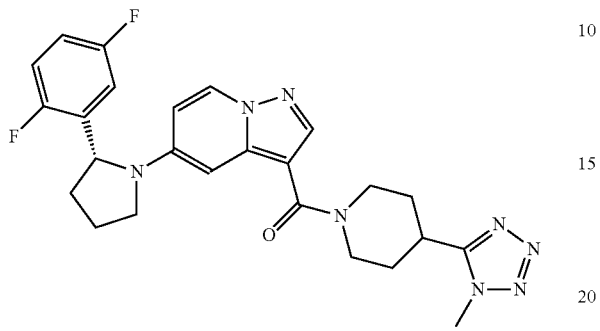

The title compound was prepared by the method substantially similar to that mentioned in Example-16, using 4-(1-Methyl-1H-tetrazol-5-yl)piperidine to afford the crude. The crude compound was purified by Preparative TLC (using Silicagel GF$_{254}$, 1000 u coated 20×20 cm dimension glass plate and 10% MeOH in CHCl$_3$ as eluent) to afford 36 mg of the title compound.

$^1$H NMR (300 MHz, CD$_3$OD) δ ppm 8.3-8.2 (1H, d, J=7.5 Hz), 8.0 (1H, s), 7.2-7.1 (1H, m), 7.05-6.95 (1H, m), 6.85-6.75 (1H, m), 6.55 (1H, s), 6.5-6.45 (1H, dd, J=2.4, 7.5 Hz), 5.2-5.1 (1H, d, J=8.1 Hz), 4.5-4.3 (2H, m), 4.1 (3H, s), 3.9-3.8 (1H, m), 3.6-3.5 (1H, m), 3.25-3.1 (2H, m), 2.6-2.45 (1H, m), 2.15-1.95 (5H, m), 1.95-1.7 (2H, m).

MS (ESI): m/z 493.5 (M+H).

Example-125

Synthesis of (R)-(5-(2-(2,5-difluorophenyl)pyrrolidin-1-yl)pyrazolo[1,5-a]pyridin-3-yl)(4-(2-methyl-2H-tetrazol-5-yl)piperidin-1-yl)methanone

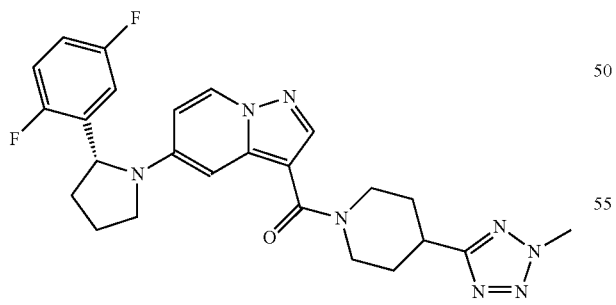

The title compound was prepared by the method substantially similar to that mentioned in Example-16, using 4-(2-Methyl-2H-tetrazol-5-yl)piperidine (Step-3 product of Example-126), to afford the crude. The crude compound was purified by Preparative TLC (using Silicagel GF$_{254}$, 1000 u coated 20×20 cm dimension glass plate and 10% MeOH in CHCl$_3$ as eluent) to 60 mg of the title compound $^1$H NMR (300 MHz, CD$_3$OD) δ ppm 8.3-8.2 (1H, d, J=8.1 Hz), 8.0 (1H, s), 7.2-7.1 (1H, m), 7.05-6.95 (1H, m), 6.85-6.75 (1H, m), 6.55-6.45 (2H, m), 5.2-5.1 (1H, d J=8.4 Hz), 4.33 (3H, s), 4.3-4.15 (1H, m), 3.9-3.8 (1H, m), 3.6-3.5 (1H, m), 3.25-3.05 (2H, m), 2.55-2.45 (1H, m), 2.2-2.0 (5H, m), 1.90-1.7 (2H, m).

MS (ESI): m/z 492.9 (M+H).

Example-126

Synthesis of (R)-5-(2-(2,5-difluorophenyl)pyrrolidin-1-yl)-N-(1-oxidotetrahydro-2H-thiopyran-4-yl)pyrazolo[1,5-a]pyridine-3-carboxamide

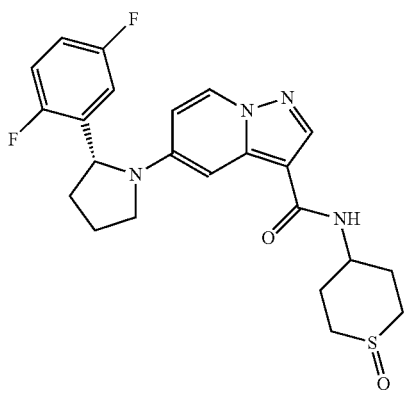 [SMILES: O=C(NC1CCS(=O)CC1)c1cnn2ccc(N3CCC[C@@H]3c3cc(F)ccc3F)cc12]

The title compound was prepared by the method substantially similar to that mentioned in Example-16, using 4-aminotetrahydro-2H-thiopyran 1-oxide hydrochloride to afford the crude. The crude compound was purified by Preparative TLC (using Silicagel GF$_{254}$, 1000 u coated 20×20 cm dimension glass plate and 5% MeOH in DCM as eluent) to afford 25 mg of the title compound.

$^1$H NMR (300 MHz, CD$_3$OD) δ ppm 8.3-8.2 (2H, m), 7.2-7.1 (1H, m), 7.1-6.95 (2H, m), 6.8-6.7 (1H, m), 6.5-6.4 (1H, dd, J=2.4, 7.8 Hz), 5.2-5.1 (1H, d, J=7.8 Hz), 4.15-3.95 (1H, m), 3.85-3.75 (1H, m), 3.60-3.45 (1H, m), 3.2-3.0 (2H, m), 2.95-2.75 (2H, m), 2.6-2.4 (1H, m), 2.4-2.2 (2H, m), 2.2-1.9 (5H, m), MS (ESI): m/z 458.8 (M+H).

Example-127

Synthesis of (5-((R)-2-(2,5-difluorophenyl)pyrrolidin-1-yl)pyrazolo[1,5-a]pyridin-3-yl)((S)-3-(pyrrolidin-1-ylmethyl)piperidin-1-yl)methanone

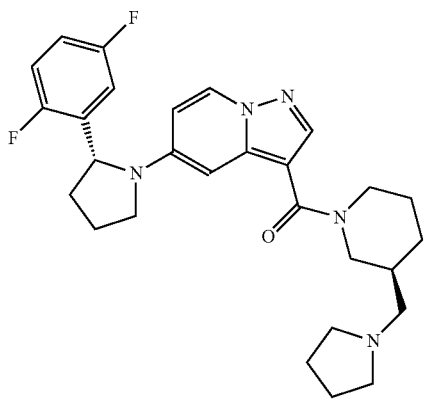 [SMILES: O=C(c1cnn2ccc(N3CCC[C@@H]3c3cc(F)ccc3F)cc12)N1CCC[C@@H](CN2CCCC2)C1]

The title compound was prepared by the method substantially similar to that mentioned in Example-16, using (S)-3-(pyrrolidin-1-ylmethyl)piperidine hydrochloride to afford the crude. The crude compound was purified by recrystallisation from a mixture of EtOAc and n-Hexane to afford 15 mg of the title compound.

$^1$H NMR (300 MHz, CD$_3$OD) δ ppm 8.3-8.2 (1H, d, J=7.5 Hz), 7.9 (1H, s), 7.25-7.15 (1H, m), 7.1-6.95 (1H, m), 6.85-6.75 (1H, m), 6.55-6.40 (2H, m), 5.16-5.13 (1H, d, J=8.4 Hz), 4.3-4.0 (2H, m), 3.9-3.8 (1H, m), 3.6-3.5 (1H, m), 3.3-3.0 (1H, m), 2.8-2.6 (1H, m), 2.6-2.2 (8H, m), 2.2-1.9 (4H, m), 1.9-1.5 (6H, m), 1.5-1.4 (1H, m), 1.35-1.1 (1H, m).

MS (ESI): m/z 494.6 (M+H).

Example-128

Synthesis of (5-((R)-2-(2,5-difluorophenyl)pyrrolidin-1-yl)pyrazolo[1,5-a]pyridin-3-yl)((R)-3-(pyrrolidin-1-ylmethyl)piperidin-1-yl)methanone

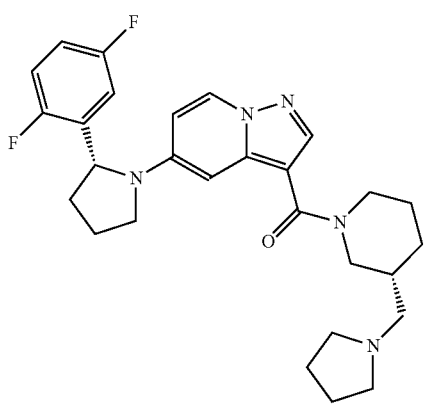 [SMILES: O=C(c1cnn2ccc(N3CCC[C@@H]3c3cc(F)ccc3F)cc12)N1CCC[C@H](CN2CCCC2)C1]

The title compound was prepared by the method substantially similar to that mentioned in Example-16, using (R)-3-(pyrrolidin-1-ylmethyl)piperidine hydrochloride to afford the crude. The crude compound was purified by recrystallisation from a mixture of EtOAc and n-Hexane to afford 355 mg of the title compound.

$^1$H NMR (300 MHz, CD$_3$OD) δ ppm 8.3-8.2 (1H, d, J=8.1 Hz), 8.0 (1H, s), 7.25-7.15 (1H, m), 7.15-6.95 (1H, m), 6.85-6.75 (1H, m), 6.55-6.45 (2H, m), 5.20-5.13 (1H, d, J=7.5 Hz), 4.45-4.20 (1H, m), 4.10-3.95 (1H, m), 3.90-3.75 (1H, m), 3.55-3.49 (1H, m), 3.12-2.85 (1H, m), 2.85-2.65 (1H, m), 2.60-2.35 (6H, m), 2.30-2.15 (1H, m), 2.15-1.85 (5H, m), 1.8-1.65 (6H, m), 1.6-1.4 (1H, m), 1.35-1.15 (1H, m).

MS (ESI): m/z 494.2 (M+H).

Example-129

Synthesis of 5-((R)-2-(2,5-difluorophenyl)pyrrolidin-1-yl)-N-((2,3-dihydrobenzo[b][1,4]dioxin-2-yl)methyl)pyrazolo[1,5-a]pyridine-3-carboxamide

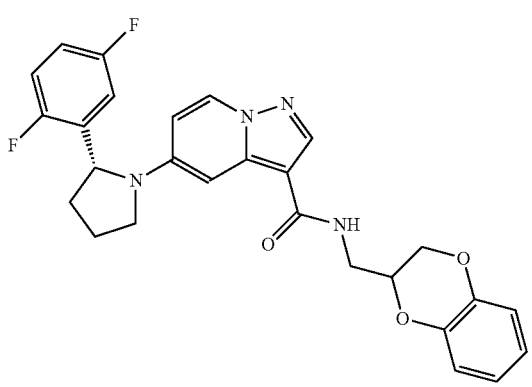 [SMILES: O=C(NCC1COc2ccccc2O1)c1cnn2ccc(N3CCC[C@@H]3c3cc(F)ccc3F)cc12]

The title compound was prepared by the method substantially similar to that mentioned in Example-6, using (2,3-dihydrobenzo[b][1,4]dioxin-2-yl)methanamine in place of NH$_4$Cl to afford the crude compound. The crude compound was purified by recrystallizing from a mixture of DCM and MeOH to afford 26 mg of the title compound.

MS (ESI): m/z 490.8 (M+H).

Example-130

Synthesis of (R)-5-(2-(2,5-difluorophenyl)pyrrolidin-1-yl)-N-((1-hydroxycyclobutyl)methyl)pyrazolo[1,5-a]pyridine-3-carboxamide

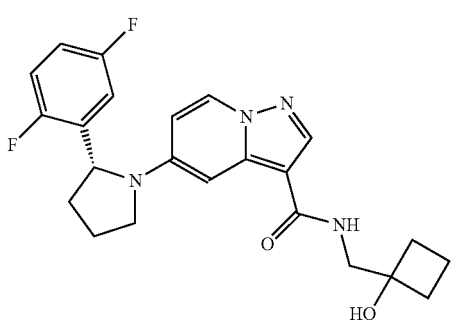 [SMILES: O=C(NCC1(O)CCC1)c1cnn2ccc(N3CCC[C@@H]3c3cc(F)ccc3F)cc12]

The title compound was prepared by the method substantially similar to that mentioned in Example-6, using 1-(aminomethyl)cyclobutanol in place of NH₄Cl to afford the crude compound. The crude compound was purified by Preparative TLC (using Silicagel GF$_{254}$, 1000 u coated 20×20 cm dimension glass plate and 8% MeOH in DCM as eluent) to afford 29.3 mg of the title compound.

$^1$H NMR (400 MHz, DMSO-d$_6$) δ ppm 8.45-8.35 (2H, m), 7.84 (1H, t), 7.38-7.30 (1H, m), 7.20-7.13 (1H, m), 6.97 (1H, s), 6.92-6.85 (1H, m), 6.34-6.33 (1H, m), 5.30 (1H, s), 5.14-5.12 (1H, d, J=8.0 Hz), 3.85 (1H, t), 3.45-3.35 (1H, m), 2.5-2.4 (1H, m), 2.10-1.84 (8H, m), 1.66-1.56 (1H, m), 1.50-1.43 (1H, m).

MS (ESI): m/z 427.5 (M+H).

Example-131

Synthesis of 5-((R)-2-(2,5-difluorophenyl)pyrrolidin-1-yl)-N—((S)-1-hydroxy-3-methylbutan-2-yl)pyrazolo[1,5-a]pyridine-3-carboxamide

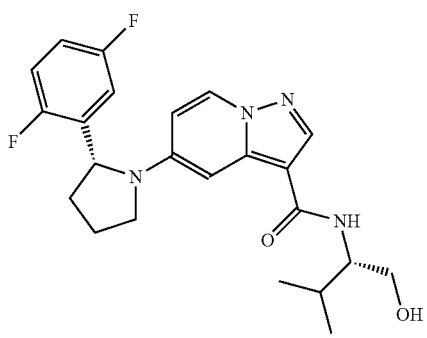 [SMILES: CC(C)[C@@H](CO)NC(=O)c1cnn2ccc(N3CCC[C@@H]3c3cc(F)ccc3F)cc12]

The title compound was prepared by the method substantially similar to that mentioned in Example-6, using (S)-2-amino-3-methylbutan-1-ol to afford the crude compound. The crude compound was purified by Preparative HPLC [Column: 21.2×150×5 um, Zorbax, XDB,C-18(#22), Mobile phase-A: 0.1% TFA in water, B:MeOH:ACN, Isocratic: A-35% and B-65% and Flow rate: 20 mL/min] to afford 19.3 mg (20.75%) of the title compound.

$^1$H NMR (400 MHz, DMSO-d$_6$) δ ppm 8.46-8.38 (2H, m), 7.38-7.28 (2H, m), 7.15 (1H, m), 6.96 (1H, s), 6.87-6.85 (1H, m), 6.376.30 (1H, m), 5.14-5.12 (1H, d, J=8.0 Hz), 3.90-3.75 (2H, m), 3.46-3.38 (3H, m), 2.51-2.40 (1H, m), 2.10-1.84 (4H, m), 0.94-0.84 (6H, m).

MS (ESI): m/z 429.1 (M+H).

Example-132

Synthesis of (R)-5-(5-(2-(2,5-difluorophenyl)pyrrolidin-1-yl)pyrazolo[1,5-a]pyridine-3-carbonyl)-4,5,6,7-tetrahydropyrazolo[1,5-a]pyrazine-2-carboxylic acid

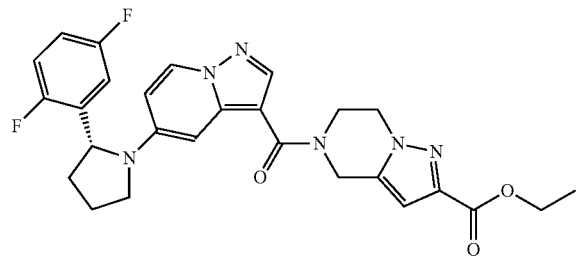 [SMILES: CCOC(=O)c1cc2n(n1)CCN(C(=O)c1cnn3ccc(N4CCC[C@@H]4c4cc(F)ccc4F)cc13)C2]

Step-1

Synthesis of (R)-ethyl 5-(5-(2-(2,5-difluorophenyl)pyrrolidin-1-yl)pyrazolo[1,5-a]pyridine-3-carbonyl)-4,5,6,7-tetrahydropyrazolo[1,5-a]pyrazine-2-carboxylate The title compound was prepared by the method substantially similar to that mentioned in Example-16, using ethyl 4,5,6,7-tetrahydropyrazolo[1,5-a]pyrazine-2-carboxylate (J. Med. Chem. 2006, 49, 4623-4637) to afford the crude compound. The crude compound was purified by recrystallisation from a mixture of EtOAc and n-Hexane to afford 150 mg of the title compound.

MS (ESI): m/z 520.9 (M+H).

149
Step-2

Synthesis of (R)-5-(5-(2-(2,5-difluorophenyl)pyrrolidin-1-yl)pyrazolo[1,5-a]pyridine-3-carbonyl)-4,5,6,7-tetrahydropyrazolo[1,5-a]pyrazine-2-carboxylic acid

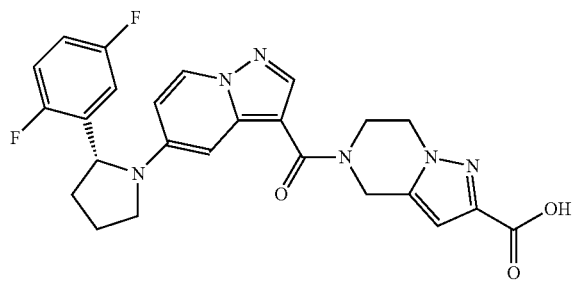 [SMILES: O=C(O)c1cc2n(n1)CCN(C(=O)c1cnn3ccc(N4CCC[C@@H]4c4cc(F)ccc4F)cc13)C2]

The title compound was prepared by a method substantially similar to that mentioned in Example-3, using (R)-ethyl 5-(5-(2-(2,5-difluorophenyl)pyrrolidin-1-yl)pyrazolo[1,5-a]pyridine-3-carbonyl)-4,5,6,7-tetrahydropyrazolo[1,5-a]pyrazine-2-carboxylate (Step-1) to afford 60 mg of the title compound.

$^1$H NMR (300 MHz, DMSO-$d_6$) δ ppm 12.8-12.2 (1H, bs), 8.49-8.46 (1H, d, J=7.5 Hz), 8.17 (1H, s), 7.40-7.25 (1H, m), 7.20-7.11 (1H, m), 6.95-6.80 (1H, m), 6.67 (1H, bs), 6.57 (1H, s), 6.45-6.35 (1H, m), 5.20-5.05 (1H, d, J=7.5 Hz), 4.84 (2H, s), 4.35-4.25 (2H, t), 4.20-4.06 (2H, m), 3.90-3.80 (1H, t) 3.50-3.35 (1H, m), 3.31 (1H, s), 2.10-2.01 (1H, m), 1.95-1.90 (2H, m).

MS ESI): m/z 493.8 (M+H).

Example-133

Synthesis of (R)-(5-(2-(2,5-difluorophenyl)pyrrolidin-1-yl)pyrazolo[1,5-a]pyridin-3-yl)(3,3-difluoropyrrolidin-1-yl)methanone

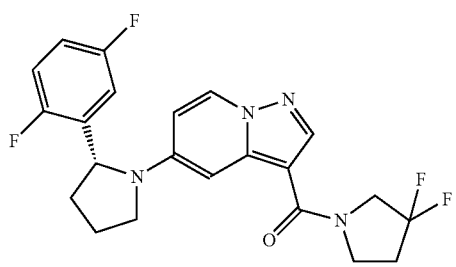 [SMILES: O=C(c1cnn2ccc(N3CCC[C@@H]3c3cc(F)ccc3F)cc12)N1CCC(F)(F)C1]

The title compound was prepared by the similar coupling method as mentioned in Example-16, using 3,3-Difluoropyrrolidine hydrochloride, to afford 24 mg of the title compound.

$^1$H NMR (300 MHz, DMSO-$d_6$) δ ppm 8.48-8.46 (1H, d, J=7.8 Hz), 8.20 (1H, s), 7.40-7.30 (1H, m), 7.20-7.11 (1H, m), 6.97 (1H, bs), 6.90-6.82 (1H, m), 6.50-6.35 (1H, m), 5.13-5.11 (1H, d, J=7.8 Hz), 4.10-3.90 (2H, m), 3.90-3.75 (3H, m), 3.55-3.40 (1H, m), 2.10-2.01 (2H, m), 1.95-1.80 (2H, m).

MS (ESI): m/z 432.8 (M+H).

150
Example-134

Synthesis of 5-((R)-2-(2,5-difluorophenyl)pyrrolidin-1-yl)-N-(2-(3-hydroxypyrrolidin-1-yl)ethyl)pyrazolo[1,5-a]pyridine-3-carboxamide

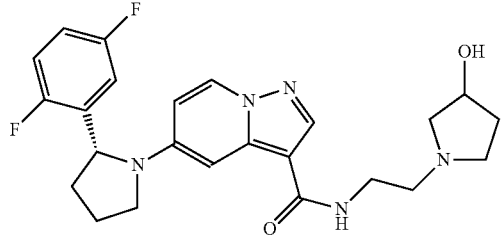 [SMILES: O=C(NCCN1CCC(O)C1)c1cnn2ccc(N3CCC[C@@H]3c3cc(F)ccc3F)cc12]

Step-1

Synthesis of 1-(2-aminoethyl)pyrrolidin-3-ol

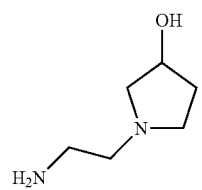

1M Solution of LAH in THF (4.38 mL, 4.38 mmol) was added to a solution of (S)-2-(3-hydroxypyrrolidin-1-yl)acetonitrile (Bio. org. Med. Chem. 15 (2007) 5369-538) (460 mg, 3.65 mmol) in THF (15 mL) at −78° C. and allowed the reaction mixture to stir at 25-35° C. for 10 minutes. The reaction mixture was refluxed for 3 h. The reaction mixture was quenched with saturated aqueous sodium sulphate solution at 0° C., heated to reflux, filtered the solid precipitate; filtrate collected was dried over anhydrous sodium sulphate and concentrated under reduced pressure to afford 250 mg of the title compound.

MS (ESI): m/z 131 (M+H).

Step-2

Synthesis of 5-((R)-2-(2,5-difluorophenyl)pyrrolidin-1-yl)-N-(2-(3-hydroxypyrrolidin-1-yl)ethyl)pyrazolo[1,5-a]pyridine-3-carboxamide

Step-1

Synthesis of (R)-ethyl 5-(5-(2-(2,5-difluorophenyl)pyrrolidin-1-yl)pyrazolo[1,5-a]pyridine-3-carbonyl)-4,5,6,7-tetrahydropyrazolo[1,5-a]pyrazine-3-carboxylate

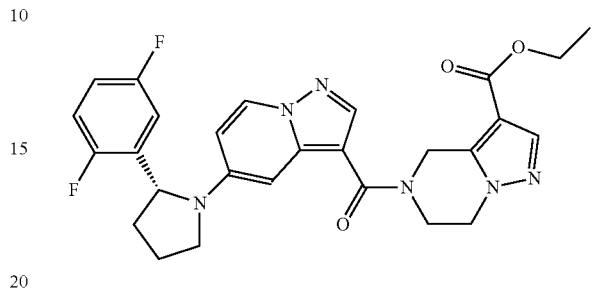

The title compound was prepared by the method substantially similar to that mentioned in Example-16, using ethyl 4,5,6,7-tetrahydropyrazolo[1,5-a]pyrazine-3-carboxylate (*J. Med. Chem.* 2006, 49, 4623-4637) to afford the crude compound. The crude compound was purified by recrystallisation from a mixture of EtOAc and n-Hexane to afford 130 mg (R)-ethyl 5-(5-(2-(2,5-difluorophenyl)pyrrolidin-1-yl)pyrazolo[1,5-a]pyridine-3-carbonyl)-4,5,6,7-tetrahydropyrazolo[1,5-a]pyrazine-3-carboxylate.

MS (ESI): m/z 521.4 (M+H).

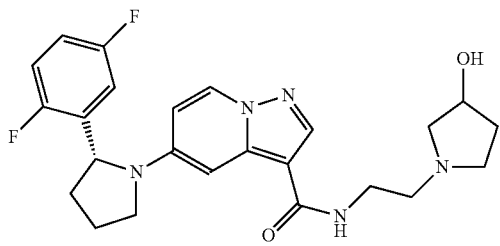 [SMILES: O=C(NCCN1CCC(O)C1)c1cnn2ccc(N3CCC[C@@H]3c3cc(F)ccc3F)cc12]

The title compound was prepared by the similar coupling method as mentioned in Example-6, using 1-(2-aminoethyl)pyrrolidin-3-ol (Step-1) to afford the crude, which was purified by Preparative TLC (using Silicagel GF$_{254}$, 1000 u coated 20×20 cm dimension glass plate and 12% MeOH in DCM as eluent) to afford 7.8 mg of the title compound.

MS (ESI): m/z 455.9 (M+H).

Step-2

Synthesis of (R)-5-(5-(2-(2,5-difluorophenyl)pyrrolidin-1-yl)pyrazolo[1,5-a]pyridine-3-carbonyl)-4,5,6,7-tetrahydropyrazolo[1,5-a]pyrazine-3-carboxylic acid

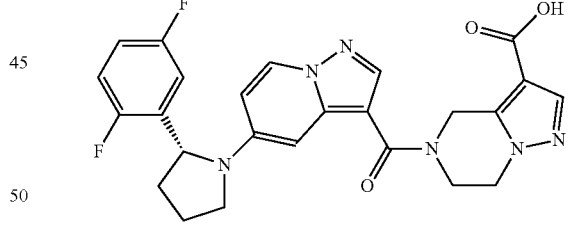

Example-135

Synthesis of (R)-5-(5-(2-(2,5-difluorophenyl)pyrrolidin-1-yl)pyrazolo[1,5-a]pyridine-3-carbonyl)-4,5,6,7-tetrahydropyrazolo[1,5-a]pyrazine-3-carboxylic acid The title compound was prepared by the method substantially similar to that mentioned in Example-3 using (R)-ethyl 5-(5-(2-(2,5-difluorophenyl)pyrrolidin-1-yl)pyrazolo[1,5-a]pyridine-3-carbonyl)-4,5,6,7-tetrahydropyrazolo[1,5-a]pyrazine-3-carboxylate (Step-1) to afford 60 mg of the title compound.

$^1$H NMR (300 MHz, DMSO-d$_6$) δ ppm 12.50-12.40 (1H, bs), 8.55-8.47 (1H, d, J=7.8 Hz), 8.16 (1H, s), 7.83 (1H, s), 7.40-7.25 (1H, m), 7.21-7.10 (1H, m), 6.95-6.80 (1H, m), 6.68 (1H, bs), 6.50-6.35 (1H, m), 5.20-5.10 (1H, d, J=7.6 Hz), 5.01 (2H, s), 4.35-4.25 (2H, t), 4.10-4.05 (2H, m), 3.90-3.75 (1H, m), 3.50-3.41 (1H, m), 3.35-3.28 (2H, m), 2.05-1.85 (2H, m).

MS (ESI): m/z 492.9 (M+H).

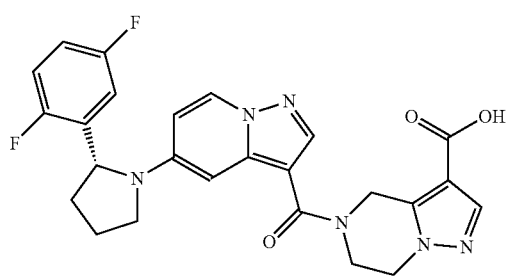 [SMILES: O=C(O)c1cnn2c1CN(C(=O)c1cnn3ccc(N4CCC[C@@H]4c4cc(F)ccc4F)cc13)CC2]

Example-136

Synthesis of N-((1r,4R)-4-(1H-tetrazol-5-yl)cyclohexyl)-5-((R)-2-(2,5-difluorophenyl)pyrrolidin-1-yl)pyrazolo[1,5-a]pyridine-3-carboxamide

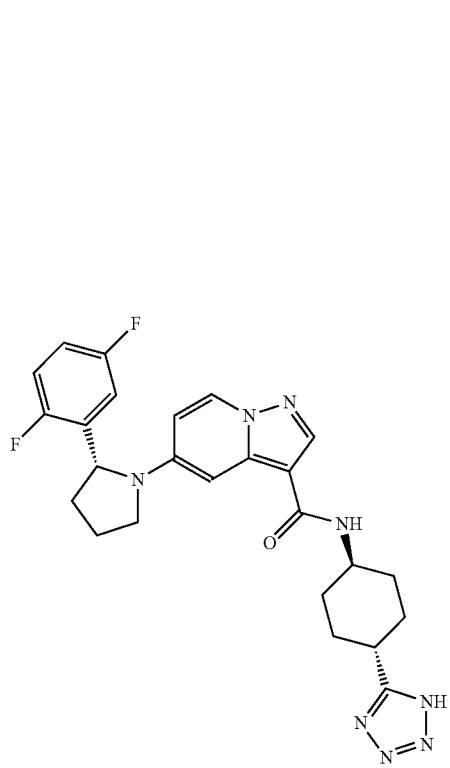 [SMILES: O=C(N[C@H]1CC[C@H](c2nnn[nH]2)CC1)c1cnn2ccc(N3CCC[C@@H]3c3cc(F)ccc3F)cc12]

The title compound was prepared by the method substantially similar to that mentioned in Example 88 using N-((1r,4R)-4-cyanocyclohexyl)-5-(R)-2-(2,5-difluorophenyl)pyrrolidin-1-yl)pyrazolo[1,5-a]pyridine-3-carboxamide (Product of Step-4 in Example-105) to afford the crude. The crude compound was purified by Preparative TLC (using Silicagel GF$_{254}$, 1000 u coated 20×20 cm dimension glass plate and 7% MeOH in DCM as eluent) to afford 60 mg of the title compound.

$^1$H NMR (300 MHz, CD$_3$OD) δ ppm 8.26-8.23 (2H, m), 7.25-7.13 (1H, m), 7.10-6.95 (2H, m), 6.81-6.71 (1H, m), 6.55-6.44 (1H, dd, J=2.7, 7.5 Hz), 5.19-5.17 (1H, d J=8.1 Hz), 4.00-3.83 (2H, m), 3.59-3.50 (1H, m), 3.15-2.95 (1H, m), 2.65-2.49 (1H, m), 2.35-1.95 (8H, m), 1.90-1.65 (2H, m), 1.65-1.45 (2H, m).

MS (ESI): m/z 493.3 (M+H).

Example-137

Synthesis of (R)-5-(2-(2,5-difluorophenyl)pyrrolidin-1-yl)-N-(3-hydroxycyclobutyl)pyrazolo[1,5-a]pyridine-3-carboxamide

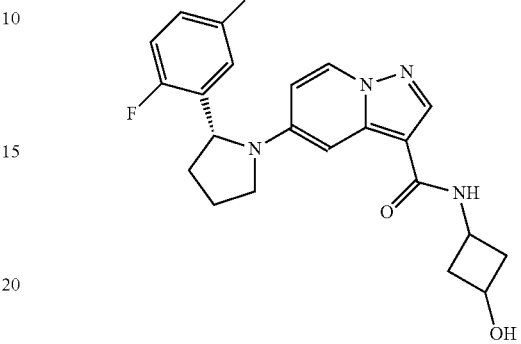

The title compound was prepared by the similar coupling method as mentioned in Example-6 using 3-aminocyclobutanol trifluoroacetate (WO 2007/115999) to afford the crude, which was purified by washing mixture of Diethyl ether and MeOH (98:2) to afford 53 mg of the title compound.

$^1$H NMR (400 MHz, DMSO-d$_6$) δ ppm 8.45-8.35 (1H, d, J=7.6 Hz), 8.33 (1H, s), 7.95-7.85 (1H, t), 7.40-7.25 (1H, m), 7.25-7.05 (1H, m), 6.93 (1H, bs), 6.90-6.80 (1H, m), 6.45-6.25 (1H, d, J=5.6 Hz), 5.20-4.95 (2H, m), 4.40-4.25 (1H, m), 3.90-3.81 (2H, m), 3.50-3.44 (1H, m), 2.23-2.15 (1H, m), 2.15-2.04 (2H, m), 2.04-1.83 (3H, m).

MS (ESI): m/z 413.2 (M+H).

Example-138

Synthesis of (R)-5-(2-(2,5-difluorophenyl)pyrrolidin-1-yl)-N-(1,1-dioxidotetrahydro-2H-thiopyran-4-yl)pyrazolo[1,5-a]pyridine-3-carboxamide

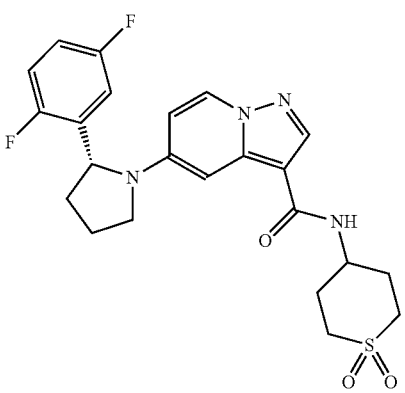

The title compound was prepared by the similar coupling method as mentioned in Example-16 using 4-aminotetrahydro-2H-thiopyran-1,1-dioxide trifluoroacetate (WO 2008033562) to afford the crude, which was purified by washing mixture of EtOAc and n-Hexane (1:1) to afford 67 mg of the title compound.

¹H NMR (400 MHz, DMSO-d₆) δ ppm 8.45-8.41 (1H, d, J=7.6 Hz), 8.32 (1H, s), 7.85-7.75 (1H, d J=8.0 Hz), 7.36-7.31 (1H, m), 7.20-7.13 (1H, m), 6.95-6.87 (2H, m), 6.45-6.35 (1H, m), 5.15-5.08 (1H, d, J=7.6 Hz), 4.25-4.05 (1H, m), 3.95-3.75 (1H, t), 3.50-3.35 (1H, m), 3.30-3.15 (2H, m), 3.15-3.06 (2H, d) 2.5-2.35 (1H, m), 2.20-1.85 (8H, m).

MS (ESI): m/z 474.8 (M+H).

Example-139

Synthesis of 5-((R)-2-(2,5-difluorophenyl)pyrrolidin-1-yl)-N-(4-((S)-3-hydroxypyrrolidin-1-yl)cyclohexyl)pyrazolo[1,5-a]pyridine-3-carboxamide

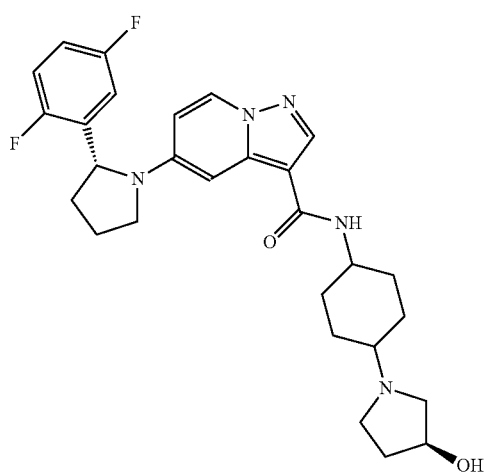 [SMILES: O=C(NC1CCC(N2CC[C@H](O)C2)CC1)c1cnn2ccc(N3CCC[C@@H]3c3cc(F)ccc3F)cc12]

Step-1

Synthesis of (S)-benzyl (4-(3-hydroxypyrrolidin-1-yl)cyclohexyl)carbamate

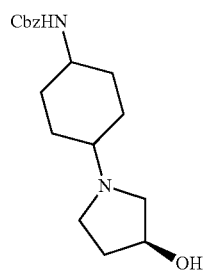 [SMILES: O=C(NC1CCC(N2CC[C@H](O)C2)CC1)OCc1ccccc1]

The title compound was prepared by the method substantially similar to that mentioned in Example-121 (Step-1), using benzyl (4-oxocyclohexyl) carbamate in place of tert-butyl-4-oxopiperidine-1-carboxylate to afford 400 mg of the title compound.

MS (ESI): m/z 319.5 (M+H)

Step-2

Synthesis of (S)-1-(4-aminocyclohexyl)pyrrolidin-3-ol

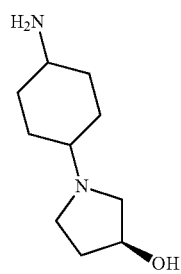 [SMILES: NC1CCC(N2CC[C@H](O)C2)CC1]

10% vPd/C (40 mg) was added to a solution of (S)-benzyl (4-(3-hydroxypyrrolidin-1-yl)cyclohexyl)carbamate (400 mg, 1.2 mmol) in MeOH (8 mL) and the mixture was stirred continuously under hydrogen atmosphere at 20-35° C. for 15 h. The reaction mixture was filtered over a celite bed and the filtrate was concentrated under reduced pressure to afford 120 g of the title compound.

MS (ESI): m/z 185.4 (M+H)

Step-3

Synthesis of 5-((R)-2-(2,5-difluorophenyl)pyrrolidin-1-yl)-N-(4-((S)-3-hydroxypyrrolidin-1-yl)cyclohexyl)pyrazolo[1,5-a]pyridine-3-carboxamide

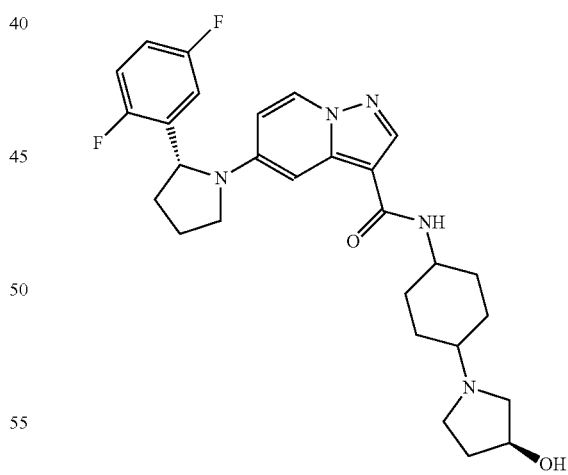

The title compound was prepared by the method substantially similar to that mentioned in Example-6, using (S)-1-(4-aminocyclohexyl)pyrrolidin-3-ol to afford the crude, which was purified by Preparative HPLC [Column: 21.2×150×5 um, Zorbax, XDB,C-18(#22), Mobile phase-A: 0.01% TFA in water, B:ACN, Gradient (Time/% B): 0/20, 2/30, 10/80 and Flow rate: 20 mL/min] to afford 12 mg of the title compound.

MS (ESI): m/z 509.9 (M+H)

Example-140

Synthesis of 5-((R)-2-(2,5-difluorophenyl)pyrrolidin-1-yl)-N-((tetrahydro-2H-pyran-3-yl)methyl)pyrazolo[1,5-a]pyridine-3-carboxamide (Diastereomer I)

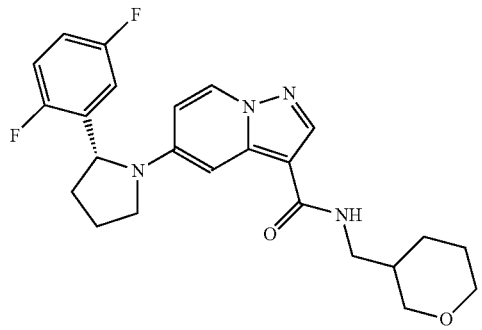 [SMILES: O=C(NCC1CCCOC1)c1cnn2ccc(N3CCC[C@@H]3c3cc(F)ccc3F)cc12]

The title compound was prepared by the similar coupling method as mentioned in Example-16, using (tetrahydro-2H-pyran-3-yl)methanamine to afford the crude, which was purified by Preparative Chiral HPLC [Column: CHIRALPAK AD-H(20×25×5 u), Mobile phase-EtOH:n-Hexane (60:40) and Flow rate:12 mL/min] to afford 22 mg of the title compound along with 14.4 mg of Example 145.

$^1$H NMR (300 MHz, CDCl$_3$) δ ppm 8.17-8.10 (1H, d, J=7.5 Hz), 7.94 (1H, s), 7.20-7.19 (1H, d J=2.4 Hz), 7.10-7.00 (1H, m), 6.89-6.82 (1H, m), 6.75-6.65 (1H, m), 6.20-6.12 (1H, dd, J=2.4, 7.5 Hz), 5.80-5.70 (1H, t), 5.12-5.11 (1H, d, J=2.4 Hz), 4.02-3.90 (1H, m), 3.90-3.79 (2H, m), 3.60-3.50 (1H, m), 3.50-3.25 (5H, m), 2.50-2.40 (1H, m), 2.15-2.00 (3H, m), 2.00-1.81 (2H, m).

MS (ESI): m/z 440.9 (M+H)

Example-141

Synthesis of 5-((R)-2-(2,5-difluorophenyl)pyrrolidin-1-yl)-N-((tetrahydro-2H-pyran-3-yl)methyl)pyrazolo[1,5-a]pyridine-3-carboxamide (Diastereomer II)

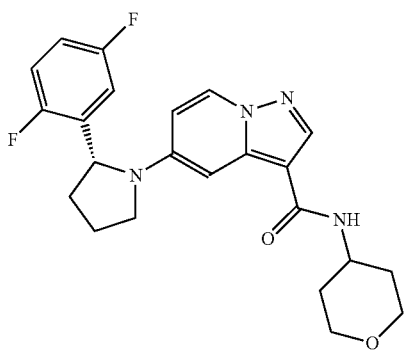 [SMILES: O=C(NC1CCOCC1)c1cnn2ccc(N3CCC[C@@H]3c3cc(F)ccc3F)cc12]

$^1$H NMR (300 MHz, CDCl$_3$) δ ppm 8.17-8.10 (1H, d, J=7.5 Hz), 7.94 (1H, s), 7.20-7.19 (1H, d, J=2.4 Hz), 7.10-7.00 (1H, m), 6.89-6.82 (1H, m), 6.70-6.60 (1H, m), 6.20-6.10 (1H, m), 5.80-5.71 (1H, t), 5.20-5.10 (1H, d, J=7.4 Hz), 4.02-3.90 (1H, m), 3.90-3.75 (2H, m), 3.60-3.40 (2H, m), 3.40-3.25 (2H, m), 2.50-2.40 (1H, m), 2.15-2.00 (3H, m), 2.00-1.82 (2H, m).

MS (ESI): m/z 440.9 (M+H)

Example-142

Synthesis of N-((1R,4R)-4-(1H-1,2,4-triazol-5-yl)cyclohexyl)-5-((R)-2-(2,5-difluorophenyl)pyrrolidin-1-yl)pyrazolo[1,5-a]pyridine-3-carboxamide

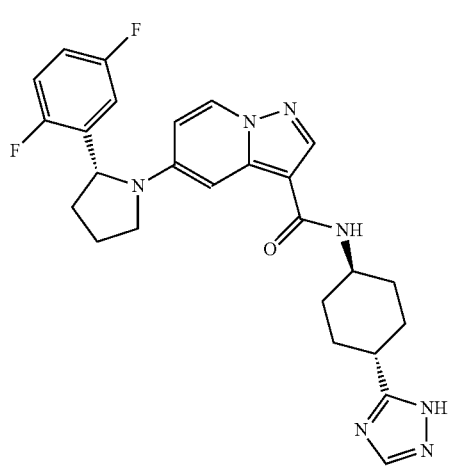 [SMILES: O=C(N[C@H]1CC[C@H](c2ncn[nH]2)CC1)c1cnn2ccc(N3CCC[C@@H]3c3cc(F)ccc3F)cc12]

Step-1

Synthesis of tert-butyl 5-((1r,4r)-4-(((benzyloxy)carbonyl)amino)cyclohexyl)-1H-1,2,4-triazole-1-carboxylate

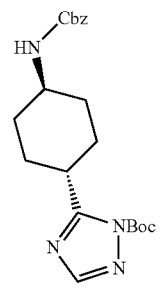 [SMILES: CC(C)(C)OC(=O)n1ncnc1[C@H]1CC[C@H](NC(=O)OCc2ccccc2)CC1]

Di-tert-butyldicarbonate (87 mg, 0.4 mmol) was added to solution of Benzyl ((1r,4r)-4-(1H-1,2,4-triazol-5-yl)cyclohexyl)carbamate (US2009/0093472 A1) (100 mg, 0.33 mmol), Et$_3$N (67 mg, 0.67 mmol) and DMAP (8 mg, 0.07 mmol) in acetonitrile (1 mL) at 0-5° C. and stirring was continued at 20-35° C. for 3 h. Reaction mixture was diluted with EtOAc, washed with water, dried over anhydrous sodium sulphate and concentrated under reduced pressure to afford 100 mg of the title compound.

¹H NMR (300 MHz, DMSO-d₆) δ ppm 9.0 (1H, s), 8.2 (1H, d) 7.4-7.2 (5H, m), 5.0 (2H, s), 4.1-4.0 (1H, m), 2.7-2.6 (1H, m), 2.1-1.8 (4H, m), 1.6 (9H, s), 1.4-0.9 (4H, m).

Step-2

Synthesis of tert-Butyl 5-((1r,4r)-4-aminocyclohexyl)-1H-1,2,4-triazole-1-carboxylate

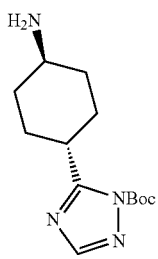

10% Pd/C (10 mg) was added to a solution of tert-butyl 5-((1r,4r)-4-(((benzyloxy)carbonyl)amino)cyclohexyl)-1H-1,2,4-triazole-1-carboxylate (100 mg, 0.25 mmol) in MeOH (1.5 mL) and the mixture was stirred continuously under hydrogen atmosphere at 20-35° C. for 2 h. The reaction mixture was filtered over a celite bed and the filtrate was concentrated under reduced pressure to afford 77 mg (crude) of the title compound.

¹H NMR (300 MHz, CD₃OD) δ ppm 8.1 (1H, s), 4.2-4.0 (1H, m), 3.4-3.2 (1H, m), 2.9-2.4 (2H, m), 2.1-1.9 (4H, m), 1.72-1.6 (2H, m), 1.5 (9H, s), 1.4-1.1 (2H, m).

Step-3

Synthesis of N-((1R,4R)-4-(1H-1,2,4-triazol-5-yl)cyclohexyl)-5-((R)-2-(2,5-difluorophenyl)pyrrolidin-1-yl)pyrazolo[1,5-a]pyridine-3-carboxamide

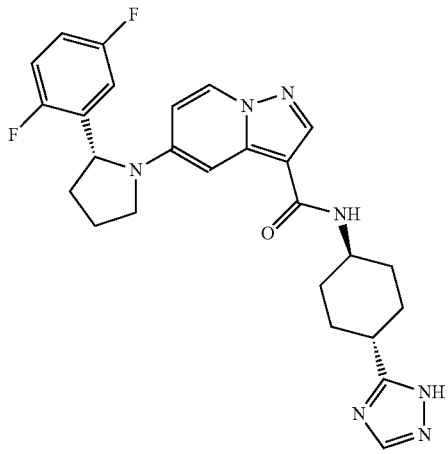 [SMILES: O=C(N[C@H]1CC[C@H](c2ncn[nH]2)CC1)c1cnn2ccc(N3CCC[C@@H]3c3cc(F)ccc3F)cc12]

The title compound was prepared by the similar coupling method as mentioned in Example-16, using tert-Butyl 5-((1r,4r)-4-aminocyclohexyl)-1H-1,2,4-triazole-1-carboxylate to afford tert-butyl-5-((1R,4r)-4-(5-((R)-2-(2,5-difluorophenyl)pyrrolidin-1-yl)pyrazolo[1,5-a]pyridine-3-carboxamido)cyclohexyl)-1H-1,2,4-triazole-1-carboxylate) as crude. The crude compound was as such dissolved in 1,4-Dioxane (0.5 mL) and 4N HCl in Dioxane (1 mL) was added to the above solution at 0-5° C. and stirring was continued at 20-35° C. for 2 h. Reaction mixture was concentrated under reduced pressure to afford the crude. The crude compound was dissolved in water, adjusted the pH to 8 with aqueous NaHCO₃ solution, filtered the solid precipitated, dried well to afford 10 mg of the title compound.

¹H NMR (300 MHz, CD₃OD) δ ppm 8.25-8.22 (2H, m), 7.22-7.12 (1H, m), 7.05-6.95 (1H, m), 6.83-6.75 (1H, m), 6.50-6.42 (1H, m), 5.20-5.16 (1H, d, J=8.4 Hz), 4.00-3.80 (2H, m), 3.60-3.50 (1H, m), 2.90-2.78 (1H, m), 2.55-2.45 (1H, m), 2.20-1.95 (7H, m), 1.89-1.45 (4H, m).

MS (ESI): m/z 491.9 (M+H).

Example-143

Synthesis of 5-((R)-2-(2,5-difluorophenyl)pyrrolidin-1-yl)-N-((1r,4R)-4-(1-methyl-1H-tetrazol-5-yl)cyclohexyl)pyrazolo[1,5-a]pyridine-3-carboxamide

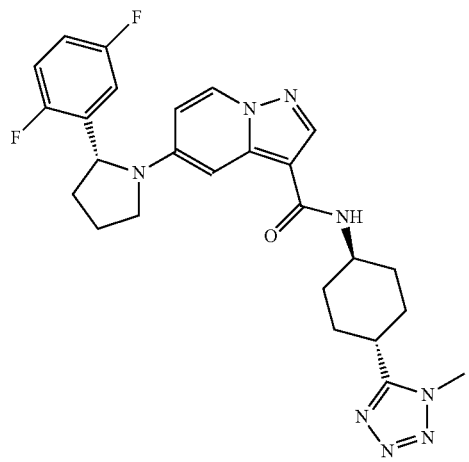 [SMILES: Cn1nnnc1[C@H]1CC[C@H](NC(=O)c2cnn3ccc(N4CCC[C@@H]4c4cc(F)ccc4F)cc23)CC1]

The title compound was prepared by the similar coupling method as mentioned in Example-16 using (1r,4r)-4-(1-methyl-1H-tetrazol-5-yl)cyclohexanamine (prepared by the method similar from Step 1 to Step-4 in Example-126) to afford the crude. The crude compound was purified by Preparative TLC (using Silicagel GF₂₅₄, 1000 u coated 20×20 cm dimension glass plate and 100% EtOAc as eluent) to afford 35 mg of the title compound.

¹H NMR (300 MHz, CD₃OD) δ ppm 8.26-8.23 (2H, m), 7.85-7.75 (1H, m), 7.20-7.12 (1H, m), 7.05-6.95 (2H, m), 6.82-6.75 (1H, m), 6.50-6.42 (1H, dd, J=2.1, 7.5 Hz), 5.20-5.17 (1H, d, J=7.8 Hz), 4.07 (3H, s), 4.05-3.90 (1H, m), 3.90-3.80 (1H, m), 3.60-3.54 (1H, m), 3.10-3.05 (1H, m), 2.55-2.45 (1H, m), 2.20-1.95 (8H, m), 1.90-1.75 (2H, m), 1.65-1.49 (2H, m).

MS (ESI): m/z 506.9 (M+H).

Example-144

Synthesis of 5-((R)-2-(2,5-difluorophenyl)pyrrolidin-1-yl)-N-((1r,4R)-4-(2-methyl-2H-tetrazol-5-yl)cyclohexyl)pyrazolo[1,5-a]pyridine-3-carboxamide

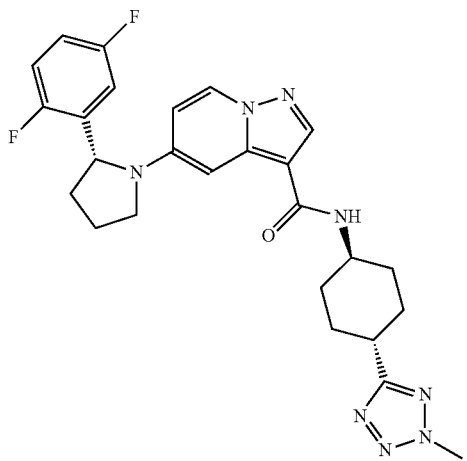 [SMILES: Cn1nnc([C@H]2CC[C@H](NC(=O)c3cnn4ccc(N5CCC[C@@H]5c5cc(F)ccc5F)cc34)CC2)n1]

The title compound was prepared by the similar coupling method as mentioned in Example-16 using (1r,4r)-4-(2-methyl-2H-tetrazol-5-yl)cyclohexanamine (prepared by the method similar from Step 1 to Step-4 in Example-126) to afford the crude. The crude compound was purified by Preparative TLC (using Silicagel GF$_{254}$, 1000 u coated 20×20 cm dimension glass plate and 100% EtOAc as eluent) to afford 55 mg of the title compound.

$^1$H NMR (300 MHz, CD$_3$OD) δ ppm 8.26-8.22 (2H, m), 7.20-7.12 (1H, m), 7.05-6.95 (2H, m), 6.82-6.75 (1H, m), 6.50-6.42 (1H, dd, J=2.4, 7.5 Hz), 5.20-5.16 (1H, d, J=8.1 Hz), 4.31 (3H, s), 4.00-3.84 (2H, m), 3.60-3.53 (1H, m), 3.00-2.85 (1H, m), 2.55-2.45 (1H, m), 2.25-1.95 (8H, m), 1.85-1.49 (4H, m).

MS (ESI): m/z 506.9 (M+H).

Example-145

Synthesis of 5-((R)-2-(2,5-difluorophenyl)pyrrolidin-1-yl)-N-(5,6,7,8-tetrahydroimidazo[1,2-a]pyridin-7-yl)pyrazolo[1,5-a]pyridine-3-carboxamide

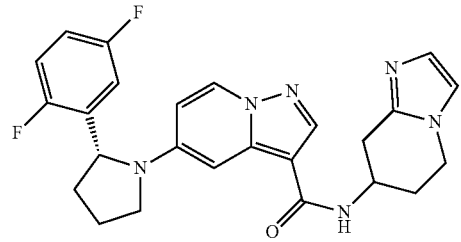 [SMILES: O=C(NC1CCn2ccnc2C1)c1cnn2ccc(N3CCC[C@@H]3c3cc(F)ccc3F)cc12]

The title compound was prepared by the similar coupling method as mentioned in Example-16 using 5,6,7,8-tetrahydroimidazo[1,2-a]pyridin-7-amine to afford the crude. The crude compound was purified by washing with mixture of DCM and n-Hexane to 45 mg of the title compound.

MS (ESI): m/z 463.3 (M+H).

Example-146

Synthesis of 5-((R)-2-(2,5-difluorophenyl)pyrrolidin-1-yl)-N-((tetrahydrofuran-3-yl)methyl)pyrazolo[1,5-a]pyridine-3-carboxamide (diastereomer 1)

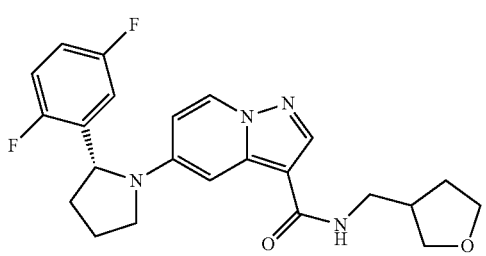 [SMILES: O=C(NCC1CCOC1)c1cnn2ccc(N3CCC[C@@H]3c3cc(F)ccc3F)cc12]

The title compound was prepared by the similar coupling method as mentioned in Example-16 using (tetrahydrofuran-3-yl)methanamine to afford the crude. The crude compound was purified by Chiral HPLC[Column: LUX AMYLOSE-2AXIA PACKED(21.2×250×5 u), Mobile Phase: Hexane/EtOH/IPA (30:35:35) Flow rate: 20 mL/min] to afford 40 mg of the title compound.

$^1$H NMR (300 MHz, CDCl$_3$) δ ppm 8.17-8.11 (1H, d, J=7.8 Hz), 7.95 (1H, s), 7.20-7.15 (1H, d, J=2.7 Hz), 7.10-7.01 (1H, m), 6.95-6.85 (1H, m), 6.71-6.65 (1H, m), 6.20-6.14 (1H, dd, J=3.0, 7.8 Hz), 5.90-5.85 (1H, t), 5.15-5.05 (1H, d, J=7.8 Hz), 3.99-3.65 (4H, m), 3.65-3.60 (1H, m), 3.60-3.40 (4H, m), 2.70-2.52 (1H, m), 2.50-2.40 (1H, m), 2.20-2.02 (5H, m).

MS (ESI): m/z 426.9 (M+H).

Example-147

Synthesis of N-((1r,4R)-4-(1,3,4-oxadiazol-2-yl)cyclohexyl)-5-((R)-2-(2,5-difluorophenyl)pyrrolidin-1-yl)pyrazolo[1,5-a]pyridine-3-carboxamide

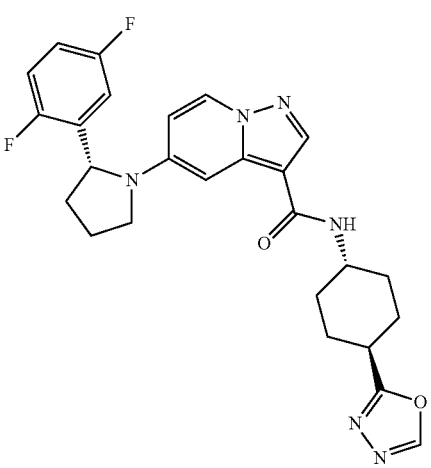 [SMILES: O=C(N[C@H]1CC[C@H](c2nnco2)CC1)c1cnn2ccc(N3CCC[C@@H]3c3cc(F)ccc3F)cc12]

The title compound was prepared by the similar coupling method as mentioned in Example-16 using (1r,4r)-4-(1,3,4-oxadiazol-2-yl)cyclohexanamine (US 2007/0155738) to afford the crude. The crude compound was purified by Preparative TLC (using Silicagel GF$_{254}$, 1000 u coated 20×20 cm dimension glass plate and 100% EtOAc as eluent) to afford 12 mg of the title compound.

$^1$H NMR (300 MHz, CD$_3$OD) δ ppm 8.86 (1H, s), 8.26-8.23 (2H, m), 7.20-7.13 (1H, m), 7.05-6.95 (2H, m), 6.82-6.75 (1H, m), 6.50-6.43 (1H, dd, J=2.4, 7.8 Hz), 5.20-5.16 (1H, d, J=7.8 Hz), 4.00-3.80 (2H, m), 3.60-3.53 (1H, m), 3.05-2.95 (1H, m), 2.55-2.45 (1H, m), 2.30-2.00 (7H, m), 1.85-1.40 (4H, m).

MS (ESI): m/z 493.3 (M+H).

Example-148

Synthesis of (R)-(5-(2-(2,5-difluorophenyl)pyrrolidin-1-yl)pyrazolo[1,5-a]pyridin-3-yl)(4-(5-methyl-1,3,4-oxadiazol-2-yl)piperidin-1-yl)methanone

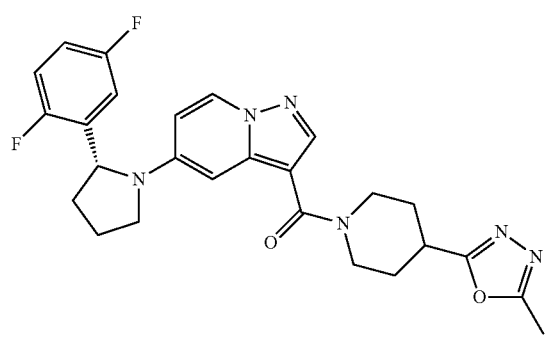 [SMILES: Cc1nnc(C2CCN(C(=O)c3cnn4ccc(N5CCC[C@@H]5c5cc(F)ccc5F)cc34)CC2)o1]

The title compound was prepared by the similar coupling method as mentioned in Example-16 using 2-methyl-5-(piperidin-4-yl)-1,3,4-oxadiazole (US 2007/0155738) to afford the crude. The crude compound was purified by Preparative TLC (using Silicagel GF$_{254}$, 1000 u coated 20×20 cm dimension glass plate and 100% EtOAc as eluent) to afford 32 mg of the title compound.

$^1$H NMR (300 MHz, CD$_3$OD) δ ppm 8.29-8.26 (1H, d, J=8.1 Hz), 7.98 (1H, s), 7.20-7.13 (1H, m), 7.05-6.95 (1H, m), 6.85-6.75 (1H, m), 6.55-6.45 (2H, m), 5.16-5.14 (1H, d, J=7.8 Hz), 4.40-4.20 (2H, m), 3.90-3.80 (1H, m), 3.61-3.50 (1H, m), 3.30-3.16 (3H, m), 2.55-2.45 (4H, m), 2.20-2.00 (5H, m), 1.90-1.70 (2H, m).

MS (ESI): m/z 492.9 (M+H).

Example-149

Synthesis of (R)-5-(2-(2,5-difluorophenyl)pyrrolidin-1-yl)-N-(4-(3-hydroxyazetidine-1-yl)cyclohexyl)pyrazolo[1,5-a]pyridine-3-carboxamide

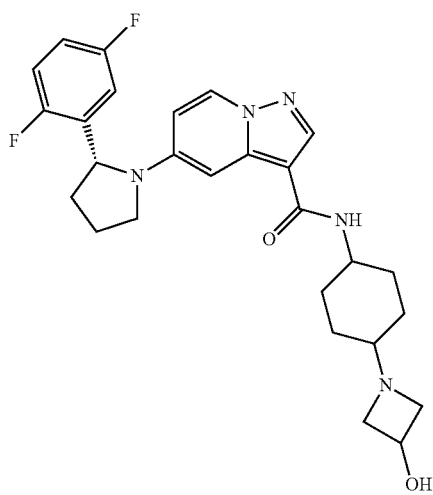 [SMILES: O=C(NC1CCC(N2CC(O)C2)CC1)c1cnn2ccc(N3CCC[C@@H]3c3cc(F)ccc3F)cc12]

The title compound was prepared by the similar coupling method as mentioned in Example-6, using 1-(4-aminocyclohexyl)azetidin-3-ol (prepared by the method similar from Step-1 to Step-2 in Example 143) to afford the crude, which was purified by Preparative HPLC [Column: LUNA-C18-250*21.2 mm, Mobile phase-A: 0.1% TFA in water, B: ACN, Gradient (Time/% B): 0/30, 2/30, 10/50 and Flow rate:20 mL/min] to afford 17 mg.

MS (ESI): m/z 496.4 (M+H).

Example-150

Synthesis of 3,8-diazabicyclo[3.2.1]octan-8-yl(5-((R)-2-(2,5-difluorophenyl)pyrrolidin-1-yl)pyrazolo[1,5-a]pyridin-3-yl)methanone

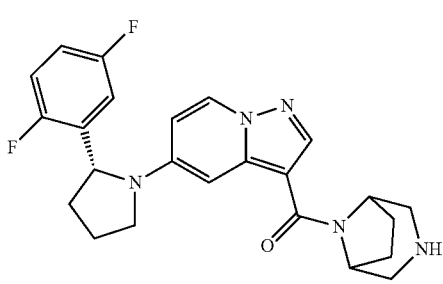 [SMILES: O=C(c1cnn2ccc(N3CCC[C@@H]3c3cc(F)ccc3F)cc12)N1C2CCC1CNC2]

Step-1

Synthesis of tert-butyl 8-(5-((R)-2-(2,5-difluorophenyl)pyrrolidin-1-yl)pyrazolo[1,5-a]pyridine-3-carbonyl)-3,8-diazabicyclo[3.2.1]octane-3-carboxylate

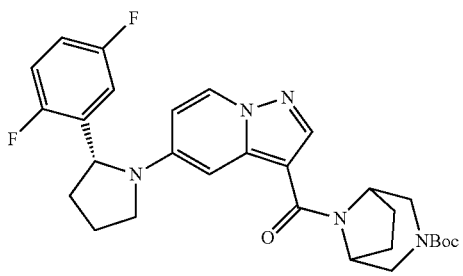 [SMILES: CC(C)(C)OC(=O)N1CC2CCC(C1)N2C(=O)c1cnn2ccc(N3CCC[C@@H]3c3cc(F)ccc3F)cc12]

The title compound was prepared by the similar coupling method as mentioned in Example-16, using tert-butyl 3,8-diazabicyclo[3.2.1]octane-3-carboxylate to afford the crude, which was purified by washing with mixture of DCM and n-Hexane to Preparative HPLC [Column:LUNA-C18-250*21.2 mm, Mobile phase-A: 0.1% TFA in water, B: ACN, Gradient (Time/% B): 0/30, 2/30, 10/50 and Flow rate:20 mL/min] to afford 200 mg of the title compound.

MS (ESI): m/z 538.9 (M+H)

Step-2

Synthesis of 3,8-diazabicyclo[3.2.1]octan-8-yl(5-((R)-2-(2,5-difluorophenyl)pyrrolidin-1-yl)pyrazolo[1,5-a]pyridin-3-yl)methanone

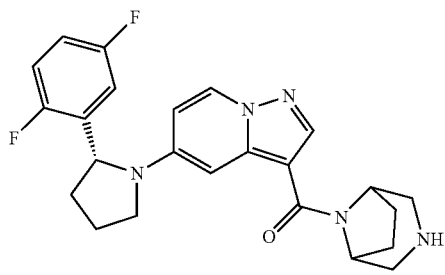 [SMILES: O=C(c1cnn2ccc(N3CCC[C@@H]3c3cc(F)ccc3F)cc12)N1C2CCC1CNC2]

TFA (1.2 mL) was added to a solution of tert-butyl 8-(5-((R)-2-(2,5-difluorophenyl)pyrrolidin-1-yl)pyrazolo[1,5-a]pyridine-3-carbonyl)-3,8-diazabicyclo[3.2.1]octane-3-carboxylate (200 mg, 0.37 mmol) in DCM (2 mL) at 0° C. and stirring was continued at 20-35° C. for 15 h. The reaction mixture was concentrated under reduced pressure to afford the crude, which was diluted with EtOAc, washed with saturated NaHCO$_3$ solution, dried over anhydrous sodium sulphate to afford the crude. The crude compound was purified by recrystallisation from mixture of DCM and n-Hexane to afford 25 mg of the title compound.

$^1$H NMR (300 MHz, CD$_3$OD) δ ppm 8.28-8.24 (1H, d, J=7.8 Hz), 7.94 (1H, s), 7.24-7.30 (1H, m), 7.06-6.96 (1H, m), 6.84-6.74 (1H, m), 6.68 (1H, s), 6.50-6.44 (1H, m), 5.18-5.12 (1H, d, J=8.4 Hz), 4.25-4.15 (2H, m), 3.90-3.80 (1H, m), 3.60-3.51 (3H, m), 3.25-3.15 (2H, m), 2.55-2.45 (1H, m), 2.20-1.95 (3H, m), 1.85-1.65 (4H, m).

MS (ESI): m/z 438.2 (M+H).

The following amides (Example-151 to Example-236) were prepared by method substantially similar to Example-4 or Example-16 by coupling with appropriate amine (either commercially available or synthesized following procedures known in the art). The coupled product was further converted to new products by modification of functional groups following procedures known in the art. Few non-limiting examples are a) functional groups like N-Boc and N-Cbz were converted to amines (NH), OTBDMS to hydroxyl (OH), ester to acid, acid to amides, cyano to tetrazole followed by methylated tetrazole etc.

Example-151

5-(5-((R)-2-(2,5-difluorophenyl)pyrrolidin-1-yl)pyrazolo[1,5-a]pyridine-3-carboxamido)-4,5,6,7-tetrahydropyrazolo[1,5-a]pyridine-3-carboxylic acid

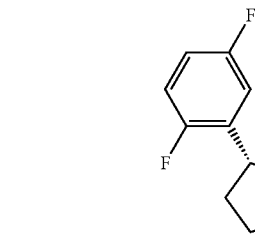 LiOH, EtOH →

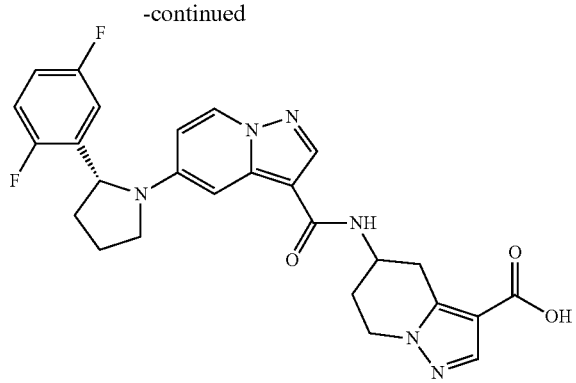

Coupled product on hydrolysis with LiOH/EtOH afforded the title product as off white solid (38.0 mg). MS (ESI): m/z 507.8 (M+H).

Example-152 (Diastereomer-I)

5-(5-((R)-2-(2,5-difluorophenyl)pyrrolidin-1-yl)pyrazolo[1,5-a]pyridine-3-carboxamido)-4,5,6,7-tetrahydropyrazolo[1,5-a]pyridine-3-carboxylic acid

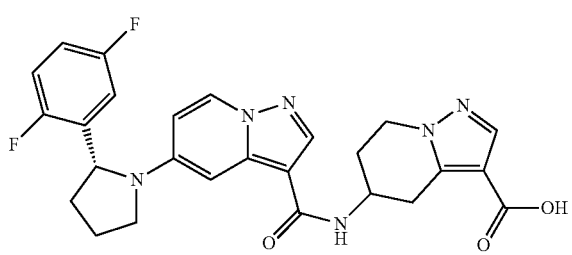 [SMILES: O=C(O)c1cnn2c1CC(NC(=O)c1cnn3ccc(N4CCC[C@@H]4c4cc(F)ccc4F)cc13)CC2]

Coupled product was a mixture of diastereomer, it was separated in chiral HPLC column: chiralpak-AD-H (10 mm×250 mm×5 u) Flow: 5 mL/min, mobile phase-20:80: Hexane:(0.1% TFA in IPA:MeOH [80:20]—Isocratic to afford the title product as off white solid (6.1 mg). MS (ESI): m/z 507.1 (M+H) and.

Example-153 (Diastereomer-II)

5-(5-((R)-2-(2,5-difluorophenyl)pyrrolidin-1-yl)pyrazolo[1,5-a]pyridine-3-carboxamido)-4,5,6,7-tetrahydropyrazolo[1,5-a]pyridine-3-carboxylic acid

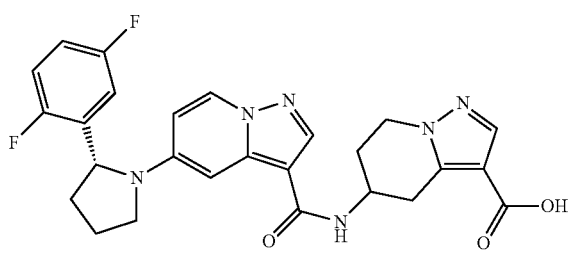 [SMILES: O=C(O)c1cnn2c1CC(NC(=O)c1cnn3ccc(N4CCC[C@@H]4c4cc(F)ccc4F)cc13)CC2]

MS (ESI): m/z 507.1 (M+H).

Example-154

5-((R)-2-(2,5-difluorophenyl)pyrrolidin-1-yl)-N-((tetrahydrofuran-3-yl)methyl)pyrazolo[1,5-a]pyridine-3-carboxamide

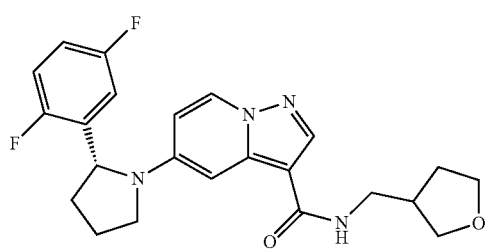 [SMILES: O=C(NCC1CCOC1)c1cnn2ccc(N3CCC[C@@H]3c3cc(F)ccc3F)cc12]

MS (ESI): m/z 426.8 (M+H).

Example-155

5-((R)-2-(2,5-difluorophenyl)pyrrolidin-1-yl)-N-(octahydroindolizin-7-yl)pyrazolo[1,5-a]pyridine-3-carboxamide

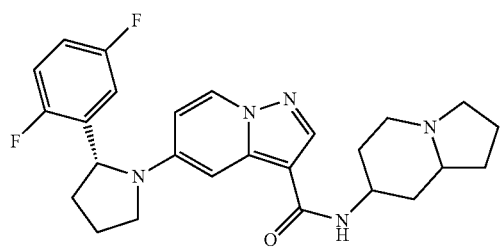 [SMILES: O=C(NC1CCN2CCCC2C1)c1cnn2ccc(N3CCC[C@@H]3c3cc(F)ccc3F)cc12]

MS (ESI): m/z 466.5 (M+H).

Example-156

(R)—N-(Benzo[d][1,3]dioxol-5-yl)-5-(2-(2,5-difluorophenyl)pyrrolidin-1-yl)pyrazolo[1,5-a]pyridine-3-carboxamide

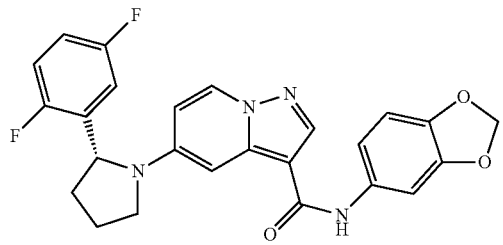 [SMILES: O=C(Nc1ccc2c(c1)OCO2)c1cnn2ccc(N3CCC[C@@H]3c3cc(F)ccc3F)cc12]

MS (ESI): m/z 463.3 (M+H).

Example-157

(R)-(5-(2-(2,5-difluorophenyl)pyrrolidin-1-yl)pyrazolo[1,5-a]pyridin-3-yl) (4-(5-(trifluoromethyl)-1,3,4-oxadiazol-2-yl)piperidin-1-yl)methanone

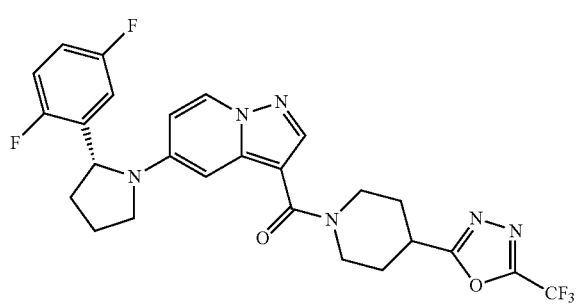 [SMILES: O=C(c1cnn2ccc(N3CCC[C@@H]3c3cc(F)ccc3F)cc12)N1CCC(c2nnc(C(F)(F)F)o2)CC1]

MS (ESI): m/z 547.4 (M+H).

Example-158

5-((R)-2-(2,5-difluorophenyl)pyrrolidin-1-yl)-N-(2,3-dihydroxy-2-methylpropyl)pyrazolo[1,5-a]pyridine-3-carboxamide

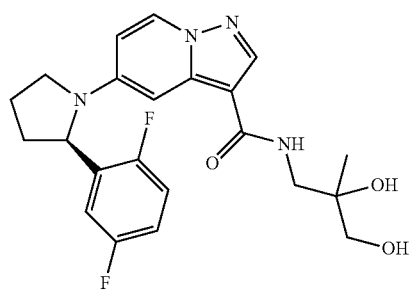 [SMILES: CC(O)(CO)CNC(=O)c1cnn2ccc(N3CCC[C@@H]3c3cc(F)ccc3F)cc12]

MS (ESI): m/z 431.2 (M+H).

Example-159

5-((R)-2-(2,5-difluorophenyl)pyrrolidin-1-yl)-N-(1,1-dioxidotetrahydrothiophen-3-yl)pyrazolo[1,5-a]pyridine-3-carboxamide

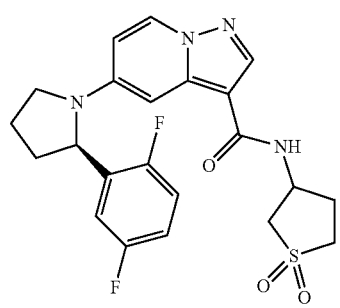 [SMILES: O=C(NC1CCS(=O)(=O)C1)c1cnn2ccc(N3CCC[C@@H]3c3cc(F)ccc3F)cc12]

MS (ESI): m/z 461.2 (M+H).

Example-160

(R)-5-(2-(2,5-difluorophenyl)pyrrolidin-1-yl)-N((1-(hydroxymethyl)cyclobutyl)methyl)pyrazolo[1,5-a]pyridine-3-carboxamide

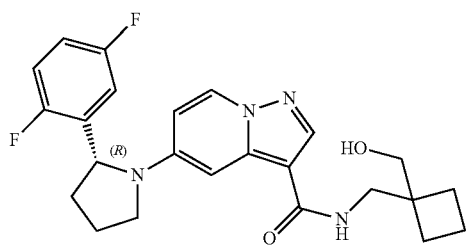

MS (ESI): m/z 441.4 (M+H).

Example-161

5-((R)-2-(2,5-difluorophenyl)pyrrolidin-1-yl)-N-((1r,4R)-4-(5-methyl-1,3,4-oxadiazol-2-yl)cyclohexyl)pyrazolo[1,5-a]pyridine-3-carboxamide

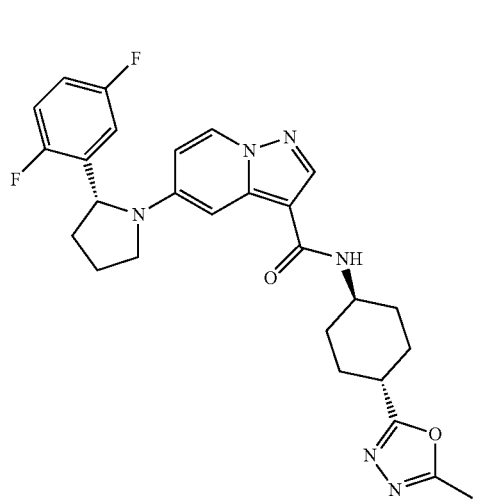 [SMILES: Cc1nnc([C@H]2CC[C@H](NC(=O)c3cnn4ccc(N5CCC[C@@H]5c5cc(F)ccc5F)cc34)CC2)o1]

MS (ESI): m/z 507.4 (M+H).

Example-162

(R)-5-(2-(2,5-difluorophenyl)pyrrolidin-1-yl)-N-(2-hydroxy-2-methylpropyl)pyrazolo[1,5-a]pyridine-3-carboxamide

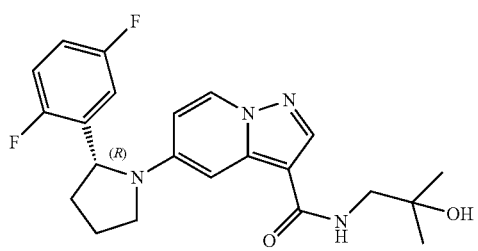

MS (ESI): m/z 415.1 (M+H).

Example-163

(R)-5-(2-(2,5-difluorophenyl)pyrrolidin-1-yl)-N-(2,3-dihydrobenzo[b][1,4]dioxin-6-yl)pyrazolo[1,5-a]pyridine-3-carboxamide

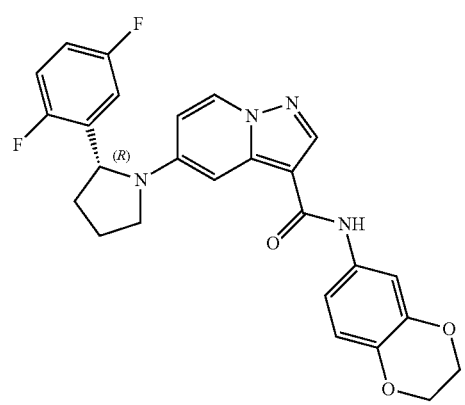

MS (ESI): m/z 477.1 (M+H).

Example-164

(R)—N-(4-(1H-1,2,4-triazol-1-yl)phenyl)-5-(2-(2,5-difluorophenyl)pyrrolidin-1-yl)pyrazolo[1,5-a]pyridine-3-carboxamide

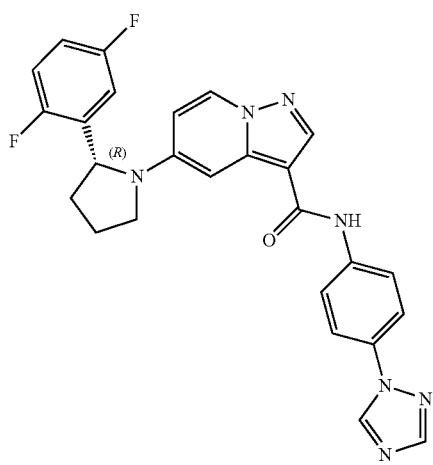

MS (ESI): m/z 486.1 (M+H).

Example-165

(R)—N-(4-cyanophenyl)-5-(2-(2,5-difluorophenyl)pyrrolidin-1-yl)pyrazolo[1,5-a]pyridine-3-carboxamide

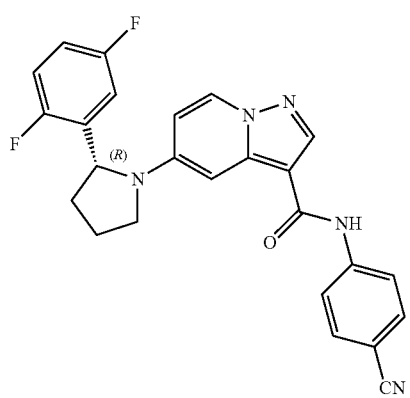

MS (ESI): m/z 444.1 (M+H).

Example-166

5-((R)-2-(2,5-difluorophenyl)pyrrolidin-1-yl)-N-(1,1-dioxidotetrahydrothiophen-3-yl)pyrazolo[1,5-a]pyridine-3-carboxamide

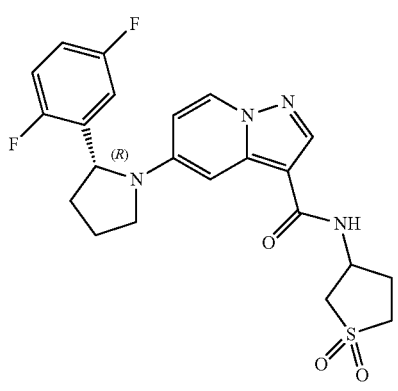

MS (ESI): m/z 461.1 (M+H).

Example-167

5-((R)-2-(2,5-difluorophenyl)pyrrolidin-1-yl)-N-(1,1-dioxidotetrahydrothiophen-3-yl)pyrazolo[1,5-a]pyridine-3-carboxamide

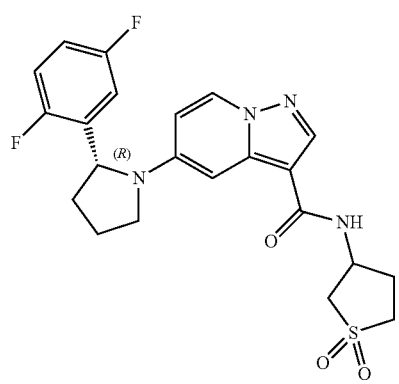

MS (ESI): m/z 461.1 (M+H).

Example-168

(R)-5-(2-(2,5-difluorophenyl)pyrrolidin-1-yl)-N-(1,3-dihydroxy-2-(hydroxymethyl) propan-2-yl)pyrazolo[1,5-a]pyridine-3-carboxamide

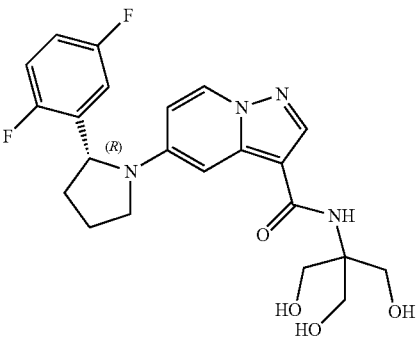

MS (ESI): m/z 447.1 (M+H).

Example-169

5-((R)-2-(2,5-difluorophenyl)pyrrolidin-1-yl)-N-((1r,4R)-4-(5-(trifluoromethyl)-1,3,4-oxadiazol-2-yl)cyclohexyl)pyrazolo[1,5-a]pyridine-3-carboxamide

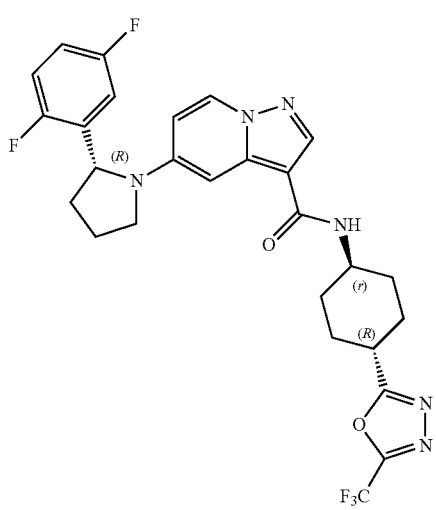

MS (ESI): m/z 561.1 (M+H).

Example-170

5-((R)-2-(2,5-difluorophenyl)pyrrolidin-1-yl)-N-(3-(dimethylcarbamoyl)-4,5,6,7-tetrahydropyrazolo[1,5-a]pyridin-6-yl)pyrazolo[1,5-a]pyridine-3-carboxamide

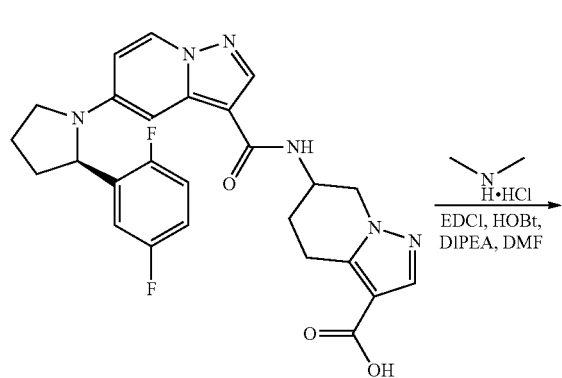

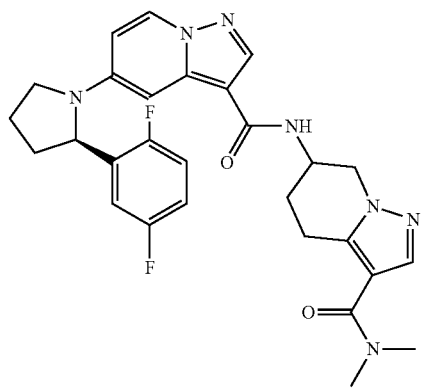

To a stirred solution of 6-(5-((R)-2-(2,5-difluorophenyl)pyrrolidin-1-yl)pyrazolo[1,5-a]pyridine-3-carboxamido)-4,5,6,7-tetrahydropyrazolo[1,5-a]pyridine-3-carboxylic acid (45 mg, 0.08 mmol) in dry DMF (1 mL) was added EDCI (28.7 mg, 0.09 mmol), HOBt (12 mg, 0.88 mmol) and stirring was continued at 25° C. for 15 min. To the above reaction added dimethylamine hydrochloride (7.8 mg, 0.1 mmol) followed by DIPEA (0.05 ml, 0.26 mmol), stirring was continued at 25° C. for 16 h. Reaction mixture was diluted with DCM (50 mL), washed it with water followed by brine, dried over anhydrous sodium sulphate and concentrated under reduced pressure to afford title compound as white solid. MS (ESI): m/z 534.2 (M+H).

Example-171

(R)-5-(2-(2,5-difluorophenyl)pyrrolidin-1-yl)-N-(2-oxo-2,3-dihydro-1H-benzo[d]imidazol-5-yl)pyrazolo[1,5-a]pyridine-3-carboxamide

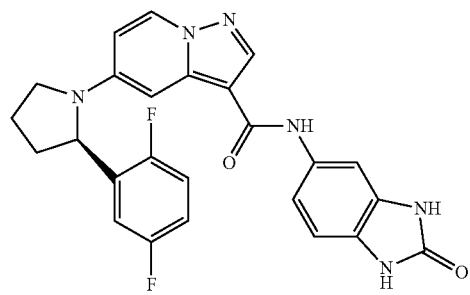 [SMILES: O=C(Nc1ccc2[nH]c(=O)[nH]c2c1)c1cnn2ccc(N3CCC[C@@H]3c3cc(F)ccc3F)cc12]

MS (ESI): m/z 475.1 (M+H).

Example-172

5-((R)-2-(2,5-difluorophenyl)pyrrolidin-1-yl)-N-(octahydro-1H-quinolizin-2-yl)pyrazolo[1,5-a]pyridine-3-carboxamide

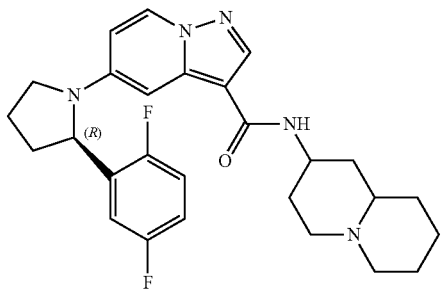

MS (ESI): m/z 480.2 (M+H).

Example-173

5-((R)-2-(2,5-difluorophenyl)pyrrolidin-1-yl)-N-(4,5,6,7-tetrahydropyrazolo[1,5-a]pyridin-6-yl)pyrazolo[1,5-a]pyridine-3-carboxamide

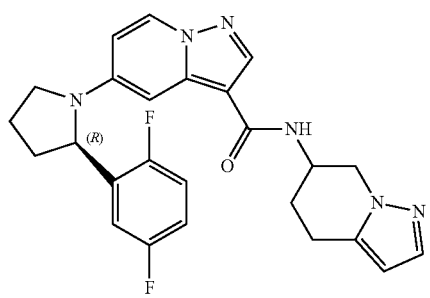

MS (ESI): m/z 463.4 (M+H).

Example-174

(5-((R)-2-(2,5-difluorophenyl)pyrrolidin-1-yl)pyrazolo[1,5-a]pyridin-3-yl) (3-(pyrrolidin-1-ylmethyl)pyrrolidin-1-yl)methanone

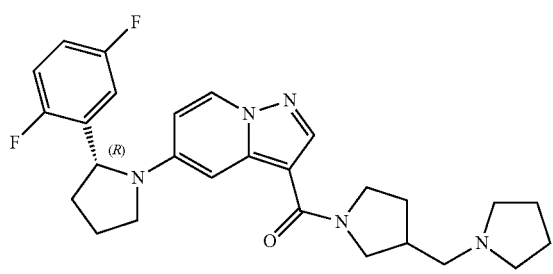

MS (ESI): m/z 480.2 (M+H).

Example-175

(R)-5-(2-(2,5-difluorophenyl)pyrrolidin-1-yl)-N-(2-methylbenzo[d]oxazol-6-yl)pyrazolo[1,5-a]pyridine-3-carboxamide

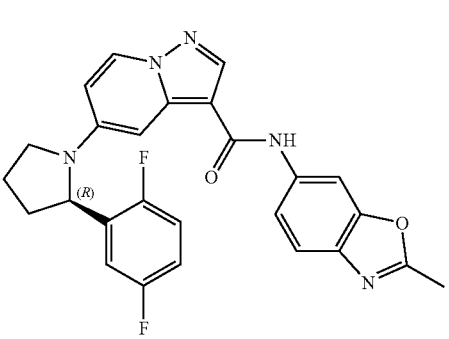

MS (ESI): m/z 474.3 (M+H).

Example-176

5-((R)-2-(2,5-difluorophenyl)pyrrolidin-1-yl)-N-((1r,4R)-4-(thiazol-2-yl)cyclohexyl)pyrazolo[1,5-a]pyridine-3-carboxamide

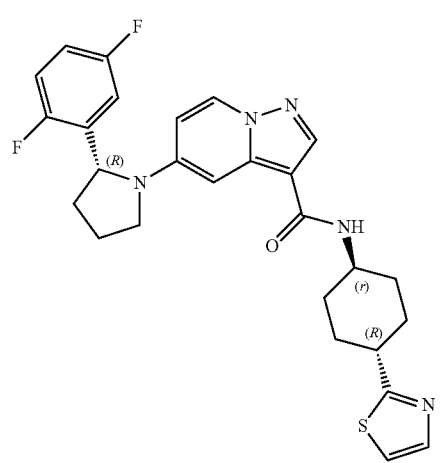

MS (ESI): m/z 508.1 (M+H).

Example-177

5-(5-((R)-2-(2,5-difluorophenyl)pyrrolidin-1-yl)pyrazolo[1,5-a]pyridine-3-carboxamido)-4,5,6,7-tetrahydropyrazolo[1,5-a]pyridine-2-carboxylic acid

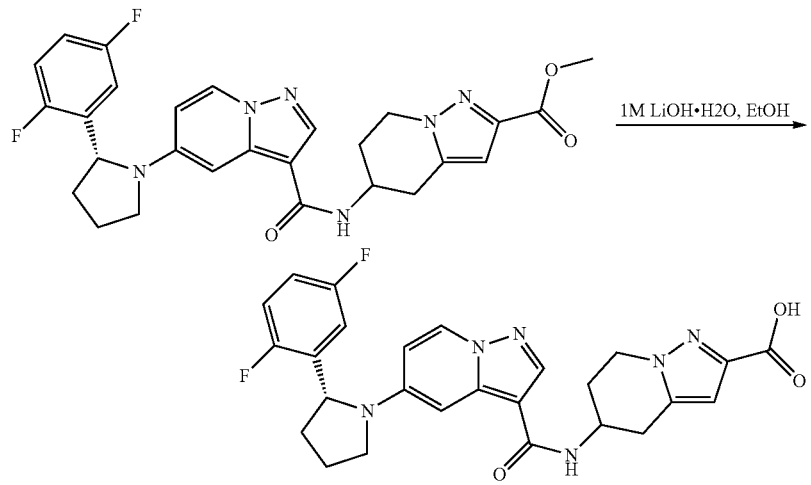

MS (ESI): m/z 507 (M+H).

Example-178

5-((R)-2-(2,5-difluorophenyl)pyrrolidin-1-yl)-N-((1r,4R)-4-(5-methyl-1,2,4-oxadiazol-3-yl)cyclohexyl)pyrazolo[1,5-a]pyridine-3-carboxamide

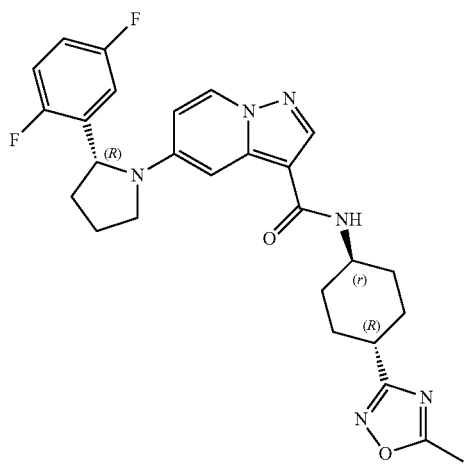

MS (ESI): m/z 507.3 (M+H).

Example-179

(R)—N-(6-(1H-1,2,4-triazol-1-yl)pyridin-3-yl)-5-(2-(2,5-difluorophenyl)pyrrolidin-1-yl)pyrazolo[1,5-a]pyridine-3-carboxamide

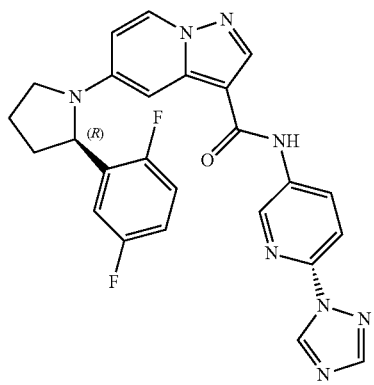

MS (ESI): m/z 487.1 (M+H).

Example-180

(R)-5-(2-(2,5-difluorophenyl)pyrrolidin-1-yl)-N-(quinoxalin-6-yl)pyrazolo[1,5-a]pyridine-3-carboxamide

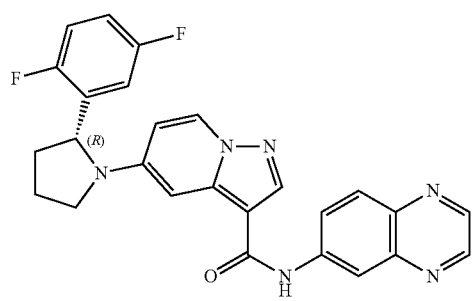

MS (ESI): m/z 471.1 (M+H).

Example-181

(R)-5-(2-(2,5-difluorophenyl)pyrrolidin-1-yl)-N-(4-(1-methyl-1H-tetrazol-5-yl)phenyl)pyrazolo[1,5-a]pyridine-3-carboxamide

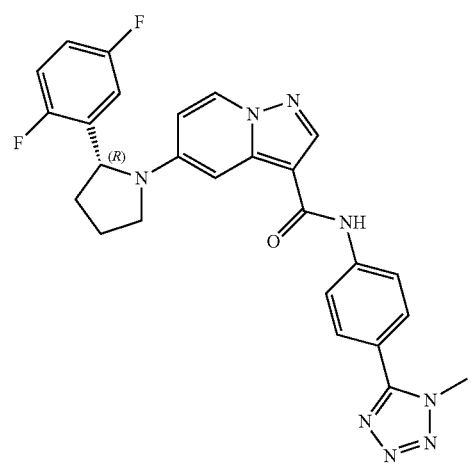

MS (ESI): m/z 501.1 (M+H).

Example-182

N-(1-(2,5-difluorophenyl)-2-hydroxyethyl)-5-((R)-2-(2,5-difluorophenyl)pyrrolidin-1-yl)pyrazolo[1,5-a]pyridine-3-carboxamide

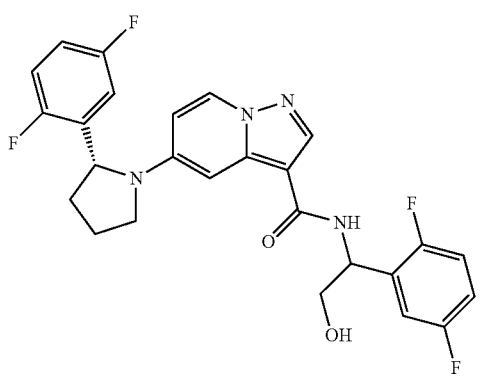 [SMILES: O=C(NC(CO)c1cc(F)ccc1F)c1cnn2ccc(N3CCC[C@@H]3c3cc(F)ccc3F)cc12]

MS (ESI): m/z 499.1 (M+H).

Example-183

(R)—N-(1-acetylindolin-6-yl)-5-(2-(2,5-difluorophenyl)pyrrolidin-1-yl)pyrazolo[1,5-a]pyridine-3-carboxamide

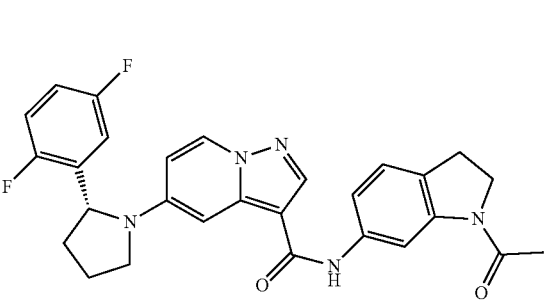 [SMILES: CC(=O)N1CCc2ccc(NC(=O)c3cnn4ccc(N5CCC[C@@H]5c5cc(F)ccc5F)cc34)cc21]

MS (ESI): m/z 502.1 (M+H).

Example-184

(R)-5-(2-(2,5-difluorophenyl)pyrrolidin-1-yl)-N-(5-methyl-1,3,4-thiadiazol-2-yl)pyrazolo[1,5-a]pyridine-3-carboxamide

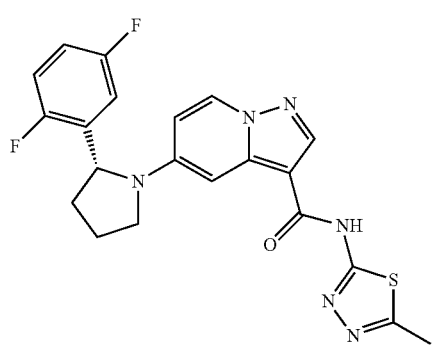 [SMILES: Cc1nnc(NC(=O)c2cnn3ccc(N4CCC[C@@H]4c4cc(F)ccc4F)cc23)s1]

MS (ESI): m/z 441.1 (M+H).

Example-185

(R)-5-(2-(2,5-difluorophenyl)pyrrolidin-1-yl)-N-(pyridin-3-yl)pyrazolo[1,5-a]pyridine-3-carboxamide

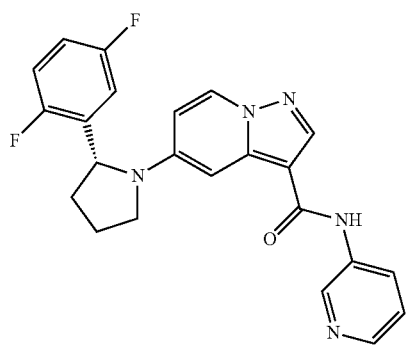 [SMILES: O=C(Nc1cccnc1)c1cnn2ccc(N3CCC[C@@H]3c3cc(F)ccc3F)cc12]

MS (ESI): m/z 420.1 (M+H).

Example-186

(R)-(5-(2-(2,5-difluorophenyl)pyrrolidin-1-yl)pyrazolo[1,5-a]pyridin-3-yl) (4-hydroxy-4-methylpiperidin-1-yl)methanone

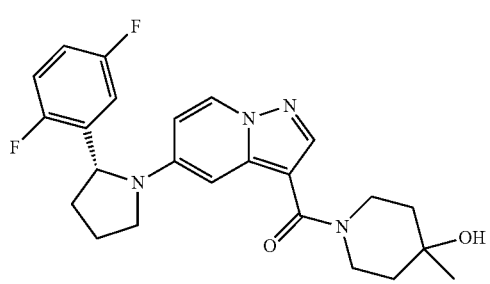 [SMILES: CC1(O)CCN(C(=O)c2cnn3ccc(N4CCC[C@@H]4c4cc(F)ccc4F)cc23)CC1]

MS (ESI): m/z 441.3 (M+H).

Example-187

5-((R)-2-(2,5-difluorophenyl)pyrrolidin-1-yl)-N-((1R,2S)-2-hydroxy-2,3-dihydro-1H-inden-1-yl)pyrazolo[1,5-a]pyridine-3-carboxamide

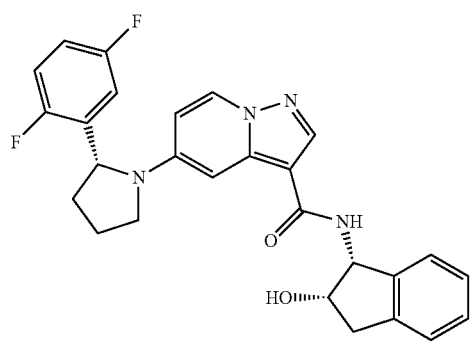 [SMILES: O=C(N[C@@H]1c2ccccc2C[C@@H]1O)c1cnn2ccc(N3CCC[C@@H]3c3cc(F)ccc3F)cc12]

MS (ESI): m/z 475.1 (M+H).

Example-188
(R)-5-(2-(2,5-difluorophenyl)pyrrolidin-1-yl)-N-(1,5-dimethyl-3-oxo-2-phenyl-2,3-dihydro-1H-pyrazol-4-yl)pyrazolo[1,5-a]pyridine-3-carboxamide
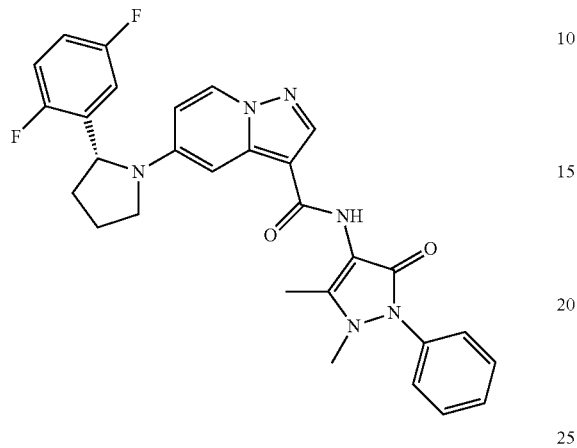
MS (ESI): m/z 529.3 (M+H).
Example-189
7-(5-((R)-2-(2,5-difluorophenyl)pyrrolidin-1-yl)pyrazolo[1,5-a]pyridine-3-carboxamido)-5,6,7,8-tetrahydroimidazo[1,2-a]pyridine-2-carboxylic acid
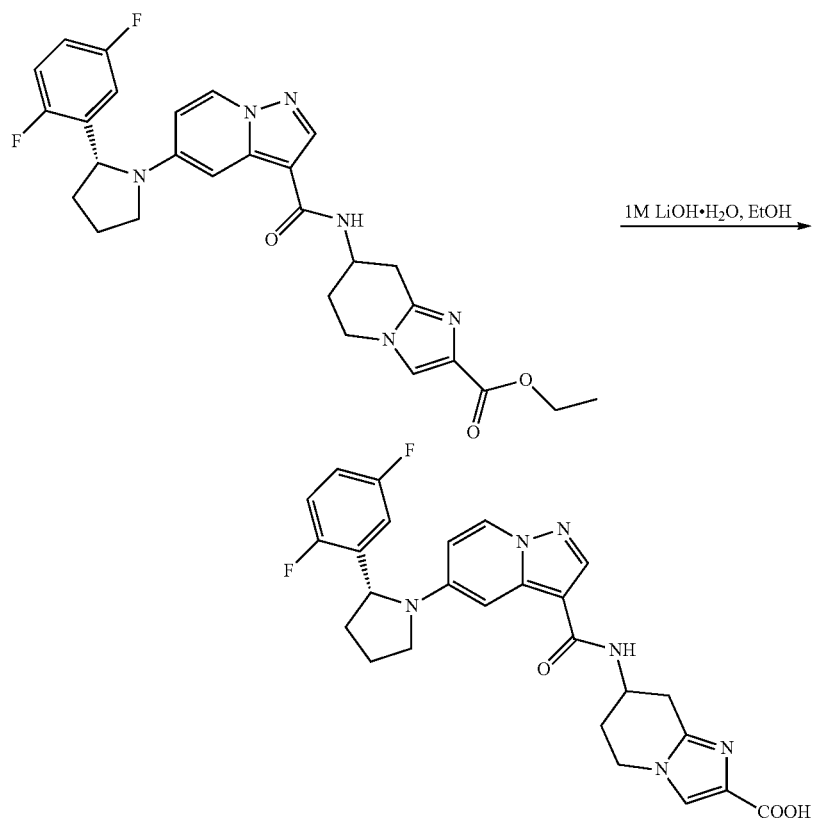
MS (ESI): m/z 507.1 (M+H).

Example-190
(R)-5-(2-(2,5-difluorophenyl)pyrrolidin-1-yl)-N-(4-methylthiazol-2-yl)pyrazolo[1,5-a]pyridine-3-carboxamide
Example-192
(1R,4r)-4-(5-((R)-2-(2,5-difluorophenyl)pyrrolidin-1-yl)pyrazolo[1,5-a]pyridine-3-carboxamido)cyclohexanecarboxylic acid
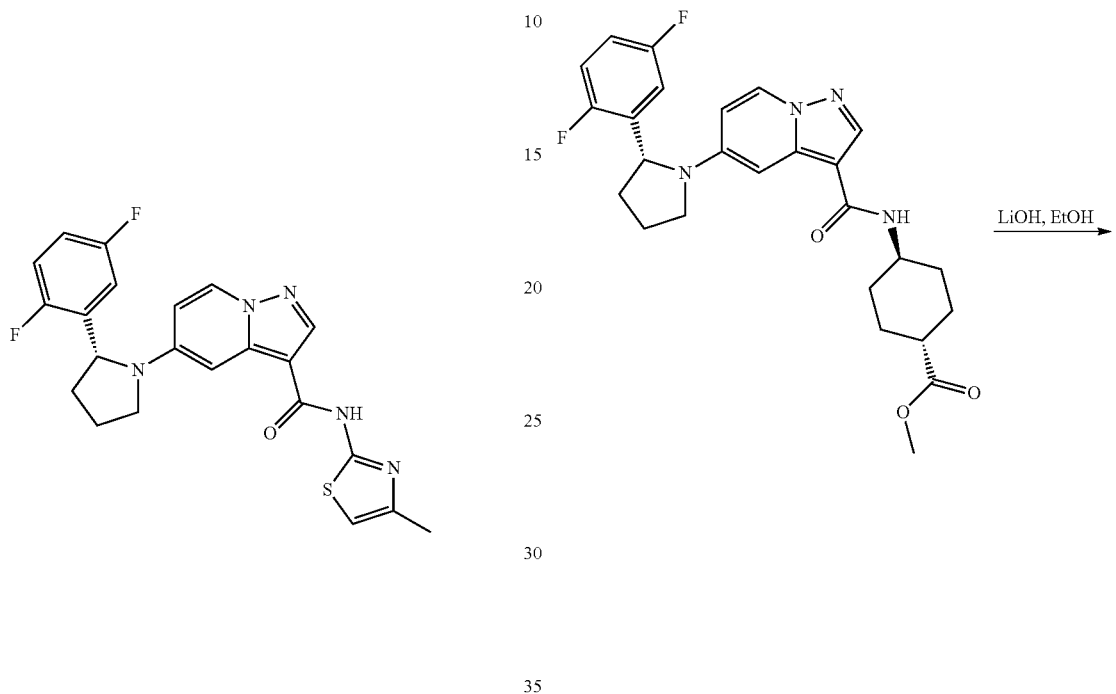
MS (ESI): m/z 440.1 (M+H).
Example-191
(R)-5-(2-(2,5-difluorophenyl)pyrrolidin-1-yl)-N-(pyridin-2-yl)pyrazolo[1,5-a]pyridine-3-carboxamide
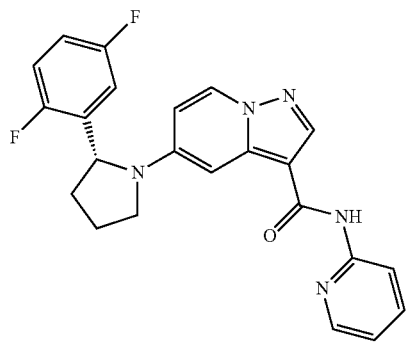 [SMILES: O=C(Nc1ccccn1)c1cnn2ccc(N3CCC[C@@H]3c3cc(F)ccc3F)cc12]
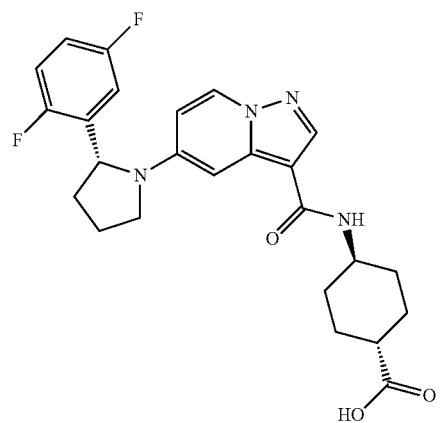
MS (ESI): m/z 420.3 (M+H).
MS (ESI): m/z 469.1 (M+H).

Example-193

(R)—N-(4-(1H-tetrazol-5-yl)phenyl)-5-(2-(2,5-difluorophenyl)pyrrolidin-1-yl)pyrazolo[1,5-a]pyridine-3-carboxamide

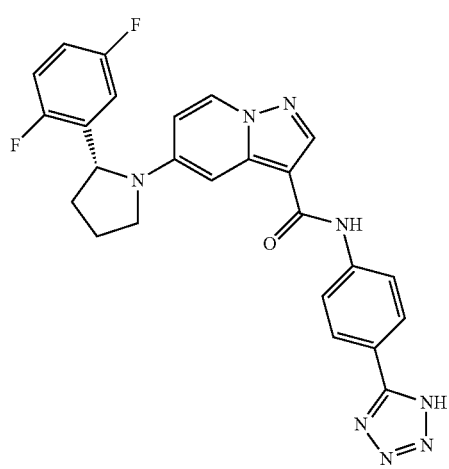 [SMILES: O=C(Nc1ccc(-c2nnn[nH]2)cc1)c1cnn2ccc(N3CCC[C@@H]3c3cc(F)ccc3F)cc12]

MS (ESI): m/z 487.3 (M+H).

Example-194

(R)—N-(3-cyanophenyl)-5-(2-(2,5-difluorophenyl)pyrrolidin-1-yl)pyrazolo[1,5-a]pyridine-3-carboxamide

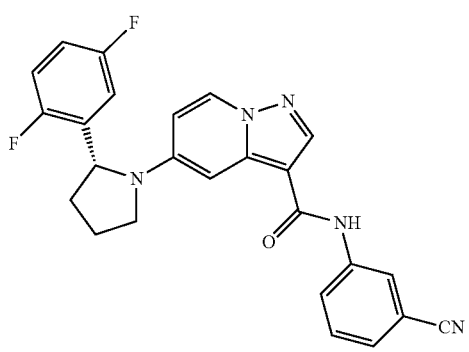 [SMILES: N#Cc1cccc(NC(=O)c2cnn3ccc(N4CCC[C@@H]4c4cc(F)ccc4F)cc23)c1]

MS (ESI): m/z 444.1 (M+H).

Example-195

(R)-5-(2-(2,5-difluorophenyl)pyrrolidin-1-yl)-N-(1H-indazol-6-yl)pyrazolo[1,5-a]pyridine-3-carboxamide

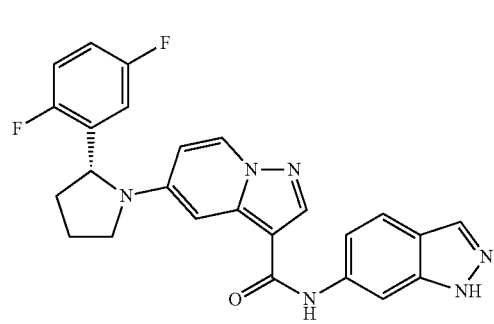 [SMILES: O=C(Nc1ccc2cn[nH]c2c1)c1cnn2ccc(N3CCC[C@@H]3c3cc(F)ccc3F)cc12]

MS (ESI): m/z 459.9 (M+H).

Example-196

(R)—N-(6-(1H-imidazol-1-yl)pyridin-3-yl)-5-(2-(2,5-difluorophenyl)pyrrolidin-1-yl)pyrazolo[1,5-a]pyridine-3-carboxamide

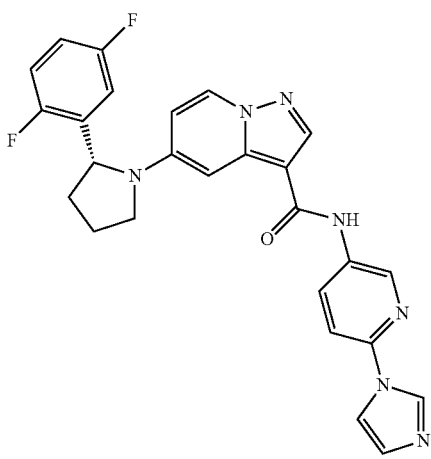 [SMILES: O=C(Nc1ccc(-n2ccnc2)nc1)c1cnn2ccc(N3CCC[C@@H]3c3cc(F)ccc3F)cc12]

MS (ESI): m/z 486 (M+H).

Example-197

(R)—N-(5-(1H-imidazol-1-yl)pyridin-2-yl)-5-(2-(2,5-difluorophenyl)pyrrolidin-1-yl)pyrazolo[1,5-a]pyridine-3-carboxamide

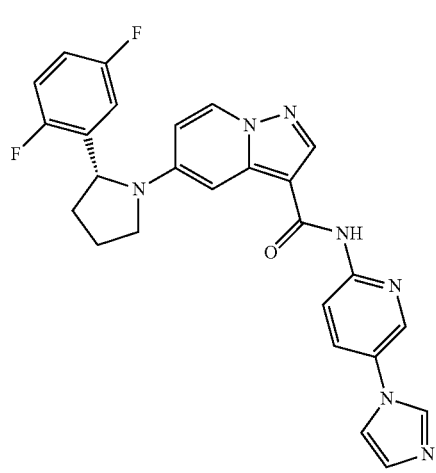 [SMILES: O=C(Nc1ccc(-n2ccnc2)cn1)c1cnn2ccc(N3CCC[C@@H]3c3cc(F)ccc3F)cc12]

MS (ESI): m/z 486 (M+H).

Example-198

(R)—N-(6-cyanopyridin-3-yl)-5-(2-(2,5-difluorophenyl)pyrrolidin-1-yl)pyrazolo[1,5-a]pyridine-3-carboxamide

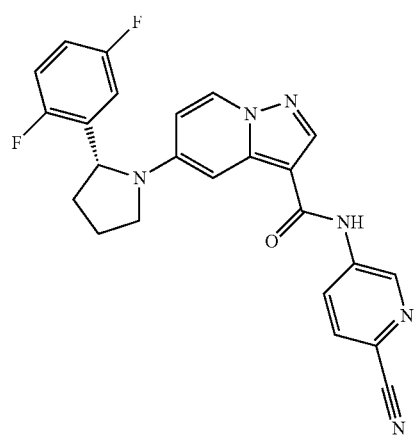 [SMILES: N#Cc1ccc(NC(=O)c2cnn3ccc(N4CCC[C@@H]4c4cc(F)ccc4F)cc23)cn1]

MS (ESI): m/z 445.1 (M+H).

Example-199

(R)—N-(3-(1H-tetrazol-5-yl)phenyl)-5-(2-(2,5-difluorophenyl)pyrrolidin-1-yl)pyrazolo[1,5-a]pyridine-3-carboxamide

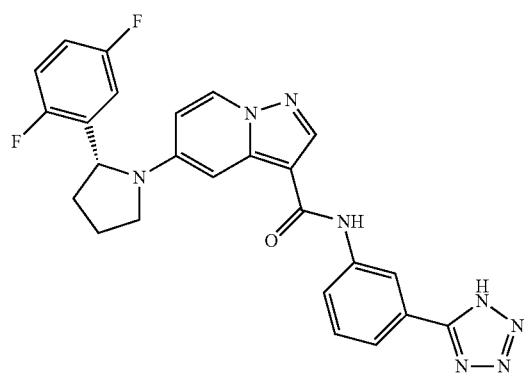 [SMILES: O=C(Nc1cccc(-c2nnn[nH]2)c1)c1cnn2ccc(N3CCC[C@@H]3c3cc(F)ccc3F)cc12]

MS (ESI): m/z 487.4 (M+H).

Example-200

(R)-5-(2-(2,5-difluorophenyl)pyrrolidin-1-yl)-N-(4-(2-methyl-2H-tetrazol-5-yl)phenyl)pyrazolo[1,5-a]pyridine-3-carboxamide

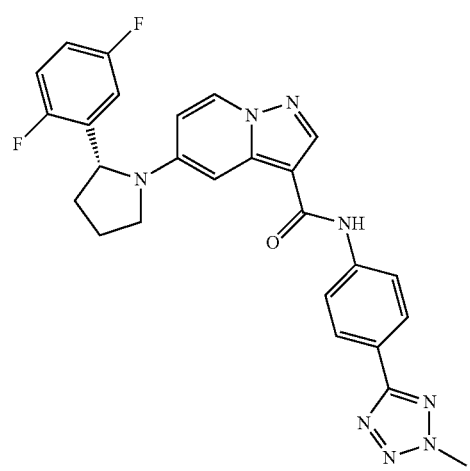 [SMILES: Cn1nnc(-c2ccc(NC(=O)c3cnn4ccc(N5CCC[C@@H]5c5cc(F)ccc5F)cc34)cc2)n1]

MS (ESI): m/z 501.1 (M+H).

Example-201

(R)—N-(benzo[d][1,3]dioxol-5-ylmethyl)-5-(2-(2,5-difluorophenyl)pyrrolidin-1-yl)pyrazolo[1,5-a]pyridine-3-carboxamide

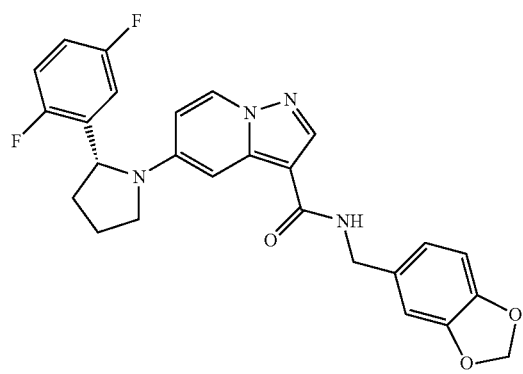 [SMILES: O=C(NCc1ccc2c(c1)OCO2)c1cnn2ccc(N3CCC[C@@H]3c3cc(F)ccc3F)cc12]

MS (ESI): m/z 476.8 (M+H).

Example-202

(R)-5-(2-(2,5-difluorophenyl)pyrrolidin-1-yl)-N-((2,3-dihydrobenzo[b][1,4]dioxin-6-yl)methyl)pyrazolo[1,5-a]pyridine-3-carboxamide

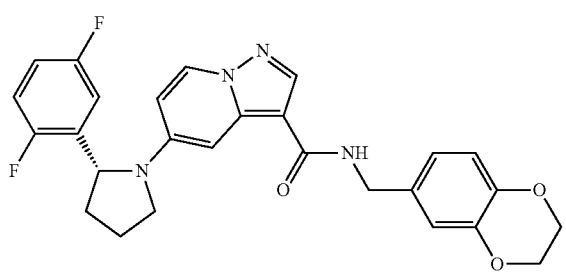 [SMILES: O=C(NCc1ccc2c(c1)OCCO2)c1cnn2ccc(N3CCC[C@@H]3c3cc(F)ccc3F)cc12]

MS (ESI): m/z 490.9 (M+H).

Example-203

(R)—N-(5-(1H-1,2,4-triazol-1-yl)pyridin-2-yl)-5-(2-(2,5-difluorophenyl)pyrrolidin-1-yl)pyrazolo[1,5-a]pyridine-3-carboxamide

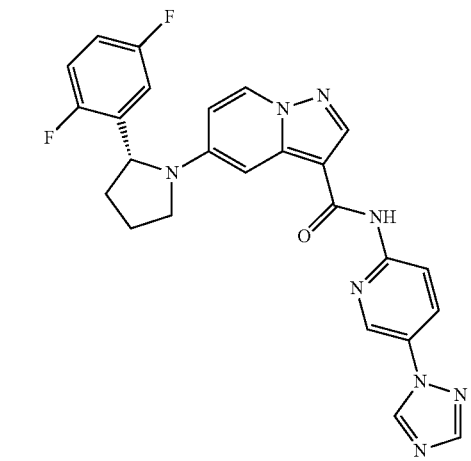 [SMILES: O=C(Nc1ccc(-n2cncn2)cn1)c1cnn2ccc(N3CCC[C@@H]3c3cc(F)ccc3F)cc12]

Step-1

5-nitro-2-(1H-1,2,4-triazol-1-yl)pyridine

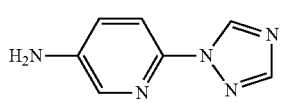 [SMILES: O=[N+]([O-])c1ccc(-n2cncn2)nc1]

2-fluoro-5-nitropyridine (30 g, 18.9 mmol) was added to a stirred solution of 1H-1,2,4-triazole (1.566 g, 22.7 mmol) and $K_2CO_3$ (5.14 g, 37.8 mmol) and stirred for 16 hrs at 25° C. Reaction mass was diluted with ice cold water and stirred for 15 min. The solid obtained was filtered and dried under vacuum to afford the desired product. MS (ESI): m/z 192 (M+H).

Step-2

6-(1H-1,2,4-triazol-1-yl)pyridin-3-amine

Raney nickel (0.650 g) was added to a solution of 5-nitro-2-(1H-1,2,4-triazol-1-yl)pyridine (3.2 g, 16.7 mmol) in a mixture of ethanol and methanol (1:1) (150 mL) followed by the addition of Hydrazine hydrate (2.51 g, 50.2 mmol) and stirring was continued at 25° C. 1 hr. The reaction mixture was filtered over celite bed and washed with methanol. The filtrate and the washings were concentrated under reduced pressure to afford title compound as pale brown liquid. MS (ESI): m/z 162.1 (M+H).

Step-3

(R)—N-(5-(1H-1,2,4-triazol-1-yl)pyridin-2-yl)-5-(2-(2,5-difluorophenyl)pyrrolidin-1-yl)pyrazolo[1,5-a]pyridine-3-carboxamide

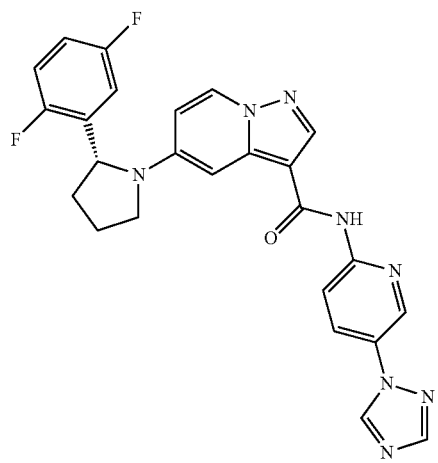 [SMILES: O=C(Nc1ccc(-n2cncn2)cn1)c1cnn2ccc(N3CCC[C@@H]3c3cc(F)ccc3F)cc12]

MS (ESI): m/z 487.3 (M+H).

Example-204

(R)-5-(2-(2,5-difluorophenyl)pyrrolidin-1-yl)-N-(3-(2-methyl-2H-tetrazol-5-yl)phenyl)pyrazolo[1,5-a]pyridine-3-carboxamide

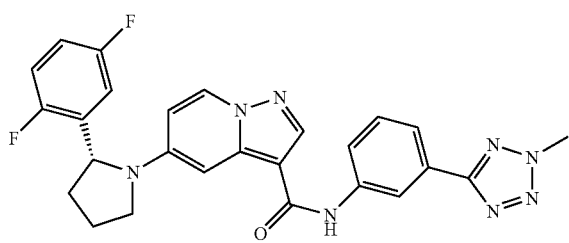 [SMILES: Cn1nnc(-c2cccc(NC(=O)c3cnn4ccc(N5CCC[C@@H]5c5cc(F)ccc5F)cc34)c2)n1]

MS (ESI): m/z 501 (M+H).

Example-205

(R)-5-(2-(2,5-difluorophenyl)pyrrolidin-1-yl)-N-(6-(1-methyl-1H-tetrazol-5-yl)pyridin-3-yl)pyrazolo[1,5-a]pyridine-3-carboxamide

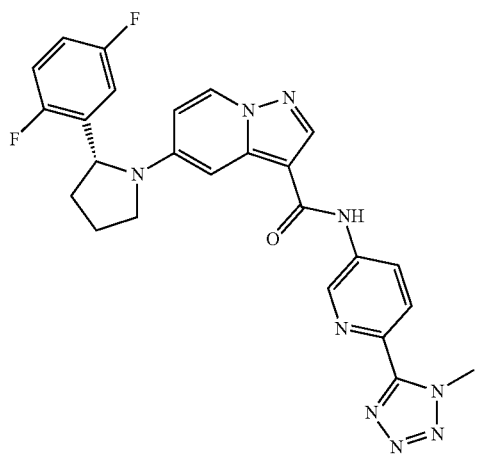 [SMILES: Cn1nnnc1-c1ccc(NC(=O)c2cnn3ccc(N4CCC[C@@H]4c4cc(F)ccc4F)cc23)cn1]

MS (ESI): m/z 502 (M+H).

Example-206

(R)-5-(2-(2,5-difluorophenyl)pyrrolidin-1-yl)-N-(6-(2-hydroxyethyl)pyridin-3-yl)pyrazolo[1,5-a]pyridine-3-carboxamide

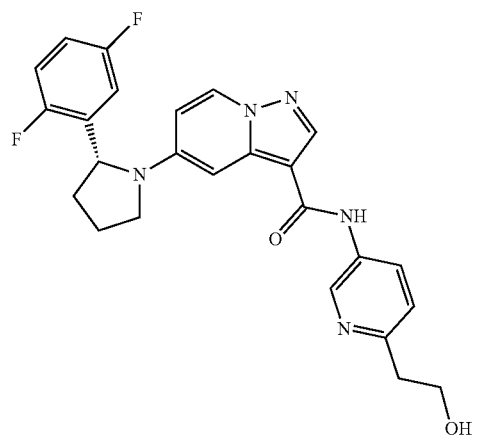 [SMILES: O=C(Nc1ccc(CCO)nc1)c1cnn2ccc(N3CCC[C@@H]3c3cc(F)ccc3F)cc12]

MS (ESI): m/z 463.9 (M+H).

Example-207

(R)-5-(2-(2,5-difluorophenyl)pyrrolidin-1-yl)-N-(3-(1-methyl-1H-tetrazol-5-yl)phenyl)pyrazolo[1,5-a]pyridine-3-carboxamide

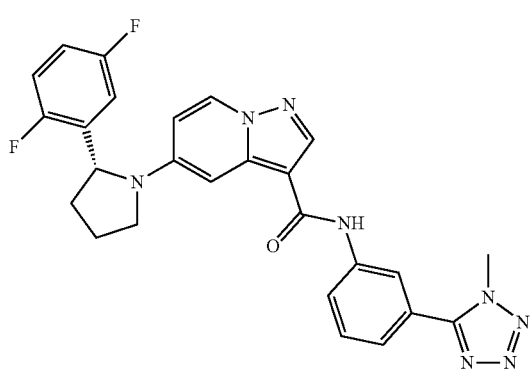 [SMILES: Cn1nnnc1-c1cccc(NC(=O)c2cnn3ccc(N4CCC[C@@H]4c4cc(F)ccc4F)cc23)c1]

MS (ESI): m/z 501 (M+H).

Example-208

(R)-5-(2-(2,5-difluorophenyl)pyrrolidin-1-yl)-N-(2-methyl-6-(trifluoromethyl)pyridin-3-yl)pyrazolo[1,5-a]pyridine-3-carboxamide

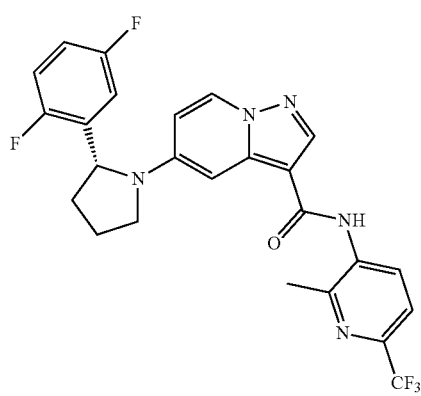 [SMILES: Cc1nc(C(F)(F)F)ccc1NC(=O)c1cnn2ccc(N3CCC[C@@H]3c3cc(F)ccc3F)cc12]

MS (ESI): m/z 502 (M+H).

Example-209

(R)-5-(2-(2,5-difluorophenyl)pyrrolidin-1-yl)-N-(6-(trifluoromethyl)pyridin-3-yl)pyrazolo[1,5-a]pyridine-3-carboxamide

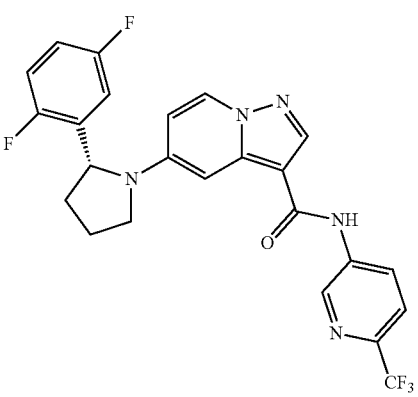 [SMILES: O=C(Nc1ccc(C(F)(F)F)nc1)c1cnn2ccc(N3CCC[C@@H]3c3cc(F)ccc3F)cc12]

MS (ESI): m/z 488 (M+H).

Example-210

(R)-5-(2-(2,5-difluorophenyl)pyrrolidin-1-yl)-N-(6-(2-methyl-2H-tetrazol-5-yl)pyridin-3-yl)pyrazolo[1,5-a]pyridine-3-carboxamide

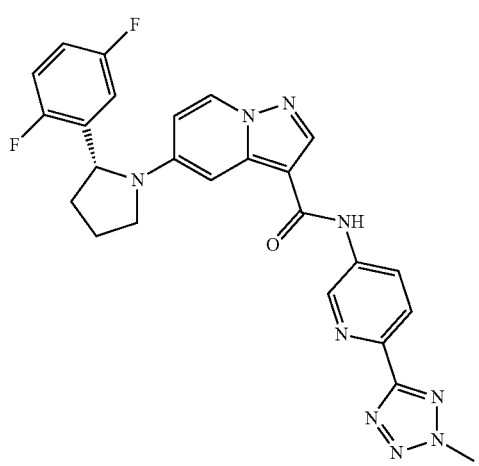 [SMILES: Cn1nnc(-c2ccc(NC(=O)c3cnn4ccc(N5CCC[C@@H]5c5cc(F)ccc5F)cc34)cn2)n1]

MS (ESI): m/z 501.9 (M+H).

Example-211

(R)—N-(2-chloro-6-(trifluoromethyl)pyridin-3-yl)-5-(2-(2,5-difluorophenyl)pyrrolidin-1-yl)pyrazolo[1,5-a]pyridine-3-carboxamide

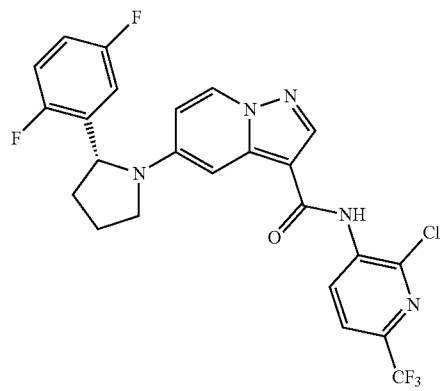 [SMILES: O=C(Nc1ccc(C(F)(F)F)nc1Cl)c1cnn2ccc(N3CCC[C@@H]3c3cc(F)ccc3F)cc12]

MS (ESI): m/z 522 (M+H).

Example-212

(R)-5-(2-(2,5-difluorophenyl)pyrrolidin-1-yl)-N-(1-(5-sulfamoylpyridin-2-yl) azetidin-3-yl)pyrazolo[1,5-a]pyridine-3-carboxamide

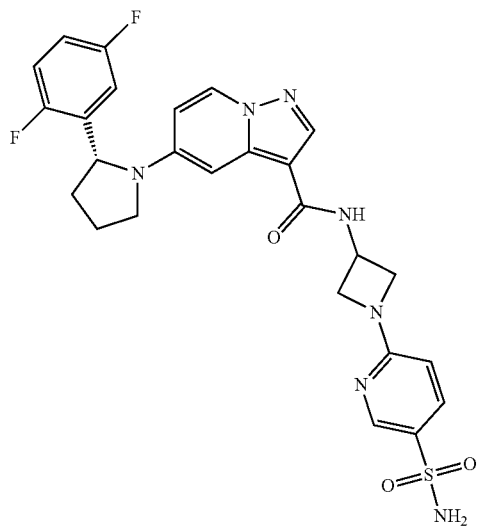 [SMILES: NS(=O)(=O)c1ccc(N2CC(NC(=O)c3cnn4ccc(N5CCC[C@@H]5c5cc(F)ccc5F)cc34)C2)nc1]

Step-1

Tert-butyl (1-(5-sulfamoylpyridin-2-yl)azetidin-3-yl) carbamate

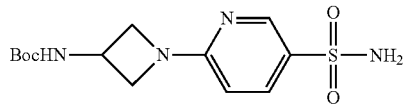 [SMILES: CC(C)(C)OC(=O)NC1CN(c2ccc(S(N)(=O)=O)cn2)C1]

6-chloropyridine-3-sulfonamide (0.32 g, 1.66 mmol) was added to a stirred solution of tert-butyl azetidin-3-ylcarbamate (0.30 g, 1.74 mmol) and DIPEA (0.9 ml, 0.65 g, 4.98 mmol) in 10 ml of ethanol and heated to reflux for 16 h. Reaction mass was cooled to 0° C. The solid formed was filtered and dried under vacuum to obtain desired product.

MS (ESI): m/z 329 (M+H).

Step-2

6-(3-aminoazetidin-1-yl)pyridine-3-sulfonamidehydrochloride

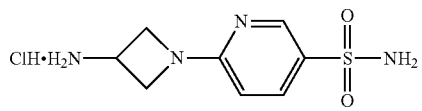

HCl solution (in Dioxane) (4 mL) was added to a stirred solution of tert-butyl 3-methyleneazetidine-1-carboxylate (0.15 g, 0.45 mmol) in Dioxane (5 mL) and stirring was continued at 20-35° C. for 18 h. The reaction mixture was concentrated under reduced pressure to afford the crude product. The crude product was purified by washing with pentane to afford the title compound (Int-77). MS (ESI): m/z 229 (M+H)

Step-3

(R)-5-(2-(2,5-difluorophenyl)pyrrolidin-1-yl)-N-(1-(5-sulfamoylpyridin-2-yl) azetidin-3-yl)pyrazolo[1,5-a]pyridine-3-carboxamide

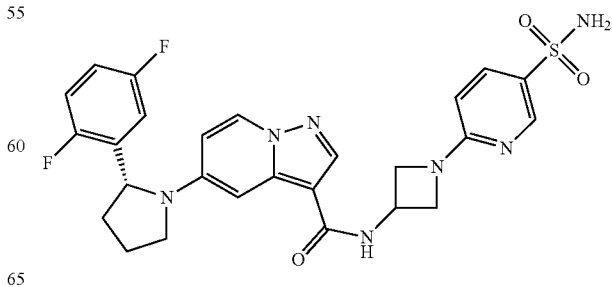

Off white solid (4.2 mg). MS (ESI): m/z 554.1 (M+H).

Example-213

DRL-23367

5-((R)-2-(2,5-difluorophenyl)pyrrolidin-1-yl)-N-(4-((S)-3-hydroxypyrrolidin-1-yl)phenyl)pyrazolo[1,5-a]pyridine-3-carboxamide

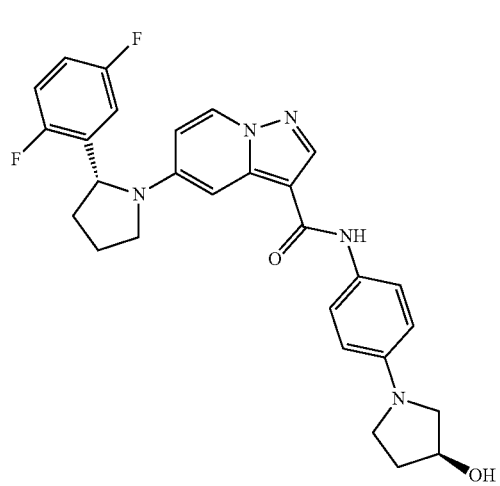 [SMILES: O=C(Nc1ccc(N2CC[C@H](O)C2)cc1)c1cnn2ccc(N3CCC[C@@H]3c3cc(F)ccc3F)cc12]

MS (ESI): m/z 504.1 (M+H).

Example-214

(R)-5-(2-(2,5-difluorophenyl)pyrrolidin-1-yl)-N-(4-(3-hydroxyazetidine-1-yl)phenyl)pyrazolo[1,5-a]pyridine-3-carboxamide

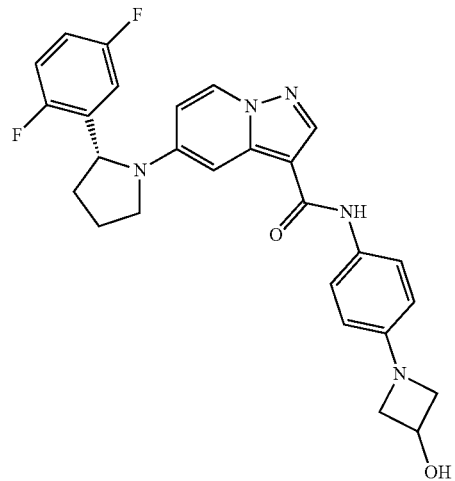 [SMILES: O=C(Nc1ccc(N2CC(O)C2)cc1)c1cnn2ccc(N3CCC[C@@H]3c3cc(F)ccc3F)cc12]

MS (ESI): m/z 490.1 (M+H).

Example-215

(R)—N-(2-(1H-imidazol-1-yl)pyrimidin-5-yl)-5-(2-(2,5-difluorophenyl)pyrrolidin-1-yl)pyrazolo[1,5-a]pyridine-3-carboxamide

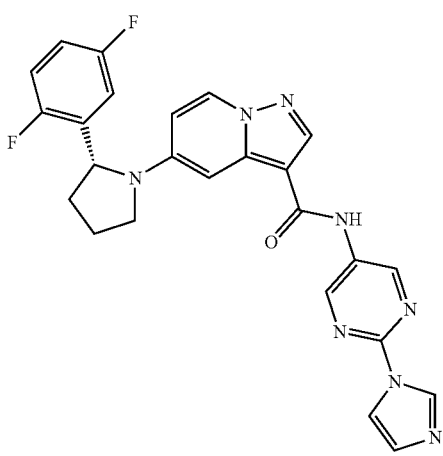 [SMILES: O=C(Nc1cnc(-n2ccnc2)nc1)c1cnn2ccc(N3CCC[C@@H]3c3cc(F)ccc3F)cc12]

MS (ESI): m/z 487 (M+H

Example-216

(R)-5-(2-(2,5-difluorophenyl)pyrrolidin-1-yl)-N-(4-(piperazin-1-yl)phenyl)pyrazolo[1,5-a]pyridine-3-carboxamide

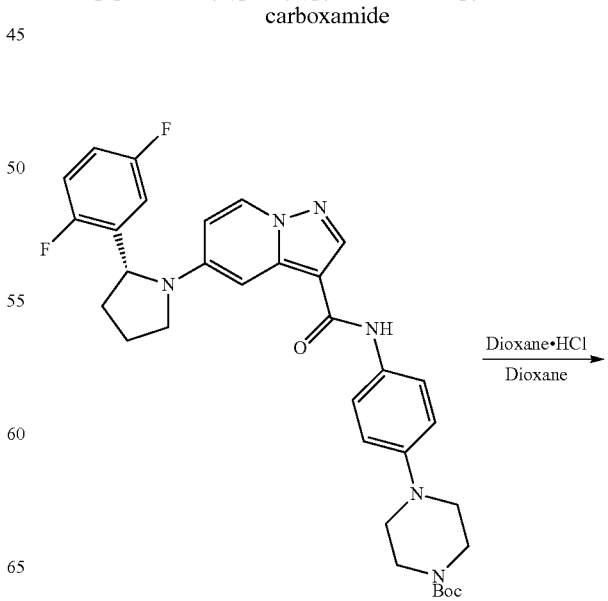

Example-217

N-(3-chloro-4-((S)-3-hydroxypyrrolidin-1-yl)phenyl)-5-((R)-2-(2,5-difluorophenyl)pyrrolidin-1-yl)pyrazolo[1,5-a]pyridine-3-carboxamide

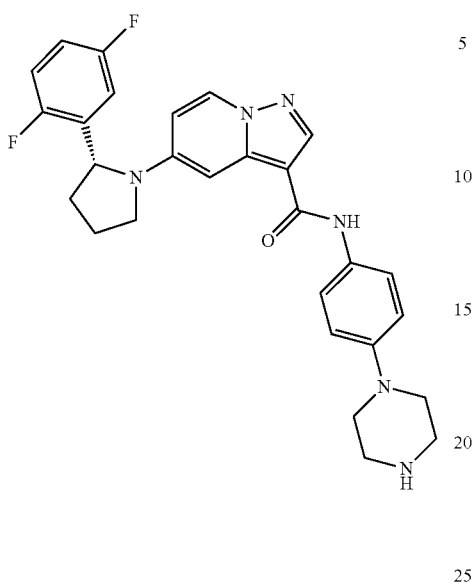

MS (ESI): m/z 503 (M+H).

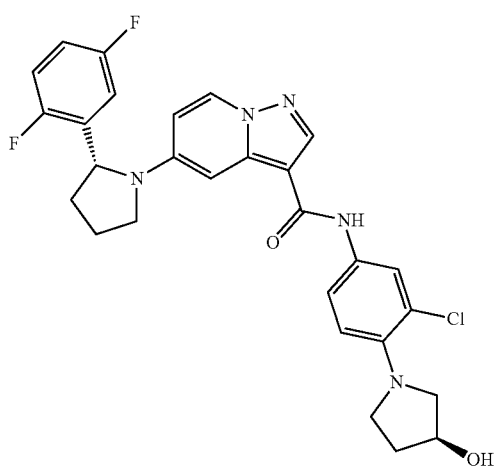 [SMILES: O=C(Nc1ccc(N2CC[C@H](O)C2)c(Cl)c1)c1cnn2ccc(N3CCC[C@@H]3c3cc(F)ccc3F)cc12]

MS (ESI): m/z 538 (M+H).

Example-218

(R)—N-(2-(1H-1,2,4-triazol-1-yl)pyrimidin-5-yl)-5-(2-(2,5-difluorophenyl)pyrrolidin-1-yl)pyrazolo[1,5-a]pyridine-3-carboxamide

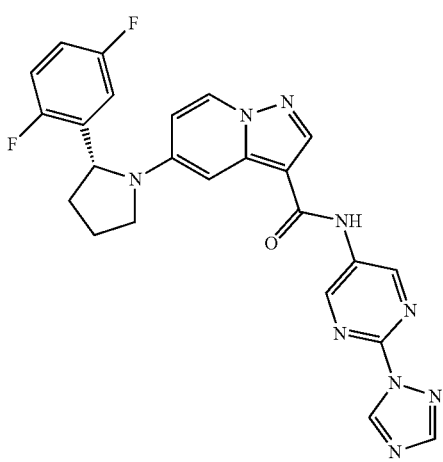 [SMILES: O=C(Nc1cnc(-n2cncn2)nc1)c1cnn2ccc(N3CCC[C@@H]3c3cc(F)ccc3F)cc12]

MS (ESI): m/z 488 (M+H).

Example-219

(5-((R)-2-(2,5-difluorophenyl)pyrrolidin-1-yl)pyrazolo[1,5-a]pyridin-3-yl)(3-hydroxy-3-methylpyrrolidin-1-yl)methanone

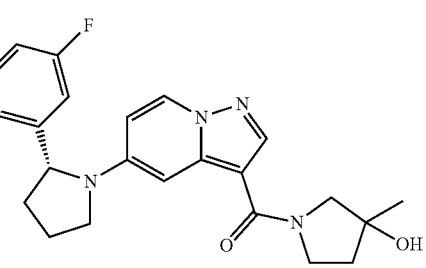

MS (ESI): m/z 427.2 (M+H).

Example-220
(R)-5-(2-(2,5-difluorophenyl)pyrrolidin-1-yl)-N-(4-(methylsulfonyl)phenyl)pyrazolo[1,5-a]pyridine-3-carboxamide
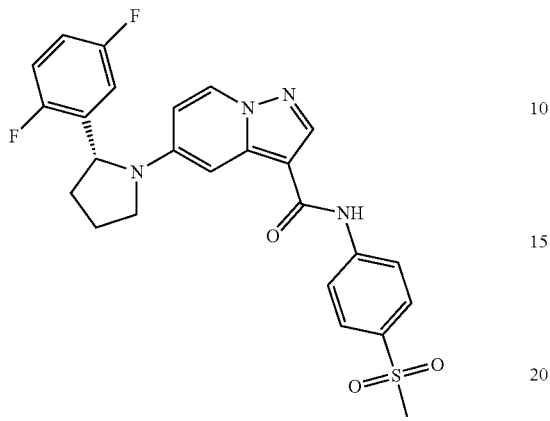
MS (ESI): m/z 497 (M+H).
Example-221
(R)-5-(2-(2,5-difluorophenyl)pyrrolidin-1-yl)-N-(4-((2-hydroxyethyl)amino)phenyl)pyrazolo[1,5-a]pyridine-3-carboxamide
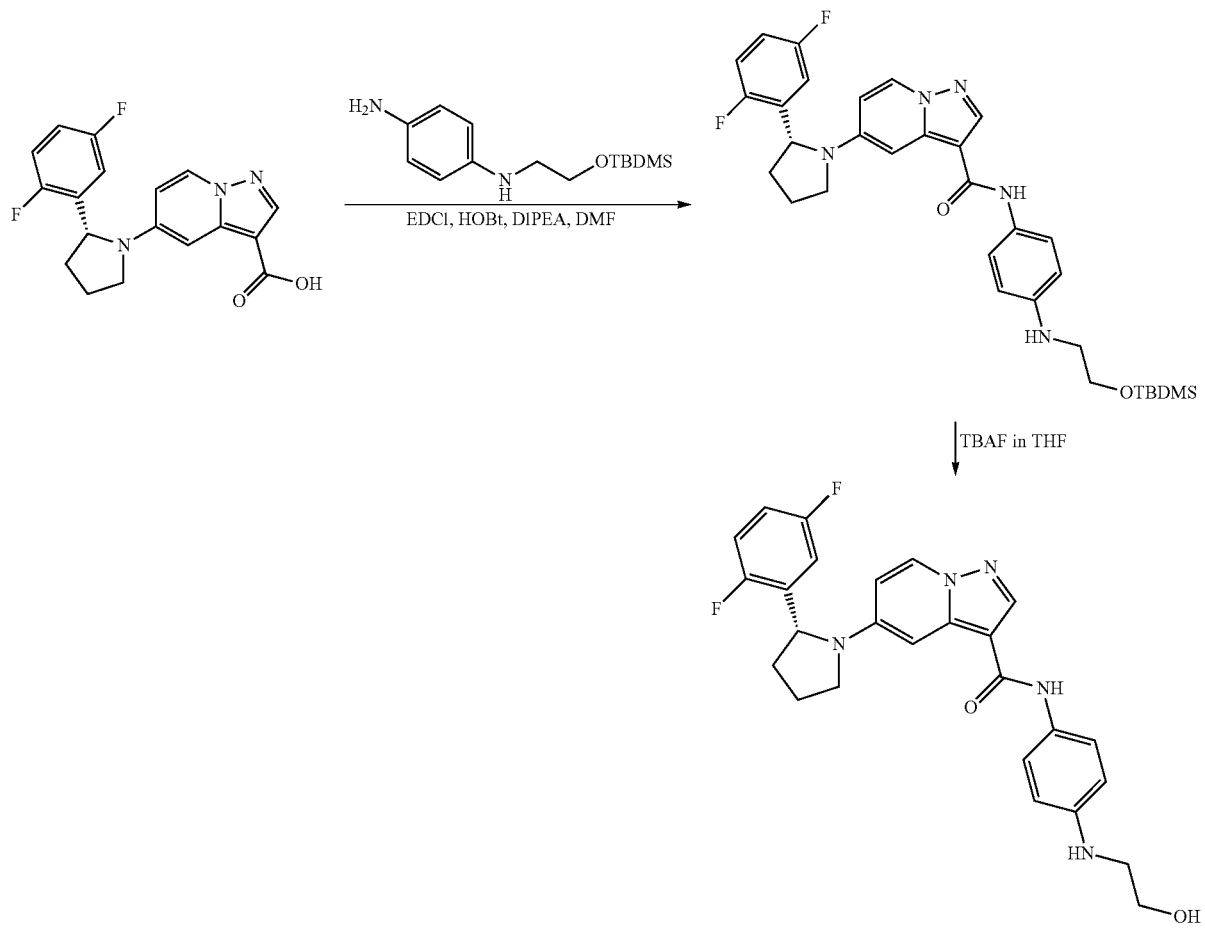 [SMILES: O=C(O)c1cnn2ccc(N3CCC[C@@H]3c3cc(F)ccc3F)cc12 ; CC(C)(C)[Si](C)(C)OCCNc1ccc(N)cc1 ; CC(C)(C)[Si](C)(C)OCCNc1ccc(NC(=O)c2cnn3ccc(N4CCC[C@@H]4c4cc(F)ccc4F)cc23)cc1 ; O=C(Nc1ccc(NCCO)cc1)c1cnn2ccc(N3CCC[C@@H]3c3cc(F)ccc3F)cc12]
MS (ESI): m/z 478.2 (M+H).

Example-222

5-((R)-2-(2,5-difluorophenyl)pyrrolidin-1-yl)-N-(4-((3S,5R)-3,5-dimethylpiperazin-1-yl)phenyl)pyrazolo[1,5-a]pyridine-3-carboxamide

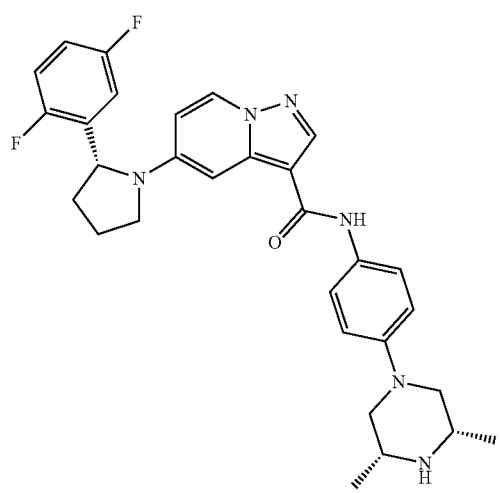 [SMILES: C[C@@H]1CN(c2ccc(NC(=O)c3cnn4ccc(N5CCC[C@@H]5c5cc(F)ccc5F)cc34)cc2)C[C@H](C)N1]

MS (ESI): m/z 430.9 (M+H).

Example-223

(R)—N-(1-(tert-butyl)-3-methyl-1H-pyrazol-5-yl)-5-(2-(2,5-difluorophenyl)pyrrolidin-1-yl)pyrazolo[1,5-a]pyridine-3-carboxamide

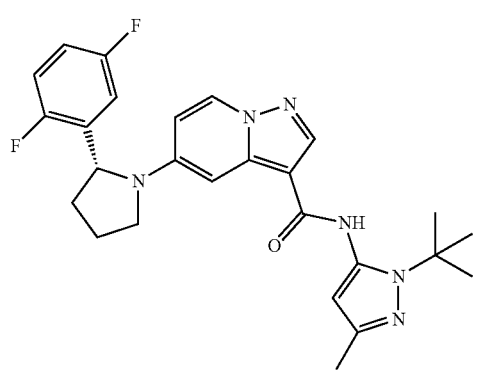 [SMILES: Cc1cc(NC(=O)c2cnn3ccc(N4CCC[C@@H]4c4cc(F)ccc4F)cc23)n(C(C)(C)C)n1]

MS (ESI): m/z 478.9 (M+H).

Example-224

(R)-5-(2-(2,5-difluorophenyl)pyrrolidin-1-yl)-N-(3-methyl-1H-pyrazol-5-yl)pyrazolo[1,5-a]pyridine-3-carboxamide

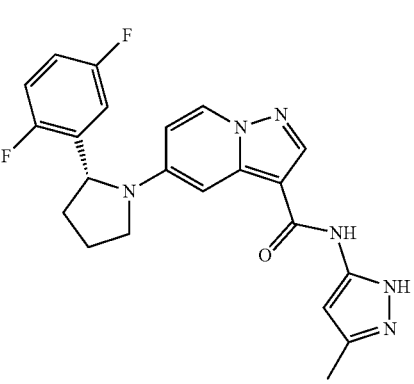 [SMILES: Cc1cc(NC(=O)c2cnn3ccc(N4CCC[C@@H]4c4cc(F)ccc4F)cc23)[nH]n1]

MS (ESI): m/z 423.9 (M+H).

Example-225

(R)-5-(2-(2,5-difluorophenyl)pyrrolidin-1-yl)-N-(6-sulfamoylpyridin-3-yl)pyrazolo[1,5-a]pyridine-3-carboxamide

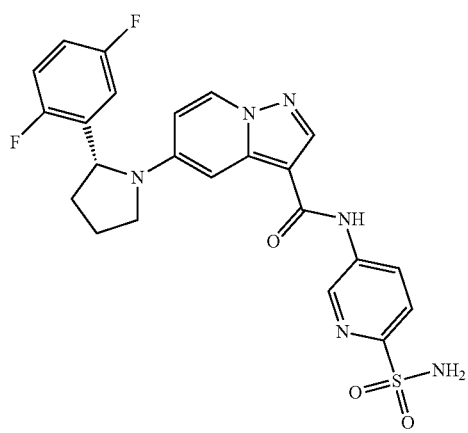 [SMILES: NS(=O)(=O)c1ccc(NC(=O)c2cnn3ccc(N4CCC[C@@H]4c4cc(F)ccc4F)cc23)cn1]

MS (ESI): m/z 499.6 (M+H).

Example-226

(R)—N-(3-chloro-4-(3-hydroxyazetidine-1-yl)phenyl)-5-(2-(2,5-difluorophenyl)pyrrolidin-1-yl)pyrazolo[1,5-a]pyridine-3-carboxamide

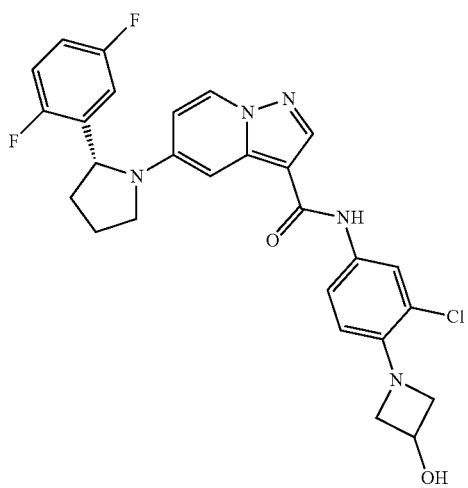 [SMILES: O=C(Nc1ccc(N2CC(O)C2)c(Cl)c1)c1cnn2ccc(N3CCC[C@@H]3c3cc(F)ccc3F)cc12]

MS (ESI): m/z 524 (M+H).

Example-227

(R)-(5-(2-(2,5-difluorophenyl)pyrrolidin-1-yl)pyrazolo[1,5-a]pyridin-3-yl)(3-hydroxy-3-(hydroxymethyl)azetidin-1-yl)methanone

Step-1

Tert-butyl 3-methyleneazetidine-1-carboxylate

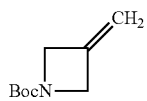

The title compound was prepared by the method similar to that mentioned in PCT/US2008/004434 to afford a off white solid. 1H NMR (300 MHz, CDCl$_3$) δ ppm 4.99-4.98 (2H, t), 4.48-4.47 (4H, m), 1.45 (9H, s).

Step-2

3-Methyleneazetidine hydrochloride

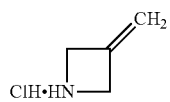

1M HCl solution (in Diethyl ether) (4 mL) was added to a stirred solution of tert-butyl 3-methyleneazetidine-1-carboxylate (0.18 g, 1.06 mmol) in Diethyl ether (5 mL) and stirring was continued at 20-35° C. for 18 h. The reaction mixture was concentrated under reduced pressure to afford the crude product. The crude product was purified by washing with pentane to afford the title compound as a white solid. $^1$H NMR (300 MHz, CDCl$_3$) δ ppm 7.66-7.55 (2H, m), 4.7 (1H, s), 4.26-4.23 (2H, d), 4.12-4.02 (2H, m).

Step-3

(R)-(5-(2-(2,5-difluorophenyl)pyrrolidin-1-yl)pyrazolo[1,5-a]pyridin-3-yl)(3-methyleneazetidine-1-yl)methanone

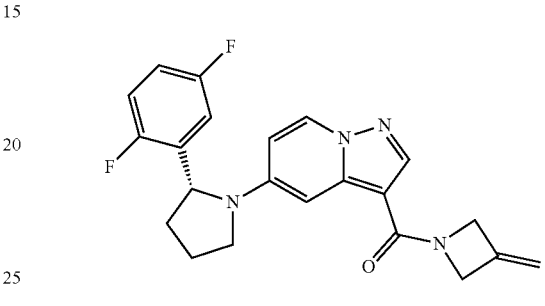

Title compound was prepared by the method substantially similar to that mentioned in example-6 to afford the product which was used without further purification to the next step.

Step-4

(R)-(5-(2-(2,5-difluorophenyl)pyrrolidin-1-yl)pyrazolo[1,5-a]pyridin-3-yl)(3-hydroxy-3-(hydroxymethyl)azetidin-1-yl)methanone

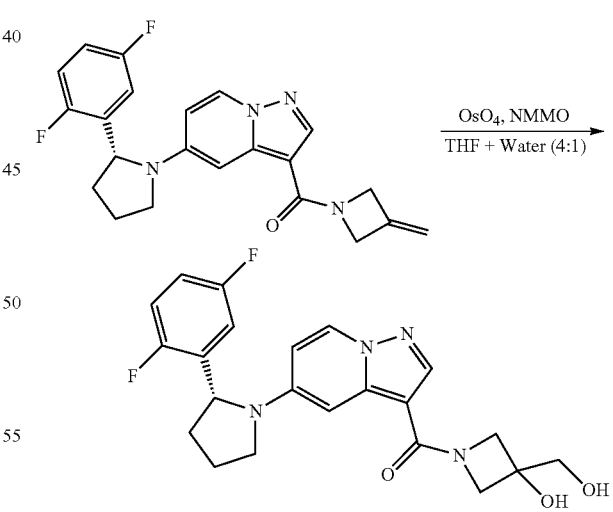

(R)-(5-(2-(2,5-difluorophenyl)pyrrolidin-1-yl)pyrazolo[1,5-a]pyridin-3-yl)(3-methyl eneazetidin-1-yl)methanone (50 mg, 0.125 mmol) and 4-methylmorpholine N-oxide (44 mg, 0.379 mmol) were dissolved in THF/Water (4:1, 2.0 ml) followed by the addition of Osmium tetroxide (1.38 mg, 0.006 mmol). Reaction mass was stirred for 16 h at 25° C., diluted with ethyl acetate and the organic layer was washed with water, NaOCl solution, followed by brine, dried over anhydrous sodium sulphate and concentrated under reduced pressure to afford the title product as brown solid. MS (ESI): m/z 429.7 (M+H).

Example-228

(5-((R)-2-(2,5-difluorophenyl)pyrrolidin-1-yl)pyrazolo[1,5-a]pyridin-3-yl) (3-hydroxy-3-(hydroxymethyl)pyrrolidin-1-yl)methanone

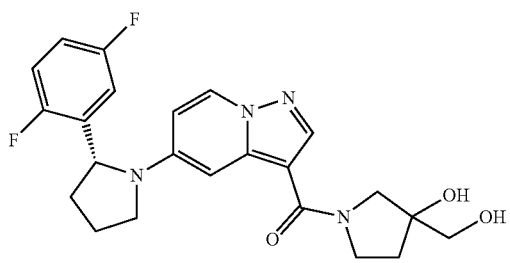 [SMILES: O=C(c1cnn2ccc(N3CCC[C@@H]3c3cc(F)ccc3F)cc12)N1CCC(O)(CO)C1]

Step-1

3-Methylenepyrrolidine hydrochloride

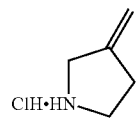

The title compound was prepared by the method similar to that of PCT/US2008/004434 to afford the product. $^1$H NMR (300 MHz, CDCl$_3$) δ ppm 9.65-9.4 (2H, s), 5.1 (2H, s), 3.72 (2H, s), 3.23 (4H, m).

Step-2

(R)-(5-(2-(2,5-difluorophenyl)pyrrolidin-1-yl)pyrazolo[1,5-a]pyridin-3-yl)(3-methylenepyrrolidin-1-yl)methanone

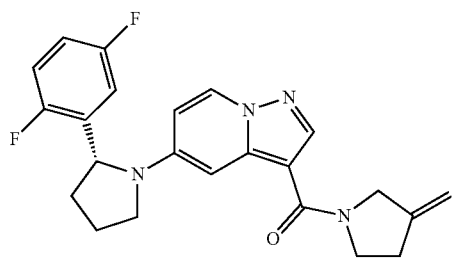 [SMILES: C=C1CCN(C(=O)c2cnn3ccc(N4CCC[C@@H]4c4cc(F)ccc4F)cc23)C1]

The title compound was prepared by a method substantially similar to that mentioned in example 6 to afford the crude product which was used as such for the next step.

Step-3

(5-((R)-2-(2,5-difluorophenyl)pyrrolidin-1-yl)pyrazolo[1,5-a]pyridin-3-yl) (3-hydroxy-3-(hydroxymethyl)pyrrolidin-1-yl)methanone

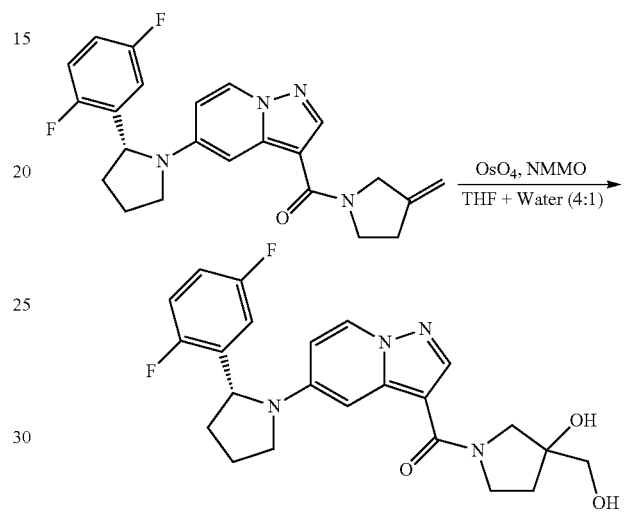

The title product was prepared by a method substantially similar to that of step-4 of example-227 to afford a dark solid (20.0 mg). MS (ESI): m/z 443.1 (M+H).

Example-229

(R)-5-(2-(2,5-difluorophenyl)pyrrolidin-1-yl)-N-(4-(2-oxoimidazolidin-1-yl)phenyl)pyrazolo[1,5-a]pyridine-3-carboxamide

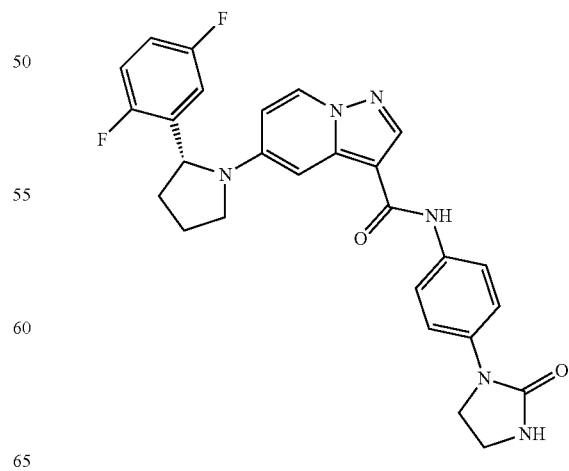

MS (ESI): m/z 503.2 (M+H).

Example-230

(R)-5-(2-(2,5-difluorophenyl)pyrrolidin-1-yl)-N-(5-(pyridin-2-yl)-1,3,4-thiadiazol-2-yl)pyrazolo[1,5-a]pyridine-3-carboxamide

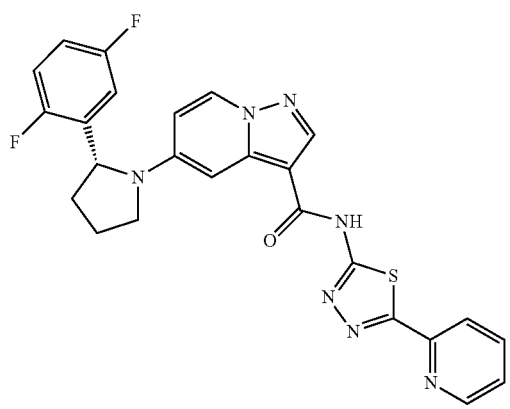 [SMILES: O=C(Nc1nnc(-c2ccccn2)s1)c1cnn2ccc(N3CCC[C@@H]3c3cc(F)ccc3F)cc12]

MS (ESI): m/z 503.4 (M+H).

Example-231

(R)-5-(2-(2,5-difluorophenyl)pyrrolidin-1-yl)-N-(4-sulfamoylphenyl)pyrazolo[1,5-a]pyridine-3-carboxamide

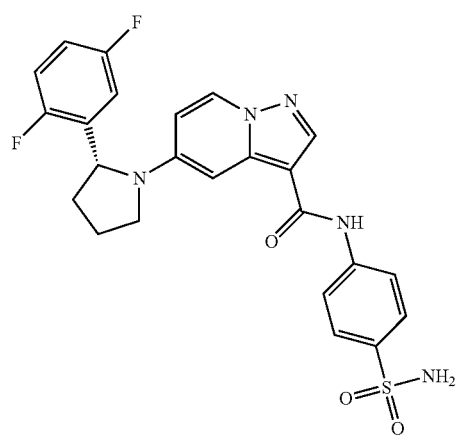 [SMILES: NS(=O)(=O)c1ccc(NC(=O)c2cnn3ccc(N4CCC[C@@H]4c4cc(F)ccc4F)cc23)cc1]

MS (ESI): m/z 497.9 (M+H).

Example-232

(R)-5-(2-(2,5-difluorophenyl)pyrrolidin-1-yl)-N-(5-(pyridin-3-yl)-1,3,4-thiadiazol-2-yl)pyrazolo[1,5-a]pyridine-3-carboxamide

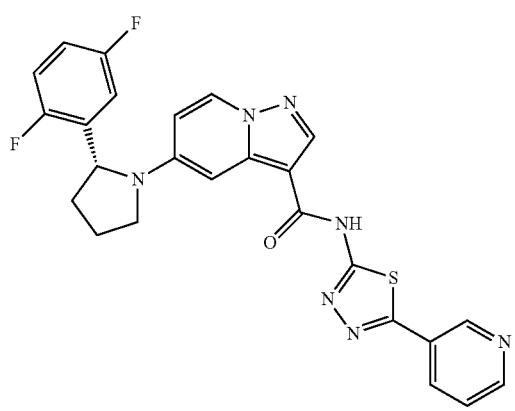 [SMILES: O=C(Nc1nnc(-c2cccnc2)s1)c1cnn2ccc(N3CCC[C@@H]3c3cc(F)ccc3F)cc12]

MS (ESI): m/504.6 (M+H).

Example-233

(R)-5-(2-(2,5-difluorophenyl)pyrrolidin-1-yl)-N-(6-(N,N-dimethylsulfamoyl)pyridin-3-yl)pyrazolo[1,5-a]pyridine-3-carboxamide

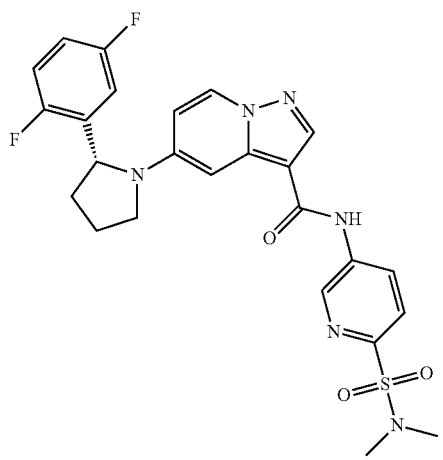 [SMILES: CN(C)S(=O)(=O)c1ccc(NC(=O)c2cnn3ccc(N4CCC[C@@H]4c4cc(F)ccc4F)cc23)cn1]

MS (ESI): m/z 526.8 (M+H).

Example-234

(R)-5-(2-(2,5-difluorophenyl)pyrrolidin-1-yl)-N-(6-(N-methylsulfamoyl)pyridin-3-yl)pyrazolo[1,5-a]pyridine-3-carboxamide

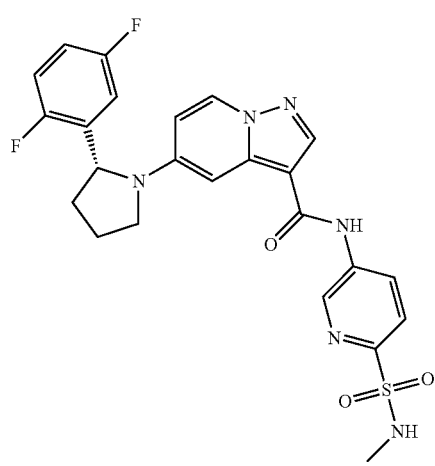 [SMILES: CNS(=O)(=O)c1ccc(NC(=O)c2cnn3ccc(N4CCC[C@@H]4c4cc(F)ccc4F)cc23)cn1]

MS (ESI): m/z 513.3 (M+H).

Example-235

(R)-5-(2-(2,5-difluorophenyl)pyrrolidin-1-yl)-N-(4-(pyridin-3-yl)thiazol-2-yl)pyrazolo[1,5-a]pyridine-3-carboxamide

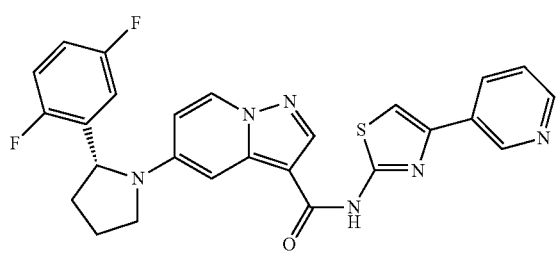 [SMILES: O=C(Nc1nc(-c2cccnc2)cs1)c1cnn2ccc(N3CCC[C@@H]3c3cc(F)ccc3F)cc12]

MS (ESI): m/z 503.3 (M+H).

Example-236

(R)-5-(2-(2,5-difluorophenyl)pyrrolidin-1-yl)-N-(4-(pyridin-2-yl)thiazol-2-yl)pyrazolo[1,5-a]pyridine-3-carboxamide

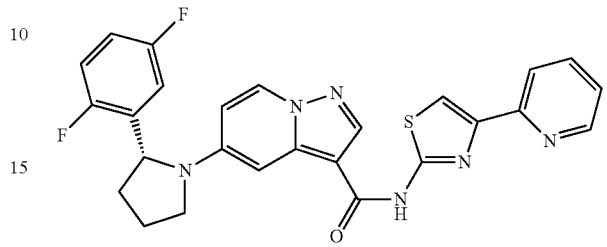

MS (ESI): m/z 503.1 (M+H).

Example-237

Synthesis of (R)-5-(2-(5-(difluoromethoxy)-2-fluorophenyl)pyrrolidin-1-yl)pyrazolo[1,5-a]pyridine-3-carboxylic acid

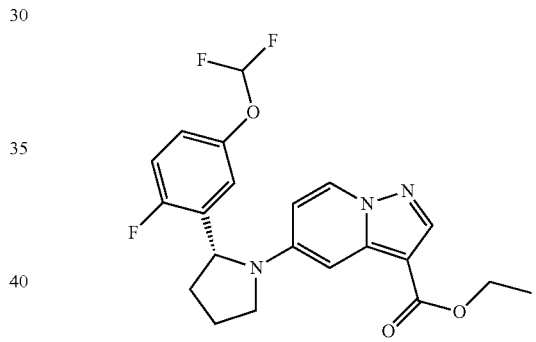

Step-1

Synthesis of (R)-2-(5-(difluoromethoxy)-2-fluorophenyl)pyrrolidine hydrochloride

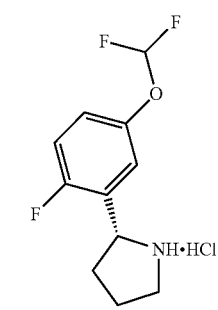

This compound was prepared by the method substantially similar to the preparation of 2,5-difluorophenyl pyrrolidine hydrochloride as mentioned in Example 1 step 5 using 2-bromo-4-(difluoromethoxy)-1-fluorobenzene (*J. Med. Chem.* 2003, 46, 1016-1030).

Step-2

Synthesis of (R)-Ethyl 5-(2-(5-(difluoromethoxy)-2-fluorophenyl)pyrrolidin-1-yl) pyrazolo[1,5a]pyridine-3-carboxylate

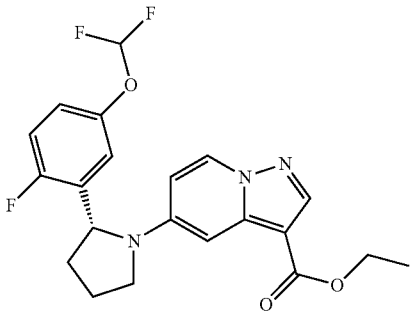 [SMILES: CCOC(=O)c1cnn2ccc(N3CCC[C@@H]3c3cc(OC(F)F)ccc3F)cc12]

The title compound was prepared by the method substantially similar to that mentioned in Example-1, to afford the crude, which was purified by column chromatography (using silica gel 60-120, and 5% EtOAc in Hexane as eluent) to afford 140 mg of the title compound.

MS (ESI): m/z 420 (M+H).

Example-238

Synthesis of (R)-5-(2-(5-(difluoromethoxy)-2-fluorophenyl)pyrrolidin-1-yl)pyrazolo[1,5-a]pyridine-3-carboxylic acid

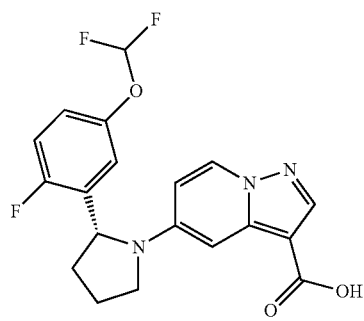 [SMILES: O=C(O)c1cnn2ccc(N3CCC[C@@H]3c3cc(OC(F)F)ccc3F)cc12]

The title compound was prepared by the method substantially similar to that mentioned in Example-3, to afford 85 mg of the title compound.

$^1$H NMR (300 MHz, DMSO-$d_6$) δ ppm 11.9 (1H, bs,), 8.47-8.45 (1H, d, J=7.5 Hz), 8.08 (1H, s), 7.37-7.30 (1H, t), 7.20-7.10 (1H, m), 6.87-6.85 (1H, m), 7.33-6.87 (1H, t, OCHF$_2$) 6.76 (1H, bs), 6.45-6.35 (1H, m), 5.16-5.14 (1H, d, J=7.5 Hz), 3.90-3.80 (1H, t), 3.55-3.45 (2H, m), 2.08-1.85 (3H, m).

MS (ESI): m/z 392.1 (M+H).

Example-239

Synthesis of 5-((R)-2-(5-(difluoromethoxy)-2-fluorophenyl)pyrrolidin-1-yl)-N—((S)-2,3-dihydroxypropyl)pyrazolo[1,5a]pyridine-3-carboxamide

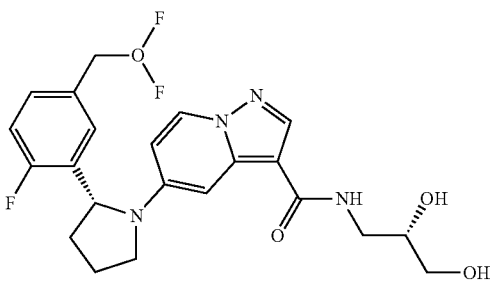

The title compound was prepared by the method substantially similar to that mentioned in Example-6, using (S)-3-aminopropane-1,2-diol in place of NH$_4$Cl to afford the crude compound. The crude compound was purified by Column chromatography (using Silica gel 60-120 and 10% MeOH in DCM as eluent) to afford 6.1 mg of the title compound.

$^1$H NMR (400 MHz, CD$_3$OD) δ ppm 8.24-8.20 (2H, m), 7.20-7.16 (1H, t), 7.08-7.04 (2H, m), 6.84-6.47 (1H, t, OCHF2) 6.82-6.80 (1H, m), 6.44-6.43 (1H, m), 5.20-5.18 (1H, d, J=8 Hz), 3.85-3.70 (2H, m), 3.60-3.47 (4H, m), 3.83-3.35 (1H, m), 2.53-2.47 (1H, m), 2.14-2.03 (3H, m), 1.37-1.33 (2H, m).

MS (ESI): m/z 464.8 (M+H).

Example-240

Synthesis of 5-((R)-2-(5-(difluoromethoxy)-2-fluorophenyl)pyrrolidin-1-yl)-N-((1r,4R)-4-hydroxy cyclo hexyl)pyrazolo[1,5a]pyridine-3-carboxamide

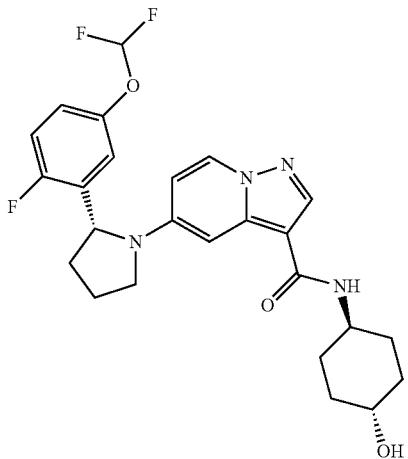 [SMILES: O=C(N[C@H]1CC[C@H](O)CC1)c1cnn2ccc(N3CCC[C@@H]3c3cc(OC(F)F)ccc3F)cc12]

The title compound was prepared by the method substantially similar to that mentioned in Example-6, using trans-4-aminocyclohexanol hydrochloride in place of NH$_4$Cl to afford the crude compound. The crude compound was purified by Preparative TLC (using Silicagel GF$_{254}$, 1000 u coated 20×20 cm dimension glass plate and 10% MeOH in DCM as eluent) to afford 48 mg of the title compound.

$^1$H NMR (400 MHz, DMSO-d$_6$) δ ppm 8.39-8.37 (1H, d, J=7.6 Hz), 8.03 (1H, s), 7.54-7.52 (1H, m), 7.36-7.31 (1H, m), 7.31-6.95 (1H, t, OCHF$_2$), 7.14-7.10 (1H, m), 6.95-6.90 (1H, m), 6.85-6.83 (1H, m), 6.40-6.35 (1H, m), 5.10-5.08 (1H, d, J=7.6 Hz), 4.56-4.55 (1H, d, J=4.8 Hz), 3.85-3.80 (1H, m), 3.70-3.60 (1H, m), 3.44-3.40 (1H, m), 2.03-1.75 (6H, m), 1.30-1.20 (4H, m).

MS (ESI): m/z 489.2 (M+H).

Example-241

Synthesis of (R)-(5-(2-(5-(difluoromethoxy)-2-fluorophenyl)pyrrolidin-1-yl)pyrazolo[1,5-a]pyridin-3-yl)(3-hydroxyazetidine-1-yl)methanone

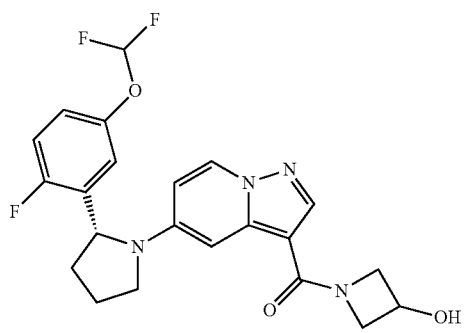 [SMILES: O=C(c1cnn2ccc(N3CCC[C@@H]3c3cc(OC(F)F)ccc3F)cc12)N1CC(O)C1]

The title compound was prepared by the method substantially similar to that mentioned in Example-6, using 3-azetidinol hydrochloride in place of NH$_4$Cl to afford the crude compound. The crude compound was purified by Preparative TLC (using Silicagel GF$_{254}$, 1000 u coated 20×20 cm dimension glass plate and 10% MeOH in DCM as eluent) to afford 65 mg of the title compound.

$^1$H NMR (400 MHz, DMSO-d$_6$) δ ppm 8.45-8.43 (1H, d, J=7.6 Hz), 8.01 (1H, s), 7.36-7.32 (1H, m), 7.31-6.95 (1H, t, OCHF$_2$), 7.14-7.10 (1H, m), 6.96-6.95 (1H, m), 6.84-6.82 (1H, m), 6.42-6.41 (1H, m), 5.71-5.69 (1H, d, J=4.7 Hz), 5.11-5.09 (1H, d, J=8.0 Hz), 4.50-4.46 (m, 1H), 3.83-3.80 (1H, m), 3.47-3.39 (1H, m), 2.44-2.40 (1H, m), 2.06-1.88 (3H, m).

MS (ESI): m/z 446.9 (M+H).

Example-242

Synthesis of (5-((R)-2-(5-(difluoromethoxy)-2-fluorophenyl)pyrrolidin-1-yl)pyrazolo[1,5-a]pyridin-3-yl)((S)-3-hydroxypyrrolidin-1-yl)methanone

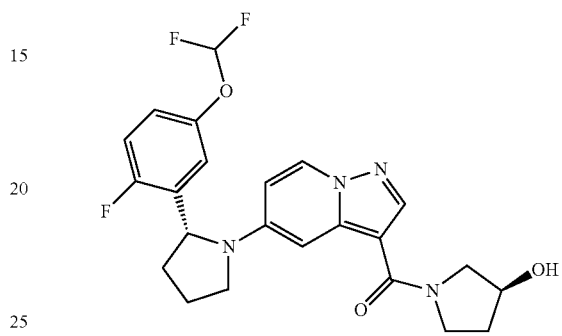

The title compound was prepared by the method substantially similar to that mentioned in Example-160, to afford the crude compound. The crude compound was purified by Preparative TLC (using Silicagel GF$_{254}$, 1000 u coated 20×20 cm dimension glass plate and 10% MeOH in DCM as eluent) to afford 20 mg of the title compound.

$^1$H NMR (300 MHz, DMSO-d$_6$) δ ppm 8.44-8.42 (1H, d, J=7.6 Hz), 8.15 (1H, s), 7.39-7.34 (1H, m), 7.30-6.90 (1H, t, OCHF$_2$) 7.13-7.10 (1H, m), 7.02 (1H, m), 6.86-6.84 (1H, m), 6.39 (1H, m), 5.12-5.10 (1H, m), 4.94 (1H, m), 2.1-1.8 (6H, m).

MS (ESI): m/z 460.9 (M+H).

Example-243

Synthesis of (R)-(5-(2-(2-(difluoromethoxy)-5-fluorophenyl)pyrrolidin-1-yl)pyrazolo[1,5-a]pyridin-3-yl)(3-hydroxyazetidine-1-yl)methanone

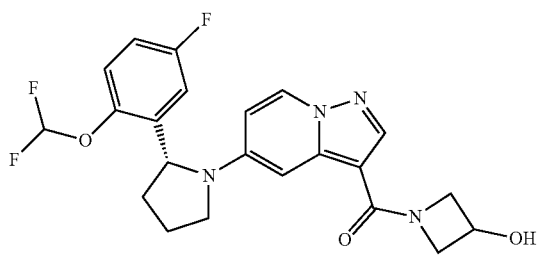 [SMILES: O=C(c1cnn2ccc(N3CCC[C@@H]3c3cc(F)ccc3OC(F)F)cc12)N1CC(O)C1]

Step-1

Synthesis of (R)-2-(2-(difluoromethoxy)-5-fluorophenyl)pyrrolidine hydrochloride

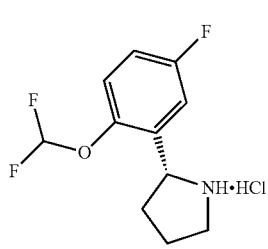

This compound was prepared by the method substantially similar to the preparation of 2,5-difluorophenyl pyrrolidine hydrochloride as mentioned in Example 1 step 5 using 3-bromo-4-(difluoromethoxy)-1-fluorobenzene (*J. Med. Chem.* 2003, 46, 1016-1030).

Step-2

Synthesis of (R)-ethyl 5-(2-(2-(difluoromethoxy)-5-fluorophenyl)pyrrolidin-1-yl)pyrazolo[1,5-a]pyridine-3-carboxylate

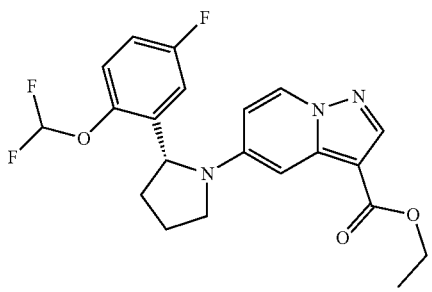 [SMILES: CCOC(=O)c1cnn2ccc(N3CCC[C@@H]3c3cc(F)ccc3OC(F)F)cc12]

The title compound was prepared by the method substantially similar to that mentioned in Example-1, to afford the crude, which was purified by column chromatography (using silica gel 60-120, and 5% EtOAc in Hexane as eluent) to afford 600 mg of the title compound(R)-ethyl 5-(2-(2-(difluoromethoxy)-5-fluorophenyl)pyrrolidin-1-yl)pyrazolo[1,5-a]pyridine-3-carboxylate.

MS (ESI): m/z 420.4 (M+H).

Step-3

Synthesis of (R)-5-(2-(2-(difluoromethoxy)-5-fluorophenyl)pyrrolidin-1-yl)pyrazolo[1,5-a]pyridine-3-carboxylic acid

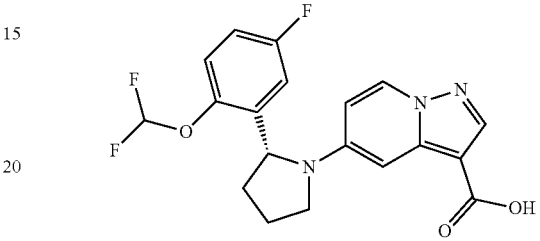

The title compound was prepared by the method substantially similar to that mentioned in Example-3, to afford 110 mg of the title compound.

MS (ESI): m/z 392.5 (M+H).

Step-4

Synthesis of (R)-(5-(2-(2-(difluoromethoxy)-5-fluorophenyl)pyrrolidin-1-yl)pyrazolo[1,5-a]pyridin-3-yl)(3-hydroxyazetidine-1-yl)methanone

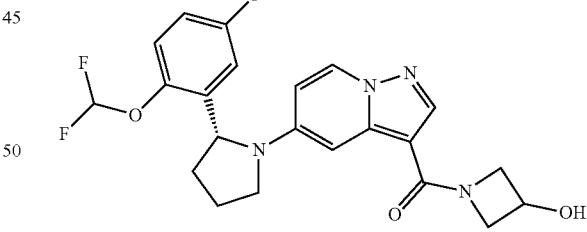

The title compound was prepared by the method substantially similar to that mentioned in Example-160, using (R)-5-(2-(2-(difluoromethoxy)-5-fluorophenyl)pyrrolidin-1-yl)pyrazolo[1,5a]pyridine-3-carboxylic acid and 3-azetidinol hydrochloride to afford 62 mg of the title compound.

$^1$H NMR (400 MHz, DMSO-d$_6$) δ ppm 8.46-8.44 (1H, d, J=7.6 Hz), 8.02 (1H, s), 7.53-7.21 (1H, t, OCHF$_2$), 7.33-7.31 (1H, m), 7.21-7.16 (1H, m), 6.92-6.88 (2H, m), 6.34 (1H, bs), 5.72-5.70 (1H, d, J=8.0 Hz), 5.07-5.05 (1H, d, J=8.0 Hz), 4.49-4.48 (1H, m), 3.89-3.85 (2H, m), 3.47-3.43 (1H, m), 3.34-3.32 (1H, m), 2.44-2.40 (1H, m), 2.03-1.86 (3H, m).

MS (ESI): m/z 447.4 (M+H).

Example-244

Synthesis of 5-((R)-2-(2-(difluoromethoxy)-5-fluorophenyl)pyrrolidin-1-yl)-N—((S)-2,3-dihydroxypropyl)pyrazolo[1,5-a]pyridine-3-carboxamide

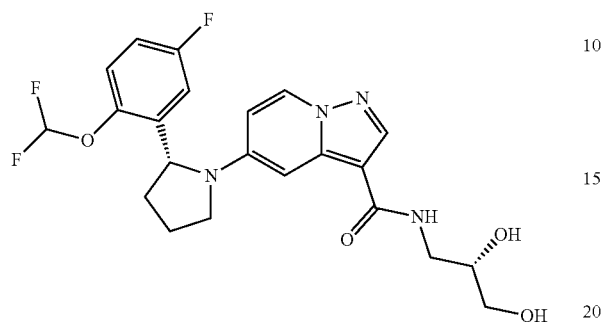

The title compound was prepared by the method substantially similar to that mentioned in Example-160, to afford the crude compound. The crude compound was purified by Column chromatography (using Silica gel 60-120 and 10% MeOH in DCM as eluent) to afford 53 mg of the title compound.

$^1$H NMR (300 MHz, DMSO-$d_6$) δ ppm 8.41-8.38 (1H, d, J=7.6 Hz), 8.32 (1H, s), 7.90-7.86 (1H, m), 7.58-7.09 (1H, t, OCHF$_2$), 7.31-7.30 (1H, m), 7.22-7.15 (1H, m), 6.94-6.87 (2H, m), 6.27-6.25 (1H, m), 5.08-5.06 (1H, d, J=8.0 Hz), 4.85-4.84 (1H, d, J=4.8 Hz), 4.62-4.58 (1H, t), 3.90-3.76 (1H, m), 3.60-3.50 (1H, m), 3.41-3.36 (1H, m), 3.18-3.13 (1H, m), 2.02-1.89 (3H, m), 1.23-1.20 (2H, m).

MS (ESI): m/z 465.5 (M+H).

Example-245

Synthesis of (5-((R)-2-(2-(difluoromethoxy)-5-fluorophenyl)pyrrolidin-1-yl)pyrazolo[1,5a]pyridin-3-yl)((S)-3-hydroxypyrrolidin-1-yl)methanone

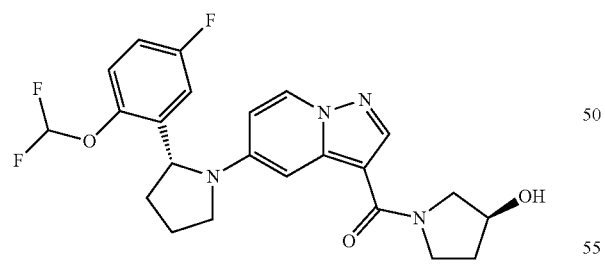

The title compound was prepared by the method substantially similar to that mentioned in Example-160, to afford the crude compound. The crude compound was purified by Column chromatography (using Silica gel 60-120 and 10% MeOH in DCM as eluent) to afford 67 mg (5-((R)-2-(2-(difluoromethoxy)-5-fluorophenyl)pyrrolidin-1-yl)pyrazolo[1,5-a]pyridin-3-yl)((S)-3-hydroxypyrrolidin-1-yl)methanone.

$^1$H NMR (400 MHz, DMSO-$d_6$) δ ppm 8.44-8.42 (1H, d, J=7.6 Hz), 8.15 (1H, bs), 7.54-7.19 (1H, t, OCHF$_2$) 7.34-7.30 (1H, m), 7.21-7.16 (1H, m), 6.99 (1H, bs), 6.91-6.88 (m, 1H) 6.31 (1H, bs), 5.08-5.06 (1H, d, J=8.0 Hz), 4.99-4.95 (1H, m), 4.30 (1H, bs), 3.88-3.84 (1H, t), 3.50-3.35 (3H, m), 2.42-2.39 (1H, m), 2.04-2.03 (1H, m), 1.98-1.86 (4H, m).

MS (ESI): m/z 460.8 (M+H).

Example-246

Synthesis of 5-((R)-2-(2-(difluoromethoxy)-5-fluorophenyl)pyrrolidin-1-yl)-N-((1r,4R)-4-hydroxycyclohexyl)pyrazolo[1,5a]pyridine-3-carboxamide

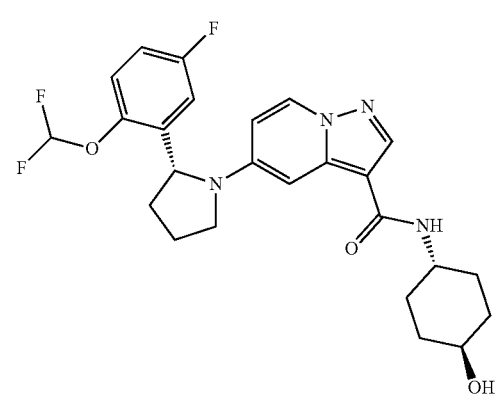 [SMILES: O=C(N[C@H]1CC[C@H](O)CC1)c1cnn2ccc(N3CCC[C@@H]3c3cc(F)ccc3OC(F)F)cc12]

The title compound was prepared by the method substantially similar to that mentioned in Example-160, to afford the crude compound. The crude compound was purified by Preparative TLC (using Silicagel GF$_{254}$, 1000 u coated 20×20 cm dimension glass plate and 10% MeOH in DCM as eluent) to afford 80 mg of the title compound.

$^1$H NMR (300 MHz, DMSO-$d_6$) δ ppm 8.39-8.37 (1H, d, J=7.6 Hz), 8.30 (1H, s), 7.59-7.10 (1H, t, OCHF$_2$) 7.54-7.51 (1H, d, J=8.1 Hz), 7.33-7.30 (1H, m), 7.21-7.18 (1H, m), 6.93 (1H, bs), 6.90-6.86 (1H, m), 6.28-6.20 (1H, m), 5.07-5.04 (1H, d, J=8.1 Hz), 4.57-4.56 (1H, d, J=4.2 Hz), 3.84-3.80 (1H, m), 3.80-3.65 (1H, m), 2.10-1.72 (8H, m), 1.35-1.15 (5H, m).

MS (ESI): m/z 488.8 (M+H).

Example-247

Synthesis of (R)-5-(2-(2-(difluoromethoxy)-5-fluorophenyl)pyrrolidin-1-yl)pyrazolo[1,5-a]pyridine-3-carboxamide

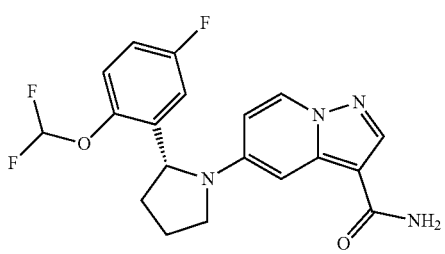 [SMILES: NC(=O)c1cnn2ccc(N3CCC[C@@H]3c3cc(F)ccc3OC(F)F)cc12]

The title compound was prepared by the method substantially similar to that mentioned in Example-6, to afford the crude compound. The crude compound was purified by Preparative TLC (using Silicagel GF$_{254}$, 1000 u coated 20×20 cm dimension glass plate and 10% MeOH in DCM as eluent) to afford 21 mg of the title compound.

¹H NMR (300 MHz, CDCl₃) δ ppm 8.16-8.13 (1H, d, J=7.6 Hz), 7.97 (1H, s), 7.25-7.15 (1H, m), 7.09 (1H, bs), 6.98-6.92 (1H, m), 6.94-6.45 (1H, t, OCHF₂) 6.76-6.69 (1H, m), 6.20-6.17 (1H, d, J=6.9 Hz), 5.39 (2H, bs), 5.17-5.14 (1H, d, J=7.8 Hz), 3.83-3.80 (1H, m), 3.61-3.53 (1H, m), 2.51-2.46 (1H, m), 2.11-1.98 (3H, m).

MS (ESI): m/z 391.2 (M+H).

Example-248

Synthesis of (R)-5-(2-(2,5-difluorophenyl)pyrrolidin-1-yl)-4-fluoro-N-(4-hydroxy-4-(hydroxymethyl)cyclohexyl)pyrazolo[1,5a]pyridine-3-carboxamide

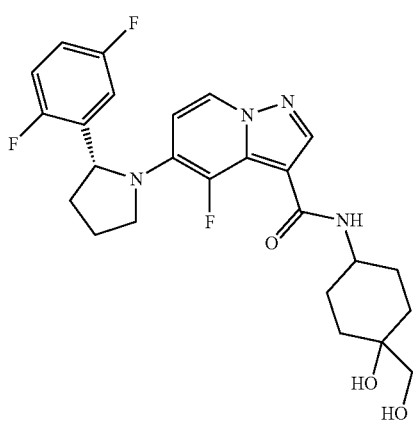 [SMILES: O=C(NC1CCC(O)(CO)CC1)c1cnn2ccc(N3CCC[C@@H]3c3cc(F)ccc3F)c(F)c12]

Step-1: 1-amino-4-((tert-butoxycarbonyl)amino)-3-fluoropyridin-1-ium 2,4-dinitrophenolate

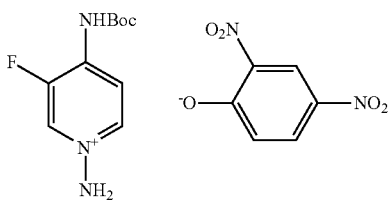

A solution of tert-butyl (3-fluoropyridin-4-yl)carbamate (25.0 g, 125 mmol) in MeCN (200 ml), was added O-(2,4-dinitrophenyl)hydroxylamine (26.64 g, 125 mmol) in MeCN (200 ml), drop wise over 30 min at RT, reaction mass was stirred at 40° C. for 12 hrs, reaction mass was concentrated at temperature below 40° C. under reduced pressure to afford 50 g of title compound as gummy solid, which was used in the next step without further purification.

Step-2: Ethyl 5-((tert-butoxycarbonyl)amino)-4-fluoropyrazolo[1,5-a]pyridine-3-carboxylate

K₂CO₃ (36.96 g, 267 mmol) was added to a solution of 1-amino-4-((tert-butoxycarbonyl)amino)-3-fluoropyridin-1-ium 2,4-dinitrophenolate (50 g, 121 mmol) in THF (500 mL) at 28° C. and continued stirring at same temperature for 30 min. Ethyl propiolate (14.3 g, 145 mmol) was added to above solution and stirring was continued at 28° C. for 16 hr. Reaction mixture was filtered to remove the salt, filtrate collected was diluted with EtOAc washed it with water followed by brine, dried over anhydrous sodium sulphate and concentrated under reduced pressure to afford crude. The crude obtained was purified by column purification (using 60-120 silicagel and 10% EtOAc in Hexane as eluant) to afford the title compound MS m/z 323.9 (M+H)

Step-3: 3-(ethoxycarbonyl)-4-fluoropyrazolo[1,5-a]pyridin-5-aminium 2,2,2-trifluoroacetate

To a solution of ethyl 5-((tert-butoxycarbonyl)amino)-4-fluoropyrazolo[1,5-a]pyridine-3-carboxylate (7 g, 21 mmol) in DCM (60 mL), TFA (12 g, 108 mmol) was added at 0-5° C. drop wise over a period of 30 min, then stirred at room temperature for 2 hrs, reaction mass was concentrated at temperature below 40° C. under reduced pressure to afford the title compound (7 g) which was used in the next step without further purification, MS m/z 223.2 (M+) Step-4: Ethyl 5-bromo-4-fluoropyrazolo[1,5-a]pyridine-3-carboxylate NaNO₂ (2.26 g, 32.89 mmol) in water (7 mL) was added dropwise at 0° C. to a solution of 3-(ethoxycarbonyl)-4-fluoropyrazolo[1,5-a]pyridin-5-aminium 2,2,2-trifluoroacetate (7 g, 97.5 mmol) in aq. 47% HBr (56 mL) and continued stirring at same temperature for 30 min. CuBr (6.29 g, 44 mmol) in aq. 47% HBr (56 mL) was added dropwise to above solution at 0° C. and stirring was continued at 28° C. for 1 hr. Reaction mixture was quenched with ice water, extracted into EtOAc, washed it with water followed by brine, dried over anhydrous sodium sulphate and concentrated under reduced pressure to afford crude. The crude obtained was purified by column purification (using 60-120 silicagel and 5% EtOAc in Hexane as eluant) to afford ethyl 5-bromo-4-fluoropyrazolo

[1,5-a]pyridine-3-carboxylate. NMR (300 MHz, DMSO-d₆) δ 9.45-9.43 (d, 1H), 8.51 (s, 1H), 8.33-8.30 (d, 1H), 4.35-4.28 (m, 2H), 1.36-1.31 (t, 3H).

Step-5: (R)-5-(2-(2,5-difluorophenyl)pyrrolidin-1-yl)-4-fluoro-N-(4-hydroxy-4-(hydroxymethyl)cyclohexyl)pyrazolo[1,5-a]pyridine-3-carboxamide

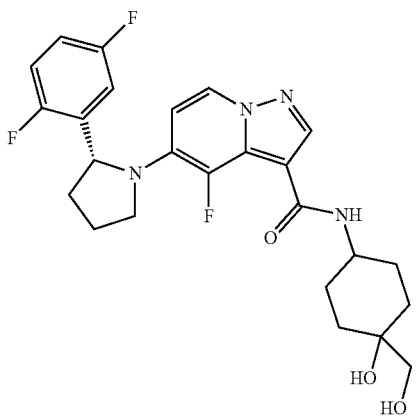 [SMILES: O=C(NC1CCC(O)(CO)CC1)c1cnn2ccc(N3CCC[C@@H]3c3cc(F)ccc3F)c(F)c12]

The title compound was prepared by the method similar to that mentioned in Example-6, using (R)-5-(2-(2,5-difluorophenyl)pyrrolidin-1-yl)-4-fluoropyrazolo[1,5-a]pyridine-3-carboxylic acid and 4-amino-1-(hydroxymethyl)cyclohexanol (instead of ammonium chloride) to afford the crude compound. The crude compound was purified by Preparative TLC (using Silicagel GF₂₅₄, 1000 u coated 20×20 cm dimension glass plate and 100% EtOAc as eluent) to afford 15 mg of the title compound.

¹H NMR (300 MHz, DMSO-d₆) δ ppm 8.80-8.74 (1H, d, J=8.4 Hz), 8.39 (1H, s), 7.70-7.67 (1H, d, J=7.8 Hz), 7.29-7.27 (1H, m), 7.19-7.11 (2H, m), 7.05-6.99 (1H, m), 5.30-5.28 (1H, m), 4.51-4.50 (1H, t), 3.93 (1H, s), 3.70-3.60 (1H, m), 3.55-3.50 (1H, m), 3.33-3.30 (2H, m), 3.17-3.15 (1H, m), 2.03-1.23 (11H, m).
MS (ESI): m/z 489.3 (M+H).

Example-249

Synthesis of (R)-(5-(2-(2,5-difluorophenyl)pyrrolidin-1-yl)-4-fluoropyrazolo[1,5-a]pyridin-3-yl)(3-hydroxyazetidine-1-yl)methanone

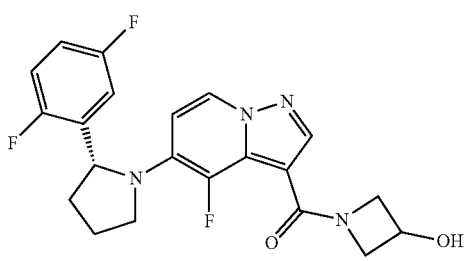 [SMILES: O=C(c1cnn2ccc(N3CCC[C@@H]3c3cc(F)ccc3F)c(F)c12)N1CC(O)C1]

The title compound was prepared by the method substantially similar to that mentioned in Example-12, using (R)-5-(2-(2,5-difluorophenyl)pyrrolidin-1-yl)-4-fluoropyrazolo[1,5-a]pyridine-3-carboxylic acid (prepared by the method mentioned in the Example 248) and 3-azetidinol hydrochloride to afford the crude compound. The crude compound was purified by Preparative TLC (using Silicagel GF₂₅₄, 1000 u coated 20×20 cm dimension glass plate and 100% EtOAc as eluent) to afford 12 mg of the title compound.

¹H NMR (300 MHz, DMSO-d₆) δ ppm 8.88-8.85 (1H, d, J=8.4 Hz), 8.06 (1H, s), 7.35-7.25 (1H, m), 7.17-7.05 (2H, m), 7.05-6.95 (1H, m), 5.80-5.78 (1H, m), 5.30-5.25 (1H, m), 4.50-4.45 (1H, m), 4.00-3.95 (2H, m), 3.60-3.50 (1H, m), 2.01-1.80 (3H, m).
MS (ESI): m/z 417.4 (M+H).

Example-250

Synthesis of (R)-5-(2-(2,5-difluorophenyl)pyrrolidin-1-yl)-4-fluoro-N-(tetrahydro-2H-pyran-4-yl)pyrazolo[1,5-a]pyridine-3-carboxamide

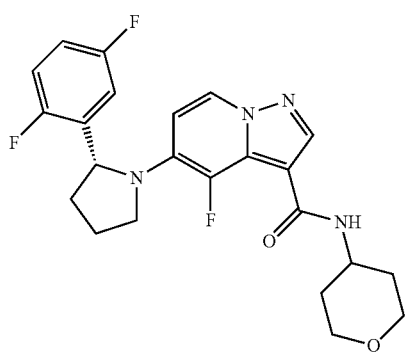

The title compound was prepared by the method substantially similar to that mentioned in Example-248, using tetrahydropyran-4-ylamine to afford the crude compound. The crude compound was purified by Preparative TLC (using Silicagel GF₂₅₄, 1000 u coated 20×20 cm dimension glass plate and 100% EtOAc as eluent) to afford 17 mg of the title compound.

¹H NMR (300 MHz, DMSO-d₆) δ ppm 8.82-8.79 (1H, d, J=8.6 Hz), 8.36 (1H, s), 7.77-7.74 (1H, m), 7.29-7.24 (1H, m), 7.16-7.10 (2H, m), 7.02-6.97 (1H, m), 5.27-5.25 (1H, m), 3.94-3.85 (4H, m), 3.55-3.53 (1H, m), 2.44-2.41 (1H, m), 2.00-1.71 (5H, m), 1.56-1.48 (2H, m).
MS (ESI): m/z 444.9 (M+H).

Example-251

Synthesis of (R)-5-(2-(2,5-difluorophenyl)pyrrolidin-1-yl)-4-fluoropyrazolo[1,5-a]pyridine-3-carboxamide

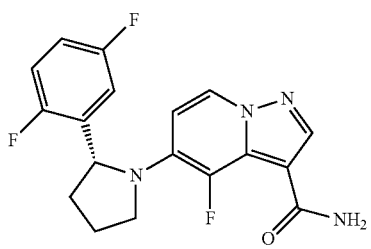 [SMILES: NC(=O)c1cnn2ccc(N3CCC[C@@H]3c3cc(F)ccc3F)c(F)c12]

The title compound was prepared by the method substantially similar to that mentioned in Example-248, using NH$_4$Cl to afford the crude compound. The crude compound was washed with diethylether followed by n-hexane to afford 30 mg of the title compound.

$^1$H NMR (400 MHz, DMSO-d$_6$) δ ppm 8.81-8.79 (1H, d, J=8.4 Hz), 8.30 (1H, s), 7.5-7.4 (1H, bs), 7.29-7.23 (1H, m), 7.16-7.08 (2H, m), 7.02-6.98 (1H, m), 6.80 (1H, bs), 5.30-5.29 (1H, m), 3.99-3.93 (1H, m), 3.54-3.52 (1H, m), 2.50-2.41 (1H, m), 2.03-1.95 (2H, m), 1.86-1.83 (1H, m).

MS (ESI): m/z 360.9 (M+H).

Example-252

Synthesis of 5-((R)-2-(2,5-difluorophenyl)pyrrolidin-1-yl)-N—((S)-2,3-dihydroxypropyl)-4-fluoropyrazolo[1,5-a]pyridine-3-carboxamide

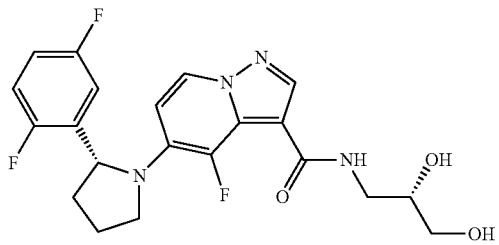 [SMILES: O=C(NC[C@H](O)CO)c1cnn2ccc(N3CCC[C@@H]3c3cc(F)ccc3F)c(F)c12]

The title compound was prepared by the method substantially similar to that mentioned in Example-248, using (S)-3-aminopropane-1,2-diol to afford the crude compound. The crude compound was purified by Preparative TLC (using Silicagel GF$_{254}$, 1000 u coated 20×20 cm dimension glass plate and 10% MeOH in DCM as eluent) to afford 34 mg of the title compound.

$^1$H NMR (400 MHz, DMSO-d$_6$) δ ppm 8.85-8.82 (1H, d, J=8.8 Hz), 8.39 (1H, s), 8.01-7.98 (1H, t), 7.33-7.27 (1H, m), 7.19-7.10 (2H, m), 7.04-7.00 (1H, m), 5.33-5.31 (1H, m), 4.87-4.86 (1H, d, J=4.4 Hz), 4.64-4.61 (1H, t), 3.96 (1H, bs), 3.61-3.42 (2H, m), 3.20-3.14 (1H, m), 2.52-2.42 (1H, m), 2.06-1.85 (3H, m).

MS (ESI): m/z 435.2 (M+H).

Example-253

Synthesis of (5-((R)-2-(2,5-difluorophenyl)pyrrolidin-1-yl)-4-fluoropyrazolo[1,5-a]pyridin-3-yl)((S)-3-hydroxypyrrolidin-1-yl)methanone

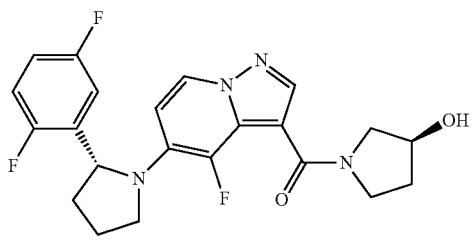 [SMILES: O=C(c1cnn2ccc(N3CCC[C@@H]3c3cc(F)ccc3F)c(F)c12)N1CC[C@H](O)C1]

The title compound was prepared by the method substantially similar to that mentioned in Example-248, using (S)-3-Pyrrolidinol to afford the crude compound. The crude compound was purified by Preparative TLC (using Silicagel GF$_{254}$, 1000 u coated 20×20 cm dimension glass plate and 10% MeOH in DCM as eluent) to afford 37 mg of the title compound.

$^1$H NMR (400 MHz, DMSO-d$_6$) δ ppm 8.85-8.83 (1H, d, J=8.4 Hz), 8.22-8.18 (1H, m), 7.31-7.26 (1H, m), 7.24-7.22 (1H, d, J=9.2 Hz), 7.24-7.08 (1H, m), 7.01-6.97 (1H, m), 5.31-5.29 (1H, m), 4.97 (1H, bs), 4.40-4.35 (1H, m), 3.93-3.90 (1H, m), 3.80-3.60 (1H, m), 3.56-3.50 (3H, m), 2.50-2.42 (1H, m), 2.04-1.83 (5H, m).

MS (ESI): m/z 430.8 (M+H).

Example-254

Synthesis of (R)-5-(2-(2,5-difluorophenyl)pyrrolidin-1-yl)-4-fluoro-N-((1-(hydroxymethyl)cyclopentyl)methyl)pyrazolo[1,5a]pyridine-3-carboxamide

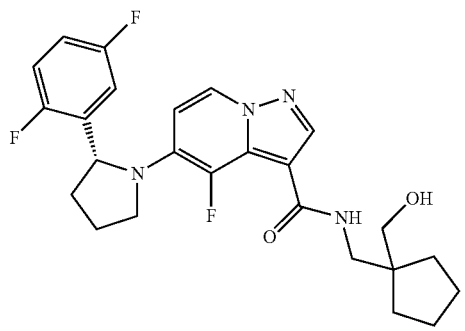 [SMILES: O=C(NCC1(CO)CCCC1)c1cnn2ccc(N3CCC[C@@H]3c3cc(F)ccc3F)c(F)c12]

The title compound was prepared by the method substantially similar to that mentioned in Example-248 (1-(aminomethyl)cyclopentyl)methanol to afford the crude compound. The crude compound was purified by Preparative TLC (using Silicagel GF$_{254}$, 1000 u coated 20×20 cm dimension glass plate and 5% MeOH in DCM as eluent) to afford 18 mg of the title compound.

$^1$H NMR (400 MHz, DMSO-d$_6$) δ ppm 8.83-8.81 (1H, d, J=8.4 Hz), 8.36 (1H, s), 8.05-8.00 (1H, t), 7.27-7.25 (1H, m), 7.16-7.13 (1H, d, J=9.6 Hz), 7.13-7.10 (1H, m), 7.02-6.99 (1H, m), 5.32-5.30 (1H, m), 4.84-4.81 (1H, t), 3.94-3.90 (1H, m), 3.55-3.53 (1H, q), 3.26-3.21 (1H, m), 3.17-3.13 (3H, m), 2.50-2.41 (1H, m), 2.04-1.84 (3H, m), 1.54-1.53 (4H, m), 1.38-1.34 (4H, m).

MS (ESI): m/z 473.4 (M+H).

The following compounds (Example-255 to Example-268) were prepared by the method substantially similar to that mentioned in Example-248.

Example-255

5-((R)-2-(2,5-difluorophenyl)pyrrolidin-1-yl)-4-fluoro-N—((S)-1-hydroxypropan-2-yl)pyrazolo[1,5-a]pyridine-3-carboxamide

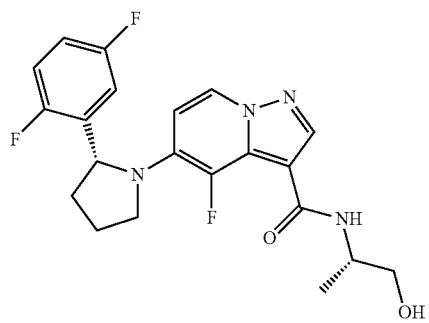 [SMILES: C[C@@H](CO)NC(=O)c1cnn2ccc(N3CCC[C@@H]3c3cc(F)ccc3F)c(F)c12]

MS (ESI): m/z 419.3 (M+H).

Example-256

N-((1r,4R)-4-(1H-1,2,4-triazol-5-yl)cyclohexyl)-5-(R)-2-(2,5-difluorophenyl)pyrrolidin-1-yl)-4-fluoro-pyrazolo[1,5-a]pyridine-3-carboxamide

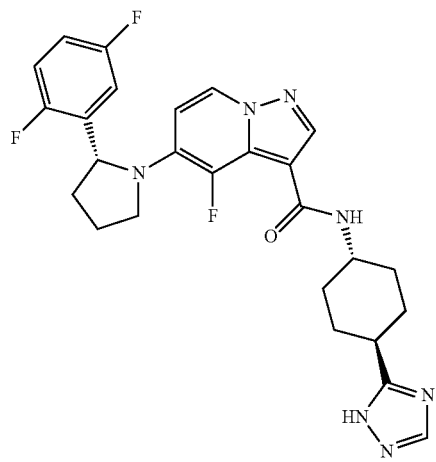 [SMILES: O=C(N[C@H]1CC[C@H](c2ncn[nH]2)CC1)c1cnn2ccc(N3CCC[C@@H]3c3cc(F)ccc3F)c(F)c12]

MS (ESI): m/z 510.4 (M+H).

Example-257

5-((R)-2-(2,5-difluorophenyl)pyrrolidin-1-yl)-4-fluoro-N—((S)-2-hydroxypropyl)pyrazolo[1,5-a]pyridine-3-carboxamide

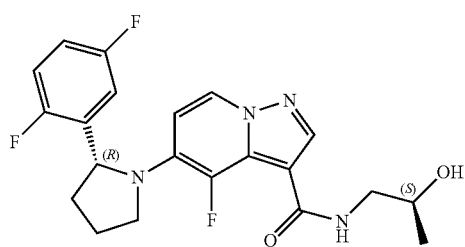

MS (ESI): m/z 419.1 (M+H).

Example-258

5-((R)-2-(2,5-difluorophenyl)pyrrolidin-1-yl)-4-fluoro-N-((1r,4R)-4-(2-methyl-2H-tetrazol-5-yl)cyclohexyl)pyrazolo[1,5-a]pyridine-3-carboxamide

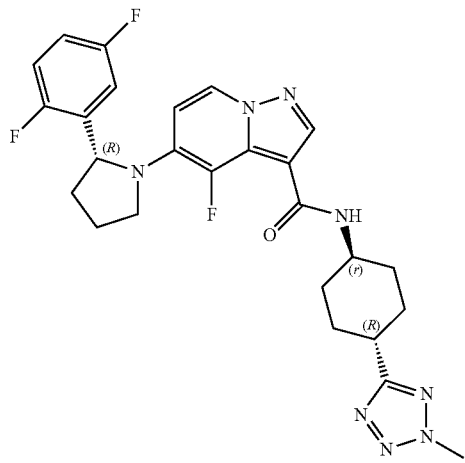

MS (ESI): m/z 486.1 (M+H).

Example-259

5-((R)-2-(2,5-difluorophenyl)pyrrolidin-1-yl)-4-fluoro-N-((1r,4R)-4-(1-methyl-1H-tetrazol-5-yl)cyclohexyl)pyrazolo[1,5-a]pyridine-3-carboxamide

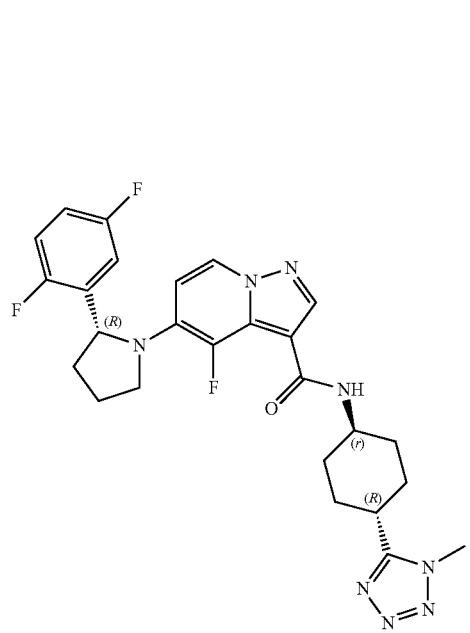

MS (ESI): m/z 525.2 (M+H).

Example-260

(R)-5-(2-(2,5-difluorophenyl)pyrrolidin-1-yl)-4-fluoro-N-((1-(hydroxymethyl)cyclobutyl)methyl)pyrazolo[1,5-a]pyridine-3-carboxamide

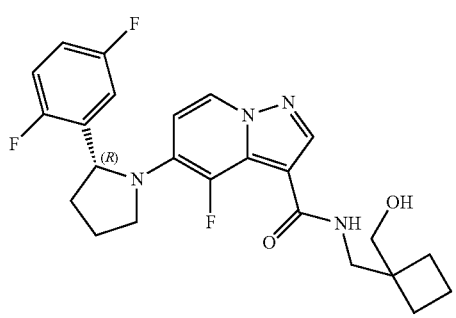

MS (ESI): m/z 459.2 (M+H).

Example-261

(R)-5-(2-(2,5-difluorophenyl)pyrrolidin-1-yl)-4-fluoro-N-(3-hydroxycyclobutyl)pyrazolo[1,5-a]pyridine-3-carboxamide

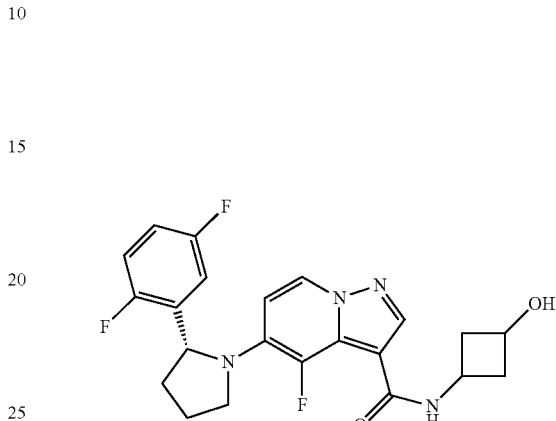

MS (ESI): m/z 431 (M+H).

Example-262

N-((1r,4R)-4-(1H-1,2,4-triazol-5-yl)cyclohexyl)-5-((R)-2-(2,5-difluorophenyl)pyrrolidin-1-yl)-4-fluoropyrazolo[1,5-a]pyridine-3-carboxamide

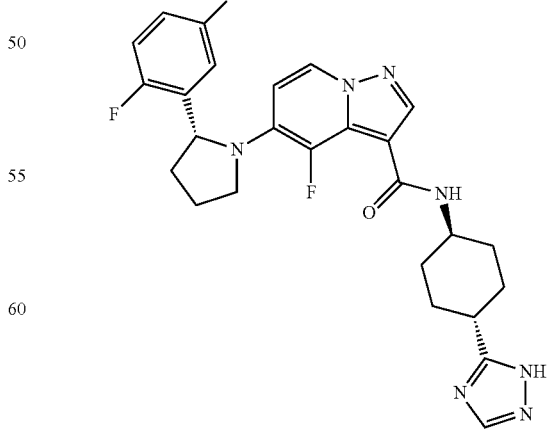

MS (ESI): m/z 510.2 (M+H).

235

Example-263

(1R,4r)-4-(5-((R)-2-(2,5-difluorophenyl)pyrrolidin-1-yl)-4-fluoropyrazolo[1,5-a]pyridine-3-carboxamido)cyclohexanecarboxylic acid

236

Example-264

5-((R)-2-(2,5-difluorophenyl)pyrrolidin-1-yl)-4-fluoro-N-((1r,4R)-4-hydroxycyclohexyl)pyrazolo[1,5-a]pyridine-3-carboxamide

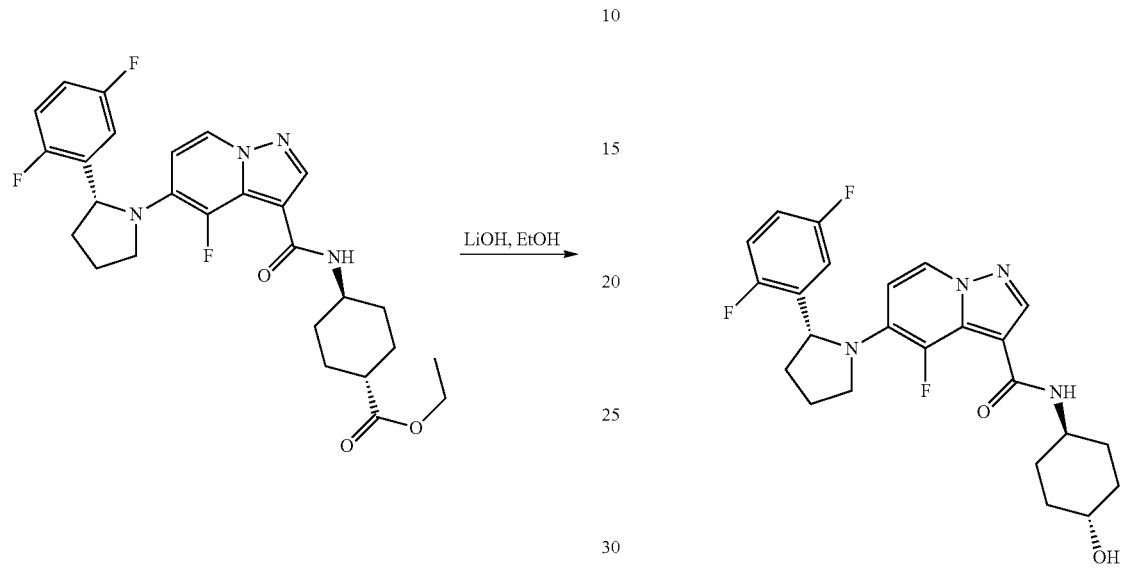

MS (ESI): m/z 425 (M+H).

Example-265

5-((R)-2-(2,5-difluorophenyl)pyrrolidin-1-yl)-4-fluoro-N-(3-hydroxycyclohexyl)pyrazolo[1,5-a]pyridine-3-carboxamide

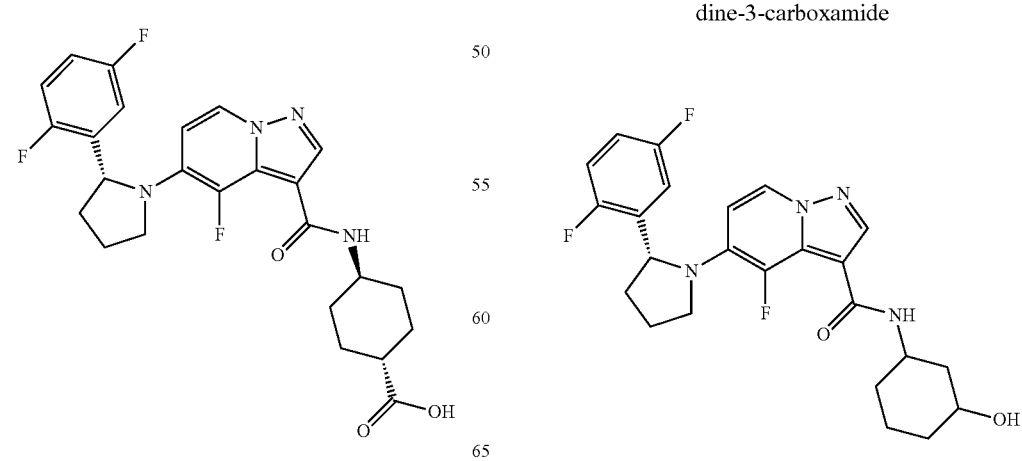

MS (ESI): m/z 487.1 (M+H).

MS (ESI): m/z 459 (M+H).

Example-266

N-((1r,4R)-4-(1H-tetrazol-5-yl)cyclohexyl)-5-((R)-2-(2,5-difluorophenyl)pyrrolidin-1-yl)-4-fluoropyrazolo[1,5-a]pyridine-3-carboxamide

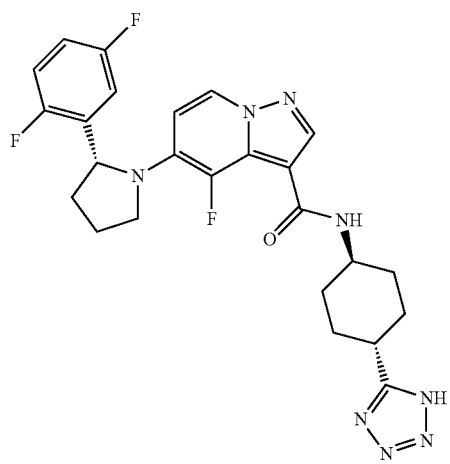 [SMILES: O=C(N[C@H]1CC[C@H](c2nnn[nH]2)CC1)c1cnn2ccc(N3CCC[C@@H]3c3cc(F)ccc3F)c(F)c12]

MS (ESI): m/z 511.2 (M+H).

Example-267

5-((R)-2-(2,5-difluorophenyl)pyrrolidin-1-yl)-4-fluoro-N-((1r,4R)-4-(methoxycarbamoyl)cyclohexyl)pyrazolo[1,5-a]pyridine-3-carboxamide

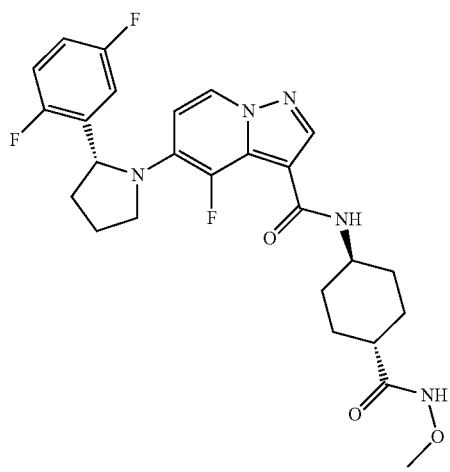 [SMILES: CONC(=O)[C@H]1CC[C@H](NC(=O)c2cnn3ccc(N4CCC[C@@H]4c4cc(F)ccc4F)c(F)c23)CC1]

MS (ESI): m/z 516.2 (M+H).

Example-268

5-((R)-2-(2,5-difluorophenyl)pyrrolidin-1-yl)-4-fluoro-N-((1r,4R)-4-(hydroxymethyl)cyclohexyl)pyrazolo[1,5-a]pyridine-3-carboxamide

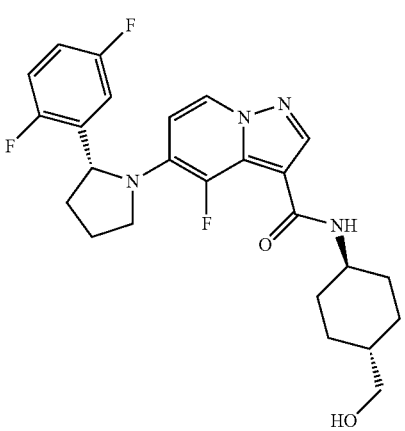 [SMILES: O=C(N[C@H]1CC[C@H](CO)CC1)c1cnn2ccc(N3CCC[C@@H]3c3cc(F)ccc3F)c(F)c12]

MS (ESI): m/z 472.8 (M+H).

Example-269

(1R,4r)-4-(4-fluoro-5-((R)-2-(5-fluoro-2-methoxyphenyl)pyrrolidin-1-yl)pyrazolo[1,5-a]pyridine-3-carboxamido)cyclohexanecarboxylic acid Step-1:
(R)-2-(5-Fluoro-2-methoxyphenyl)pyrrolidine hydrochloride

The title compound was prepared by the method similar to that mentioned in step-5 of example-1 using 2-Bromo-4- fluoro-anisole in place of 2,5-difluoro-1-bromobenzene to afford the title compound as white solid. MS (ESI): m/z 195.9 (M+H).

Step-2: (R)-4-fluoro-5-(2-(5-fluoro-2-methoxyphenyl)pyrrolidin-1-yl)pyrazolo[1,5-a]pyridine-3-carboxylic acid

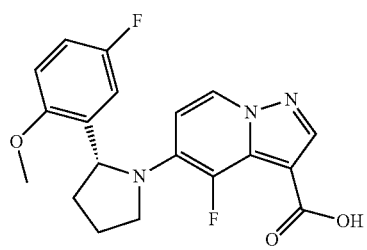 [SMILES: COc1ccc(F)cc1[C@H]1CCCN1c1ccn2ncc(C(=O)O)c2c1F]

The title compound was prepared by a method substantially similar to that mentioned in step-5 and step-6 of example-3 using (R)-2-(5-Fluoro-2-methoxyphenyl)pyrrolidine hydrochloride (step-1) and Ethyl 5-bromo-4-fluoropyrazolo[1,5-a]pyridine-3-carboxylate (step-4 of example-248) to afford the product as white solid. MS (ESI): m/z 374.12 (M+H).

Step 3 (1R,4r)-ethyl 4-(4-fluoro-5-((R)-2-(5-fluoro-2-methoxyphenyl)pyrrolidin-1-yl)pyrazolo[1,5-a]pyridine-3-carboxamido)cyclohexanecarboxylate

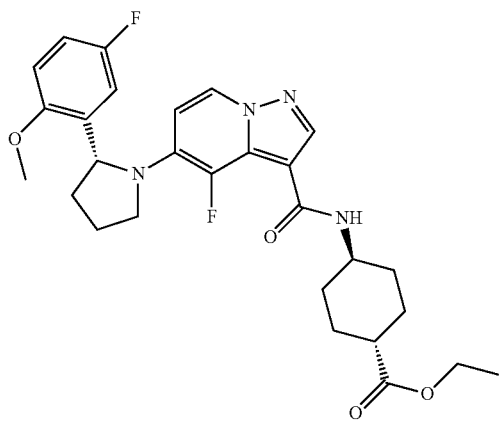 [SMILES: CCOC(=O)[C@H]1CC[C@H](NC(=O)c2cnn3ccc(N4CCC[C@@H]4c4cc(F)ccc4OC)c(F)c23)CC1]

The title compound was prepared by a method substantially similar to Example-4 to afford the product as white solid MS (ESI): m/z 527.2 (M+H)

Step-4: (1R,4r)-4-(4-fluoro-5-((R)-2-(5-fluoro-2-methoxyphenyl)pyrrolidin-1-yl)pyrazolo[1,5-a]pyridine-3-carboxamido)cyclohexanecarboxylic acid

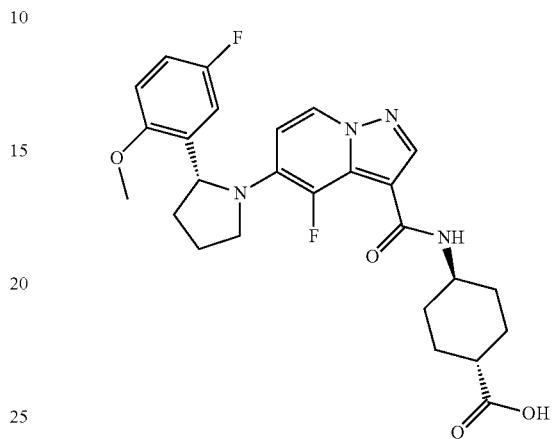

A method substantially similar to that of example 31 was used to afford the title compound as white solid (70.0 mg). MS (ESI): m/z 499.1 (M+H).

Example-270

5-((R)-2-(3-(difluoromethoxy)-5-fluorophenyl)pyrrolidin-1-yl)-N—((S)-2,3-dihydroxypropyl)pyrazolo[1,5-a]pyridine-3-carboxamide

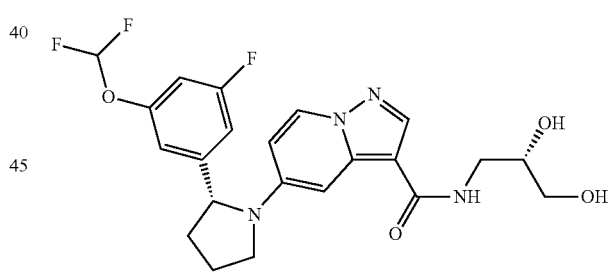

Step-1: 1-Bromo-3-(difluoromethoxy)-5-fluorobenzene

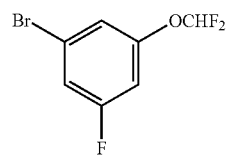

To a solution of 3-bromo-5-fluorophenol (0.5 g, 2.6 mmol) in DMF (4.5 mL) was added $K_2CO_3$ (0.9 g, 6.54 mmol) and stirred at 25° C. for 10 min. Water (0.5 mL) was added to the above mixture followed by addition of 2-Chloro-2,2,-difluoroacetic acid sodium salt (0.6 g, 3.93 mmol) and stirring was continued at 100° C. for 3 h. The reaction mixture was cooled to 25° C. and diluted with ethyl acetate, washed with brine, dried over anhydrous sodium sulphate and concentrated under reduced pressure to afford the crude, which was purified by column chromatography (using silica gel and 2% ethyl acetate in Hexane as eluent) to afford the desired compound. $^1$H NMR (400 MHz, CDCl$_3$) δ ppm 7.2-6.9 (2H, m), 6.8-6.7 (1H, d), 6.7-6.2 (1H, m).

Step-2: (R)-2-(3-(Difluoromethoxy)-5-fluorophenyl) pyrrolidine hydrochloride (Int-46)

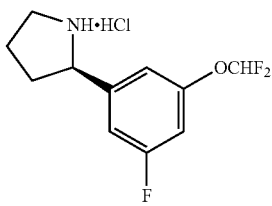

The title compound was prepared by the method similar to that mentioned in step 1 to 5 of example-1, using 1-bromo-3-(difluoromethoxy)-5-fluorobenzene in place of 2,5-difluoro-1-bromobenzene to afford the title compound as a thick brown liquid. MS (ESI):

m/z 232.2 (M+H).

Step-3: 5-((R)-2-(3-(difluoromethoxy)-5-fluorophenyl)pyrrolidin-1-yl)-N—((S)-2,3-dihydroxypropyl) pyrazolo[1,5-a]pyridine-3-carboxamide

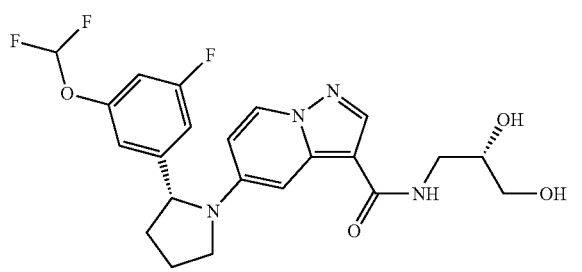 [SMILES: O=C(NC[C@H](O)CO)c1cnn2ccc(N3CCC[C@@H]3c3cc(F)cc(OC(F)F)c3)cc12]

Brown colour solid (35.0 mg). MS (ESI): m/z 503.1 (M+H).

Example-271

(5-((R)-2-(3-(difluoromethoxy)-5-fluorophenyl)pyrrolidin-1-yl)pyrazolo[1,5-a]pyridin-3-yl) ((S)-3-hydroxypyrrolidin-1-yl)methanone

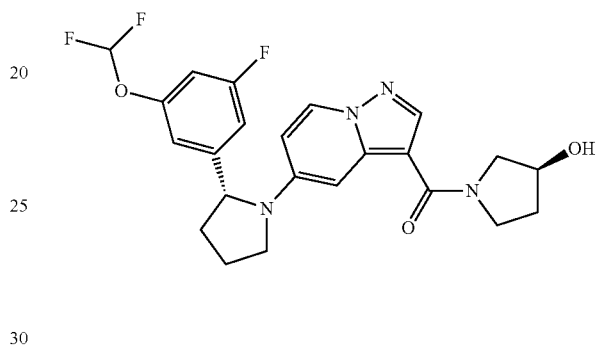

MS (ESI): m/z 460.9 (M+H).

Example-272

(R)-5-(2-(3-(difluoromethoxy)-5-fluorophenyl)pyrrolidin-1-yl)-N-(3-hydroxycyclobutyl)pyrazolo[1,5-a]pyridine-3-carboxamide

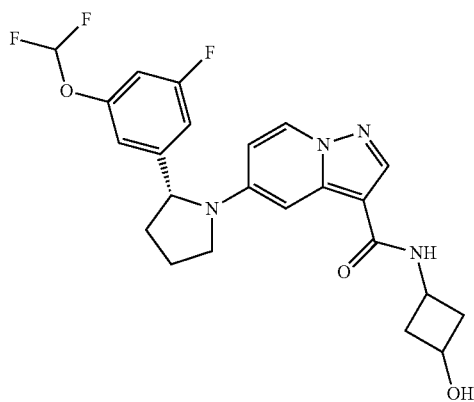 [SMILES: O=C(NC1CC(O)C1)c1cnn2ccc(N3CCC[C@@H]3c3cc(F)cc(OC(F)F)c3)cc12]

MS (ESI): m/z 459 (M+H).

Example-273

5-((R)-2-(3-(difluoromethoxy)-5-fluorophenyl)pyrrolidin-1-yl)-N-((1r,4R)-4-(2-methyl-2H-tetrazol-5-yl)cyclohexyl)pyrazolo[1,5-a]pyridine-3-carboxamide

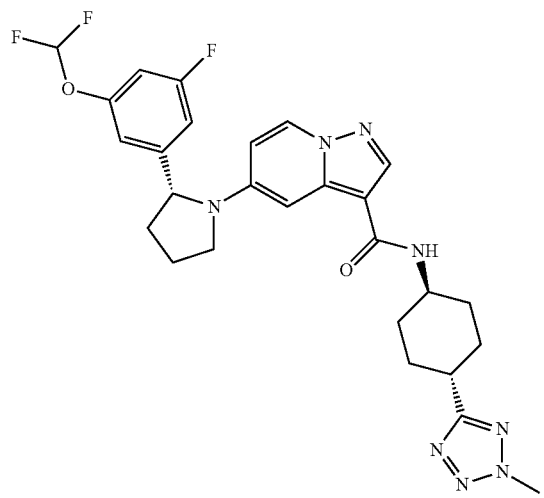 [SMILES: Cn1nnc([C@H]2CC[C@H](NC(=O)c3cnn4ccc(N5CCC[C@@H]5c5cc(F)cc(OC(F)F)c5)cc34)CC2)n1]

MS (ESI): m/z 555.2 (M+H).

Example-274

(R)-5-(2-(3-(difluoromethoxy)-5-fluorophenyl)pyrrolidin-1-yl)-N-(4-hydroxy-4-(hydroxy methyl)cyclohexyl)pyrazolo[1,5-a]pyridine-3-carboxamide

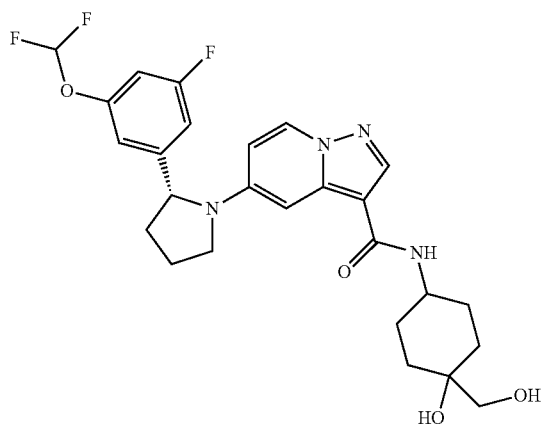 [SMILES: O=C(NC1CCC(O)(CO)CC1)c1cnn2ccc(N3CCC[C@@H]3c3cc(F)cc(OC(F)F)c3)cc12]

MS (ESI): m/z 519 (M+H).

Example-275

5-((R)-2-(3-(difluoromethoxy)-5-fluorophenyl)pyrrolidin-1-yl)-N-((1r,4R)-4-hydroxycyclohexyl)pyrazolo[1,5-a]pyridine-3-carboxamide

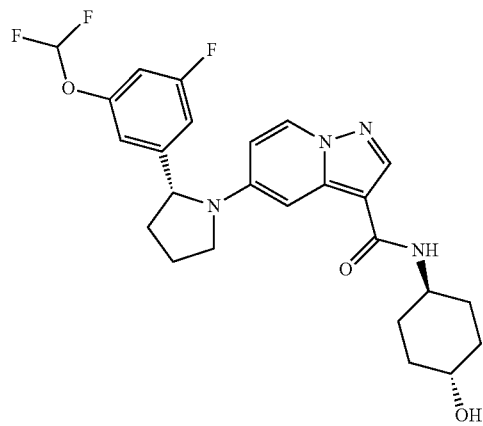 [SMILES: O=C(N[C@H]1CC[C@H](O)CC1)c1cnn2ccc(N3CCC[C@@H]3c3cc(F)cc(OC(F)F)c3)cc12]

MS (ESI): m/z 489.2 (M+H).

Example-276

(1R,4r)-4-(5-((R)-2-(3-(difluoromethoxy)-5-fluorophenyl)pyrrolidin-1-yl)pyrazolo[1,5-a]pyridine-3-carboxamido)cyclohexanecarboxylic acid

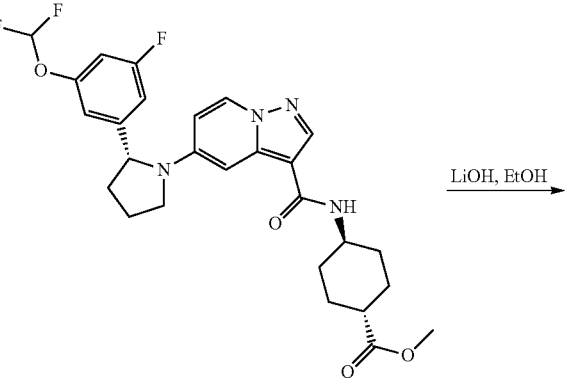

LiOH, EtOH →

-continued

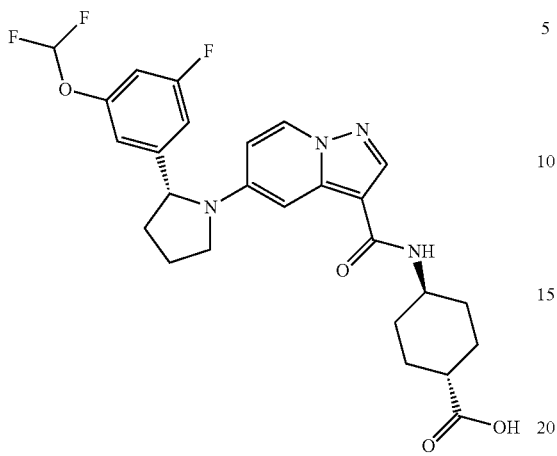

Hydrolysis of (1R,4r)-methyl 4-(5-((R)-2-(3-(difluoromethoxy)-5-fluorophenyl)pyrrolidin-1-yl)pyrazolo[1,5-a]pyridine-3-carboxamido)cyclohexanecarboxylate with LiOH in ethanol at room temperature provided the title compound as a gray solid (48.0 mg). MS (ESI): m/z 517.3 (M+H).

Example-277

5-((R)-2-(3-(difluoromethoxy)-5-fluorophenyl)pyrrolidin-1-yl)-N-((1r,4R)-4-(1-methyl-1H-tetrazol-5-yl)cyclohexyl)pyrazolo[1,5-a]pyridine-3-carboxamide

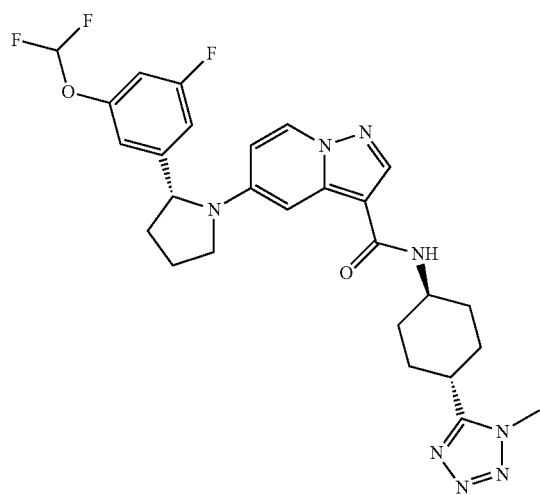 [SMILES: Cn1nnnc1[C@H]1CC[C@H](NC(=O)c2cnn3ccc(N4CCC[C@@H]4c4cc(F)cc(OC(F)F)c4)cc23)CC1]

MS (ESI): m/z 555.2 (M+H).

Example-278

5-((R)-2-(5-fluoro-2-methoxyphenyl)pyrrolidin-1-yl)-N-((1r,4R)-4-hydroxycyclohexyl)pyrazolo[1,5-a]pyridine-3-carboxamide

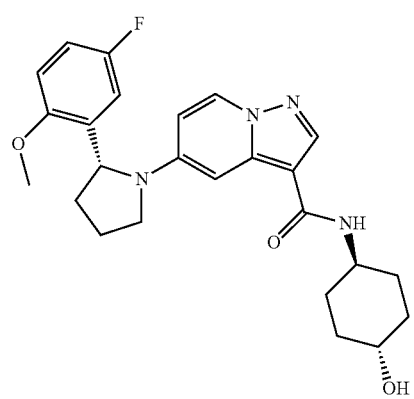 [SMILES: COc1ccc(F)cc1[C@H]1CCCN1c1ccn2ncc(C(=O)N[C@H]3CC[C@H](O)CC3)c2c1]

Step-1: (R)-5-(2-(5-fluoro-2-methoxyphenyl)pyrrolidin-1-yl)pyrazolo[1,5-a]pyridine-3-carboxylic acid

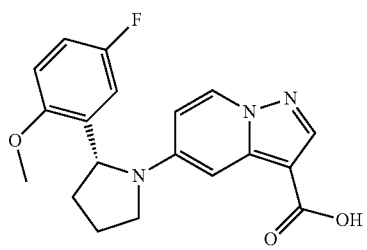 [SMILES: COc1ccc(F)cc1[C@H]1CCCN1c1ccn2ncc(C(=O)O)c2c1]

The title compound was prepared by a method substantially similar to that mentioned in step-5 and step-6 of example-3 using (R)-2-(5-Fluoro-2-methoxyphenyl)pyrrolidine hydrochloride (step-1 of example-269) and Ethyl 5-bromo-pyrazolo[1,5-a]pyridine-3-carboxylate to afford the product as white solid. MS (ESI): m/z 356.1 (M+H).

Step-2: 5-((R)-2-(5-fluoro-2-methoxyphenyl)pyrrolidin-1-yl)-N-((1r,4R)-4-hydroxycyclohexyl)pyrazolo[1,5-a]pyridine-3-carboxamide

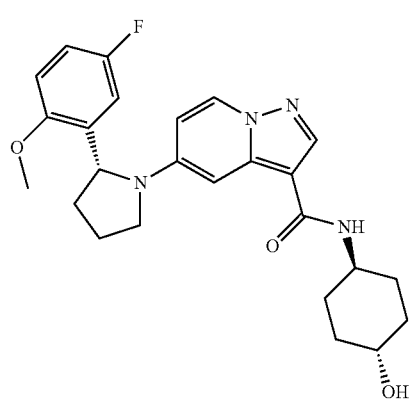 [SMILES: COc1ccc(F)cc1[C@H]1CCCN1c1ccn2ncc(C(=O)N[C@H]3CC[C@H](O)CC3)c2c1]

The title compound was prepared by a method substantially similar to that Example-4 to afford the product as off white solid (55.0 mg). MS (ESI): m/z 453.2 (M+H).

Example-279

N—((S)-2,3-dihydroxypropyl)-5-((R)-2-(5-fluoro-2-methoxyphenyl)pyrrolidin-1-yl)pyrazolo[1,5-a]pyridine-3-carboxamide

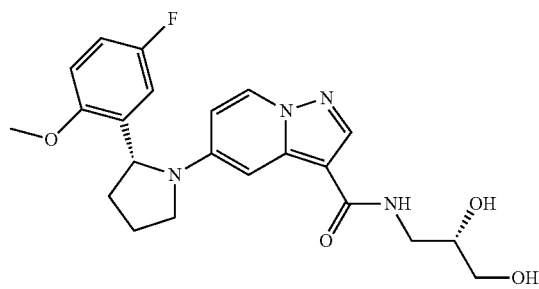 [SMILES: COc1ccc(F)cc1[C@H]1CCCN1c1ccn2ncc(C(=O)NC[C@H](O)CO)c2c1]

MS (ESI): m/z 429.1 (M+H).

Example-280

(1R,4r)-4-(5-((R)-2-(5-fluoro-2-methoxyphenyl)pyrrolidin-1-yl)pyrazolo[1,5-a]pyridine-3-carboxamido)cyclohexanecarboxylic acid

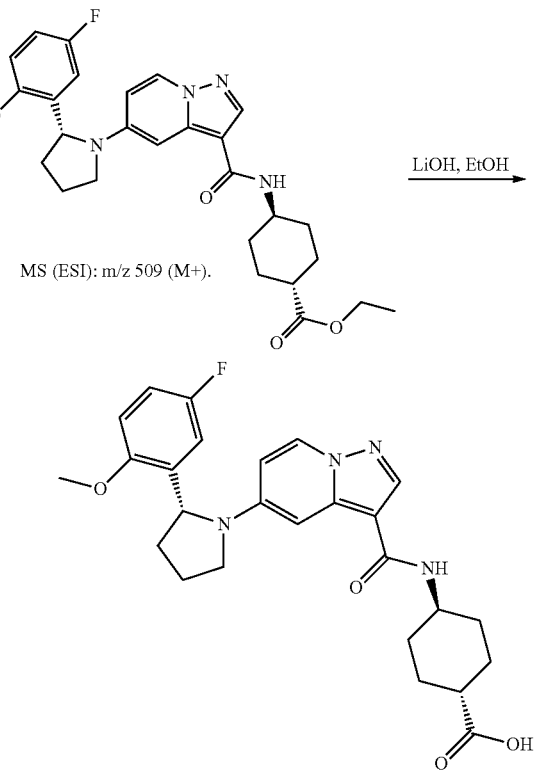

MS (ESI): m/z 481.2 (M+H).

Example-281

(5-((R)-2-(5-fluoro-2-methoxyphenyl)pyrrolidin-1-yl)pyrazolo[1,5-a]pyridin-3-yl)((S)-3-hydroxypyrrolidin-1-yl)methanone

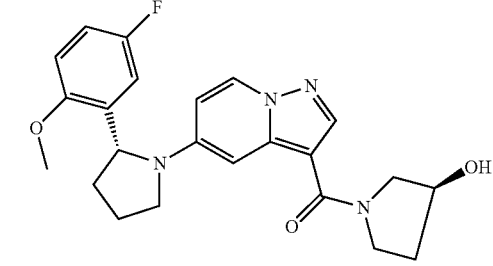 [SMILES: COc1ccc(F)cc1[C@H]1CCCN1c1ccn2ncc(C(=O)N3CC[C@H](O)C3)c2c1]

MS (ESI): m/z 425 (M+H).

Example-282

(R)-5-(2-(5-fluoro-2-methoxyphenyl)pyrrolidin-1-yl)-N-(3-hydroxycyclobutyl)pyrazolo[1,5-a]pyridine-3-carboxamide

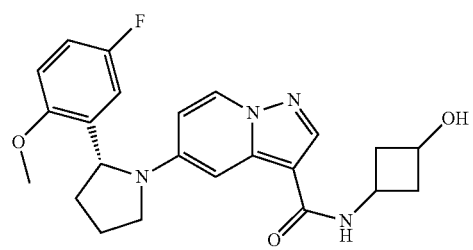 [SMILES: COc1ccc(F)cc1[C@H]1CCCN1c1ccn2ncc(C(=O)NC3CC(O)C3)c2c1]

MS (ESI): m/z 425.1 (M+H).

Example-283

5-((R)-2-(5-fluoro-2-methoxyphenyl)pyrrolidin-1-yl)-N-((1r,4R)-4-(2-methyl-2H-tetrazol-5-yl)cyclohexyl)pyrazolo[1,5-a]pyridine-3-carboxamide

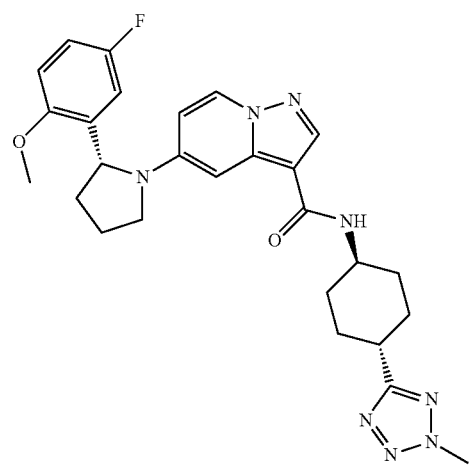 [SMILES: COc1ccc(F)cc1[C@H]1CCCN1c1ccn2ncc(C(=O)N[C@H]3CC[C@H](c4nnn(C)n4)CC3)c2c1]

MS (ESI): m/z 519.4 (M+H).

Example-284

5-((R)-2-(5-fluoro-2-methoxyphenyl)pyrrolidin-1-yl)-N-((1r,4R)-4-(1-methyl-1H-tetrazol-5-yl)cyclohexyl)pyrazolo[1,5-a]pyridine-3-carboxamide

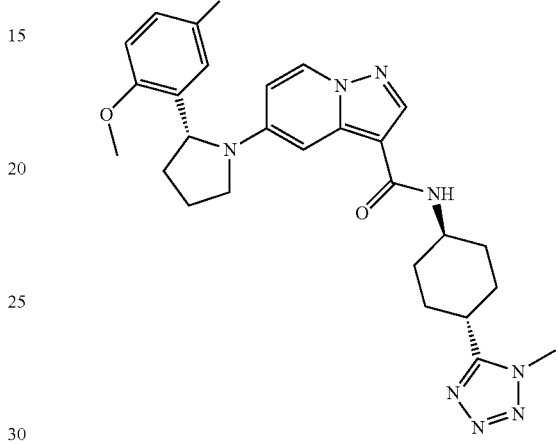

MS (ESI): m/z 519 (M+H).

Example-285

5-((R)-2-(5-fluoro-2-methoxyphenyl)pyrrolidin-1-yl)-N-((1r,4R)-4-(methoxycarbamoyl)cyclohexyl)pyrazolo[1,5-a]pyridine-3-carboxamide

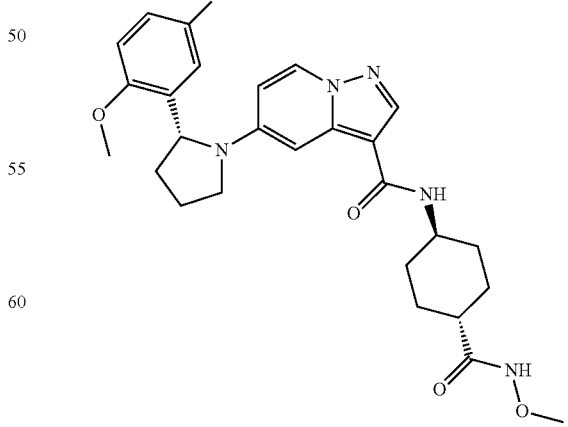

MS (ESI): m/z 510 (M+H).

Example-286 (Isomer-I)

5-((R)-2-(5-fluoro-2-methoxyphenyl)pyrrolidin-1-yl)-N-(3-hydroxycyclohexyl)pyrazolo[1,5-a]pyridine-3-carboxamide (Isomer-I)

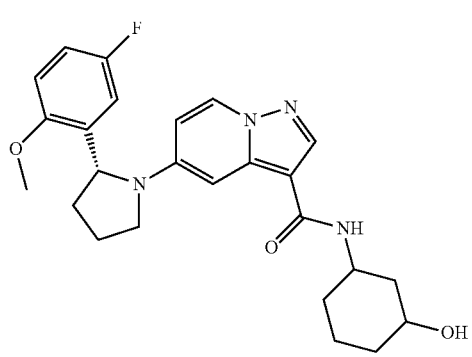 [SMILES: COc1ccc(F)cc1[C@H]1CCCN1c1ccn2ncc(C(=O)NC3CCCC(O)C3)c2c1]

HPLC separation of the mixture using mobile phase:A:10 mm ammonium acetate in water and B:CAN, Column:Zorbaz-C18-150×21.2) [flow rate: 20 mL/min., Isocratic:53:35] afforded diastereomer-I (example 286) and diastereomer-II (example 287).

MS (ESI): m/z 453.3 (M+H).

Example-287 (Isomer-II)

5-((R)-2-(5-fluoro-2-methoxyphenyl)pyrrolidin-1-yl)-N-(3-hydroxycyclohexyl)pyrazolo[1,5-a]pyridine-3-carboxamide (Isomer-II)

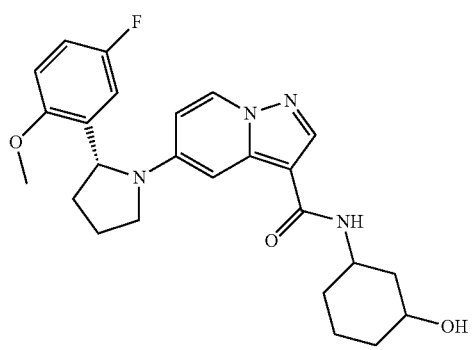 [SMILES: COc1ccc(F)cc1[C@H]1CCCN1c1ccn2ncc(C(=O)NC3CCCC(O)C3)c2c1]

MS (ESI): m/z 453.3 (M+H).

Example-288

N-((1r,4R)-4-(1H-1,2,4-triazol-5-yl)cyclohexyl)-5-((R)-2-(5-fluoro-2-methoxyphenyl)pyrrolidin-1-yl)pyrazolo[1,5-a]pyridine-3-carboxamide

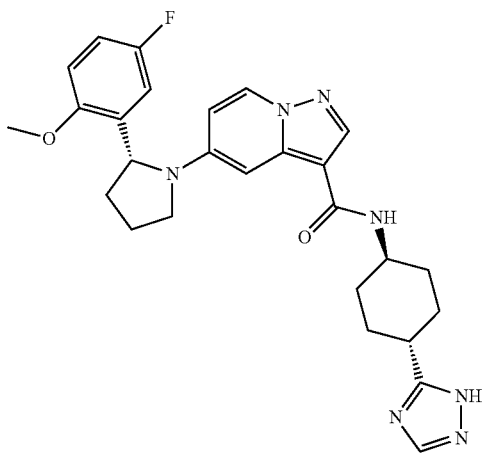 [SMILES: COc1ccc(F)cc1[C@H]1CCCN1c1ccn2ncc(C(=O)N[C@H]3CC[C@H](c4ncn[nH]4)CC3)c2c1]

MS (ESI): m/z 504.2 (M+H).

Example-289

N-((1r,4R)-4-(1H-tetrazol-5-yl)cyclohexyl)-5-((R)-2-(5-fluoro-2-methoxyphenyl)pyrrolidin-1-yl)pyrazol[1,5-a]pyridine-3-carboxamide

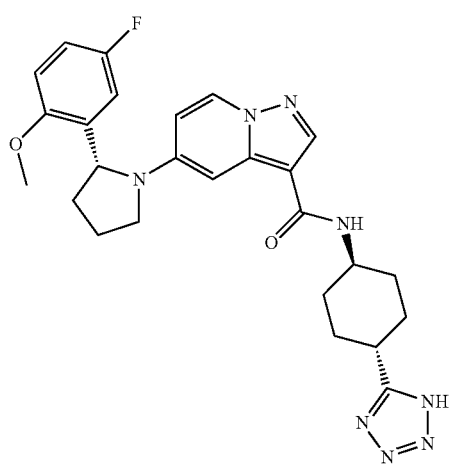 [SMILES: COc1ccc(F)cc1[C@H]1CCCN1c1ccn2ncc(C(=O)N[C@H]3CC[C@H](c4nnn[nH]4)CC3)c2c1]

MS (ESI): m/z 504.8 (M+H).

Example-290 (Isomer-I)

3-(5-((R)-2-(5-fluoro-2-methoxyphenyl)pyrrolidin-1-yl)pyrazolo[1,5-a]pyridine-3-carboxamido)cyclohexanecarboxylic acid (Isomer-I)

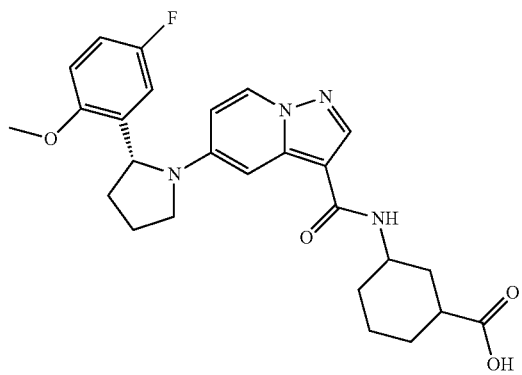 [SMILES: COc1ccc(F)cc1[C@H]1CCCN1c1ccn2ncc(C(=O)NC3CCCC(C(=O)O)C3)c2c1]

Hydrolysis of ethyl 3-(5-((R)-2-(5-fluoro-2-methoxyphenyl)pyrrolidin-1-yl)pyrazolo[1,5-a]pyridine-3-carboxamido)cyclohexanecarboxylate afforded diastereomeric mixture of 3-(5-((R)-2-(5-fluoro-2-methoxyphenyl)pyrrolidin-1-yl)pyrazolo[1,5-a]pyridine-3-carboxamido) cyclohexanecarboxylic acid which was separated using chiral column (Mobile phase:A:Hexane, B:Ethanol; Column:Chiral Pak AO-H(10 mm×250 mm, 5 g) semi prep column, Flow rate: 6 mL/min., Isocratic:80:20) to obtain diastereomer-I (example 290) as off white solid, MS MS (ESI): m/z 481.2 (M+H) and diastereomer-II (example 291)

Example-291 (Isomer-II)

3-(5-((R)-2-(5-fluoro-2-methoxyphenyl)pyrrolidin-1-yl)pyrazolo[1,5-a]pyridine-3-carboxamido)cyclohexanecarboxylic acid (Isomer-II)

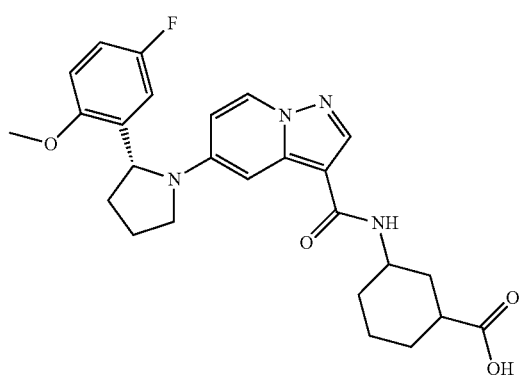 [SMILES: COc1ccc(F)cc1[C@H]1CCCN1c1ccn2ncc(C(=O)NC3CCCC(C(=O)O)C3)c2c1]

MS (ESI): m/z 480.9 (M+H).

Example-292

(5-((R)-2-(3,5-difluorophenyl)pyrrolidin-1-yl)pyrazolo[1,5-a]pyridin-3-yl)((S)-3-hydroxypyrrolidin-1-yl)methanone

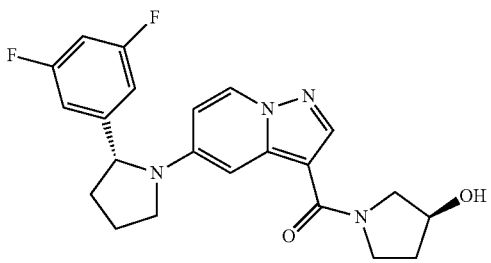 [SMILES: O=C(c1cnn2ccc(N3CCC[C@@H]3c3cc(F)cc(F)c3)cc12)N1CC[C@H](O)C1]

Step-1: (R)-2-(3,5-Difluorophenyl)pyrrolidine hydrochloride

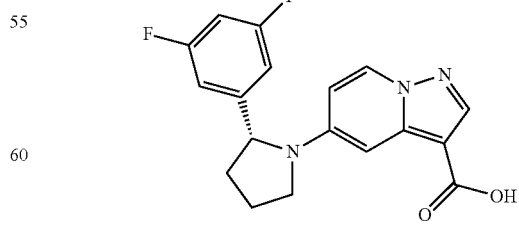

The title intermediate was prepared by the method similar to that mentioned in step-1 to 5 of example-1 using 3,5-difluoro-1-bromobenzene in place of 2,5-difluoro-1-bromobenzene to afford the title compound as white solid. MS (ESI): m/z 184 (M+H).

Step-2: (R)-5-(2-(3,5-difluorophenyl)pyrrolidin-1-yl) pyrazolo[1,5-a]pyridine-3-carboxylic acid The title compound was prepared by a method substantially similar to that mentioned in step-5 and step-6 of example-3 using (R)-2-(3,5-Difluorophenyl)pyrrolidine hydrochloride (step-1) and Ethyl 5-bromo-pyrazolo[1,5-a]pyridine-3-carboxylate to afford the product as white solid. MS (ESI): m/z 344.1 (M+H).

Step-3: (5-((R)-2-(3,5-difluorophenyl)pyrrolidin-1-yl)pyrazolo[1,5-a]pyridin-3-yl)((S)-3-hydroxypyrrolidin-1-yl)methanone

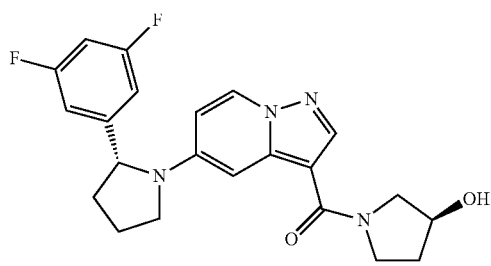 [SMILES: O=C(c1cnn2ccc(N3CCC[C@@H]3c3cc(F)cc(F)c3)cc12)N1CC[C@H](O)C1]

The title compound was prepared by a method substantially similar to that Example-4 to afford the product as tan solid (92.0 mg). MS (ESI): m/z 413.1 (M+H).

Example-293

5-((R)-2-(3,5-difluorophenyl)pyrrolidin-1-yl)-N—((S)-2,3-dihydroxypropyl)pyrazolo[1,5-a]pyridine-3-carboxamide

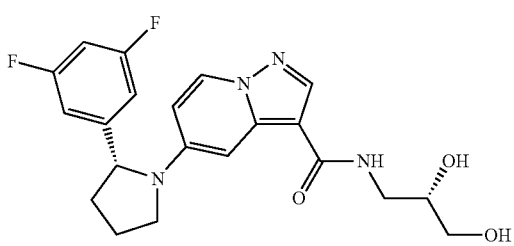 [SMILES: O=C(NC[C@H](O)CO)c1cnn2ccc(N3CCC[C@@H]3c3cc(F)cc(F)c3)cc12]

MS (ESI): m/z 417.1 (M+H).

Example-294

5-((R)-2-(3,5-difluorophenyl)pyrrolidin-1-yl)-N-((1r,4R)-4-(1-methyl-1H-tetrazol-5-yl)cyclohexyl)pyrazolo[1,5-a]pyridine-3-carboxamide

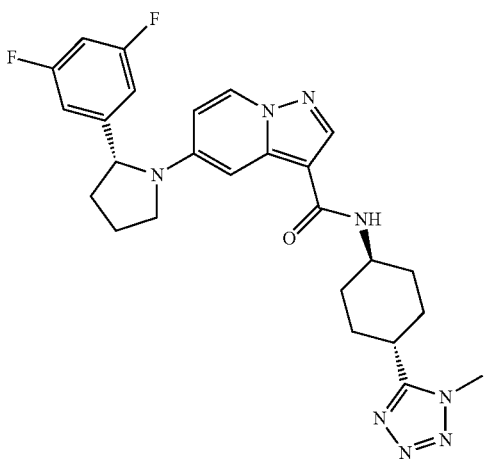 [SMILES: Cn1nnnc1[C@H]1CC[C@H](NC(=O)c2cnn3ccc(N4CCC[C@@H]4c4cc(F)cc(F)c4)cc23)CC1]

MS (ESI): m/z 507.2 (M+H).

Example-295

5-((R)-2-(3,5-difluorophenyl)pyrrolidin-1-yl)-N-((1r,4R)-4-(2-methyl-2H-tetrazol-5-yl)cyclohexyl)pyrazolo[1,5-a]pyridine-3-carboxamide

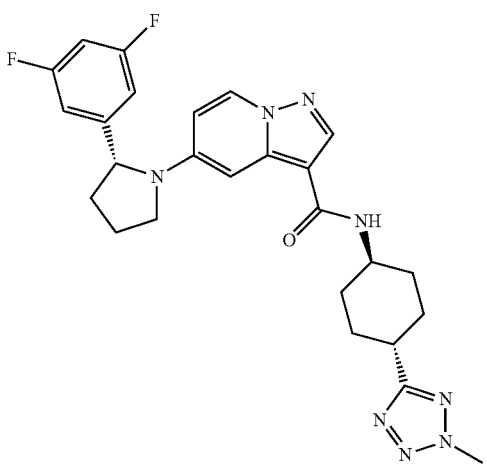 [SMILES: Cn1nnc([C@H]2CC[C@H](NC(=O)c3cnn4ccc(N5CCC[C@@H]5c5cc(F)cc(F)c5)cc34)CC2)n1]

MS (ESI): m/z 507 (M+H).

Example-296

(R)-5-(2-(3,5-difluorophenyl)pyrrolidin-1-yl)-N-((1-(hydroxymethyl)cyclopentyl)methyl)pyrazolo[1,5-a]pyridine-3-carboxamide

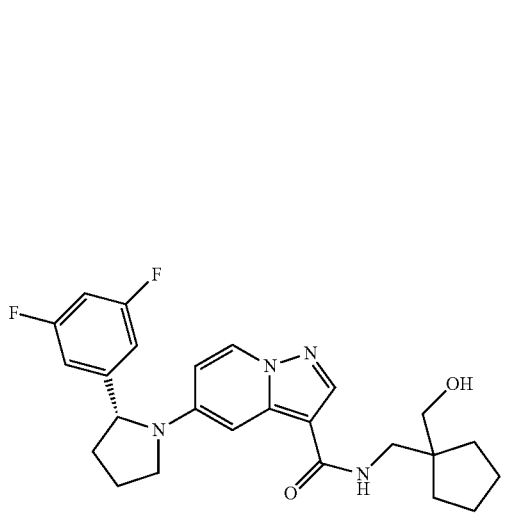 [SMILES: O=C(NCC1(CO)CCCC1)c1cnn2ccc(N3CCC[C@@H]3c3cc(F)cc(F)c3)cc12]

MS (ESI): m/z 455 (M+H).

Example-297

(R)-5-(2-(3,5-difluorophenyl)pyrrolidin-1-yl)-N-(1,3-dihydroxy-2-(hydroxymethyl) propan-2-yl)pyrazolo[1,5-a]pyridine-3-carboxamide

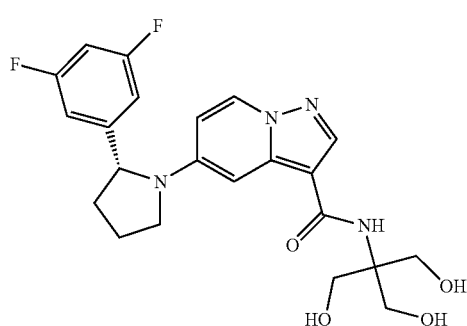 [SMILES: O=C(NC(CO)(CO)CO)c1cnn2ccc(N3CCC[C@@H]3c3cc(F)cc(F)c3)cc12]

MS (ESI): m/z 447.1 (M+H).

Example-298

(R)-5-(2-(3,5-difluorophenyl)pyrrolidin-1-yl)-N((1-(hydroxymethyl)cyclobutyl)methyl)pyrazolo[1,5-a]pyridine-3-carboxamide

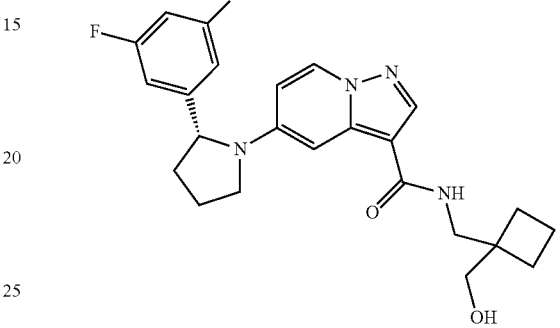

MS (ESI): m/z 440.9 (M+H).

Example-299 (Isomer-I)

5-((R)-2-(3,5-difluorophenyl)pyrrolidin-1-yl)-N-(1,1-dioxidotetrahydrothiophen-3-yl)pyrazolo[1,5-a]pyridine-3-carboxamide (Isomer-I)

A diastereomeric mixture obtained from the amide coupling reaction between (R)-5-(2-(3,5-difluorophenyl)pyrrolidin-1-yl)pyrazolo[1,5-a]pyridine-3-carboxylic acid and 3-aminotetrahydrothiophene 1,1-dioxide was purified by chiral column (Mobile phase:A:Hexane,B: Ethanol; Column: Chiral Pak AO-H(10 mm×250 mm, 5µ) semi prep column, Flow rate: 6 mL/min., Isocratic:50:50) to obtain diastereomer-I (example 299) and diastereomer-II (example-300).

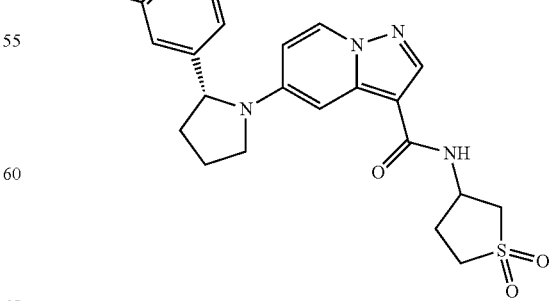

Off white solid (40.0 mg). MS (ESI): m/z 461.1 (M+H).

Example-300 (Isomer-II)

5-((R)-2-(3,5-difluorophenyl)pyrrolidin-1-yl)-N-(1,1-dioxidotetrahydrothiophen-3-yl)pyrazolo[1,5-a]pyridine-3-carboxamide (Isomer-II)

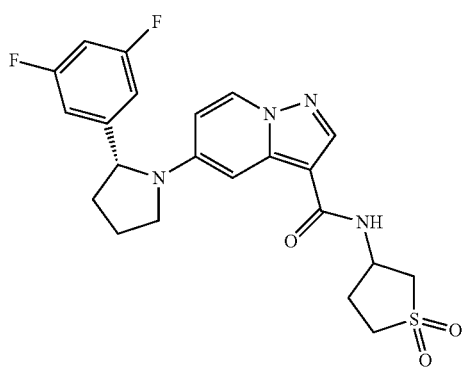 [SMILES: O=C(NC1CCS(=O)(=O)C1)c1cnn2ccc(N3CCC[C@@H]3c3cc(F)cc(F)c3)cc12]

MS (ESI): m/z 461.2 (M+H).

Example-301

(R)-5-(2-(3,5-difluorophenyl)pyrrolidin-1-yl)-N-(4-hydroxy-4-(hydroxymethyl)cyclohexyl)pyrazolo[1,5-a]pyridine-3-carboxamide

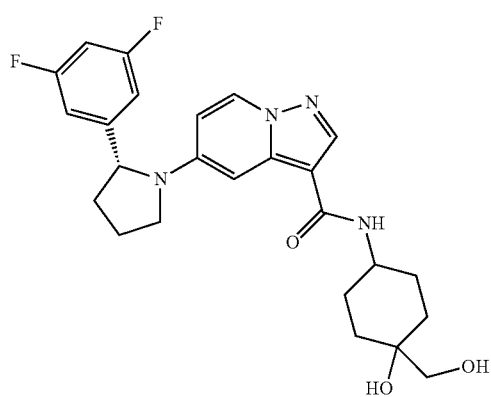 [SMILES: O=C(NC1CCC(O)(CO)CC1)c1cnn2ccc(N3CCC[C@@H]3c3cc(F)cc(F)c3)cc12]

MS (ESI): m/z 471.2 (M+H).

Example-302

5-((R)-2-(3,5-difluorophenyl)pyrrolidin-1-yl)-N—((R)-1-hydroxypropan-2-yl)pyrazolo[1,5-a]pyridine-3-carboxamide

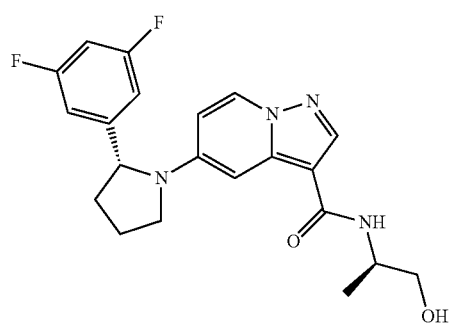 [SMILES: C[C@H](CO)NC(=O)c1cnn2ccc(N3CCC[C@@H]3c3cc(F)cc(F)c3)cc12]

MS (ESI): m/z 401.1 (M+H).

Example-303

(R)—N-(6-(1H-1,2,4-triazol-1-yl)pyridin-3-yl)-5-(2-(3,5-difluorophenyl)pyrrolidin-1-yl)pyrazolo[1,5-a]pyridine-3-carboxamide

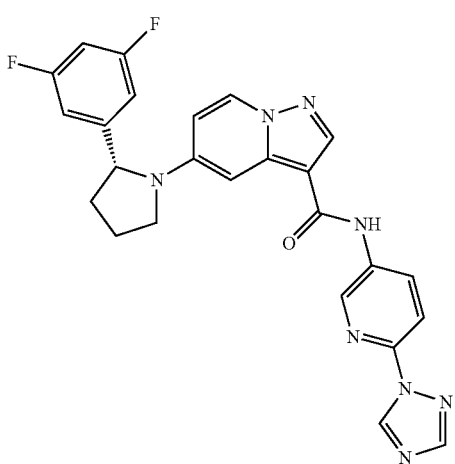 [SMILES: O=C(Nc1ccc(-n2cncn2)nc1)c1cnn2ccc(N3CCC[C@@H]3c3cc(F)cc(F)c3)cc12]

MS (ESI): m/z 487.1 (M+H).

Example-304

(R)-5-(2-(3,5-difluorophenyl)pyrrolidin-1-yl)-N-(1-(5-sulfamoylpyridin-2-yl)azetidin-3-yl)pyrazolo[1,5-a]pyridine-3-carboxamide

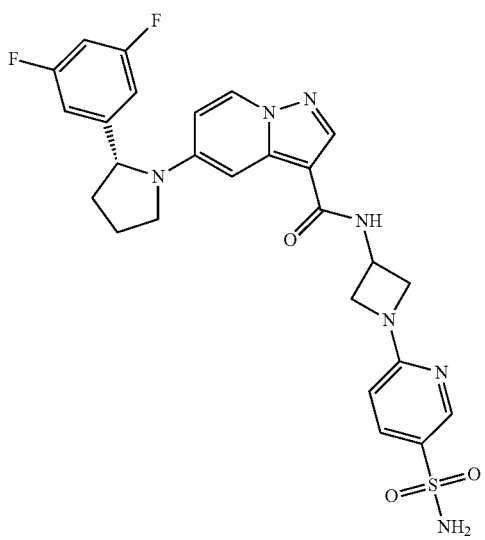 [SMILES: NS(=O)(=O)c1ccc(N2CC(NC(=O)c3cnn4ccc(N5CCC[C@@H]5c5cc(F)cc(F)c5)cc34)C2)nc1]

MS (ESI): m/z 554(M+H).

Example-305 (Isomer-I)

5-((R)-2-(3,5-difluorophenyl)pyrrolidin-1-yl)-N-(2,3-dihydroxy-2-methylpropyl)pyrazolo[1,5-a]pyridine-3-carboxamide (Isomer-I)

The crude product (obtained by the coupling of (R)-5-(2-(3,5-difluorophenyl)pyrrolidin-1-yl)pyrazolo[1,5-a]pyridine-3-carboxylic acid and 3-amino-2-methylpropane-1,2-diol) was purified by preparative HPLC (21.2×150×5C18-28, Flow rate: 20 mL/min., Mobile phase: 0.1% TFA in water (A): ACN+MeOH1:1 (B), Gradient—Time:% B=0:40, 2:50, 10:80) to obtain diastereomer-I (example 305) and diastereomer-II (example 306).

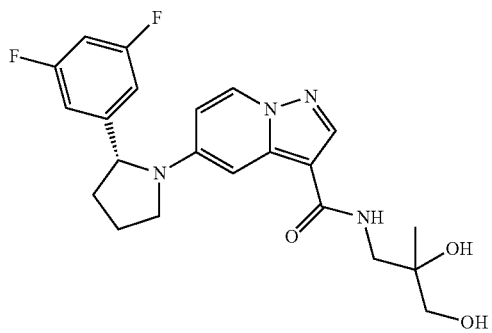 [SMILES: CC(O)(CO)CNC(=O)c1cnn2ccc(N3CCC[C@@H]3c3cc(F)cc(F)c3)cc12]

Brown solid (7.0 mg). MS (ESI): m/z 431.1 (M+H).

Example-306 (Isomer-II)

5-((R)-2-(3,5-difluorophenyl)pyrrolidin-1-yl)-N-(2,3-dihydroxy-2-methylpropyl)pyrazolo[1,5-a]pyridine-3-carboxamide

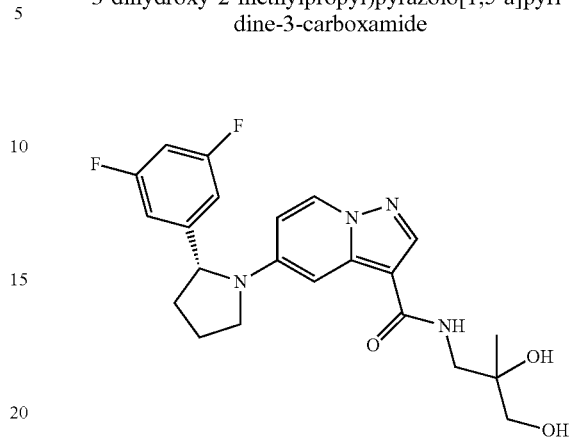

MS (ESI): m/z 431.1 (M+H).

It is understood that examples described above for which experimental procedures are not provided can be made by the procedures disclosed in or more of the other examples application.

Example-307

Determination of in vitro TrkA inhibitory activity using TR-FRET assay

Compounds were screened in the TR-FRET assay with TrkA kinase. 5 ng of TrkA [Upstate, USA] kinase was used for assay. The compound was incubated with the kinase for 30 minutes at 20-35° C. After the incubation, substrate mix [40 nM Ultra light poly GT (Perkin Elmer, USA) and 500 µM ATP] was added. The above reaction was stopped by the addition of 40 mM EDTA after 30 minutes. The Eu-labelled antiphospho-tyrosine antibody [Perkin Elmer, USA] was added at 0.5 nM and the fluorescence emission at 615 nm/665 nm [excitation at 340 nm] was measured. The compounds were initially screened at 100 nM, 1 µM and 10 µM concentrations. The potent compounds with >25% inhibition at 1 µM of TrkA were taken for the full dose response studies. The final DMSO concentration in the assay was 1%. For $IC_{50}$ determination, $\frac{1}{3}^{rd}$ serial dilution was made from the 20 mM DMSO stock solution. 2 µl of these were transferred to the test wells containing 20 µl reaction mixture [Total reaction volume 22 µl]. The fluorescence was measured in Perkin Elmer Wallac 1420 Multilabel Counter Victor 3. The $IC_{50}$ was determined by fitting the dose response data to a sigmoidal curve fitting equation using GraphPad Prism software version 5.

Using this protocol, various compounds as described herein and further as exemplified above, were found to exhibit inhibitory effect on TrkA. Examples 1-306 (other than examples 20, 31, 38, 42, 45, 47, 55, 59, 71, 77, 103, 108, 117, 118, 120, 121, 127, 134, 223 and 271), as described herein, exhibited a TrkA inhibition in-vitro 1050 values less than or equal to about 1 µM.

Examples, as described herein, 20, 31, 38, 42, 45, 47, 55, 59, 71, 77, 103, 108, 117, 118, 120, 121, 127, 134, 223 and 271 exhibited a TrkA inhibitory activity in-vitro 1050 values between about 1 µM to about 10 µM.

Although the present application has been illustrated by certain of the preceding examples, it is not to be construed as being limited thereby; but rather, the present application encompasses the generic area as hereinbefore disclosed. Various modifications and embodiments can be made without departing from the spirit and scope thereof. For example, the following compounds, their pharmaceutically acceptable salts or their stereoisomers thereof are also included in the scope of the present application:

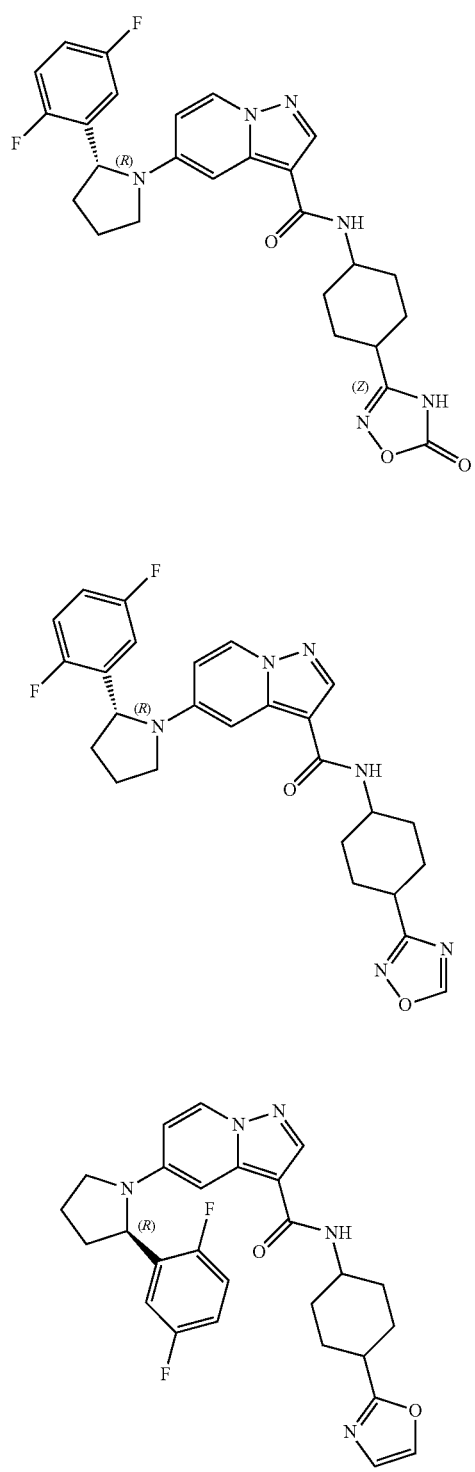
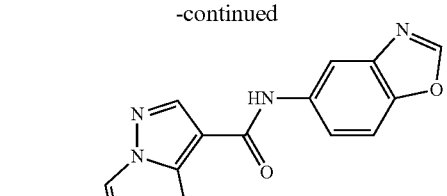
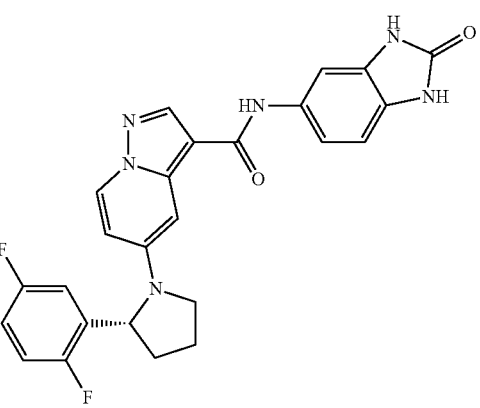
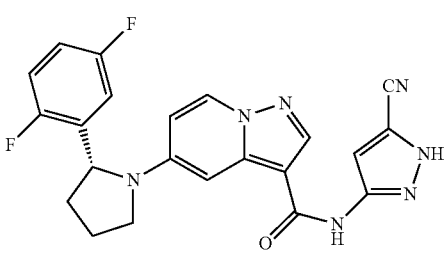
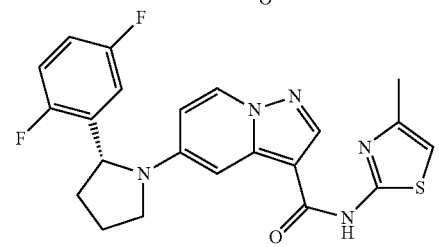
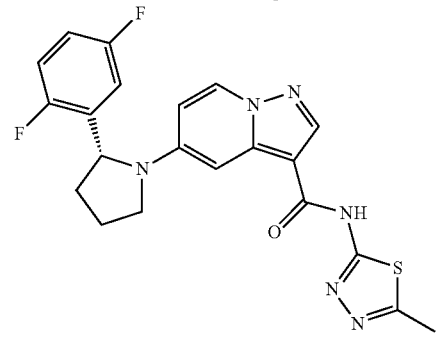

What is claimed is:

1. A compound having the formula (I),

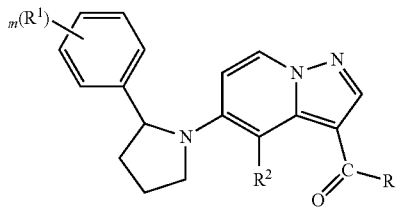

their pharmaceutically acceptable salts, pharmaceutically acceptable solvates or stereoisomers thereof, wherein $R^1$ is independently selected from hydrogen, alkyl, halogen, alkoxy or haloalkoxy;

$R^2$ is selected from hydrogen or fluorine;

wherein when $R^2$ is hydrogen, R is —$NR^3R^4$; and when $R^2$ is fluorine, R is —$NR^3R^4$ or —$OR^x$ wherein $R^x$ is hydrogen or alkyl;

$R^3$ is hydrogen, alkyl, hydroxyalkyl or alkoxyalkyl;

$R^4$ is selected from (i) —$(CR^yR^z)_m$—CN, —$(CR^yR^z)_m COOR^b$, —$(CR^yR^z)_m CONR^cR^d$, —$(CR^yR^z)_m$—$NR^eR^f$, —$(CR^yR^z)_m OR^g$, —$(CR^yR^z)_n$—O—$(CH_2)_n$—$OR^h$, alkoxy, haloalkoxy, alkoxyalkyl, thiazolyl, 1,3,4-thiadiazolyl, tetrahydro-2H-thiopyranyl, tetrahydro-2H-thiopyran-1-oxide, tetrahydro-2H-thiopyran-1,1-dioxide, tetrahydrothiophene 1,1-dioxide, (ii) cycloalkyl substituted with hydroxyalkyl, hydroxyalkyl and hydroxyl together, —$(CR^yR^z)_m$—$COOR^b$, —$CONR^cR^d$, —$NR^eR^f$, —$COR^g$, optionally substituted heterocyclyl, wherein the optional substituent is selected from alkyl or haloalkyl, (iii) heterocyclyl substituted with haloalkyl, alkyl and haloalkyl together, halogen and haloalkyl together, hydroxyalkyl, —$SO_2$-alkyl, —$SO_2$-aryl, —$SO_2$—$NR^eR^f$, —CO—$NR^eR^f$, —$COOR^b$, —$COR^g$, aralkyl, —$(CR^yR^z)_n$—$NR^eR^f$, optionally substituted heterocyclyl wherein optional substituent is selected from alkyl or $SO_2$—$NR^eR^f$, (iv) —$(CR^yR^z)_m$-aryl substituted with hydroxyalkyl, —$SO_2$-alkyl, —$SO_2$-aryl, —$SO_2$—$NR^eR^f$, —CO—$NR^eR^f$, —$COOR^b$, aralkyl, —$NR^3R^4$, —$(CR^yR^z)_n$—$NR^eR^f$ optionally substituted heterocyclyl wherein optional substituent is selected from halogen, hydroxyl or alkyl; halogen and optionally substituted heterocyclyl together, (v) optionally substituted —$(CR^yR^z)_n$-heterocyclyl, optionally substituted $(C_7-C_{12})$cycloalkyl, optionally substituted —$(CR^yR^z)_n$-cycloalkyl, optionally substituted heterocycle containing 3-4 heteroatoms or heterogroups selected from O, S, N, CO, SO or $SO_2$, wherein the optional substituent is selected from cyano, halogen, hydroxy, alkyl, haloalkyl, hydroxyalkyl, alkoxy, haloalkoxy, ¯$COOR^b$, —$(CR^yR^z)_n$—$CONR^cR^d$, —$(CR^yR^z)_n$_$NR^eR^f$, —$SO_2R^g$ or —$(CHR^j)_p$—$R^5$, Provided that when $R^2$ is Fluorine, $R^4$ can alternatively be hydroxyalkyl;

Alternatively $R^3$ and $R^4$ together with the nitrogen atom to which they are attached form an optionally substituted 3-10 membered heterocyclic ring wherein the optional substituent is selected from hydroxy, cyano, halogen, alkyl, haloalkyl, hydroxyalkyl, alkoxy, haloalkoxy, —$COOR^b$, —$CONR^cR^d$, —$NR^eR^f$, —$COR^g$, —$O(CH_2)_o$—$OR^h$, —$SO_2R^i$, —$(CHR^j)_p$—$R^5$ or heterocyclyl optionally substituted with hydroxyl or alkyl;

$R^5$ is independently selected from an optionally substituted group selected from cycloalkyl, aryl, heterocyclyl; wherein the optional substituent is hydroxyl, alkyl, haloalkyl or $SO_2R^g$;

$R^b$ is independently selected from hydrogen or alkyl;

$R^c$ is independently selected from hydrogen or alkyl;

$R^d$ is independently selected from hydrogen, alkyl or alkoxy;

$R^e$ is independently selected from hydrogen, alkyl or hydroxyalkyl;

$R^f$ is independently selected from hydrogen or alkyl;

Alternatively $R^e$ and $R^f$, in each occurrence, independent of each other, together with the nitrogen atom to which they are attached form optionally substituted 3-6 membered heterocyclic ring, wherein the optional substituent is selected from hydroxyl, alkyl, acyl, mesyl or $COOR^b$;

$R^g$ is independently selected from alkyl, aryl, heterocyclyl or —$NR^eR^f$;

$R^h$ is independently represents alkyl;

$R^i$ is independently selected from alkyl, aryl or —$NR^eR^d$;

$R^j$ is independently selected from hydrogen or alkyl;

$R^y$ is independently selected from hydrogen, hydroxy, hydroxyalkyl, alkyl or aryl;

$R^z$ is independently selected from hydrogen or alkyl;

m is independently selected from 0, 1, 2, 3 or 4;

n is independently selected from 1, 2, 3 or 4; and p is 0, 1, 2, 3 or 4.

2. The compound according to claim 1 having the formula (Ia):

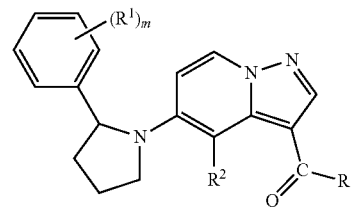

their pharmaceutically acceptable salts, pharmaceutically acceptable solvates or stereoisomers thereof.

3. The compound according to claim 2, having the formula (Ib):

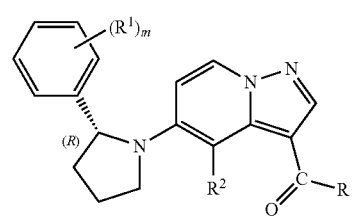

their pharmaceutically acceptable salts, pharmaceutically acceptable solvates or stereoisomers thereof.

4. The compound according to claim 1, having the formula (Ic):

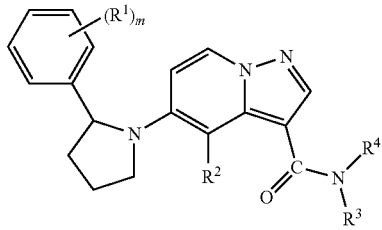

their pharmaceutically acceptable salts, pharmaceutically acceptable solvates or stereoisomers thereof.

5. The compound according to claim 1, having the formula (Id):

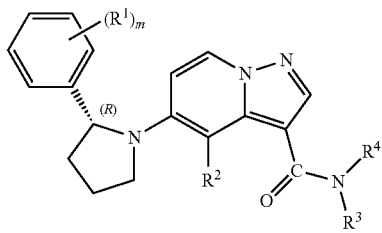

their pharmaceutically acceptable salts, pharmaceutically acceptable solvates or stereoisomers thereof.

6. The compound according to claim 1, having the formula (Ie):

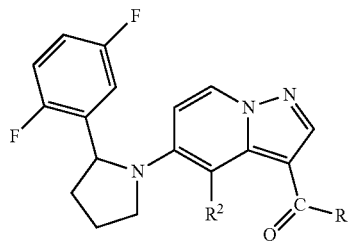

their pharmaceutically acceptable salts, pharmaceutically acceptable solvates or stereoisomers thereof.

7. The compound according to claim 1, having the formula (If):

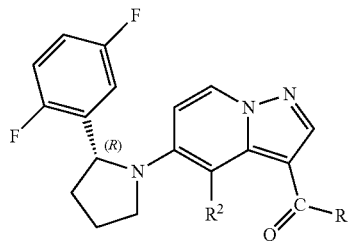

their pharmaceutically acceptable salts, pharmaceutically acceptable solvates or stereoisomers thereof.

8. The compound according to claim 1, wherein when $R^2$ is hydrogen, R is $NR^3R^4$.

9. The compound according to claim 1, wherein when $R^2$ is fluorine, R is $NR^3R^4$ or —$OR^x$.

10. The compound according to claim 1, wherein $R^1$ is fluorine and m is 1 or 2.

11. A compound which is
   (5-(2-(2,5-difluorophenyl)pyrrolidin-1-yl)pyrazolo[1,5-a]pyridin-3-yl)((S)-3-hydroxypyrrolidin-1-yl)methanone;
   (5-(2-(2,5-difluorophenyl)pyrrolidin-1-yl)pyrazolo[1,5-a]pyridin-3-yl)(3-hydroxyazetidine-1-yl)methanone;
   (5-(2-(2,5-difluorophenyl)pyrrolidin-1-yl)pyrazolo[1,5-a]pyridin-3-yl)(4-hydroxypiperidin-1-yl)methanone;
   (5-(2-(2,5-difluorophenyl)pyrrolidin-1-yl)pyrazolo[1,5-a]pyridin-3-yl)(4-methylpiperazin-1-yl)methanone;
   (R)-(5-(2-(2,5-difluorophenyl)pyrrolidin-1-yl)pyrazolo[1,5-a]pyridin-3-yl) (3-hydroxyazetidine-1-yl)methanone;
   (5-((R)-2-(2,5-difluorophenyl)pyrrolidin-1-yl)pyrazolo[1,5-a]pyridin-3-yl)((S)-3-hydroxypyrrolidin-1-yl)methanone;
   (5-((S)-2-(2,5-difluorophenyl)pyrrolidin-1-yl)pyrazolo[1,5-a]pyridin-3-yl) ((S)-3-hydroxypyrrolidin-1-yl)methanone;
   (S)-(5-(2-(2,5-difluorophenyl)pyrrolidin-1-yl)pyrazolo[1,5-a]pyridin-3-yl) (3-hydroxyazetidine-1-yl)methanone;
   (5-((R)-2-(2,5-difluorophenyl)pyrrolidin-1-yl)pyrazolo[1,5-a]pyridin-3-yl)(Hexahydro-1H-pyrido[1,2-a]pyrazin-2 (6H)-yl)methanone;
   (R)-(5-(2-(2,5-difluorophenyl)pyrrolidin-1-yl)pyrazolo[1,5-a]pyridin-3-yl)(5,6-dihydroimidazo[1,2-a]pyrazin-7(8H)-yl)methanone;
   (R)-ethyl 7-(5-(2-(2,5-difluorophenyl)pyrrolidin-1-yl)pyrazolo[1,5-a]pyridine-3-carbonyl)-5,6,7,8-tetrahydroimidazo[1,2-a]pyrazine-2-carboxylate;
   (5-((R)-2-(2,5-difluorophenyl)pyrrolidin-1-yl)pyrazolo[1,5-a]pyridin-3-yl)(Hexahydropyrrolo[1,2-a]pyrazin-2 (1H)-yl)methanone;
   (5-((R)-2-(2,5-difluorophenyl)pyrrolidin-1-yl)pyrazolo[1,5-a]pyridin-3-yl)(5-methylhexahydropyrrolo[3,4-c]pyrrol-2 (1H)-yl)methanone;
   (R)-(5-(2-(2,5-difluorophenyl)pyrrolidin-1-yl)pyrazolo[1,5-a]pyridin-3-yl)(3-(trifluoromethyl)-5,6-dihydro-[1,2,4]triazolo[4,3-a]pyrazin-7(8H)-yl)methanone;
   (R)-(5-(2-(2,5-difluorophenyl)pyrrolidin-1-yl)pyrazolo[1,5-a]pyridin-3-yl) (3-hydroxy-3-methylazetidin-1-yl)methanone;
   5-((R)-2-(2,5-difluorophenyl)pyrrolidin-1-yl)-N-((S)-1-phenyl-2-(pyrrolidin-1-yl)ethyl)pyrazolo[1,5-a]pyridine-3-carboxamide;
   (5-((R)-2-(2,5-difluorophenyl)pyrrolidin-1-yl)pyrazolo[1,5-a]pyridin-3-yl)(3-(hydroxymethyl)pyrrolidin-1-yl)methanone;
   Ethyl 1-(5-((R)-2-(2,5-difluorophenyl)pyrrolidin-1-yl)pyrazolo[1,5-a]pyridine-3-carbonyl)pyrrolidine-3-carboxylate;
   1-(5-((R)-2-(2,5-difluorophenyl)pyrrolidin-1-yl)pyrazolo[1,5-a]pyridine-3-carbonyl)pyrrolidine-3-carboxylic acid;
   5-((R)-2-(2,5-difluorophenyl)pyrrolidin-1-yl)-N-((S)-2-((S)-3-hydroxypyrrolidin-1-yl)-1-phenylethyl)pyrazolo[1,5-a]pyridine-3-carboxamide;
   (R)-Ethyl 2-(5-(2-(2,5-difluorophenyl)pyrrolidin-1-yl)pyrazolo[1,5-a]pyridine-3-carboxamido)acetate;
   (R)-2-(5-(2-(2,5-difluorophenyl)pyrrolidin-1-yl)pyrazolo[1,5-a]pyridine-3-carboxamido) acetic acid;

5-((R)-2-(2,5-difluorophenyl)pyrrolidin-1-yl)-N-(3-hydroxyadamantan-1-yl)pyrazolo[1,5-a]pyridine-3-carboxamide (R)-(5-(2-(2,5-difluorophenyl)pyrrolidin-1-yl)pyrazolo[1,5-a]pyridin-3-yl) (piperazin-1-yl)methanone;

2,5-diazabicyclo[2.2.1]heptan-2-yl(5-((R)-2-(2,5-difluorophenyl)pyrrolidin-1-yl)pyrazolo[1,5-a]pyridin-3-yl)methanone;

(R)-Methyl 4-(5-(2-(2,5-difluorophenyl)pyrrolidin-1-yl)pyrazolo[1,5-a]pyridine-3-carboxamido)cyclohexanecarboxylate;

(R)-4-(5-(2-(2,5-difluorophenyl)pyrrolidin-1-yl)pyrazolo[1,5-a]pyridine-3-carboxamido)cyclohexanecarboxylic acid;

(R)-4-amino-1-(5-(2-(2,5-difluorophenyl)pyrrolidin-1-yl)pyrazolo[1,5-a]pyridine-3-carbonyl)piperidine-4-carboxylic acid hydrochloride;

(5-((R)-2-(2,5-difluorophenyl)pyrrolidin-1-yl)pyrazolo[1,5-a]pyridin-3-yl)(8-(((S)-3-hydroxypyrrolidin-1-yl)methyl)-5,6-dihydroimidazo[1,2-a]pyrazin-7(8H)-yl)methanone 2,2,2-trifluoroacetate;

(5-((R)-2-(2,5-difluorophenyl)pyrrolidin-1-yl)pyrazolo[1,5-a]pyridin-3-yl)(4-hydroxyazepan-1-yl)methanone;

(R)-5-(2-(2,5-difluorophenyl)pyrrolidin-1-yl)-N-(2-(pyrrolidin-1-yl)ethyl)pyrazolo[1,5-a]pyridine-3-carboxamide;

(R)-Methyl 4-(5-(2-(2,5-difluorophenyl)pyrrolidin-1-yl)pyrazolo[1,5-a]pyridine-3-carboxamido)tetrahydro-2H-pyran-4-carboxylate;

(R)-(5-(2-(2,5-difluorophenyl)pyrrolidin-1-yl)pyrazolo[1,5-a]pyridin-3-yl)(6,7-dimethoxy-3,4-dihydroisoquinolin-2 (1H)-yl)methanone;

Ethyl 3-(5-((R)-2-(2,5-difluorophenyl)pyrrolidin-1-yl)pyrazolo[1,5-a]pyridine-3-carboxamido)cyclohexanecarboxylate;

3-(5-((R)-2-(2,5-difluorophenyl)pyrrolidin-1-yl)pyrazolo[1,5-a]pyridine-3-carboxamido)cyclohexanecarboxylic acid;

(R)-7-(5-(2-(2,5-difluorophenyl)pyrrolidin-1-yl)pyrazolo[1,5-a]pyridine-3-carbonyl)-5,6,7,8-tetrahydroimidazo[1,2-a]pyrazine-2-carboxylic acid;

(R)-5-(2-(2,5-difluorophenyl)pyrrolidin-1-yl)-N-(2-(dimethylamino)-2-oxoethyl)pyrazolo[1,5-a]pyridine-3-carboxamide;

(R)-5-(2-(2,5-difluorophenyl)pyrrolidin-1-yl)-N-(2-(dimethylamino)ethyl)pyrazolo[1,5-a]pyridine-3-carboxamide;

5-((R)-2-(2,5-difluorophenyl)pyrrolidin-1-yl)-N-(1-(5-fluoropyridin-2-yl)ethyl)pyrazolo[1,5-a]pyridine-3-carboxamide;

(5-Benzylhexahydropyrrolo[3,4-c]pyrrol-2 (1H)-yl)(5-((R)-2-(2,5-difluorophenyl)pyrrolidin-1-yl)pyrazolo[1,5-a]pyridin-3-yl)methanone;

(5-((R)-2-(2,5-difluorophenyl)pyrrolidin-1-yl)pyrazolo[1,5-a]pyridin-3-yl)((S)-2-(hydroxymethyl)pyrrolidin-1-yl)methanone;

(R)-Methyl 4-amino-1-(5-(2-(2,5-difluorophenyl)pyrrolidin-1-yl)pyrazolo[1,5-a]pyridine-3-carbonyl)piperidine-4-carboxylate;

(R)-5-(2-(2,5-difluorophenyl)pyrrolidin-1-yl)-N-(2-morpholinoethyl)pyrazolo[1,5-a]pyridine-3-carboxamide;

(5-((R)-2-(2,5-difluorophenyl)pyrrolidin-1-yl)pyrazolo[1,5-a]pyridin-3-yl)((S)-3-(dimethylamino)pyrrolidin-1-yl)methanone;

(R)-4-(5-(2-(2,5-difluorophenyl)pyrrolidin-1-yl)pyrazolo[1,5-a]pyridine-3-carboxamido)tetrahydro-2H-pyran-4-carboxylic acid;

((S)-3-aminopyrrolidin-1-yl)(5-((R)-2-(2,5-difluorophenyl)pyrrolidin-1-yl)pyrazolo[1,5-a]pyridin-3-yl)methanone;

(R)-5-(2-(2,5-difluorophenyl)pyrrolidin-1-yl)-N-(1-(methylsulfonyl)piperidin-4-yl)pyrazolo[1,5-a]pyridine-3-carboxamide;

(R)-5-(2-(2,5-difluorophenyl)pyrrolidin-1-yl)-N-(1-(methylsulfonyl)piperidin-4-yl)pyrazolo[1,5-a]pyridine-3-carboxamide;

5-((R)-2-(2,5-difluorophenyl)pyrrolidin-1-yl)-N—((S)-1-(2-hydroxyethyl)pyrrolidin-3-yl)pyrazolo[1,5-a]pyridine-3-carboxamide;

(R)-5-(2-(2,5-difluorophenyl)pyrrolidin-1-yl)-N-(4-(pyrrolidin-1-ylmethyl)tetrahydro-2H-pyran-4-yl)pyrazolo[1,5-a]pyridine-3-carboxamide;

(R)-5-(2-(2,5-difluorophenyl)pyrrolidin-1-yl)-N-(4-(hydroxymethyl)tetrahydro-2H-pyran-4-yl)pyrazolo[1,5-a]pyridine-3-carboxamide;

(R)-Ethyl 4-(5-(2-(2,5-difluorophenyl)pyrrolidin-1-yl)pyrazolo[1,5-a]pyridine-3-carboxamido) piperidine-1-carboxylate;

(R)-5-(2-(2,5-difluorophenyl)pyrrolidin-1-yl)-N-(1-(2-hydroxyethyl)piperidin-4-yl)pyrazolo[1,5-a]pyridine-3-carboxamide;

(5-((R)-2-(2,5-difluorophenyl)pyrrolidin-1-yl)pyrazolo[1,5-a]pyridin-3-yl)((S)-3-(hydroxymethyl)piperidin-1-yl)methanone;

(5-((R)-2-(2,5-difluorophenyl)pyrrolidin-1-yl)pyrazolo[1,5-a]pyridin-3-yl)((R)-3-(hydroxymethyl)piperidin-1-yl)methanone;

5-((R)-2-(2,5-difluorophenyl)pyrrolidin-1-yl)-N—((S)-1-(methylsulfonyl)pyrrolidin-3-yl)pyrazolo[1,5-a]pyridine-3-carboxamide;

(R)-Methyl 1-benzyl-4-(5-(2-(2,5-difluorophenyl)pyrrolidin-1-yl)pyrazolo[1,5-a]pyridine-3-carboxamido) piperidine-4-carboxylate;

(R)-Methyl 4-(5-(2-(2,5-difluorophenyl)pyrrolidin-1-yl)pyrazolo[1,5-a]pyridine-3-carboxamido) piperidine-4-carboxylate;

(R)—N-(cyanomethyl)-5-(2-(2,5-difluorophenyl)pyrrolidin-1-yl)pyrazolo[1,5-a]pyridine-3-carboxamide;

(R)—N-((2H-tetrazol-5-yl)methyl)-5-(2-(2,5-difluorophenyl)pyrrolidin-1-yl)pyrazolo[1,5-a]pyridine-3-carboxamide;

(R)-1-(5-(2-(2,5-difluorophenyl)pyrrolidin-1-yl)pyrazolo[1,5-a]pyridine-3-carbonyl)piperidine-4-carbonitrile;

5-((R)-2-(2,5-difluorophenyl)pyrrolidin-1-yl)-N-((1r,4R)-4-(methoxycarbamoyl)cyclohexyl)pyrazolo[1,5-a]pyridine-3-carboxamide;

(R)-5-(2-(2,5-difluorophenyl)pyrrolidin-1-yl)-N-((1-(hydroxymethyl)cyclopentyl)methyl)pyrazolo[1,5-a]pyridine-3-carboxamide;

(R)-5-(2-(2,5-difluorophenyl)pyrrolidin-1-yl)-N-(2-methoxyethyl)pyrazolo[1,5-a]pyridine-3-carboxamide;

(5-((R)-2-(2,5-difluorophenyl)pyrrolidin-1-yl)pyrazolo[1,5-a]pyridin-3-yl)(3-(hydroxymethyl)piperazin-1-yl)methanone;

5-((R)-2-(2,5-difluorophenyl)pyrrolidin-1-yl)-N-(1-(5-fluoropyridin-2-yl)ethyl)pyrazolo[1,5-a]pyridine-3-carboxamide (Diastereomer I);

5-((R)-2-(2,5-difluorophenyl)pyrrolidin-1-yl)-N-(1-(5-fluoropyridin-2-yl)ethyl)pyrazolo[1,5-a]pyridine-3-carboxamide (Diastereomer II);

5-((R)-2-(2,5-difluorophenyl)pyrrolidin-1-yl)-N-((1r,4R)-4-(1-ethyl-1H-1,2,4-triazol-5-yl)cyclohexyl)pyrazolo[1,5-a]pyridine-3-carboxamide;

(R)-5-(2-(2,5-difluorophenyl)pyrrolidin-1-yl)-N-(1-sulfamoylpiperidin-4-yl)pyrazolo[1,5-a]pyridine-3-carboxamide;

5-((R)-2-(2,5-difluorophenyl)pyrrolidin-1-yl)-N-(3-(hydroxymethyl)cyclohexyl)pyrazolo[1,5-a]pyridine-3-carboxamide;

(R)-5-(2-(2,5-difluorophenyl)pyrrolidin-1-yl)-N-(1-(hydroxymethyl)cyclopropyl)pyrazolo[1,5-a]pyridine-3-carboxamide;

(R)-5-(2-(2,5-difluorophenyl)pyrrolidin-1-yl)-N-(2-(2-hydroxyethoxy)ethyl)pyrazolo[1,5-a]pyridine-3-carboxamide;

(R)-(4-(1H-tetrazol-5-yl)piperidin-1-yl)(5-(2-(2,5-difluorophenyl)pyrrolidin-1-yl)pyrazolo[1,5-a]pyridin-3-yl)methanone;

5-((R)-2-(2,5-difluorophenyl)pyrrolidin-1-yl)-N-4(((S)-tetrahydrofuran-2-yl)methyl)pyrazolo[1,5-a]pyridine-3-carboxamide;

(R)-5-(2-(2,5-difluorophenyl)pyrrolidin-1-yl)-N-(tetrahydro-2H-thiopyran-4-yl)pyrazolo[1,5-a]pyridine-3-carboxamide;

(R)-5-(2-(2,5-difluorophenyl)pyrrolidin-1-yl)-N-(1-(hydroxymethyl)cyclohexyl)pyrazolo[1,5-a]pyridine-3-carboxamide;

5-((R)-2-(2,5-difluorophenyl)pyrrolidin-1-yl)-N—((S)-1-sulfamoylpyrrolidin-3-yl)pyrazolo[1,5-a]pyridine-3-carboxamide;

(R)-5-(2-(2,5-difluorophenyl)pyrrolidin-1-yl)-N-((2-methyl-2H-tetrazol-5-yl)methyl)pyrazolo[1,5-a]pyridine-3-carboxamide;

(R)-5-(2-(2,5-difluorophenyl)pyrrolidin-1-yl)-N-((1-methyl-1H-tetrazol-5-yl)methyl)pyrazolo[1,5-a]pyridine-3-carboxamide (R)-5-(2-(2,5-difluorophenyl)pyrrolidin-1-yl)-N-(2-(4-hydroxypiperidin-1-yl)ethyl)pyrazolo[1,5-a]pyridine-3-carboxamide;

(R)-5-(2-(2,5-difluorophenyl)pyrrolidin-1-yl)-N-(2-(4-methylpiperazin-1-yl)ethyl)pyrazolo[1,5-a]pyridine-3-carboxamide;

5-((R)-2-(2,5-difluorophenyl)pyrrolidin-1-yl)-N-((1r,4R)-4-(hydroxymethyl)cyclohexyl)pyrazolo[1,5-a]pyridine-3-carboxamide;

(5-((R)-2-(2,5-difluorophenyl)pyrrolidin-1-yl)pyrazolo[1,5-a]pyridin-3-yl)(3-(hydroxymethyl)morpholino)methanone;

(5-((R)-2-(2,5-difluorophenyl)pyrrolidin-1-yl)pyrazolo[1,5-a]pyridin-3-yl)(2-(hydroxymethyl)morpholino)methanone;

(R)-5-(2-(2,5-difluorophenyl)pyrrolidin-1-yl)-N-(4-hydroxy-4-(hydroxymethyl)cyclohexyl)pyrazolo[1,5-a]pyridine-3-carboxamide;

(5-((R)-2-(2,5-difluorophenyl)pyrrolidin-1-yl)pyrazolo[1,5-a]pyridin-3-yl)(4-((S)-3-hydroxypyrrolidin-1-yl)piperidin-1-yl)methanone;

(R)-(5-(2-(2,5-difluorophenyl)pyrrolidin-1-yl)pyrazolo[1,5-a]pyridin-3-yl)(4-(3-hydroxyazetidine-1-yl)piperidin-1-yl)methanone;

5-((R)-2-(2,5-difluorophenyl)pyrrolidin-1-yl)-N—((S)-2-hydroxypropyl)pyrazolo[1,5-a]pyridine-3-carboxamide;

(R)-(5-(2-(2,5-difluorophenyl)pyrrolidin-1-yl)pyrazolo[1,5-a]pyridin-3-yl)(4-(1-methyl-1H-tetrazol-5-yl)piperidin-1-yl)methanone;

(R)-(5-(2-(2,5-difluorophenyl)pyrrolidin-1-yl)pyrazolo[1,5-a]pyridin-3-yl)(4-(2-methyl-2H-tetrazol-5-yl)piperidin-1-yl)methanone;

(R)-5-(2-(2,5-difluorophenyl)pyrrolidin-1-yl)-N-(1-oxidotetrahydro-2H-thiopyran-4-yl)pyrazolo[1,5-a]pyridine-3-carboxamide;

(5-((R)-2-(2,5-difluorophenyl)pyrrolidin-1-yl)pyrazolo[1,5-a]pyridin-3-yl)((S)-3-(pyrrolidin-1-ylmethyl)piperidin-1-yl)methanone;

(5-((R)-2-(2,5-difluorophenyl)pyrrolidin-1-yl)pyrazolo[1,5-a]pyridin-3-yl)((R)-3-(pyrrolidin-1-ylmethyl)piperidin-1-yl)methanone;

5-((R)-2-(2,5-difluorophenyl)pyrrolidin-1-yl)-N-((2,3-dihydrobenzo[b][1,4]dioxin-2-yl)methyl)pyrazolo[1,5-a]pyridine-3-carboxamide;

(R)-5-(2-(2,5-difluorophenyl)pyrrolidin-1-yl)-N-((1-hydroxycyclobutyl)methyl)pyrazolo[1,5-a]pyridine-3-carboxamide;

(R)-5-(5-(2-(2,5-difluorophenyl)pyrrolidin-1-yl)pyrazolo[1,5-a]pyridine-3-carbonyl)-4,5,6,7-tetrahydropyrazolo[1,5-a]pyrazine-2-carboxylic acid;

(R)-(5-(2-(2,5-difluorophenyl)pyrrolidin-1-yl)pyrazolo[1,5-a]pyridin-3-yl)(3,3-difluoropyrrolidin-1-yl)methanone;

5-((R)-2-(2,5-difluorophenyl)pyrrolidin-1-yl)-N-(2-(3-hydroxypyrrolidin-1-yl)ethyl)pyrazolo[1,5-a]pyridine-3-carboxamide;

(R)-5-(5-(2-(2,5-difluorophenyl)pyrrolidin-1-yl)pyrazolo[1,5-a]pyridine-3-carbonyl)-4,5,6,7-tetrahydropyrazolo[1,5-a]pyrazine-3-carboxylic acid;

N-((1r,4R)-4-(1H-tetrazol-5-yl)cyclohexyl)-5-((R)-2-(2,5-difluorophenyl)pyrrolidin-1-yl)pyrazolo[1,5-a]pyridine-3-carboxamide;

(R)-5-(2-(2,5-difluorophenyl)pyrrolidin-1-yl)-N-(1,1-dioxidotetrahydro-2H-thiopyran-4-yl)pyrazolo[1,5-a]pyridine-3-carboxamide;

5-((R)-2-(2,5-difluorophenyl)pyrrolidin-1-yl)-N-(4-((S)-3-hydroxypyrrolidin-1-yl)cyclohexyl)pyrazolo[1,5-a]pyridine-3-carboxamide;

5-((R)-2-(2,5-difluorophenyl)pyrrolidin-1-yl)-N-((tetrahydro-2H-pyran-3-yl)methyl)pyrazolo[1,5-a]pyridine-3-carboxamide (Diastereomer I);

5-((R)-2-(2,5-difluorophenyl)pyrrolidin-1-yl)-N-((tetrahydro-2H-pyran-3-yl)methyl)pyrazolo[1,5-a]pyridine-3-carboxamide (Diastereomer II);

N-((1R,4R)-4-(1H-1,2,4-triazol-5-yl)cyclohexyl)-5-((R)-2-(2,5-difluorophenyl)pyrrolidin-1-yl)pyrazolo[1,5-a]pyridine-3-carboxamide;

5-((R)-2-(2,5-difluorophenyl)pyrrolidin-1-yl)-N-((1r,4R)-4-(1-methyl-1H-tetrazol-5-yl)cyclohexyl)pyrazolo[1,5-a]pyridine-3-carboxamide;

5-((R)-2-(2,5-difluorophenyl)pyrrolidin-1-yl)-N-((1r,4R)-4-(2-methyl-2H-tetrazol-5-yl)cyclohexyl)pyrazolo[1,5-a]pyridine-3-carboxamide;

5-((R)-2-(2,5-difluorophenyl)pyrrolidin-1-yl)-N-(5,6,7,8-tetrahydroimidazo[1,2-a]pyridin-7-yl)pyrazolo[1,5-a]pyridine-3-carboxamide;

5((R)-2-(2,5-difluorophenyl)pyrrolidin-1-yl)-N-((tetrahydrofuran-3-yl)methyl)pyrazolo[1,5-a]pyridine-3-carboxamide (diastereomer 1);

N-((1r,4R)-4-(1,3,4-oxadiazol-2-yl)cyclohexyl)-5-((R)-2-(2,5-difluorophenyl)pyrrolidin-1-yl)pyrazolo[1,5-a]pyridine-3-carboxamide;

(R)-(5-(2-(2,5-difluorophenyl)pyrrolidin-1-yl)pyrazolo[1,5-a]pyridin-3-yl)(4-(5-methyl-1,3,4-oxadiazol-2-yl)piperidin-1-yl)methanone;

(R)-5-(2-(2,5-difluorophenyl)pyrrolidin-1-yl)-N-(4-(3-hydroxyazetidine-1-yl)cyclohexyl)pyrazolo[1,5-a]pyridine-3-carboxamide;

3,8-diazabicyclo[3.2.1]octan-8-yl(5-((R)-2-(2,5-difluorophenyl)pyrrolidin-1-yl)pyrazolo[1,5-a]pyridin-3-yl)methanone;

5-(5-((R)-2-(2,5-difluorophenyl)pyrrolidin-1-yl)pyrazolo[1,5-a]pyridine-3-carboxamido)-4,5,6,7-tetrahydropyrazolo[1,5-a]pyridine-3-carboxylic acid (Diastereomer-I);

5-(5-((R)-2-(2,5-difluorophenyl)pyrrolidin-1-yl)pyrazolo[1,5-a]pyridine-3-carboxamido)-4,5,6,7-tetrahydropyrazolo[1,5-a]pyridine-3-carboxylic acid (Diastereomer-II);

5-((R)-2-(2,5-difluorophenyl)pyrrolidin-1-yl)-N-((tetrahydrofuran-3-yl)methyl)pyrazolo[1,5-a]pyridine-3-carboxamide;

5-((R)-2-(2,5-difluorophenyl)pyrrolidin-1-yl)-N-(octahydroindolizin-7-yl)pyrazolo[1,5-a]pyridine-3-carboxamide;

(R)—N-(Benzo[d][1,3]dioxol-5-yl)-5-(2-(2,5-difluorophenyl)pyrrolidin-1-yl)pyrazolo[1,5-a]pyridine-3-carboxamide;

(R)-(5-(2-(2,5-difluorophenyl)pyrrolidin-1-yl)pyrazolo[1,5-a]pyridin-3-yl)(4-(5-(trifluoromethyl)-1,3,4-oxadiazol-2-yl)piperidin-1-yl)methanone;

5-((R)-2-(2,5-difluorophenyl)pyrrolidin-1-yl)-N-(1,1-dioxidotetrahydrothiophen-3-yl)pyrazolo[1,5-a]pyridine-3-carboxamide;

(R)-5-(2-(2,5-difluorophenyl)pyrrolidin-1-yl)-N-((1-(hydroxymethyl)cyclobutyl)methyl)pyrazolo[1,5-a]pyridine-3-carboxamide;

5-((R)-2-(2,5-difluorophenyl)pyrrolidin-1-yl)-N-((1r,4R)-4-(5-methyl-1,3,4-oxadiazol-2-yl)cyclohexyl)pyrazolo[1,5-a]pyridine-3-carboxamide;

(R)-5-(2-(2,5-difluorophenyl)pyrrolidin-1-yl)-N-(2,3-dihydrobenzo[b][1,4]dioxin-6-yl)pyrazolo[1,5-a]pyridine-3-carboxamide;

(R)—N-(4-(1H-1,2,4-triazol-1-yl)phenyl)-5-(2-(2,5-difluorophenyl)pyrrolidin-1-yl)pyrazolo[1,5-a]pyridine-3-carboxamide;

5-((R)-2-(2,5-difluorophenyl)pyrrolidin-1-yl)-N-(1,1-dioxidotetrahydrothiophen-3-yl)pyrazolo[1,5-a]pyridine-3-carboxamide;

5-((R)-2-(2,5-difluorophenyl)pyrrolidin-1-yl)-N-(1,1-dioxidotetrahydrothiophen-3-yl)pyrazolo[1,5-a]pyridine-3-carboxamide;

5-((R)-2-(2,5-difluorophenyl)pyrrolidin-1-yl)-N-((1r,4R)-4-(5-(trifluoromethyl)-1,3,4-oxadiazol-2-yl)cyclohexyl)pyrazolo[1,5-a]pyridine-3-carboxamide;

5-((R)-2-(2,5-difluorophenyl)pyrrolidin-1-yl)-N-(3-(dimethylcarbamoyl)-4,5,6,7-tetrahydropyrazolo[1,5-a]pyridin-6-yl)pyrazolo[1,5-a]pyridine-3-carboxamide;

(R)-5-(2-(2,5-difluorophenyl)pyrrolidin-1-yl)-N-(2-oxo-2,3-dihydro-1H-benzo[d]imidazol-5-yl)pyrazolo[1,5-a]pyridine-3-carboxamide;

5-((R)-2-(2,5-difluorophenyl)pyrrolidin-1-yl)-N-(octahydro-1H-quinolizin-2-yl)pyrazolo[1,5-a]pyridine-3-carboxamide;

5-((R)-2-(2,5-difluorophenyl)pyrrolidin-1-yl)-N-(4,5,6,7-tetrahydropyrazolo[1,5-a]pyridin-6-yl)pyrazolo[1,5-a]pyridine-3-carboxamide;

(5-((R)-2-(2,5-difluorophenyl)pyrrolidin-1-yl)pyrazolo[1,5-a]pyridin-3-yl)(3-(pyrrolidin-1-ylmethyl)pyrrolidin-1-yl)methanone;

(R)-5-(2-(2,5-difluorophenyl)pyrrolidin-1-yl)-N-(2-methylbenzo[d]oxazol-6-yl)pyrazolo[1,5-a]pyridine-3-carboxamide;

5-((R)-2-(2,5-difluorophenyl)pyrrolidin-1-yl)-N-((1r,4R)-4-(thiazol-2-yl)cyclohexyl) pyrazolo[1,5-a]pyridine-3-carboxamide;

5-(5-((R)-2-(2,5-difluorophenyl)pyrrolidin-1-yl)pyrazolo[1,5-a]pyridine-3-carboxamido)-4,5,6,7-tetrahydropyrazolo[1,5-a]pyridine-2-carboxylic acid;

5-((R)-2-(2,5-difluorophenyl)pyrrolidin-1-yl)-N-((1r,4R)-4-(5-methyl-1,2,4-oxadiazol-3-yl)cyclohexyl) pyrazolo[1,5-a]pyridine-3-carboxamide;

(R)—N-(6-(1H-1,2,4-triazol-1-yl)pyridin-3-yl)-5-(2-(2,5-difluorophenyl)pyrrolidin-1-yl)pyrazolo[1,5-a]pyridine-3-carboxamide;

(R)-5-(2-(2,5-difluorophenyl)pyrrolidin-1-yl)-N-(quinoxalin-6-yl)pyrazolo[1,5-a]pyridine-3-carboxamide;

(R)-5-(2-(2,5-difluorophenyl)pyrrolidin-1-yl)-N-(4-(1-methyl-1H-tetrazol-5-yl)phenyl)pyrazolo[1,5-a]pyridine-3-carboxamide;

N-(1-(2,5-difluorophenyl)-2-hydroxyethyl)-5-((R)-2-(2,5-difluorophenyl)pyrrolidin-1-yl)pyrazolo[1,5-a]pyridine-3-carboxamide;

(R)—N-(1-acetylindolin-6-yl)-5-(2-(2,5-difluorophenyl) pyrrolidin-1-yl)pyrazolo[1,5-a]pyridine-3-carboxamide;

(R)-5-(2-(2,5-difluorophenyl)pyrrolidin-1-yl)-N-(5-methyl-1,3,4-thiadiazol-2-yl)pyrazolo[1,5-a]pyridine-3-carboxamide;

(R)-(5-(2-(2,5-difluorophenyl)pyrrolidin-1-yl)pyrazolo[1,5-a]pyridin-3-yl)(4-hydroxy-4-methylpiperidin-1-yl)methanone;

5-((R)-2-(2,5-difluorophenyl)pyrrolidin-1-yl)-N-((1R,2S)-2-hydroxy-2,3-dihydro-1H-inden-1-yl)pyrazolo[1,5-a]pyridine-3-carboxamide;

(R)-5-(2-(2,5-difluorophenyl)pyrrolidin-1-yl)-N-(1,5-dimethyl-3-oxo-2-phenyl-2,3-dihydro-1H-pyrazol-4-yl)pyrazolo[1,5-a]pyridine-3-carboxamide;

7-(5-((R)-2-(2,5-difluorophenyl)pyrrolidin-1-yl)pyrazolo[1,5-a]pyridine-3-carboxamido)-5,6,7,8-tetrahydroimidazo[1,2-a]pyridine-2-carboxylic acid;

(1R,4r)-4-(5-((R)-2-(2,5-difluorophenyl)pyrrolidin-1-yl)pyrazolo[1,5-a]pyridine-3-carboxamido)cyclohexanecarboxylic acid;

(R)—N-(4-(1H-tetrazol-5-yl)phenyl)-5-(2-(2,5-difluorophenyl)pyrrolidin-1-yl)pyrazolo[1,5-a]pyridine-3-carboxamide;

(R)-5-(2-(2,5-difluorophenyl)pyrrolidin-1-yl)-N-(1H-indazol-6-yl)pyrazolo[1,5-a]pyridine-3-carboxamide;

(R)—N-(6-(1H-imidazol-1-yl)pyridin-3-yl)-5-(2-(2,5-difluorophenyl)pyrrolidin-1-yl) pyrazolo[1,5-a]pyridine-3-carboxamide;

(R)—N-(5-(1H-imidazol-1-yl)pyridin-2-yl)-5-(2-(2,5-difluorophenyl)pyrrolidin-1-yl)pyrazolo[1,5-a]pyridine-3-carboxamide;

(R)—N-(3-(1H-tetrazol-5-yl)phenyl)-5-(2-(2,5-difluorophenyl)pyrrolidin-1-yl)pyrazolo[1,5-a]pyridine-3-carboxamide;

(R)-5-(2-(2,5-difluorophenyl)pyrrolidin-1-yl)-N-(4-(2-methyl-2H-tetrazol-5-yl)phenyl)pyrazolo[1,5-a]pyridine-3-carboxamide;

(R)—N-(benzo[d][1,3]dioxol-5-ylmethyl)-5-(2-(2,5-difluorophenyl)pyrrolidin-1-yl)pyrazolo[1,5-a]pyridine-3-carboxamide;

(R)-5-(2-(2,5-difluorophenyl)pyrrolidin-1-yl)-N-((2,3-dihydrobenzo[b][1,4]dioxin-6-yl)methyl)pyrazolo[1,5-a]pyridine-3-carboxamide;

(R)—N-(5-(1H-1,2,4-triazol-1-yl)pyridin-2-yl)-5-(2-(2,5-difluorophenyl)pyrrolidin-1-yl)pyrazolo[1,5-a]pyridine-3-carboxamide;
(R)-5-(2-(2,5-difluorophenyl)pyrrolidin-1-yl)-N-(3-(2-methyl-2H-tetrazol-5-yl)phenyl)pyrazolo[1,5-a]pyridine-3-carboxamide;
(R)-5-(2-(2,5-difluorophenyl)pyrrolidin-1-yl)-N-(6-(1-methyl-1H-tetrazol-5-yl)pyridin-3-yl)pyrazolo[1,5-a]pyridine-3-carboxamide;
(R)-5-(2-(2,5-difluorophenyl)pyrrolidin-1-yl)-N-(6-(2-hydroxyethyl)pyridin-3-yl)pyrazolo[1,5-a]pyridine-3-carboxamide;
(R)-5-(2-(2,5-difluorophenyl)pyrrolidin-1-yl)-N-(3-(1-methyl-1H-tetrazol-5-yl)phenyl)pyrazolo[1,5-a]pyridine-3-carboxamide;
(R)-5-(2-(2,5-difluorophenyl)pyrrolidin-1-yl)-N-(2-methyl-6-(trifluoromethyl)pyridin-3-yl)pyrazolo[1,5-a]pyridine-3-carboxamide;
(R)-5-(2-(2,5-difluorophenyl)pyrrolidin-1-yl)-N-(6-(trifluoromethyl)pyridin-3-yl)pyrazolo[1,5-a]pyridine-3-carboxamide
(R)-5-(2-(2,5-difluorophenyl)pyrrolidin-1-yl)-N-(6-(2-methyl-2H-tetrazol-5-yl)pyridin-3-yl)pyrazolo[1,5-a]pyridine-3-carboxamide;
(R)—N-(2-chloro-6-(trifluoromethyl)pyridin-3-yl)-5-(2-(2,5-difluorophenyl)pyrrolidin-1-yl)pyrazolo[1,5-a]pyridine-3-carboxamide;
(R)-5-(2-(2,5-difluorophenyl)pyrrolidin-1-yl)-N-(1-(5-sulfamoylpyridin-2-yl) azetidin-3-yl)pyrazolo[1,5-a]pyridine-3-carboxamide;
5-((R)-2-(2,5-difluorophenyl)pyrrolidin-1-yl)-N-(4-((S)-3-hydroxypyrrolidin-1-yl) phenyl)pyrazolo[1,5-a]pyridine-3-carboxamide;
(R)-5-(2-(2,5-difluorophenyl)pyrrolidin-1-yl)-N-(4-(3-hydroxyazetidine-1-yl)phenyl)pyrazolo[1,5-a]pyridine-3-carboxamide;
(R)—N-(2-(1H-imidazol-1-yl)pyrimidin-5-yl)-5-(2-(2,5-difluorophenyl)pyrrolidin-1-yl)pyrazolo[1,5-a]pyridine-3-carboxamide;
(R)-5-(2-(2,5-difluorophenyl)pyrrolidin-1-yl)-N-(4-(piperazin-1-yl)phenyl)pyrazolo[1,5-a]pyridine-3-carboxamide;
N-(3-chloro-4-((S)-3-hydroxypyrrolidin-1-yl)phenyl)-5-((R)-2-(2,5-difluorophenyl)pyrrolidin-1-yl)pyrazolo[1,5-a]pyridine-3-carboxamide;
(R)—N-(2-(1H-1,2,4-triazol-1-yl)pyrimidin-5-yl)-5-(2-(2,5-difluorophenyl)pyrrolidin-1-yl)pyrazolo[1,5-a]pyridine-3-carboxamide;
(5-((R)-2-(2,5-difluorophenyl)pyrrolidin-1-yl)pyrazolo[1,5-a]pyridin-3-yl)(3-hydroxy-3-methylpyrrolidin-1-yl)methanone;
(R)-5-(2-(2,5-difluorophenyl)pyrrolidin-1-yl)-N-(4-(methylsulfonyl)phenyl)pyrazolo[1,5-a]pyridine-3-carboxamide;
5-((R)-2-(2,5-difluorophenyl)pyrrolidin-1-yl)-N-(4-((3S,5R)-3,5-dimethylpiperazin-1-yl)phenyl)pyrazolo[1,5-a]pyridine-3-carboxamide;
(R)-5-(2-(2,5-difluorophenyl)pyrrolidin-1-yl)-N-(3-methyl-1H-pyrazol-5-yl)pyrazolo[1,5-a]pyridine-3-carboxamide;
(R)-5-(2-(2,5-difluorophenyl)pyrrolidin-1-yl)-N-(6-sulfamoylpyridin-3-yl)pyrazolo[1,5-a]pyridine-3-carboxamide;
(R)—N-(3-chloro-4-(3-hydroxyazetidine-1-yl)phenyl)-5-(2-(2,5-difluorophenyl)pyrrolidin-1-yl)pyrazolo[1,5-a]pyridine-3-carboxamide;
(R)-(5-(2-(2,5-difluorophenyl)pyrrolidin-1-yl)pyrazolo[1,5-a]pyridin-3-yl)(3-hydroxy-3-(hydroxymethyl)azetidin-1-yl)methanone;
(5-((R)-2-(2,5-difluorophenyl)pyrrolidin-1-yl)pyrazolo[1,5-a]pyridin-3-yl) (3-hydroxy-3-(hydroxymethyl)pyrrolidin-1-yl)methanone;
(R)-5-(2-(2,5-difluorophenyl)pyrrolidin-1-yl)-N-(4-(2-oxoimidazolidin-1-yl)phenyl)pyrazolo[1,5-a]pyridine-3-carboxamide;
(R)-5-(2-(2,5-difluorophenyl)pyrrolidin-1-yl)-N-(5-(pyridin-2-yl)-1,3,4-thiadiazol-2-yl)pyrazolo[1,5-a]pyridine-3-carboxamide;
(R)-5-(2-(2,5-difluorophenyl)pyrrolidin-1-yl)-N-(4-sulfamoylphenyl)pyrazolo[1,5-a]pyridine-3-carboxamide;
(R)-5-(2-(2,5-difluorophenyl)pyrrolidin-1-yl)-N-(5-(pyridin-3-yl)-1,3,4-thiadiazol-2-yl)pyrazolo[1,5-a]pyridine-3-carboxamide;
(R)-5-(2-(2,5-difluorophenyl)pyrrolidin-1-yl)-N-(6-(N,N-dimethylsulfamoyl)pyridin-3-yl)pyrazolo[1,5-a]pyridine-3-carboxamide;
(R)-5-(2-(2,5-difluorophenyl)pyrrolidin-1-yl)-N-(6-(N-methylsulfamoyl)pyridin-3-yl)pyrazolo[1,5-a]pyridine-3-carboxamide;
(R)-5-(2-(2,5-difluorophenyl)pyrrolidin-1-yl)-N-(4-(pyridin-3-yl)thiazol-2-yl)pyrazolo[1,5-a]pyridine-3-carboxamide;
(R)-5-(2-(2,5-difluorophenyl)pyrrolidin-1-yl)-N-(4-(pyridin-2-yl)thiazol-2-yl)pyrazolo[1,5-a]pyridine-3-carboxamide;
(R)-5-(2-(5-(difluoromethoxy)-2-fluorophenyl)pyrrolidin-1-yl)pyrazolo[1,5-a]pyridine-3-carboxylic acid;
(R)-(5-(2-(5-(difluoromethoxy)-2-fluorophenyl)pyrrolidin-1-yl)pyrazolo[1,5-a]pyridin-3-yl)(3-hydroxyazetidine-1-yl)methanone;
(5-((R)-2-(5-(difluoromethoxy)-2-fluorophenyl)pyrrolidin-1-yl)pyrazolo[1,5-a]pyridin-3-yl)((S)-3-hydroxypyrrolidin-1-yl)methanone;
(R)-(5-(2-(2-(difluoromethoxy)-5-fluorophenyl)pyrrolidin-1-yl)pyrazolo[1,5-a]pyridin-3-yl)(3-hydroxyazetidine-1-yl)methanone;
(5-((R)-2-(2-(difluoromethoxy)-5-fluorophenyl)pyrrolidin-1-yl)pyrazolo[1,5a]pyridin-3-yl)((S)-3-hydroxypyrrolidin-1-yl)methanone;
(R)-5-(2-(2,5-difluorophenyl)pyrrolidin-1-yl)-4-fluoro-N-(4-hydroxy-4-(hydroxymethyl)cyclohexyl)pyrazolo[1,5a]pyridine-3-carboxamide;
(R)-(5-(2-(2,5-difluorophenyl)pyrrolidin-1-yl)-4-fluoropyrazolo[1,5-a]pyridin-3-yl)(3-hydroxyazetidine-1-yl)methanone;
(R)-5-(2-(2,5-difluorophenyl)pyrrolidin-1-yl)-4-fluoro-N-(tetrahydro-2H-pyran-4-yl)pyrazolo[1,5-a]pyridine-3-carboxamide;
(R)-5-(2-(2,5-difluorophenyl)pyrrolidin-1-yl)-4-fluoropyrazolo[1,5-a]pyridine-3-carboxamide;
5-((R)-2-(2,5-difluorophenyl)pyrrolidin-1-yl)-N—((S)-2,3-dihydroxypropyl)-4-fluoropyrazolo[1,5-a]pyridine-3-carboxamide;
(5-((R)-2-(2,5-difluorophenyl)pyrrolidin-1-yl)-4-fluoropyrazolo[1,5-a]pyridin-3-yl)((S)-3-hydroxypyrrolidin-1-yl)methanone;
(R)-5-(2-(2,5-difluorophenyl)pyrrolidin-1-yl)-4-fluoro-N-((1-(hydroxymethyl)cyclopentyl)methyl)pyrazolo[1,5a]pyridine-3-carboxamide;
5-((R)-2-(2,5-difluorophenyl)pyrrolidin-1-yl)-4-fluoro-N-((S)-1-hydroxypropan-2-yl)pyrazolo[1,5-a]pyridine-3-carboxamide;

N-((1r,4R)-4-(1H-1,2,4-triazol-5-yl)cyclohexyl)-5-(R)-2-(2,5-difluorophenyl)pyrrolidin-1-yl)-4-fluoropyrazolo[1,5-a]pyridine-3-carboxamide;

5-((R)-2-(2,5-difluorophenyl)pyrrolidin-1-yl)-4-fluoro-N—((S)-2-hydroxypropyl)pyrazolo[1,5-a]pyridine-3-carboxamide;

5-((R)-2-(2,5-difluorophenyl)pyrrolidin-1-yl)-4-fluoro-N-((1r,4R)-4-(2-methyl-2H-tetrazol-5-yl)cyclohexyl)pyrazolo[1,5-a]pyridine-3-carboxamide;

5-((R)-2-(2,5-difluorophenyl)pyrrolidin-1-yl)-4-fluoro-N-((1r,4R)-4-(1-methyl-1H-tetrazol-5-yl)cyclohexyl)pyrazolo[1,5-a]pyridine-3-carboxamide;

(R)-5-(2-(2,5-difluorophenyl)pyrrolidin-1-yl)-4-fluoro-N-((1-(hydroxymethyl)cyclobutyl)methyl)pyrazolo[1,5-a]pyridine-3-carboxamide;

(R)-5-(2-(2,5-difluorophenyl)pyrrolidin-1-yl)-4-fluoro-N-(3-hydroxycyclobutyl)pyrazolo[1,5-a]pyridine-3-carboxamide;

N-((1r,4R)-4-(1H-1,2,4-triazol-5-yl)cyclohexyl)-5-((R)-2-(2,5-difluorophenyl)pyrrolidin-1-yl)-4-fluoropyrazolo[1,5-a]pyridine-3-carboxamide;

(1R,4r)-4-(5-((R)-2-(2,5-difluorophenyl)pyrrolidin-1-yl)-4-fluoropyrazolo[1,5-a]pyridine-3-carboxamido)cyclohexanecarboxylic acid;

5-((R)-2-(2,5-difluorophenyl)pyrrolidin-1-yl)-4-fluoro-N-((1r,4R)-4-hydroxycyclohexyl)pyrazolo[1,5-a]pyridine-3-carboxamide;

5-((R)-2-(2,5-difluorophenyl)pyrrolidin-1-yl)-4-fluoro-N-(3-hydroxycyclohexyl)pyrazolo[1,5-a]pyridine-3-carboxamide;

N-((1r,4R)-4-(1H-tetrazol-5-yl)cyclohexyl)-5-((R)-2-(2,5-difluorophenyl)pyrrolidin-1-yl)-4-fluoropyrazolo[1,5-a]pyridine-3-carboxamide;

5-((R)-2-(2,5-difluorophenyl)pyrrolidin-1-yl)-4-fluoro-N-((1r,4R)-4-(methoxycarbamoyl)cyclohexyl)pyrazolo[1,5-a]pyridine-3-carboxamide;

5-((R)-2-(2,5-difluorophenyl)pyrrolidin-1-yl)-4-fluoro-N-((1r,4R)-4-(hydroxymethyl)cyclohexyl)pyrazolo[1,5-a]pyridine-3-carboxamide;

(1R,4r)-4-(4-fluoro-5-((R)-2-(5-fluoro-2-methoxyphenyl)pyrrolidin-1-yl)pyrazolo[1,5-a]pyridine-3-carboxamido)cyclohexanecarboxylic acid;

(5-((R)-2-(3-(difluoromethoxy)-5-fluorophenyl)pyrrolidin-1-yl)pyrazolo[1,5-a]pyridin-3-yl)((S)-3-hydroxypyrrolidin-1-yl)methanone;

5-((R)-2-(3-(difluoromethoxy)-5-fluorophenyl)pyrrolidin-1-yl)-N-((1r,4R)-4-(2-methyl-2H-tetrazol-5-yl)cyclohexyl)pyrazolo[1,5-a]pyridine-3-carboxamide;

(R)-5-(2-(3-(difluoromethoxy)-5-fluorophenyl)pyrrolidin-1-yl)-N-(4-hydroxy-4-(hydroxymethyl)cyclohexyl)pyrazolo[1,5-a]pyridine-3-carboxamide;

(1R,4r)-4-(5-((R)-2-(3-(difluoromethoxy)-5-fluorophenyl)pyrrolidin-1-yl)pyrazolo[1,5-a]pyridine-3-carboxamido)cyclohexanecarboxylic acid;

5-((R)-2-(3-(difluoromethoxy)-5-fluorophenyl)pyrrolidin-1-yl)-N-((1r,4R)-4-(1-methyl-1H-tetrazol-5-yl)cyclohexyl)pyrazolo[1,5-a]pyridine-3-carboxamide;

(1r,4r)-4-(5-((R)-2-(5-fluoro-2-methoxyphenyl)pyrrolidin-1-yl)pyrazolo[1,5-a]pyridine-3-carboxamido)cyclohexanecarboxylic acid;

(5-((R)-2-(5-fluoro-2-methoxyphenyl)pyrrolidin-1-yl)pyrazolo[1,5-a]pyridin-3-yl) ((S)-3-hydroxypyrrolidin-1-yl)methanone;

5-((R)-2-(5-fluoro-2-methoxyphenyl)pyrrolidin-1-yl)-N-((1r,4R)-4-(2-methyl-2H-tetrazol-5-yl)cyclohexyl)pyrazolo[1,5-a]pyridine-3-carboxamide;

5-((R)-2-(5-fluoro-2-methoxyphenyl)pyrrolidin-1-yl)-N-((1r,4R)-4-(1-methyl-1H-tetrazol-5-yl)cyclohexyl)pyrazolo[1,5-a]pyridine-3-carboxamide;

5-((R)-2-(5-fluoro-2-methoxyphenyl)pyrrolidin-1-yl)-N-((1r,4R)-4-(methoxycarbamoyl)cyclohexyl)pyrazolo[1,5-a]pyridine-3-carboxamide;

N-((1r,4R)-4-(1H-1,2,4-triazol-5-yl)cyclohexyl)-5-((R)-2-(5-fluoro-2-methoxyphenyl)pyrrolidin-1-yl)pyrazolo[1,5-a]pyridine-3-carboxamide;

N-((1r,4R)-4-(1H-tetrazol-5-yl)cyclohexyl)-5-((R)-2-(5-fluoro-2-methoxyphenyl)pyrrolidin-1-yl)pyrazol[1,5-a]pyridine-3-carboxamide;

3-(5-((R)-2-(5-fluoro-2-methoxyphenyl)pyrrolidin-1-yl)pyrazolo[1,5-a]pyridine-3-carboxamido)cyclohexanecarboxylic acid (Isomer-I);

3-(5-((R)-2-(5-fluoro-2-methoxyphenyl)pyrrolidin-1-yl)pyrazolo[1,5-a]pyridine-3-carboxamido)cyclohexanecarboxylic acid (Isomer-II);

(5-((R)-2-(3,5-difluorophenyl)pyrrolidin-1-yl)pyrazolo[1,5-a]pyridin-3-yl)((S)-3-hydroxypyrrolidin-1-yl)methanone;

5-((R)-2-(3,5-difluorophenyl)pyrrolidin-1-yl)-N-((1r,4R)-4-(1-methyl-1H-tetrazol-5-yl)cyclohexyl)pyrazolo[1,5-a]pyridine-3-carboxamide;

5-((R)-2-(3,5-difluorophenyl)pyrrolidin-1-yl)-N-((1r,4R)-4-(2-methyl-2H-tetrazol-5-yl)cyclohexyl)pyrazolo[1,5-a]pyridine-3-carboxamide;

(R)-5-(2-(3,5-difluorophenyl)pyrrolidin-1-yl)-N-((1-(hydroxymethyl)cyclopentyl)methyl)pyrazolo[1,5-a]pyridine-3-carboxamide;

(R)-5-(2-(3,5-difluorophenyl)pyrrolidin-1-yl)-N-((1-(hydroxymethyl)cyclobutyl)methyl)pyrazolo[1,5-a]pyridine-3-carboxamide;

5-((R)-2-(3,5-difluorophenyl)pyrrolidin-1-yl)-N-(1,1-dioxidotetrahydrothiophen-3-yl)pyrazolo[1,5-a]pyridine-3-carboxamide (Isomer-I);

5-((R)-2-(3,5-difluorophenyl)pyrrolidin-1-yl)-N-(1,1-dioxidotetrahydrothiophen-3-yl)pyrazolo[1,5-a]pyridine-3-carboxamide (Isomer-II);

(R)-5-(2-(3,5-difluorophenyl)pyrrolidin-1-yl)-N-(4-hydroxy-4-(hydroxymethyl)cyclohexyl)pyrazolo[1,5-a]pyridine-3-carboxamide;

(R)—N-(6-(1H-1,2,4-triazol-1-yl)pyridin-3-yl)-5-(2-(3,5-difluorophenyl)pyrrolidin-1-yl)pyrazolo[1,5-a]pyridine-3-carboxamide; or (R)-5-(2-(3,5-difluorophenyl)pyrrolidin-1-yl)-N-(1-(5-sulfamoylpyridin-2-yl)azetidin-3-yl)pyrazolo[1,5-a]pyridine-3-carboxamide;

or their pharmaceutically acceptable salts, pharmaceutically acceptable solvates or stereoisomers thereof.

12. The compound according to claim 1 is
(R)-5-(2-(2,5-difluorophenyl)pyrrolidin-1-yl)-4-fluoro-N-(4-hydroxy-4-(hydroxymethyl)cyclohexyl)pyrazolo[1,5a]pyridine-3-carboxamide;

(R)-(5-(2-(2,5-difluorophenyl)pyrrolidin-1-yl)-4-fluoropyrazolo[1,5-a]pyridin-3-yl)(3-hydroxyazetidine-1-yl)methanone;

(R)-5-(2-(2,5-difluorophenyl)pyrrolidin-1-yl)-4-fluoro-N-(tetrahydro-2H-pyran-4-yl)pyrazolo[1,5-a]pyridine-3-carboxamide;

(R)-5-(2-(2,5-difluorophenyl)pyrrolidin-1-yl)-4-fluoropyrazolo[1,5-a]pyridine-3-carboxamide;

5-((R)-2-(2,5-difluorophenyl)pyrrolidin-1-yl)-N—((S)-2,3-dihydroxypropyl)-4-fluoropyrazolo[1,5-a]pyridine-3-carboxamide;

(5-((R)-2-(2,5-difluorophenyl)pyrrolidin-1-yl)-4-fluoropyrazolo[1,5-a]pyridin-3-yl)((S)-3-hydroxypyrrolidin-1-yl)methanone;

(R)-5-(2-(2,5-difluorophenyl)pyrrolidin-1-yl)-4-fluoro-N-((1-(hydroxymethyl)cyclopentyl)methyl)pyrazolo[1,5a]pyridine-3-carboxamide;

5-((R)-2-(2,5-difluorophenyl)pyrrolidin-1-yl)-4-fluoro-N—((S)-1-hydroxypropan-2-yl)pyrazolo[1,5-a]pyridine-3-carboxamide;

N-((1r,4R)-4-(1H-1,2,4-triazol-5-yl)cyclohexyl)-5-(R)-2-(2,5-difluorophenyl)pyrrolidin-1-yl)-4-fluoropyrazolo[1,5-a]pyridine-3-carboxamide;

5-((R)-2-(2,5-difluorophenyl)pyrrolidin-1-yl)-4-fluoro-N—((S)-2-hydroxypropyl)pyrazolo[1,5-a]pyridine-3-carboxamide;

5-((R)-2-(2,5-difluorophenyl)pyrrolidin-1-yl)-4-fluoro-N-((1r,4R)-4-(2-methyl-2H-tetrazol-5-yl)cyclohexyl)pyrazolo[1,5-a]pyridine-3-carboxamide;

5-((R)-2-(2,5-difluorophenyl)pyrrolidin-1-yl)-4-fluoro-N-((1r,4R)-4-(1-methyl-1H-tetrazol-5-yl)cyclohexyl)pyrazolo[1,5-a]pyridine-3-carboxamide;

(R)-5-(2-(2,5-difluorophenyl)pyrrolidin-1-yl)-4-fluoro-N-((1-(hydroxymethyl)cyclobutyl)methyl)pyrazolo[1,5-a]pyridine-3-carboxamide;

(R)-5-(2-(2,5-difluorophenyl)pyrrolidin-1-yl)-4-fluoro-N-(3-hydroxycyclobutyl)pyrazolo[1,5-a]pyridine-3-carboxamide;

N-((1r,4R)-4-(1H-1,2,4-triazol-5-yl)cyclohexyl)-5-((R)-2-(2,5-difluorophenyl)pyrrolidin-1-yl)-4-fluoropyrazolo[1,5-a]pyridine-3-carboxamide;

(1R,4r)-4-(5-((R)-2-(2,5-difluorophenyl)pyrrolidin-1-yl)-4-fluoropyrazolo[1,5-a]pyridine-3-carboxamido)cyclohexanecarboxylic acid;

5-((R)-2-(2,5-difluorophenyl)pyrrolidin-1-yl)-4-fluoro-N-((1r,4R)-4-hydroxycyclohexyl)pyrazolo[1,5-a]pyridine-3-carboxamide;

5-((R)-2-(2,5-difluorophenyl)pyrrolidin-1-yl)-4-fluoro-N-(3-hydroxycyclohexyl)pyrazolo[1,5-a]pyridine-3-carboxamide;

N-((1r,4R)-4-(1H-tetrazol-5-yl)cyclohexyl)-5-((R)-2-(2,5-difluorophenyl)pyrrolidin-1-yl)-4-fluoropyrazolo[1,5-a]pyridine-3-carboxamide;

5-((R)-2-(2,5-difluorophenyl)pyrrolidin-1-yl)-4-fluoro-N-((1r,4R)-4-(methoxycarbamoyl)cyclohexyl)pyrazolo[1,5-a]pyridine-3-carboxamide;

5-((R)-2-(2,5-difluorophenyl)pyrrolidin-1-yl)-4-fluoro-N-((1r,4R)-4-(hydroxymethyl)cyclohexyl)pyrazolo[1,5-a]pyridine-3-carboxamide; or (1R,4r)-4-(4-fluoro-5-((R)-2-(5-fluoro-2-methoxyphenyl)pyrrolidin-1-yl)pyrazolo[1,5-a]pyridine-3-carboxamido)cyclohexanecarboxylic acid;

or their pharmaceutically acceptable salts, pharmaceutically acceptable solvates or stereoisomers thereof.

13. A pharmaceutical composition comprising at least one compound as claimed in claim 1 and at least one pharmaceutically acceptable excipient.

14. A method of inhibiting tropomyosin receptor kinase A (TrkA) in a patient comprising administering to said patient a therapeutically effective amount of a compound as claimed in claim 1.

15. The compound of claim 1 having TrkA inhibitory activity using TR-FRET assay of less than about 1 μM.

* * * * *